US007897157B2

(12) United States Patent
Steward et al.

(10) Patent No.: US 7,897,157 B2
(45) Date of Patent: Mar. 1, 2011

(54) ACTIVATABLE CLOSTRIDIAL TOXINS

(75) Inventors: Lance E. Steward, Irvine, CA (US);
Joseph Francis, Aliso Viejo, CA (US);
Ester Fernandez-Salas, Fullerton, CA (US); Sanjiv Ghanshani, Irvine, CA (US); Marcella A. Gilmore, Santa Ana, CA (US); Shengwen Li, Irvine, CA (US); J. Oliver Dolly, Portmarnock (IE); Kei Roger Aoki, Coto de Caza, CA (US)

(73) Assignee: Allergan, Inc., Irvine, CA (US)

( * ) Notice: Subject to any disclaimer, the term of this patent is extended or adjusted under 35 U.S.C. 154(b) by 536 days.

(21) Appl. No.: 11/845,252

(22) Filed: Aug. 27, 2007

(65) Prior Publication Data
US 2008/0221012 A1 Sep. 11, 2008

Related U.S. Application Data

(60) Continuation of application No. 11/832,173, filed on Aug. 1, 2007, now Pat. No. 7,740,868, which is a continuation-in-part of application No. 11/326,265, filed on Jan. 5, 2006, now Pat. No. 7,419,676, which is a division of application No. 09/648,692, filed on Aug. 25, 2000, now Pat. No. 7,132,259, application No. 11/845,252, which is a continuation-in-part of application No. 11/776,075, filed on Jul. 11, 2007.

(60) Provisional application No. 60/150,710, filed on Aug. 25, 1999, provisional application No. 60/807,059, filed on Jul. 11, 2006.

(51) Int. Cl.
A61K 38/00 (2006.01)
C07K 14/33 (2006.01)

(52) U.S. Cl. .................... 424/239.1; 424/236.1; 424/9.1; 435/252.7; 514/2; 514/12; 530/350

(58) Field of Classification Search .............. 424/239.1, 424/236.1, 9.1; 514/2, 12; 530/350; 435/252.7
See application file for complete search history.

(56) References Cited

U.S. PATENT DOCUMENTS

| | | | |
|---|---|---|---|
| 4,683,202 | A | 7/1987 | Mullis |
| 4,800,159 | A | 1/1989 | Mullis |
| 5,919,665 | A | 7/1999 | Williams |
| 5,939,070 | A | 8/1999 | Johnson et al. |
| 5,989,545 | A | 11/1999 | Foster et al. |
| 6,395,513 | B1 | 5/2002 | Foster et al. |
| 6,461,617 | B1 | 10/2002 | Shone et al. |
| 6,632,440 | B1 | 10/2003 | Quinn et al. |
| 6,962,703 | B2 | 11/2005 | Foster et al. |
| 7,052,702 | B1 | 5/2006 | Duggan et al. |
| 7,132,259 | B1 | 11/2006 | Dolly et al. |
| 7,192,596 | B2 | 3/2007 | Shone et al. |
| 2003/0180289 | A1 | 9/2003 | Foster et al. |
| 2004/0071736 | A1 | 4/2004 | Quinn et al. |
| 2006/0099672 | A1 | 5/2006 | Dolly et al. |
| 2008/0032930 | A1 | 2/2008 | Steward et al. |
| 2008/0032931 | A1 | 2/2008 | Steward et al. |
| 2008/0081355 | A1 | 4/2008 | Dolly et al. |
| 2008/0161226 | A1 | 7/2008 | Steward et al. |
| 2008/0161543 | A1 | 7/2008 | Steward et al. |
| 2008/0182294 | A1 | 7/2008 | Dolly et al. |

FOREIGN PATENT DOCUMENTS

| | | |
|---|---|---|
| WO | WO 94/21300 | 9/1994 |
| WO | WO 95/32738 | 12/1995 |
| WO | WO 96/33273 | 10/1996 |
| WO | WO 98/07864 | 2/1998 |
| WO | WO 98/08540 | 3/1998 |
| WO | WO 99/17806 | 4/1999 |
| WO | WO 99/55359 | 11/1999 |
| WO | WO 00/23427 | 8/2000 |
| WO | WO 2004/024909 | 3/2004 |
| WO | WO 2005/023309 | 3/2005 |
| WO | WO 2006/027207 | 3/2006 |
| WO | WO 2006/059093 | 6/2006 |
| WO | WO 2006/059105 | 6/2006 |
| WO | WO2006/059113 | 6/2006 |

OTHER PUBLICATIONS

Herreros et al., Biochemical Journal 347, No. 1, 199-204 (Apr. 2001).*
U.S. Appl. No. 11/610,440, filed Dec. 13, 2006, Dolly et al.
U.S. Appl. No. 11/781,359, filed Jul. 23, 2007, Dolly et al.
U.S. Appl. No. 11/782,112, filed Jul. 24, 2007, Dolly et al.
U.S. Appl. No. 11/832,108, filed Aug. 1, 2007, Steward et al.
U.S. Appl. No. 11/845,167, filed Aug. 27, 2007, Steward et al.
U.S. Appl. No. 11/832,173, filed Aug. 1, 2007, Steward et al.
U.S. Appl. No. 11/833,142, filed Aug. 2, 2007, Steward et al.
U.S. Appl. No. 11/833,720, filed Aug. 3, 2007, Steward et al.
U.S. Appl. No. 11/834,068, filed Aug. 6, 2007, Steward et al.
U.S. Appl. No. 11/844,780, filed Aug. 24, 2007, Steward et al.
U.S. Appl. No. 11/844,850, filed Aug. 24, 2007, Steward et al.
U.S. Appl. No. 11/844,885, filed Aug. 24, 2007, Steward et al.
U.S. Appl. No. 11/844,929, filed Aug. 24, 2007, Steward et al.
U.S. Appl. No. 11/844,919, filed Aug. 24, 2007, Steward et al.
U.S. Appl. No. 11/844,899, filed Aug. 24, 2007, Steward et al.
U.S. Appl. No. 11/844,517, filed Aug. 24, 2007, Steward et al.
U.S. Appl. No. 11/844,546, filed Aug. 24, 2007, Steward et al.
U.S. Appl. No. 11/845,252, filed Aug. 27, 2007, Steward et al.
U.S. Appl. No. 11/845,284, filed Aug. 27, 2007, Steward et al.
U.S. Appl. No. 11/845,320, filed Aug. 27, 2007, Steward et al.
U.S. Appl. No. 11/845,345, filed Aug. 27, 2007, Steward et al.
U.S. Appl. No. 11/845,466, filed Aug. 27, 2007, Steward et al.
Herreros et al, "C-Terminal Half of Tetanus Toxin Fragment C is Sufficient for Neuronal Binding and Interaction with a Putative Protein Receptor", Biochemical Journal, vol. 347, No. Part 1, pp. 199-204, Apr. 1, 2001.
Rummel et al, "The Hcc-domain of botulinum neurotoxins A and B exhibits a singular ganglioside binding site displaying serotype specific carbohydrate interation", Molecular Microbiology, pp. 631-643, Dec. 15, 2003.
Halpern et al, "Characterization of the receptor-binding domain of tetanus toxin", Journal of Biological Chemistry, pp. 11188-11192, May 25, 1993.

(Continued)

Primary Examiner — Chih-Min Kam
(74) Attorney, Agent, or Firm — Kenton Abel; Dean Stathakis; Debra Condino

(57) ABSTRACT

Compositions comprising activatable recombinant neurotoxins and polypeptides derived therefrom. The invention also comprises nucleic acids encoding such polypeptides, and methods of making such polypeptides and nucleic acids.

29 Claims, 25 Drawing Sheets

OTHER PUBLICATIONS

Borodic et al, "Pharmacology and Histology of the Therapeutic Application of Botulinum Toxin Application of Botulinum Toxins", pp. 119-157-1994.

Tonello et al, "Tetanus and Botulinum Neurotoxins a Novel Group of Zinc-Endopeptidases", Intracellular Protein Catabolism, Adv. Exp. Med. & Biol. 389, pp. 251-260 (1996).

Li, Yan et al., "A Single Mutation in the Recombinant Light Chain of Tetanus Toxin Abolishes Its Proteolytic Activity and Removes the Toxicity Seen After Reconstitution with Native Heavy Chain", *Biochemistry* (1994), 33(22), 7014-20 CODEN: Bichaw; Issn: 0006-2960: pp. 7014-7020.

Coffield et al., "The Site and Mechanism of Action of Botulinum Neurotoxin", *Neurological Disease and Therapy*, pp. 3-13, 25 (Jankovic J. & Hallett M. eds. 1994).

Foran et al, "Botulinum Neurotoxin C1 Cleaves both Syntaxin and SNAP-25 in Intact and Permeabilized Chromaffin Cells: Correlation with Its Blockade of Catecholamine Release", Biochem. 35: pp. 2630-2636 (1996).

Dolly et al, "Probing the process of transmitter release with botulinum and tetanus neurotoxins" Seminars in Neuroscience, 6(3): pp. 149-158 (1994).

Zhou et al, "Expression and Purification of the Light Chain of Botulinum Neurotoxin A: A Single Mutation Abolishes Its Cleavage of SNAP-25 and Neurotoxiicity after Reconstitution with the Heavy Chain", Biochemistry 34: pp. 15175-15181 (1995).

Lacy et al, "Crystal structure of botulinum neurotoxin type A and implications for toxicity" Nature Struct. Biol. Oct; 5 (10): pp. 898-902 (1998).

Kurazono et al, "Minimal Essential Domains Specifying Toxicity of the Light Cahins of Tetanus Toxin and Botulinum Neurotoxin Type A", J. Biol. Chem.: pp. 14721-14729 (1992).

Hutchison et al, "Mutagenesis at a Specific Position in a DNA Sequence", J. Biol. Chem. 253: No. 18, Sep. 25 issue, pp. 6651-6560 (1978).

Li et al, "Expression and Characterization of the Heavy Chain of Tetanus Toxin: Reconstution of the Fully-Recombinant Dichain Proetin in Active Form", J. Biochem. 125: pp. 1200-1208 (1999).

\* cited by examiner

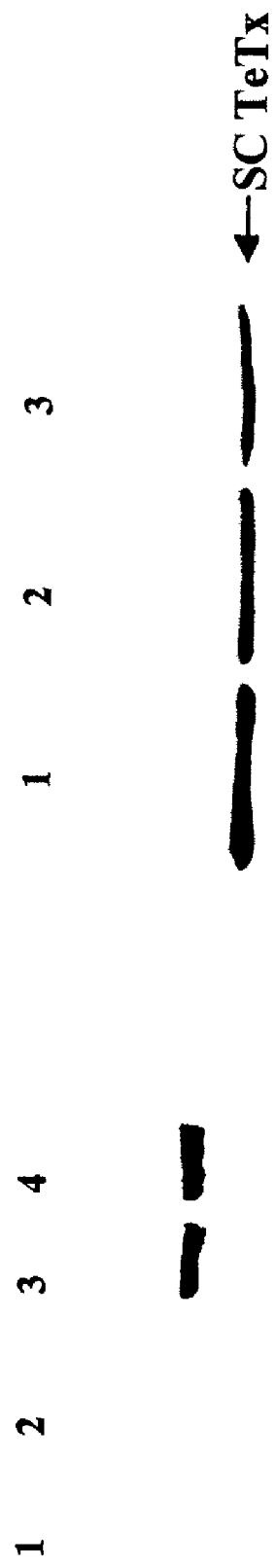

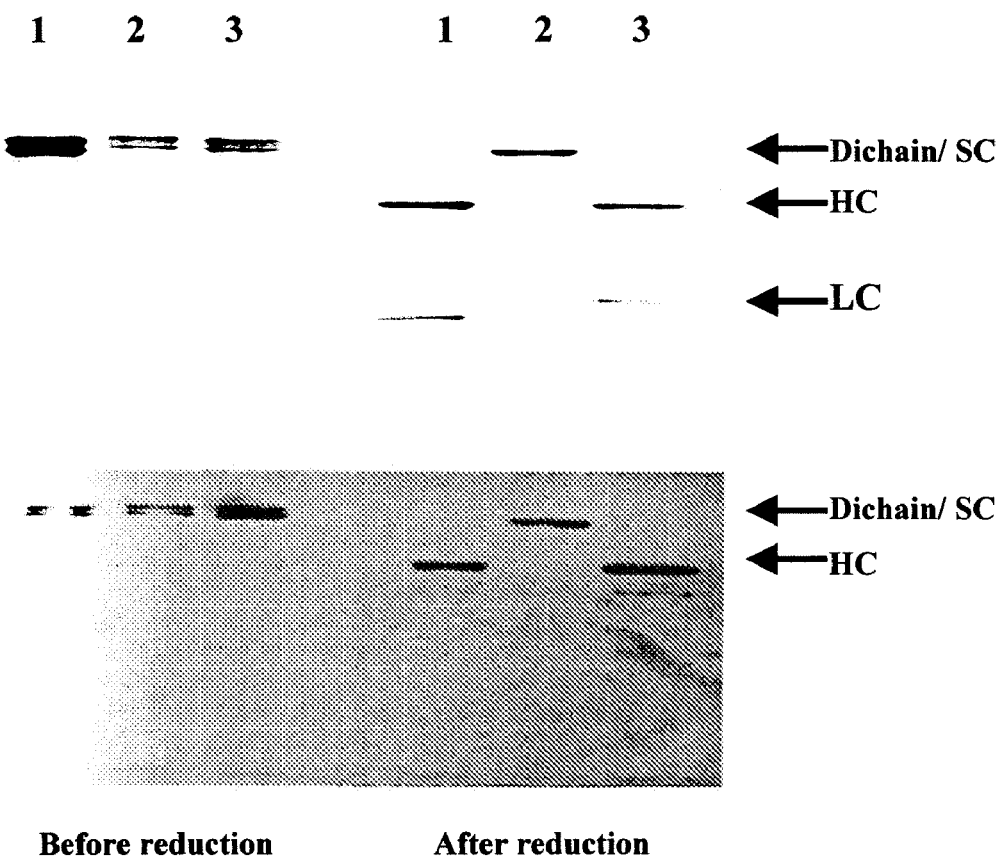

← SC TeTx WT

HC → Stained with Ponceau red
↓
HC band cut from the gel
↓
N-terminal sequencing
↓

← LC

No enzyme | Trypsin

Arg-C

GEKLYDDDDKDRWGSSR$^{496}$ $^{497}$SLTDLGGELCIKIKNEDLT

Linker sequence    HC

Arg-C and trypsin cleavage site

FIG.5

NICKED MUTANT

K$^+$-EVOKED Ca$^{2+}$-DEP. RELEASE OF [$^{14}$C] GLUTAMATE/5 MIN. (% TOXIN-FREE CONTROL)

| NATIVE TeTx (0.2 nM) | − | + | + | + | + |
|---|---|---|---|---|---|
| PRE-INCUBATED WITH MUTANT TeTx (nM) | 52 | 0 | 10 | 30 | 60 |

FIG. 7A

SINGLE-CHAIN MUTANT

K$^+$-EVOKED Ca$^{2+}$-DEP. RELEASE OF [$^{14}$C] GLUTAMATE/5 MIN. (% TOXIN-FREE CONTROL)

| NATIVE TeTx (0.2 nM) | + | + | + | + |
|---|---|---|---|---|
| PRE-INCUBATED WITH MUTANT TeTx (nM) | 0 | 7 | 20 | 40 |

CLOSTRIDIUM BOTULINUM TYPE E
(STRAIN BELUGA) CHROMOSOMAL DNA

PCR WITH A PROOF READING
THERMOPOLYMERASE 1 2 3

1: MARKERS
2: NEGATIVE CONTROL
3: SAMPLE 3.5-kB DNA FRAGMENT PURIFIED
AND CLONED INTO BamHI AND PstI
SITES OF pQE30 EXPRESSION VECTOR

HIS TAG — BamHI — BoNT/E — PstI

ATG AGA GGA TCG CAT CAC CAT CAC CAT CAC GGA TCC CCA AAA ATT AAT AGT TTT
 M   R   G   S   H   H   H   H   H   H   G   S   P   K   I   N   S   T
START           POLY HISTIDINE TAG              Bam HI    BoNT/E LIGHT CHAIN

FIG. 13

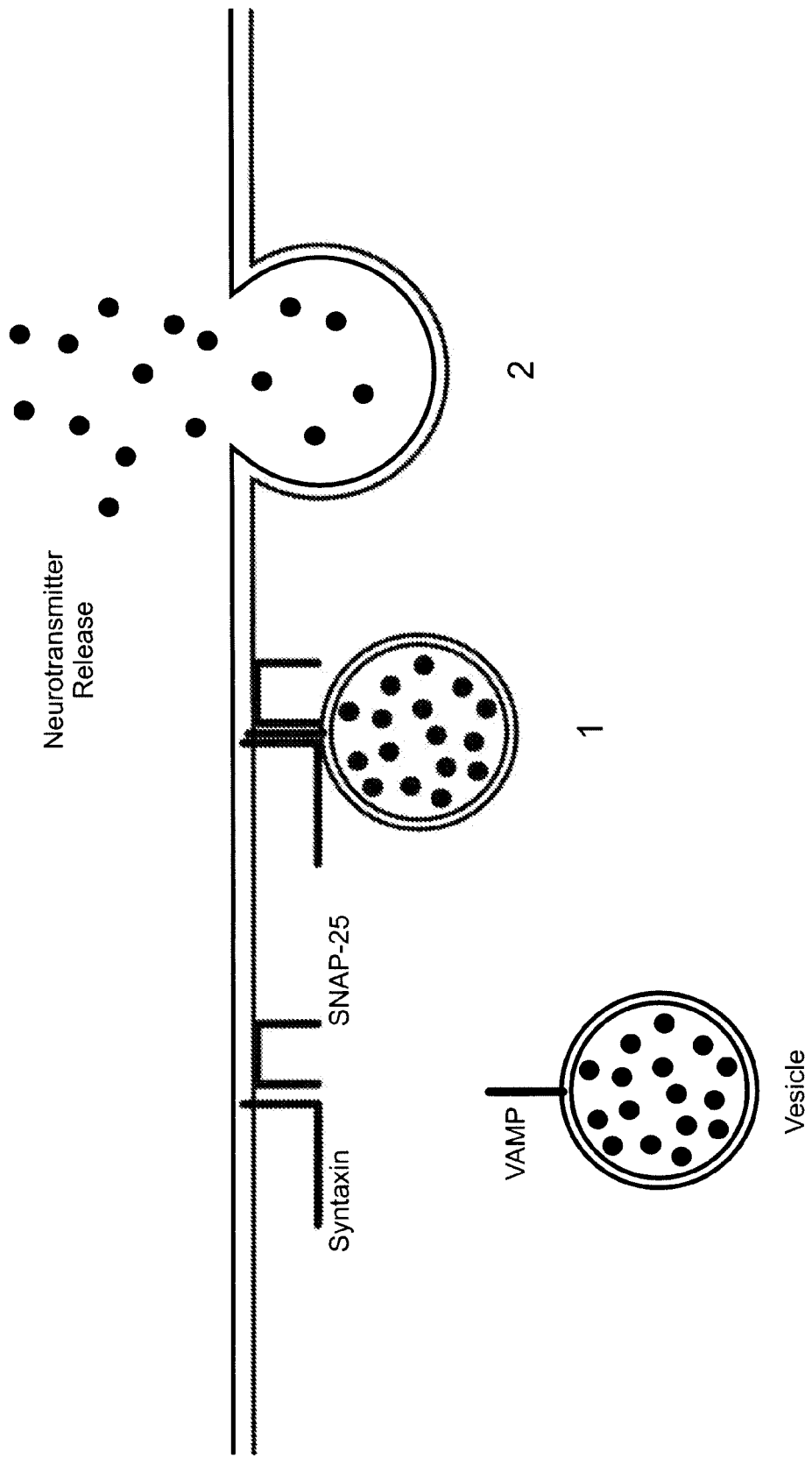

FIG. 18B.

ACTIVATABLE CLOSTRIDIAL TOXINS

This application is a continuation and claims priority pursuant to 35 U.S.C. §120 to U.S. patent application Ser. No. 11/832,173, filed Aug. 1, 2007, now U.S. Pat. No. 7,740,868, which is a continuation-in-part application that claims priority pursuant to 35 U.S.C. §120 to U.S. patent application Ser. No. 11/326,265, filed Jan. 5, 2006, now U.S. Pat. No. 7,419,676, which is a divisional application that claims priority pursuant to 35 U.S.C. §120 to U.S. patent application Ser. No. 09/648,692, filed Aug. 8, 2000, now U.S. Pat. No. 7,132,259, which claims priority pursuant to 35 U.S.C. §119(e) to U.S. Provisional Patent Application Ser. No. 60/150,710 filed on Aug. 5, 1999; and this application is a continuation-in-part application that claims priority pursuant to 35 U.S.C. §120 to U.S. patent application Ser. No. 11/776,075 filed on Jul. 11, 2007, which claims priority pursuant to 35 U.S.C. §119(e) to U.S. Provisional Patent Application Ser. No. 60/807,059 filed Jul. 11, 2006, each of which is hereby incorporated by reference in its entirety.

FIELD OF THE INVENTION

This invention concerns methods and compositions useful in the fields of neurobiology, molecular biology, and medicine, as well as methods for the production of potentially toxic therapeutic agents and derivatives thereof. The invention also concerns recombinant clostridial neurotoxins (particular botulinum neurotoxins), modified versions thereof, and methods of making such molecules, for use as therapeutic agents, transporter molecules, adducts, and the like.

BACKGROUND OF THE INVENTION

Neurotoxins, such as those obtained from *Clostridium botulinum* and *Clostridium tetani*, are highly potent and specific poisons of neural cells, and other cells when delivered within such cells for therapeutic purposes. These Gram positive bacteria express two related but distinct toxins types, each comprising two disulfide-linked amino acid chains: a light chain (L) of about 50 KDa and a heavy chain (H) of about 100 KDa, which are wholly responsible for the symptoms of these diseases. The holotoxin is synthesised in vivo as a single-chain, then nicked in a post-translational modification to form the active neurotoxin comprising the separate L and H chains.

The tetanus and botulinum toxins are among the most lethal substances known to man, having a lethal dose in humans of between 0.1 ng and 1 ng per kilogram of body weight. Tonello et al., *Adv. Exp. Med. & Biol.* 389:251-260 (1996). Both toxins function by inhibiting neurotransmitter release in affected neurons. The tetanus neurotoxin (TeNT) acts mainly in the central nervous system, while botulinum neurotoxin (BoNT) acts at the neuromuscular junction and other cholinergic synapses in the peripheral nervous system; both act by inhibiting neurotransmitter release from the axon of the affected neuron into the synapse, resulting in paralysis.

The tetanus neurotoxin (TeNT) is known to exist in one immunologically distinct type; the botulinum neurotoxins (BoNT) are known to occur in seven different immunogenic types, termed BoNT/A through BoNT/G. While all of these types are produced by isolates of *C. botulinum*, two other species, *C. baratii* and *C. butyricum* also produce toxins similar to /F and /E, respectively. See e.g., Coffield et al., *The Site and Mechanism of Action of Botulinum Neurotoxin in Therapy with Botulinum Toxin* 3-13 (Jankovic J. & Hallett M. eds. 1994), the disclosure of which is incorporated herein by reference.

Regardless of type, the molecular mechanism of intoxication appears to be similar. In the first step of the process, the toxin binds to the presynaptic membrane of the target neuron through a specific interaction between the heavy (H) chain and a cell surface receptor; the receptor is thought to be different for each type of botulinum toxin and for TeNT. Dolly et al., *Seminars in Neuroscience* 6:149-158 (1994), incorporated by reference herein. The carboxyl terminus of the heavy chain appears to be important for targeting of the toxin to the cell surface. Id.

In the second step, the toxin crosses the plasma membrane of the poisoned cell. The toxin is first engulfed by the cell through receptor-mediated endocytosis, and an endosome containing the toxin is formed. The toxin then escapes the endosome into the cytoplasm of the cell. This last step is thought to be mediated by the amino terminus of the H chain, which triggers a conformational change of the toxin in response to a pH of about 5.5 or lower. Endosomes are known to possess a proton pump which decreases intra endosomal pH. The conformational shift exposes hydrophobic residues in the toxin, which permits the toxin to embed itself in the endosomal membrane. The toxin then translocates through the endosomal membrane into the cytosol.

The last step of the mechanism of botulinum toxin activity appears to involve reduction of the disulfide bond joining the H and light (L) chain. The entire toxic activity of botulinum and tetanus toxins is contained in the L chain of the holotoxin; the L chain is a zinc ($Zn^{++}$) endopeptidase which selectively cleaves proteins essential for recognition and docking of neurotransmitter-containing vesicles with the cytoplasmic surface of the plasma membrane, and fusion of the vesicles with the plasma membrane. TxNT, BoNT/B BoNT/D, BoNT/F, and BoNT/G cause degradation of synaptobrevin, also called vesicle-associated membrane protein (VAMP), a synaptosomal membrane protein. Most of the cytosolic domain of VAMP extending from the surface of the synaptic vesicle is removed as a result of any one of these cleavage events. Each toxin (except TeNT and BoNT/B) specifically cleaves a different bond.

BoNT/A and /E selectively cleave the plasma membrane-associated protein SNAP-25; this protein, which is also cleaved by BoNT/C1 (Foran et al., *Biochem.* 35:2630-2636 (1996)), is predominantly bound to and present on the cytosolic surface of the plasma membrane. BoNT/C cleaves syntaxin, an integral protein having most of its mass exposed to the cytosol. Syntaxin interacts with the calcium channels at presynaptic terminal active zones. See Tonello et al., *Tetanus and Botulinum Neurotoxins in Intracellular Protein Catabolism* 251-260 (Suzuki K. & Bond J. eds. 1996), the disclosure of which is incorporated by reference as part of this specification.

Both TeNT and BoNT are taken up at the neuromuscular junction. BoNT remains within peripheral neurons, and blocks release of the neurotransmitter acetylcholine from these cells. Through its receptor, TeNT enters vesicles that move in a retrograde manner along the axon to the soma, and is discharged into the intersynaptic space between motor neurons and the inhibitory neurons of the spinal cord. At this point, TeNT binds receptors of the inhibitory neurons, is again internalized, and the light chain enters the cytosol to block the release of the inhibitory neurotransmitters 4-aminobutyric acid (GABA) and glycine from these cells.

Because of its specifically localized effects, minute doses of BoNT have been used since 1981 as therapeutic agents in the treatment of patients suffering from dystonias, including strabismus (misalignment of the eye), bephlarospasm (involuntary eyelid closure) and hemifacial spasm. See e.g., Borodic et al, *Pharmacology and Histology of the Therapeutic Application of Botulinum Toxin in Therapy with Botulinum Toxin* 119-157 (Jankovic J. & Hallett eds. 1994), hereby incorporated by reference herein. Of the seven toxin types, BoNT/A is the most potent of the BoNTs, and the best characterized. Intramuscular injection of spastic tissue with small quantities of BoNT/A has also been used effectively to treat spasticity due to brain injury, spinal cord injury, stroke, multiple sclerosis and cerebral palsy. The extent of paralysis depends on both the dose and volume delivered to the target site.

Although the L chain is the moiety responsible for neural intoxication, it must be delivered to the neural cytoplasm in order to be toxic. Similarly, the single-chain holotoxin proforms exhibit relatively low toxicity until they are cleaved at one or more peptide bonds in an exposed loop region between their H and L chains to create the fully-active mature neurotoxins. As implied in the mechanism provided above, the H chain of each neurotoxin is essential for cell receptor binding and endocytosis, while both the L and the H chains (and an intact disulfide bond) are required for translocation of the toxin into the cytoplasm. As indicated above, the L chain alone is responsible for the toxicity caused by inhibition of acetylcholine secretion.

Despite the clear therapeutic efficacy of clostridial neurotoxin preparations, industrial production of the toxin is difficult. Production of neurotoxin from anaerobic *Clostridium* cultures is a cumbersome and time-consuming process including a multi-step purification protocol involving several protein precipitation steps and either prolonged and repeated crystallisation of the toxin or several stages of column chromatography. Significantly, the high toxicity of the product dictates that the procedure must be performed under strict containment (BL-3). During the fermentation process, the folded single-chain neurotoxins are activated by endogenous clostridial proteases through a process termed nicking. This involves the removal of approximately 10 amino acid residues from the single-chain to create the di-chain form in which the two chains remain covalently linked through the interchain disulfide bond.

The nicked neurotoxin is much more active than the unnicked form. The amount and precise location of nicking varies with the serotypes of the bacteria producing the toxin. The differences in single-chain neurotoxin activation and, hence, the yield of nicked toxin, are due to variations in the type and amounts of proteolytic activity produced by a given strain. For example, greater than 99% of *C. botulinum* type A single-chain neurotoxin is activated by the Hall A *C. botulinum* strain, whereas type B and E strains produce toxins with lower amounts of activation (0 to 75% depending upon the fermentation time). Thus, the high toxicity of the mature neurotoxin plays a major part in the commercial manufacture of neurotoxins as therapeutic agents.

The degree of activation of engineered clostridial toxins is, therefore, an important consideration for manufacture of these materials. It would be a major advantage if neurotoxins such as BoNT and TeNT could be expressed in high yield in rapidly-growing bacteria (such as heterologous *E. coli* cells) as relatively non-toxic single-chains (or single-chains having reduced toxic activity) which are safe, easy to isolate and simple to convert to the fully-active form.

With safety being a prime concern, previous work has concentrated on the expression in *E. coli* and purification of individual H and L chains of TeNT and BoNT; these isolated chains are, by themselves, non-toxic; see Li et al., *Biochemistry* 33:7014-7020 (1994); Zhou et al., *Biochemistry* 34:15175-15181 (1995), hereby incorporated by reference herein. Following the separate production of these peptide chains and under strictly controlled conditions the H and L subunits can be combined by oxidative disulphide linkage to form the neuroparalytic di-chains. Unfortunately, this strategy has several drawbacks.

Firstly, it is not practical to express and isolate large amounts of the individual chains; in particular, in the absence of the L chain the isolated H chain is quite insoluble in aqueous solution and is highly susceptible to proteolytic degradation. Secondly, the in vitro oxidation of the individually expressed and purified H and L chains to produce the active di-chain is very inefficient, and leads to low yields of active toxin and the production of many inactive incorrectly folded or oxidized forms. The purification of the correctly folded and oxidized H and L chain-containing toxin is difficult, as is its separation from these inactive forms and the unreacted separate H and L chains.

It would therefore be useful and advantageous to express clostridial neurotoxins as inactive (or less active) single-chain forms, to eliminate the need for the time-consuming and inefficient reconstitution of the constituent chains, to maintain solubility of the protein chains, to reduce protein misfolding and consequent susceptibility to protease attack, to improve toxin yield, and/or to provide a simple method for the purification of the toxin.

Additionally, it would be useful to engineer these toxins to provide single-chain, modified neurotoxin molecules having novel therapeutic properties and/or longer duration of action, or toxic or non-toxic forms for use as transport molecules capable of delivering a therapeutic moiety to nerve or other cell types. By expressing such proteins as a single-chain, the yield and purification of the engineered proteins would be vastly improved.

SUMMARY OF THE INVENTION

The present invention is directed to recombinant and isolated proteins comprising a functional binding domain, translocation domain, and therapeutic domain in which such proteins also include an amino acid sequence that is susceptible to specific cleavage in vitro following expression as a single-chain. Such proteins may include clostridial neurotoxins and derivatives thereof, such as those proteins disclosed in Dolly et al., *Modified Clostridial Toxins for Use as Transport Proteins*, International Patent Publication WO 95/32738 (Dec. 7, 1995); and Foster et al., *Clostridial Toxin Derivatives Able to Modify Peripheral Sensory Afferent Functions*, U.S. Pat. No. 5,989,545 (Nov. 23, 1999), both incorporated by reference herein.

In one embodiment of the invention the protein comprises the functional domains of a clostridial neurotoxin H chain and some or all of the functions of a clostridial neurotoxin L chain in a single polypeptide chain, and having an inserted proteolytic cleavage site located between the H domain and the L domain by which the single-chain protein may be cleaved to produce the individual chains, preferably covalently linked by a disulfide linkage. The invention also includes methods of making such proteins and expressing them within a cell, as well as nucleic acid vectors for the transfer and expression of the nucleotide sequence regions encoding such proteins and cells containing such vectors. The proteolytic cleavage sites comprise amino acid sequences that are selectively recognized and cleaved by a specific enzyme.

In a preferred aspect of the invention, the expressed single-chain proteins comprise the biologically active domains of the H chain and L chain of a clostridial neurotoxin. Scission at the internal proteolytic cleavage site separating the chain domains thus results in the activation of a neurotoxin having full activity.

In another aspect of the invention the single-chain proteins comprise a binding domain targeted to a cell receptor other than one borne by a motor neuron. Such a binding domain may specific bind to, for example, a sensory afferent neuron, or to a non-neuronal cell type or tissue, such as pancreatic acinar cells. The single-chain proteins will contain a translocation domain similar to that of clostridial neurotoxins, and a therapeutic moiety. The therapeutic moiety may be a clostridial neurotoxin light chain, or may be a different therapeutic moiety such as an enzyme, a transcribable nucleotide sequence, growth factor, an antisense nucleotide sequence and the like.

Preferably, the toxins and toxin-based proteins of the present invention will be tailored to contain an additional amino acid sequence comprising a binding tag able to bind a target compound at sufficiently high efficiency to facilitate rapid isolation of the toxin protein. Proteins containing such binding sites are many and well known to those of skill in the art, and may comprise, without limitation, monoclonal antibodies, maltose binding protein, glutathione-S-transferase, protein A, a His$_6$ tag, and the like.

Because such proteins exhibit binding selectivity to a certain compound or compound type, the target compound may be immobilized to a solid support, including without limitation, a chromotography resin or microtiter well and used for affinity purification of the modified toxin. The toxin molecule can then be eluted by standard methods, such as through the use of a high salt solution or specific antagonist.

To minimize the safety risk associated with handling neurotoxin, the toxins of the this aspect of the present invention are expressed as their low activity (or inactive) single-chain proforms, then, by a carefully controlled proteolytic reaction in vitro, they are activated, preferably to the same potency level as the native neurotoxin from which they were derived. To improve the efficiency and rate of proteolytic cleavage the engineered proteolytic cleavage sites can be designed to occur in a specially-designed loop between the H and L portions of the single amino acid chain that promotes accessibility of the protease to the holotoxin substrate.

To reduce the risk of unintentional activation of the toxin by human or commonly encountered proteases, the amino acid sequences of the cleavage site are preferably designed to have a high degree of specificity to proteolytic enzymes which do not normally occur in humans (as either human proteases or occurring in part of the foreseeable human fauna and flora). A non-exclusive list of examples of such proteases includes a protease isolated or derived from a non-human Enterokinase, like bovine enterokinase, a protease isolated or derived from plant legumain, a protease isolated or derived from plant papain, such as, e.g., like from *Carica papaya*, a protease isolated or derived from insect papain, like from the silkworm *Sitophilus zeamatus*, a protease isolated or derived from crustacian papain, a protease isolated or derived from Tobacco etch virus (TEV), a protease isolated or derived from a Tobacco Vein Mottling Virus (TVMV), a protease isolated or derived from *Bacillus amyliquifaciens*, such as, e.g., subtilisin and GENENASE®, a protease isolated or derived from 3c protease from human rhinovirus (HRV), such as, e.g., PRESCISSION®, a protease isolated or derived from 3c protease from human enteroviruses (HEV), and a protease isolated or derived from a non-human Caspase 3.

In an aspect of the invention the single-chain polypeptide is an isolated polypeptide. By "isolated" is meant removed from its natural environment. For example, for a protein expressed within the cell, isolation includes preparation of a cell lysate as well as subsequent purification steps. A protein expressed extracellularly may be isolated by, for example, separation of the supernatant from the cells as well as any subsequent purification steps.

In another aspect of the invention the interchain loop region of the *C. botulinum* subtype E neurotoxin, which is normally resistant to proteolytic nicking in the bacterium and mammals, is modified to include the inserted proteolytic cleavage site, and this loop region used as the interchain loop region in the single-chain toxin or modified toxin molecules of the present invention. It is believed that using the loop from *C. botulinum* subtype E will stabilize the unnicked toxin molecule in vivo, making it resistant to undesired cleavage until activated through the use of the selected protease.

In yet another aspect of the invention compositions are contemplated comprising recombinant forms of BoNT/E expressed as a single-chain polypeptide.

In still another aspect contemplate recombinant chimeric and/or modified toxin derivatives expressed as a single-chain polypeptide. Such polypeptide may be molecular transporters, such as, without limitation, those disclosed in Dolly et al., European Patent Specification EP 0 760 681 B1, incorporated by reference herein.

In a further aspect the invention includes neurotoxin derivatives comprising at least a portion of a light chain from one clostridial neurotoxin or subtype thereof, and at least a portion of a heavy chain from another neurotoxin or neurotoxin subtype, as well as methods for their production. In one embodiment the hybrid neurotoxin may contain the entire light chain of a light chain from one neurotoxin subtype and the heavy chain from another neurotoxin subtype. In another embodiment, a chimeric neurotoxin derivative may contain a portion (e.g., the binding domain) of the heavy chain of one neurotoxin subtype, with another portion of the heavy chain being from another neurotoxin subtype. Similarly or alternatively, the therapeutic element may comprise light chain portions from different neurotoxins.

Such hybrid or chimeric neurotoxin derivatives are useful, for example, as a means of delivering the therapeutic benefits of such neurotoxins to patients who are immunologically resistant to a given neurotoxin subtype, to patients who may have a lower than average concentration of receptors to a given neurotoxin heavy chain binding moiety, or to patients who may have a protease-resistant variant of the membrane or vesicle toxin substrate (e.g., SNAP-25, VAMP and syntaxin). Creation of recombinant chimeric or hybrid neurotoxin derivatives having a light chain with different substrate would permit such patients to respond to neurotoxin therapy.

With regard to immunological resistance, it is known that most neurotoxin epitopes exist on the heavy chain portion of the toxin. Thus if a patient has neutralizing antibodies to, for example BoNT/A, a chimeric neurotoxin containing the heavy chain from BoNT/E and the light chain from BoNT/A (which has a longer duration of therapeutic activity than other neurotoxin light chains) would overcome this resistance. Likewise if the patient has few cell surface receptors for BoNT/A, the chance are great that the same patient would have adequate receptors to another BoNT subtype. By creating a hybrid or chimeric neurotoxin (such as one containing at least a portion of a heavy chain selected from the group consisting of $HC_A$, $HC_B$, $HC_{C1}$, $HC_D$, $HC_E$, $HC_F$, and $HC_G$ and a at least a portion of a light chain selected from a different clostridial neurotoxin subtype, said light chain being selected from the group consisting of $LC_A$, $LC_B$, $LC_{C1}$, $LC_D$, $LC_E$, $LC_F$, and $LC_G$) combining the heavy chain of that subtype with the most therapeutically appropriate light chain (for example, the BoNT/A light chain) the patient could better respond to neurotoxin therapy.

Another advantage of the hybrid or chimeric neurotoxin derivatives described above is related to the fact that certain of the light chains (e.g., $LC_A$) have a long duration of action, others having a short duration of action (e.g., $LC_E$ and $LC_F$) while still others have an intermediate duration of activity (e.g., $LC_B$). Thus, hybrid and chimeric neurotoxins represent second and third generation neurotoxin drugs in which the neurotoxin activity may be tailored to a specific therapeutic need or condition, with different drugs having different activities, substrate specificities or duration of activity.

Such hybrid or chimeric neurotoxins would also be useful in treating a patient (such as a soldier or laboratory worker) who has been inoculated with the pentavalent BoNT vaccine. Such vaccines do not contain BoNT/F; thus, combining the appropriate light chain with the BoNT/F heavy chain would create a therapeutic agent which is effective in such a patient where current therapeutic neurotoxins may not be.

The same strategy may be useful in using derivatives of clostridial neurotoxins with a therapeutic moiety other than an active neurotoxin light chain. As the heavy chain of such an agent would be derived from a neurotoxin, it may be advantageous to use a lesser known, or rarer heavy chain to avoid resistance mechanisms neutralizing the effectiveness of the therapeutic neurotoxin derivative.

By the same token, the binding moiety may be one other than a binding moiety derived from a clostridial neurotoxin heavy chain, thus providing a targeting function to cell types other than motor neurons.

Also included herein are methods for the construction, expression, and purification of such molecules in high yield as biologically active entities.

BRIEF DESCRIPTION OF THE DRAWINGS

FIG. 2A is a representation of a Western blot of an SDS-PAGE gel of cell extracts of *E. coli* JM 109 transformants containing 2 different recombinant single-chain toxins, either before or after induction of plasmid protein expression with IPTG. The antibody used for detection is an anti-His$_6$ monoclonal antibody.

FIG. 2B is a Western blot of IPTG-induced cell extracts from cells transformed with the E234A construct.

FIG. 3A shows the results of an experiment in which affinity purified recombinant single-chain (SC) TeNT is nicked with enterokinase, then separated using SDS-PAGE and visualized using Commassie Brilliant Blue under reducing and non-reducing conditions.

FIG. 3B shows the results of an experiment in which affinity purified recombinant single-chain (SC) TeNT is nicked with enterokinase, then separated using SDS-PAGE under reducing and non-reducing conditions and subjected to a Western blot using anti TeNT heavy chain antibody.

FIG. 5 is a depiction of the peptide fragments generated upon incubation of the recombinant single-chain TeNT with trypsin and Arg C protease, and deduction, from the N-terminal sequences of one of the resulting fragments, of the amino acid sequence recognized by these agents.

FIG. 7 shows the inhibitory effect upon TeNT stimulated inhibition of $Ca^{++}$-dependent neurotransmitter release of pre-incubating cerebellar cells with the E234A mutant TeNT. Pre-incubation of cerebellar neurons with nicked (FIG. 7A) or unnicked (FIG. 7B) TeTx E234A at 4° C. followed by the addition of 0.2 nM native toxin, antagonized the native toxin's inhibition of transmitter release at 37° C. to similar extents.

FIG. 10 shows the scheme for construction of a plasmid encoding single-chain BoNT/E, and an agarose gel electrophoretogram of the PCR fragment obtained during the construction of the plasmid.

FIG. 13 shows SDS-PAGE electrophoretograms under reducing and non-reducing conditions of native recombinant unnicked, and recombinant nicked BoNT/E, and Western Blots directed towards the heavy and light chains of the toxin.

FIG. 18 shows a schematic of the current paradigm of neurotransmitter release and Clostridial toxin intoxication in a central and peripheral neuron. FIG. 18A shows a schematic for the neurotransmitter release mechanism of a central and peripheral neuron. The release process can be described as comprising two steps: 1) vesicle docking, where the vesicle-bound SNARE protein of a vesicle containing neurotransmitter molecules associates with the membrane-bound SNARE proteins located at the plasma membrane; and 2) neurotransmitter release, where the vesicle fuses with the plasma membrane and the neurotransmitter molecules are exocytosed. FIG. 18B shows a schematic of the intoxication mechanism for tetanus and botulinum toxin activity in a central and peripheral neuron. This intoxication process can be described as comprising four steps: 1) receptor binding, where a Clostridial toxin binds to a Clostridial receptor system and initiates the intoxication process; 2) complex internalization, where after toxin binding, a vesicle containing the toxin/receptor system complex is endocytosed into the cell; 3) light chain translocation, where multiple events are thought to occur, including, e.g., changes in the internal pH of the vesicle, formation of a channel pore comprising the HN domain of the Clostridial toxin heavy chain, separation of the Clostridial toxin light chain from the heavy chain, and release of the active light chain and 4) enzymatic target modification, where the activate light chain of Clostridial toxin proteolytically cleaves its target SNARE substrate, such as, e.g., SNAP-25, VAMP or Syntaxin, thereby preventing vesicle docking and neurotransmitter release.

FIG. 20 shows modified Clostridial toxins with an enhanced targeting domain located at the amino terminus of the modified toxin.

FIG. 21 shows modified Clostridial toxins with an enhanced targeting domain located between the other two domains.

FIG. 22 shows modified Clostridial toxins with an enhanced targeting domain located at the carboxyl terminus of the modified toxin.

DETAILED DESCRIPTION OF THE INVENTION

Figure 1A:
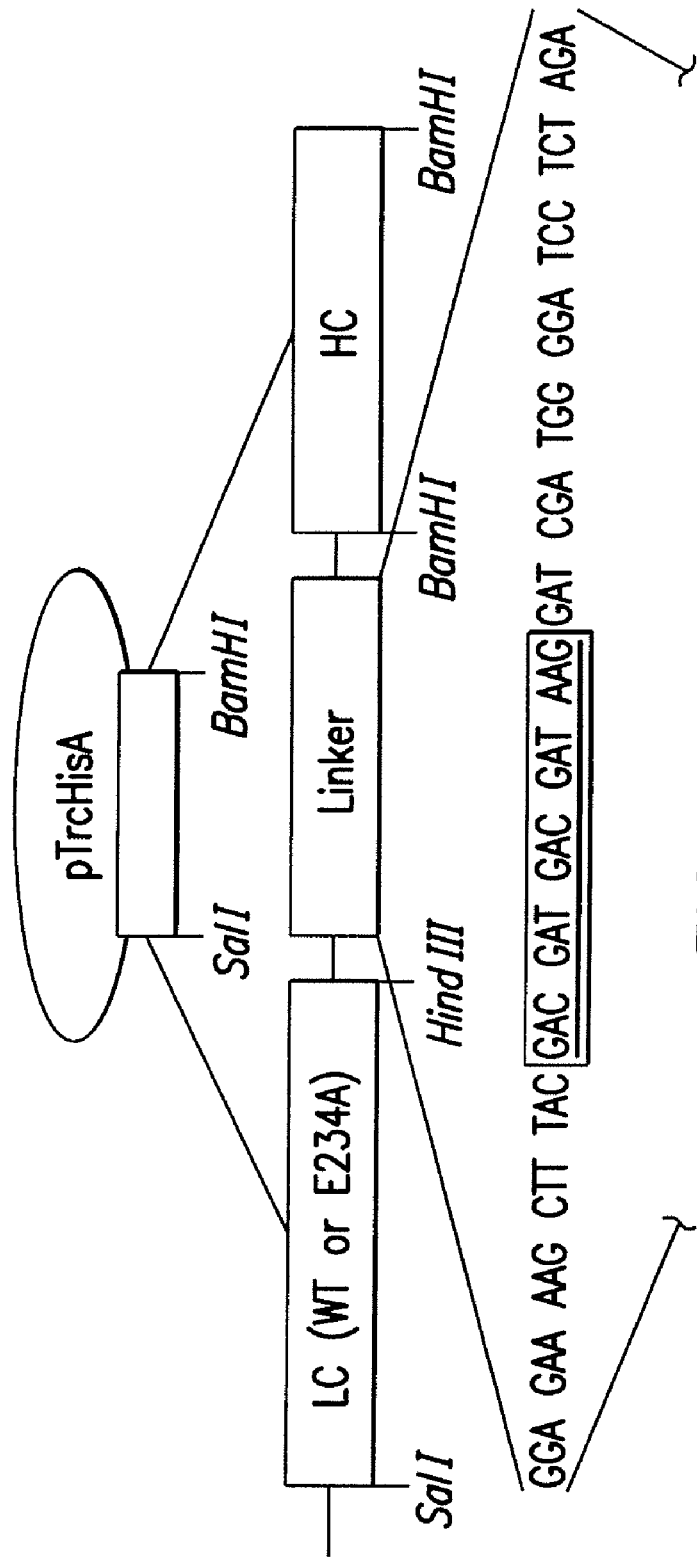
FIG. 1A is a diagrammatic view of the single-chain TeNT construct in plasmid pTrcHisA and the nucleotide sequence of the junction region.

Clostridia toxins produced by *Clostridium botulinum, Clostridium tetani, Clostridium baratii* and *Clostridium butyricum* are the most widely used in therapeutic and cosmetic treatments of humans and other mammals. Strains of *C. botulinum* produce seven antigenically-distinct types of Botulinum toxins (BoNTs), which have been identified by investigating botulism outbreaks in man (BoNT/A, /B, /E and /F), animals (BoNT/C1 and /D), or isolated from soil (BoNT/G). BoNTs possess approximately 35% amino acid identity with each other and share the same functional domain organization and overall structural architecture. It is recognized by those of skill in the art that within each type of Clostridial toxin there can be subtypes that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific subtypes showing approximately 89% amino acid identity when compared to another BoNT/A subtype. While all seven BoNT serotypes have similar structure and pharmacological properties, each also displays heterogeneous bacteriological characteristics. In contrast, tetanus toxin (TeNT) is produced by a uniform group of *C. tetani*. Two other species of *Clostridia, C. baratii* and *C. butyricum*, also produce toxins, BaNT and BuNT respectively, which are similar to BoNT/F and BoNT/E, respectively.

Each mature di-chain molecule comprises three functionally distinct domains: 1) an enzymatic domain located in the LC that includes a metalloprotease region containing a zinc-dependent endopeptidase activity which specifically targets core components of the neurotransmitter release apparatus; 2) a translocation domain contained within the amino-terminal half of the HC ($H_N$) that facilitates release of the LC from intracellular vesicles into the cytoplasm of the target cell; and 3) a binding domain found within the carboxyl-terminal half of the HC ($H_C$) that determines the binding activity and binding specificity of the toxin to the receptor complex located at the surface of the target cell. The $H_C$ domain comprises two distinct structural features of roughly equal size that indicate function and are designated the $H_{CN}$ and $H_{CC}$ subdomains. Table 1 gives approximate boundary regions for each domain found in exemplary Clostridial toxins.

TABLE 1

Clostridial Toxin Reference Sequences and Regions

| Toxin | SEQ ID NO: | LC | $H_N$ | $H_C$ |
|---|---|---|---|---|
| BoNT/A | 1 | M1-K448 | A449-K871 | N872-L1296 |
| BoNT/B | 2 | M1-K441 | A442-S858 | E859-E1291 |
| BoNT/C1 | 3 | M1-K449 | T450-N866 | N867-E1291 |
| BoNT/D | 4 | M1-R445 | D446-N862 | S863-E1276 |
| BoNT/E | 5 | M1-R422 | K423-K845 | R846-K1252 |
| BoNT/F | 6 | M1-K439 | A440-K864 | K865-E1274 |
| BoNT/G | 7 | M1-K446 | S447-S863 | N864-E1297 |
| TeNT | 8 | M1-A457 | S458-V879 | I880-D1315 |
| BaNT | 9 | M1-K431 | N432-I857 | I858-E1268 |
| BuNT | 10 | M1-R422 | K423-I847 | Y1086-K1251 |

The binding, translocation and enzymatic activity of these three functional domains are all necessary for toxicity. While all details of this process are not yet precisely known, the overall cellular intoxication mechanism whereby Clostridial toxins enter a neuron and inhibit neurotransmitter release is similar, regardless of serotype or subtype. Although the applicants have no wish to be limited by the following description, the intoxication mechanism can be described as comprising at least four steps: 1) receptor binding, 2) complex internalization, 3) light chain translocation, and 4) enzymatic target modification (see FIG. 18). The process is initiated when the $H_C$ domain of a Clostridial toxin binds to a toxin-specific receptor system located on the plasma membrane surface of a target cell. The binding specificity of a receptor complex is thought to be achieved, in part, by specific combinations of gangliosides and protein receptors that appear to distinctly comprise each Clostridial toxin receptor complex. Once bound, the toxin/receptor complexes are internalized by endocytosis and the internalized vesicles are sorted to specific intracellular routes. The translocation step appears to be triggered by the acidification of the vesicle compartment. This process seems to initiate two important pH-dependent structural rearrangements that increase hydrophobicity and promote formation di-chain form of the toxin. Once activated, light chain endopeptidase of the toxin is released from the intracellular vesicle into the cytosol where it appears to specifically targets one of three known core components of the neurotransmitter release apparatus. These core proteins, vesicle-associated membrane protein (VAMP)/synaptobrevin, synaptosomal-associated protein of 25 kDa (SNAP-25) and Syntaxin, are necessary for synaptic vesicle docking and fusion at the nerve terminal and constitute members of the soluble N-ethylmaleimide-sensitive factor-attachment protein-receptor (SNARE) family. BoNT/A and BoNT/E cleave SNAP-25 in the carboxyl-terminal region, releasing a nine or twenty-six amino acid segment, respectively, and BoNT/C1 also cleaves SNAP-25 near the carboxyl-terminus. The botulinum serotypes BoNT/B, BoNT/D, BoNT/F and BoNT/G, and tetanus toxin, act on the conserved central portion of VAMP, and release the amino-terminal portion of VAMP into the cytosol. BoNT/C1 cleaves syntaxin at a single site near the cytosolic membrane surface. The selective proteolysis of synaptic SNAREs accounts for the block of neurotransmitter release caused by Clostridial toxins in vivo. The SNARE protein targets of Clostridial toxins are common to exocytosis in a variety of non-neuronal types; in these cells, as in neurons, light chain peptidase activity inhibits exocytosis, see, e.g., Yann Humeau et al., *How Botulinum and Tetanus Neurotoxins Block Neurotransmitter Release*, 82(5) Biochimie. 427-446 (2000); Kathryn Turton et al., *Botulinum and Tetanus Neurotoxins: Structure, Function and Therapeutic Utility*, 27(11) Trends Biochem. Sci. 552-558. (2002); Giovanna Lalli et al., *The Journey of Tetanus and Botulinum Neurotoxins in Neurons*, 11(9) Trends Microbiol. 431-437, (2003).

Figure 18B:
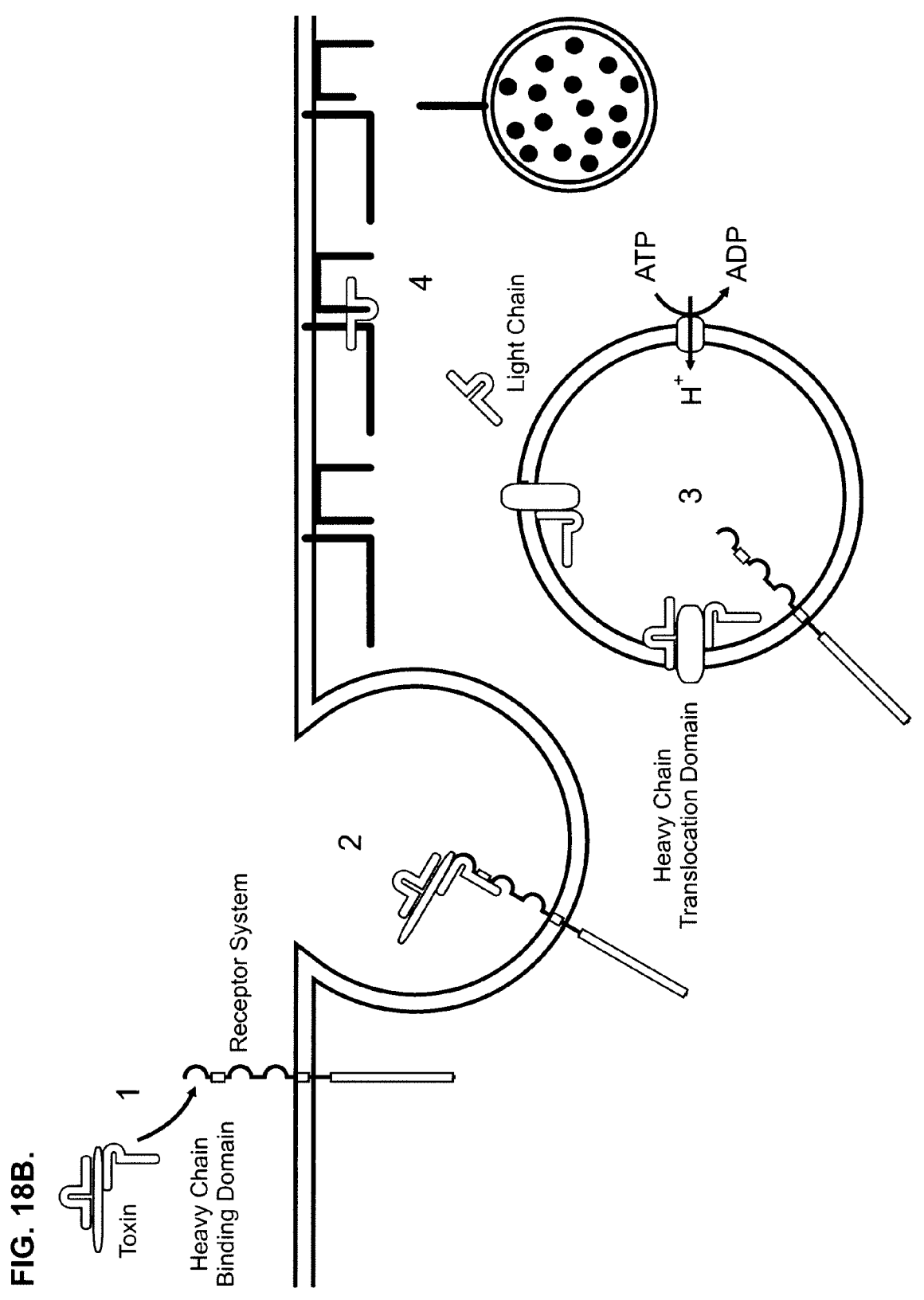

Clostridial toxins are each translated as a single-chain polypeptide of approximately 150 kDa that is subsequently cleaved by proteolytic scission within a disulfide loop by a naturally-occurring protease (FIG. 18). This cleavage occurs within the discrete di-chain loop region created between two cysteine residues that form a disulfide bridge. This posttranslational processing yields a di-chain molecule comprising an approximately 50 kDa light chain (LC) and an approximately 100 kDa heavy chain (HC) held together by the single disulfide bond and non-covalent interactions between the two chains. The naturally-occurring protease used to convert the single-chain molecule into the di-chain is currently not known. In some bacterial serotypes, such as, e.g., a BoNT/A, a BoNT/B proteolytic, a BoNT/F proteolytic, a BaNT proteolytic strain, or a TeNT, the naturally-occurring protease is produced endogenously by the bacteria serotype and cleavage occurs within the cell before the toxin is release into the environment. However, in other bacterial serotypes, such as, e.g., a BoNT/B nonproteolytic, a BoNT/C1, a BoNT/D, a BoNT/E, a BoNT/F nonproteolytic, a BoNT/G, a BaNT nonproteolytic, or a BuNT, the bacterial strain appears not to produce appreciable amounts of an endogenous protease capable of converting the single-chain form of the toxin into the di-chain form. In these situations, the toxin is released from the cell as a single-chain toxin which is subsequently converted into the di-chain form by a naturally-occurring protease found in the environment.

The compositions and methods of the present invention involve modified neurotoxins, their synthesis and use. Di-chain neurotoxins that are normally activated by scission of a single-chain polypeptide by indigenous proteases can be modified at the nucleic acid level by alteration or removal of the nucleotide sequence encoding the indigenous protease cleavage site and insertion of a nucleotide sequence encoding another different proteolytic cleavage site resistant to cleavage by host cell or human proteases. The inserted amino acid sequence is designed to be cleaved in vitro through the use of a cleaving agent chosen in advance of expression that is, absent from both human and host cell tissue.

The amino acid sequences recognized by many proteases, and their cleavage specificity are well-known to those of skill in the art. Thus, both the design of a specific proteolytic cleavage site in the loop region between the L and H chain portions of the single-chain toxin and the modification of incidental protease sites in the polypeptide to be protease-resistant is a routine matter of comparing the specificity and recognition sequences for various proteins. In the first case, the specificity of a candidate proteolytic site need not be totally exclusive, but merely needs to exclude cleavage sites for human and/or host cell proteases that might be present during the handling, storage and purification of the single-chain neurotoxin. Of course, it is preferable that the protease site is as specific as possible. In the latter case, the modification of the proteolytic cleavage site need only be sufficient to render the site resistant to the activator protease and to human and host cell proteases.

As mentioned above, a Clostridial toxin is converted from a single polypeptide form into a di-chain molecule by proteolytic cleavage. While the naturally-occurring protease is currently not known, cleavage occurs within the di-chain loop region between the two cysteine residues that form the disulfide bridge (Table 2). As used herein, the term "di-chain loop region" means the amino acid sequence of a Clostridial toxin containing a protease cleavage site used to convert the single-chain polypeptide form of a Clostridial toxin into the di-chain form. Non-limiting examples of a Clostridial toxin di-chain loop region, include, a di-chain loop region of BoNT/A comprising SEQ ID NO: 11; a di-chain loop region of BoNT/B comprising SEQ ID NO: 12; a di-chain loop region of BoNT/C1 comprising SEQ ID NO: 13; a di-chain loop region of BoNT/D comprising SEQ ID NO: 14; a di-chain loop region of BoNT/E comprising SEQ ID NO: 15; a di-chain loop region of BoNT/F comprising SEQ ID NO: 16; a di-chain loop region of BoNT/G comprising SEQ ID NO: 17; a di-chain loop region of TeNT comprising SEQ ID NO: 18, a di-chain loop region of BaNT comprising SEQ ID NO: 19, and a di-chain loop region of BuNT comprising SEQ ID NO: 20 (Table 2).

TABLE 2

Di-chain Loop Region of Clostridial Toxins

| Toxin | SEQ ID NO: | Di-Chain Loop Region Including a Di-Chain Protease Cleavage Site |
|---|---|---|
| BoNT/A | 11 | CVRGIITSKTKSLDKGYNK*----ALNDLC |
| BoNT/B | 12 | CKSVK*------------------APGIC |
| BoNT/C1 | 13 | CHKAIDGRSLYNK*------------TLDC |
| BoNT/D | 14 | CLRLTKNSR*---------------DDSTC |
| BoNT/E | 15 | CKNIVSVKGIR*--------------KSIC |
| BoNT/F | 16 | CKSVIPRKGTK*-----------APPRLC |
| BoNT/G | 17 | CKPVMYKNTGK*--------------SEQC |
| TeNT | 18 | CKKIIPPTNIRENLYNRTA*SLTDLGGELC |
| BaNT | 19 | CKSIVSKKGTK*--------------NSLC |
| BuNT | 20 | CKNIVSVKGIR*--------------KSIC |

The amino acid sequence displayed are as follows:
BoNT/A, residues 430-454 of SEQ ID NO: 1;
BoNT/B, residues 437-446 of SEQ ID NO: 2;
BoNT/C1, residues 437-453 of SEQ ID NO: 3;
BoNT/D, residues 437-450 of SEQ ID NO: 4;
BoNT/E, residues 412-426 of SEQ ID NO: 5;
BoNT/F, residues 429-445 of SEQ ID NO: 6;
BoNT/G, residues 436-450 of SEQ ID NO: 7;
TeNT, residues 439-467 of SEQ ID NO: 8;
BaNT, residues 421-435 of SEQ ID NO: 9; and
BuNT, residues 412-426 of SEQ ID NO: 10.
An asterisks (*) indicates the peptide bond of the $P_1$-$P_1$ cleavage site that is believed to be cleaved by a Clostridial toxin di-chain loop protease.

The inserted amino acid sequence may be chosen to confer susceptibility to a chemical agent capable of cleaving peptide bonds, such as cyanogen bromide. However, and much more preferably, the encoded amino acid sequence may comprise a proteolytic cleavage site highly specific for a selected protease. The selected protease may be any protease that recognizes a specific amino acid sequence and cleaves a peptide bond near or at that location, but the selected protease is very preferably not a human protease such as, e.g., human trypsin, chymotrypsin or pepsin, or a protease expressed in the host cell. Moreover, the selected protease does not recognize the same amino acid sequence as the endogenous protease (i.e., the naturally-occurring di-chain loop protease cleavage site). Finally, the selected protease should not be one expressed by the host cell that contains the plasmid encoding the recombinant neurotoxin. Any non-human protease recognizing a relatively rare amino acid sequence may be used, provided that the amino acid recognition sequence is also known. Examples of proteases to be selected as activators may include any of the following, without limitation: a protease isolated or derived from non-human Enterokinase, such as, e.g., a bovine enterokinase, a protease isolated or derived from plant legumain, a protease isolated or derived from plant papain, such as, e.g., like from *Carica papaya*, a protease isolated or derived from insect papain, like from the silkworm *Sitophilus zeamatus*, a protease isolated or derived from crustacian papain, a protease isolated or derived from Tobacco etch virus (TEV), a protease isolated or derived from a Tobacco Vein Mottling Virus (TVMV), a protease isolated or derived from *Bacillus amyliquifaciens*, such as, e.g., subtilisin and GENENASE®, a protease isolated or derived from 3c protease from human rhinovirus (HRV), such as, e.g., PRESCISSION®, a protease isolated or derived from 3c protease from human enteroviruses (HEV) and a protease isolated or derived from a non-human Caspase 3, such as, e.g., a mouse Caspase 3.

In another aspect of the invention, a modified Clostridial toxin comprises, in part, an exogenous protease cleavage site within a di-chain loop region. As used herein, the term "exogenous protease cleavage site" is synonymous with a "non-naturally occurring protease cleavage site" or "non-native protease cleavage site" and means a protease cleavage site that is not normally present in a di-chain loop region from a naturally occurring Clostridial toxin, with the proviso that the exogenous protease cleavage site is not a human protease cleavage site or a protease cleavage site that is susceptible to a protease being expressed in the host cell that is expressing a construct encoding an activatable polypeptide disclosed in the present specification. It is envisioned that any and all exogenous protease cleavage sites can be used to convert the single-chain polypeptide form of a Clostridial toxin into the di-chain form are useful to practice aspects of the present invention. Non-limiting examples of exogenous protease cleavage sites include, e.g., a plant papain cleavage site, an insect papain cleavage site, a crustacian papain cleavage site, a non-human enterokinase cleavage site, a human rhinovirus 3C protease cleavage site, human enterovirus 3C protease cleavage site, a tobacco etch virus (TEV) protease cleavage site, a Tobacco Vein Mottling Virus (TVMV) cleavage site, a subtilisin cleavage site, a hydroxylamine cleavage site, or a non-human Caspase 3 cleavage site.

It is envisioned that an exogenous protease cleavage site of any and all lengths can be useful in aspects of the present invention with the proviso that the exogenous protease cleavage site is capable of being cleaved by its respective protease. Thus, in aspects of this embodiment, an exogenous protease cleavage site can be, e.g., at least 6 amino acids in length, at least 7 amino acids in length, at least 8 amino acids in length, at least 9 amino acids in length, at least 10 amino acids in length, at least 15 amino acids in length, at least 20 amino acids in length, at least 25 amino acids in length, at least 30 amino acids in length, at least 40 amino acids in length, at least 50 amino acids in length or at least 60 amino acids in length. In other aspects of this embodiment, an exogenous protease cleavage site can be, e.g., at most 6 amino acids in length, at most 7 amino acids in length, at most 8 amino acids in length, at most 9 amino acids in length, at most 10 amino acids in length, at most 15 amino acids in length, at most 20 amino acids in length, at most 25 amino acids in length, at most 30 amino acids in length, at most 40 amino acids in length, at most 50 amino acids in length or at most 60 amino acids in length.

In an embodiment, an exogenous protease cleavage site is located within the di-chain loop of a modified Clostridial toxin. In aspects of this embodiment, a modified Clostridial toxin comprises an exogenous protease cleavage site comprises, e.g., a plant papain cleavage site, an insect papain cleavage site, a crustacian papain cleavage site, a non-human enterokinase protease cleavage site, a Tobacco Etch Virus protease cleavage site, a Tobacco Vein Mottling Virus protease cleavage site, a human rhinovirus 3C protease cleavage site, a human enterovirus 3C protease cleavage site, a subtilisin cleavage site, a hydroxylamine cleavage site, a SUMO/ULP-1 protease cleavage site, and a non-human Caspase 3 cleavage site. In other aspects of this embodiment, an exogenous protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In an aspect of this embodiment, an exogenous protease cleavage site can comprise, e.g., a non-human enterokinase cleavage site is located within the di-chain loop of a modified Clostridial toxin. In other aspects of the embodiment, an exogenous protease cleavage site can comprise, e.g., a bovine enterokinase protease cleavage site located within the di-chain loop of a modified Clostridial toxin. In other aspects of the embodiment, an exogenous protease cleavage site can comprise, e.g., a bovine enterokinase protease cleavage site located within the di-chain loop of a modified Clostridial toxin comprises SEQ ID NO: 21. In still other aspects of this embodiment, a bovine enterokinase protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In another aspect of this embodiment, an exogenous protease cleavage site can comprise, e.g., a Tobacco Etch Virus protease cleavage site is located within the di-chain loop of a modified Clostridial toxin. In other aspects of the embodiment, an exogenous protease cleavage site can comprise, e.g., a Tobacco Etch Virus protease cleavage site located within the di-chain loop of a modified Clostridial toxin comprises the consensus sequence E-P5-P4-Y-P2-Q*-G (SEQ ID NO: 22) or E-P5-P4-Y-P2-Q*-S (SEQ ID NO: 23), where P2, P4 and P5 can be any amino acid. In other aspects of the embodiment, an exogenous protease cleavage site can comprise, e.g., a Tobacco Etch Virus protease cleavage site located within the di-chain loop of a modified Clostridial toxin comprises SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33. In still other aspects of this embodiment, a Tobacco Etch Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In another aspect of this embodiment, an exogenous protease cleavage site can comprise, e.g., a Tobacco Vein Mottling Virus protease cleavage site is located within the di-chain loop of a modified Clostridial toxin. In other aspects of the embodiment, an exogenous protease cleavage site can comprise, e.g., a Tobacco Vein Mottling Virus protease cleavage site located within the di-chain loop of a modified Clostridial toxin comprises the consensus sequence P6-P5-V-R-F-Q*-G (SEQ ID NO: 34) or P6-P5-V-R-F-Q*-S (SEQ ID NO: 35), where P5 and P6 can be any amino acid. In other aspects of the embodiment, an exogenous protease cleavage site can comprise, e.g., a Tobacco Vein Mottling Virus protease cleavage site located within the di-chain loop of a modified Clostridial toxin comprises SEQ ID NO: 36, SEQ ID NO: 37, SEQ ID NO: 38, or SEQ ID NO: 39. In still other aspects of this embodiment, a Tobacco Vein Mottling Virus protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In still another aspect of this embodiment, an exogenous protease cleavage site can comprise, e.g., a human rhinovirus 3C protease cleavage site is located within the di-chain loop of a modified Clostridial toxin. In other aspects of the embodiment, an exogenous protease cleavage site can comprise, e.g., a human rhinovirus 3C protease cleavage site located within the di-chain loop of a modified Clostridial toxin comprises the consensus sequence P5-P4-L-F-Q*-G-P (SEQ ID NO: 40), where P4 is G, A, V, L, I, M, S or T and P5 can any amino acid, with D or E preferred. In other aspects of the embodiment, an exogenous protease cleavage site can comprise, e.g., a human rhinovirus 3C protease cleavage site located within the di-chain loop of a modified Clostridial toxin comprises SEQ ID NO: 41, SEQ ID NO: 42, SEQ ID NO: 43, SEQ ID NO: 44, SEQ ID NO: 45 or SEQ ID NO: 46. In other aspects of the embodiment, an exogenous protease cleavage site can comprise, e.g., a human rhinovirus 3C protease located within the di-chain loop of a modified Clostridial toxin that can be cleaved by PRESCISSION®. In still other aspects of this embodiment, a human rhinovirus 3C protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In yet another aspect of this embodiment, an exogenous protease cleavage site can comprise, e.g., a subtilisin cleavage site is located within the di-chain loop of a modified Clostridial toxin. In other aspects of the embodiment, an exogenous protease cleavage site can comprise, e.g., a subtilisin cleavage site located within the di-chain loop of a modified Clostridial toxin comprises the consensus sequence P6-P5-P4-P3-H*-Y (SEQ ID NO: 47) or P6-P5-P4-P3-Y-H* (SEQ ID NO: 48), where P3, P4 and P5 and P6 can be any amino acid. In other aspects of the embodiment, an exogenous protease cleavage site can comprise, e.g., a subtilisin cleavage site located within the di-chain loop of a modified Clostridial toxin comprises SEQ ID NO: 49, SEQ ID NO: 50, or SEQ ID NO: 51. In other aspects of the embodiment, an exogenous protease cleavage site can comprise, e.g., a subtilisin cleavage site located within the di-chain loop of a modified Clostridial toxin that can be cleaved by GENENASE®. In still other aspects of this embodiment, a subtilisin cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In yet another aspect of this embodiment, an exogenous protease cleavage site can comprise, e.g., a hydroxylamine cleavage site is located within the di-chain loop of a modified Clostridial toxin. In other aspects of the embodiment, an exogenous protease cleavage site can comprise, e.g., a hydroxylamine cleavage site comprising multiples of the dipeptide N*G. In other aspects of the embodiment, an exogenous protease cleavage site can comprise, e.g., a hydroxylamine cleavage site located within the di-chain loop of a modified Clostridial toxin comprises SEQ ID NO: 52, SEQ ID NO: 53, or SEQ ID NO: 54. In still other aspects of this embodiment, a hydroxylamine cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In yet another aspect of this embodiment, an exogenous protease cleavage site can comprise, e.g., a SUMO/ULP-1 protease cleavage site is located within the di-chain loop of a modified Clostridial toxin. In other aspects of the embodiment, an exogenous protease cleavage site can comprise, e.g., a SUMO/ULP-1 protease cleavage site located within the di-chain loop of a modified Clostridial toxin comprising the consensus sequence G-G*-P1'-P2'-P3' (SEQ ID NO: 55), where P1', P2', and P3' can be any amino acid. In other aspects of the embodiment, an exogenous protease cleavage site can comprise, e.g., a SUMO/ULP-1 protease cleavage site located within the di-chain loop of a modified Clostridial toxin comprises SEQ ID NO: 56. In still other aspects of this embodiment, a SUMO/ULP-1 protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

In an aspect of this embodiment, an exogenous protease cleavage site can comprise, e.g., a non-human Caspase 3 cleavage site is located within the di-chain loop of a modified Clostridial toxin. In other aspects of the embodiment, an exogenous protease cleavage site can comprise, e.g., a mouse Caspase 3 protease cleavage site located within the di-chain loop of a modified Clostridial toxin. In other aspects of the embodiment, an exogenous protease cleavage site can comprise, e.g., a non-human Caspase 3 protease cleavage site located within the di-chain loop of a modified Clostridial toxin comprises the consensus sequence D-P3-P2-D*P1' (SEQ ID NO: 57), where P3 can be any amino acid, with E preferred, P2 can be any amino acid and P1' can any amino acid, with G or S preferred. In other aspects of the embodiment, an exogenous protease cleavage site can comprise, e.g., a non-human Caspase 3 protease cleavage site located within the di-chain loop of a modified Clostridial toxin comprising SEQ ID NO: 58, SEQ ID NO: 59, SEQ ID NO: 60, SEQ ID NO: 61, SEQ ID NO: 62 or SEQ ID NO: 63. In still other aspects of this embodiment, a bovine enterokinase protease cleavage site is located within the di-chain loop of, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

A di-chain loop region is modified to replace a naturally-occurring di-chain loop protease cleavage site for an exogenous protease cleavage site. In this modification, the naturally-occurring di-chain loop protease cleavage site is made inoperable and thus can not be cleaved by its protease. Only the exogenous protease cleavage site can be cleaved by its corresponding exogenous protease. In this type of modification, the exogenous protease site is operably-linked in-frame to a modified Clostridial toxin as a fusion protein and the site can be cleaved by its respective exogenous protease. Replacement of an endogenous di-chain loop protease cleavage site with an exogenous protease cleavage site can be a substitution of the sites where the exogenous site is engineered at the position approximating the cleavage site location of the endogenous site. Replacement of an endogenous di-chain loop protease cleavage site with an exogenous protease cleavage site can be an addition of an exogenous site where the exogenous site is engineered at the position different from the cleavage site location of the endogenous site, the endogenous site being engineered to be inoperable. The location and kind of protease cleavage site may be critical because certain binding domains require a free amino-terminal or carboxyl-terminal amino acid. For example, when a binding domain is placed between two other domains, e.g., see FIG. 22, a criterion for selection of a protease cleavage site could be whether the protease that cleaves its site leaves a flush cut, exposing the free amino-terminal or carboxyl-terminal of the binding domain necessary for selective binding of the binding domain to its receptor.

A naturally-occurring protease cleavage site can be made inoperable by altering at least the two amino acids flanking the peptide bond cleaved by the naturally-occurring di-chain loop protease. More extensive alterations can be made, with the proviso that the two cysteine residues of the di-chain loop region remain intact and the region can still form the disulfide bridge. Non-limiting examples of an amino acid alteration include deletion of an amino acid or replacement of the original amino acid with a different amino acid. Thus, in one embodiment, a naturally-occurring protease cleavage site is made inoperable by altering the two amino acids flanking the peptide bond cleaved by a naturally-occurring protease. In other aspects of this embodiment, a naturally-occurring protease cleavage site is made inoperable by altering, e.g., at least three amino acids including the two amino acids flanking the peptide bond cleaved by a naturally-occurring protease; at least four amino acids including the two amino acids flanking the peptide bond cleaved by a naturally-occurring protease; at least five amino acids including the two amino acids flanking the peptide bond cleaved by a naturally-occurring protease; at least six amino acids including the two amino acids flanking the peptide bond cleaved by a naturally-occurring protease; at least seven amino acids including the two amino acids flanking the peptide bond cleaved by a naturally-occurring protease; at least eight amino acids including the two amino acids flanking the peptide bond cleaved by a naturally-occurring protease; at least nine amino acids including the two amino acids flanking the peptide bond cleaved by a naturally-occurring protease; at least ten amino acids including the two amino acids flanking the peptide bond cleaved by a naturally-occurring protease; at least 15 amino acids including the two amino acids flanking the peptide bond cleaved by a naturally-occurring protease; or at least 20 amino acids including the two amino acids flanking the peptide bond cleaved by a naturally-occurring protease.

In still other aspects of this embodiment, a naturally-occurring di-chain protease cleavage site is made inoperable by altering, e.g., at most three amino acids including the two amino acids flanking the peptide bond cleaved by a naturally-occurring protease; at most four amino acids including the two amino acids flanking the peptide bond cleaved by a naturally-occurring protease; at most five amino acids including the two amino acids flanking the peptide bond cleaved by a naturally-occurring protease; at most six amino acids including the two amino acids flanking the peptide bond cleaved by a naturally-occurring protease; at most seven amino acids including the two amino acids flanking the peptide bond cleaved by a naturally-occurring protease; at most eight amino acids including the two amino acids flanking the peptide bond cleaved by a naturally-occurring protease; at most nine amino acids including the two amino acids flanking the peptide bond cleaved by a naturally-occurring protease; at most ten amino acids including the two amino acids flanking the peptide bond cleaved by a naturally-occurring protease; at most 15 amino acids including the two amino acids flanking the peptide bond cleaved by a naturally-occurring protease; or at most 20 amino acids including the two amino acids flanking the peptide bond cleaved by a naturally-occurring protease.

It is understood that a modified Clostridial toxin disclosed in the present specification can optionally further comprise a flexible region comprising a flexible spacer. Non-limiting examples of a flexible spacer include, e.g., a G-spacer GGGGS (SEQ ID NO: 64) or an A-spacer EAAAK (SEQ ID NO: 65). A flexible region comprising flexible spacers can be used to adjust the length of a polypeptide region in order to optimize a characteristic, attribute or property of a polypeptide. Such a flexible region is operably-linked in-frame to the modified Clostridial toxin as a fusion protein. As a non-limiting example, a polypeptide region comprising one or more flexible spacers in tandem can be use to better expose a protease cleavage site thereby facilitating cleavage of that site by a protease. As another non-limiting example, a polypeptide region comprising one or more flexible spacers in tandem can be use to better present a binding domain, thereby facilitating the binding of that binding domain to its receptor.

Thus, in an embodiment, a modified Clostridial toxin disclosed in the present specification can further comprise a flexible region comprising a flexible spacer. In another embodiment, a modified Clostridial toxin disclosed in the present specification can further comprise flexible region comprising a plurality of flexible spacers in tandem. In aspects of this embodiment, a flexible region can comprise in tandem, e.g., at least 1 G-spacer, at least 2 G-spacers, at least 3 G-spacers, at least 4 G-spacers or at least 5 G-spacers. In other aspects of this embodiment, a flexible region can comprise in tandem, e.g., at most 1 G-spacer, at most 2 G-spacers, at most 3 G-spacers, at most 4 G-spacers or at most 5 G-spacers. In still other aspects of this embodiment, a flexible region can comprise in tandem, e.g., at least 1 A-spacer, at least 2 A-spacers, at least 3 A-spacers, at least 4 A-spacers or at least 5 A-spacers. In still other aspects of this embodiment, a flexible region can comprise in tandem, e.g., at most 1 A-spacer, at most 2 A-spacers, at most 3 A-spacers, at most 4 A-spacers or at most 5 A-spacers. In another aspect of this embodiment, a modified Clostridial toxin can comprise a flexible region comprising one or more copies of the same flexible spacers, one or more copies of different flexible-spacer regions, or any combination thereof.

In other aspects of this embodiment, a modified Clostridial toxin comprising a flexible spacer can be, e.g., a modified BoNT/A, a modified BoNT/B, a modified BoNT/C1, a modified BoNT/D, a modified BoNT/E, a modified BoNT/F, a modified BoNT/G, a modified TeNT, a modified BaNT, or a modified BuNT.

It is envisioned that a modified Clostridial toxin disclosed in the present specification can comprise a flexible spacer in any and all locations with the proviso that modified Clostridial toxin is capable of performing the intoxication process. In aspects of this embodiment, a flexible spacer is positioned between, e.g., a therapeutic element and a translocation element, a therapeutic element and a binding element, a therapeutic element and an exogenous protease cleavage site. In other aspects of this embodiment, a G-spacer is positioned between, e.g., a therapeutic element and a translocation element, a therapeutic element and a binding element, a therapeutic element and an exogenous protease cleavage site. In other aspects of this embodiment, an A-spacer is positioned between, e.g., a therapeutic element and a translocation element, a therapeutic element and a binding element, a therapeutic element and an exogenous protease cleavage site.

In other aspects of this embodiment, a flexible spacer is positioned between, e.g., a binding element and a translocation element, a binding element and a therapeutic element, a binding element and an exogenous protease cleavage site. In other aspects of this embodiment, a G-spacer is positioned between, e.g., a binding element and a translocation element, a binding element and a therapeutic element, a binding element and an exogenous protease cleavage site. In other aspects of this embodiment, an A-spacer is positioned between, e.g., a binding element and a translocation element, a binding element and a therapeutic element, a binding element and an exogenous protease cleavage site.

In yet other aspects of this embodiment, a flexible spacer is positioned between, e.g., a translocation element and a therapeutic element, a translocation element and a binding element, a translocation element and an exogenous protease cleavage site. In other aspects of this embodiment, a G-spacer is positioned between, e.g., a translocation element and a therapeutic element, a translocation element and a binding element, a translocation element and an exogenous protease cleavage site. In other aspects of this embodiment, an A-spacer is positioned between, e.g., a translocation element and a therapeutic element, a translocation element and a binding element, a translocation element and an exogenous protease cleavage site.

In another aspect, the invention is drawn to recombinant single-chain modified clostridial neurotoxins that may be cleaved at will by a protease to provide an active di-chain molecule. Such modified neurotoxins need not be toxic; in certain of these proteins the enzymatic activity of the toxin L chain may be abrogated, and the toxin joined to a drug or other bioactive agent having therapeutic activity. Alternatively, in certain other modified neurotoxins the L chain is enzymatically active, but portions of the H chain are modified to provide specificity to target cells other than the natural target of the neurotoxin, while maintaining the translocation and endocytosis-stimulating activities of the native toxin. Modified neurotoxins such as those described in this aspect of the invention are disclosed in, for example, Dolly et al., Modified Clostridial Toxins for Use as Transport Proteins, International Patent Publication WO 95/32738 (Dec. 7, 1995); Foster et al., Botulinum Toxin Derivatives Able to Modify Peripheral Sensory Afferent Functions, International Patent Publication WO96/33273 (Oct. 24, 1996); Shone et al., Recombinant Toxin Fragments, International Patent Application WO 98/07864 (98/07864); and Duggan and Chaddock, Conjugates of Galactose-Binding Lectins and Clostridial Neurotoxins as Analgesics, International Patent Publication WO 99/17806 (Apr. 15, 1999); Dolly et al., Compositions and Methods for Extending the Action of Clostridial Neurotoxin, International Patent Publication WO 99/55359 (Nov. 4, 1999); Keith A. Foster et al., Clostridial Toxin Derivatives Able To Modify Peripheral Sensory Afferent Functions, U.S. Pat. No. 5,989,545 (Nov. 23, 1999); Clifford C. Shone et al., Recombinant Toxin Fragments, U.S. Pat. No. 6,461,617 (Oct. 8, 2002); Conrad P. Quinn et al., Methods and Compounds for the Treatment of Mucus Hypersecretion, U.S. Pat. No. 6,632, 440 (Oct. 14, 2003); Lance E. Steward et al., Methods And Compositions For The Treatment Of Pancreatitis, U.S. Pat. No. 6,843,998 (Jan. 18, 2005); Stephan Donovan, Clostridial Toxin Derivatives and Methods For Treating Pain, U.S. Pat. No. 7,138,127 (Nov. 21, 2006); Keith A. Foster et al., Inhibition of Secretion from Non-Neural Cells, U.S. Patent Publication 2003/0180289 (Sep. 25, 2003); these publications are incorporated by reference herein. The present invention provides single-chain, cleavable versions of these molecules and improved methods of making such molecules.

In another aspect, the invention comprises a modified clostridial neurotoxin derived from tetanus toxin (TeNT), or one or more of the botulinum toxin (BoNT) subtypes in which the naturally-occurring interchain loop region has been replace with a modified loop region comprising a different amino acid sequence conferring 1) resistance to cleavage by host proteases or autolytic action, and/or 2) lability to a selected protease. Preferably the cleavage site is highly specific for the selected protease. The interchain loop region of certain clostridial neurotoxins, for example, BoNT/E, is naturally resistant to proteolytic cleavage in vivo. This protease resistance may reflect a secondary or tertiary structure that makes the loop more resistant to indigenous proteases than other clostridial neurotoxins. In one embodiment of the present invention, therefore, the inter-chain loop region of BoNT/E is substituted for the natural loop region occurring an another BoNT having greater therapeutic activity or duration of action, for example BoNT/A or /B. In another embodiment of the invention the loop region of BoNT/E is modified to contain a proteolytic cleavage site highly specific to a selected protease prior to the subcloning. The otherwise highly conserved BoNT/E loop region would be resistant to indigenous proteases, or those encountered within a human, but would retain the ability to be activated by digestion with the selected protease.

Unless indicated otherwise, the following terms have the following meanings in this specification:

The "therapeutic element" of the present invention may comprise, without limitation: active or inactive (i.e., modified) hormone receptors (such as androgen, estrogen, retinoid, perioxysome proliferator and ecdysone receptors etc.), and hormone-agonists and antagonists, nucleic acids capable being of being used as replication, transcription, or translational templates (e.g., for expression of a protein drug having the desired biological activity or for synthesis of a nucleic acid drug as an antisense agent), enzymes, toxins (including apoptosis-inducing or -preventing agents), and the like.

In a preferred embodiment, the therapeutic element is a polypeptide comprising a clostridial neurotoxin light chain or a portion thereof retaining the SNARE-protein sequence-specific endopeptidase activity of a clostridial neurotoxin light chain. The amino acid sequences of the light chain of botulinum neurotoxin (BoNT) subtypes A-G have been determined, as has the amino acid sequence of the light chains of the tetanus neurotoxin (TeNT), Baratii neurotoxin (BaNT), and butyricum neurotoxin (BuNT). Each chain contains the $Zn^{++}$-binding motif His-Glu-Xaa-Xaa-His (SEQ ID NO: 66).

Recent studies of the BoNT/A light chain have revealed certain features important for the activity and specificity of the toxin towards its target substrate, SNAP-25. Thus, studies by Zhou et al. *Biochemistry* 34:15175-15181 (1995) have indicated that when the light chain amino acid residue $His_{227}$ is substituted with tyrosine, the resulting polypeptide is unable to cleave SNAP-25; Kurazono et al., *J. Biol. Chem.* 14721-14729 (1992) performed studies in the presynaptic cholinergic neurons of the buccal ganglia of *Aplysia californica* using recombinant BoNT/A light chain that indicated that the removal of 8 N-terminal or 32 C-terminal residues did not abolish toxicity, but that removal of 10 N-terminal or 57 C-terminal residues abolished toxicity in this system. Most recently, the crystal structure of the entire BoNT/A holotoxin has been solved; the active site is indicated as involving the participation of $His_{222}$, $Glu_{223}$, $His_{226}$, $Glu_{26}$, and $Tyr_{365}$. Lacy et al., supra. (These residues correspond to $His_{223}$, $Glu_{224}$, $His_{227}$, $Glu_{262}$ and $Tyr_{366}$ of the BoNT/A L chain of Kurazono et al., supra.) Interestingly, an alignment of BoNT/A through E and TeNT light chains reveals that every such chain invariably has these residues in positions analogous to BoNT/A. Kurazono et al., supra.

The catalytic domain of BoNT/A is very specific for the C-terminus of SNAP-25 and appears to require a minimum of 17 SNAP-25 amino acids for cleavage to occur. The catalytic site resembles a pocket; when the light chained is linked to the heavy chain via the disulfide bond between $Cys_{429}$ and $Cys_{453}$, the translocation domain of the heavy chain appears to block access to the catalytic pocket until the light chain gains entry to the cytosol. When the disulfide bond is then reduced, the catalytic pocket is "opened" and the light chain is fully active.

The substrate specificities of the various clostridial neurotoxin light chains other than BoNT/A are known. As described above, VAMP and syntaxin are cleaved by BoNT/B, D, F, G and TeNT, and BoNT/$C_1$, respectively, while SNAP-25 is cleaved by BoNT/A E and C1. Therefore, the person of ordinary skill in the art could easily determine the toxin residues essential in these subtypes for cleavage and substrate recognition (for example, by site-directed mutagenesis or deletion of various regions of the toxin molecule followed by testing of proteolytic activity and substrate specificity), and could therefore easily design variants of the native neurotoxin light chain that retain or lack the same or similar activity.

Aspects of the present invention provide, in part, a Clostridial toxin enzymatic domain. As used herein, the term "Clostridial toxin enzymatic domain" means any Clostridial toxin polypeptide that can execute the enzymatic target modification step of the intoxication process. Thus, a Clostridial toxin enzymatic domain specifically targets a Clostridial toxin substrate and encompasses the proteolytic cleavage of a Clostridial toxin substrate, such as, e.g., SNARE proteins like a SNAP-25 substrate, a VAMP substrate and a Syntaxin substrate. Non-limiting examples of a Clostridial toxin enzymatic domain include, e.g., a BoNT/A enzymatic domain, a BoNT/B enzymatic domain, a BoNT/C1 enzymatic domain, a BoNT/D enzymatic domain, a BoNT/E enzymatic domain, a BoNT/F enzymatic domain, a BoNT/G enzymatic domain, a TeNT enzymatic domain, a BaNT enzymatic domain, and a BuNT enzymatic domain. Other non-limiting examples of a Clostridial toxin enzymatic domain include, e.g., amino acids 1-448 of SEQ ID NO: 1, amino acids 1-441 of SEQ ID NO: 2, amino acids 1-449 of SEQ ID NO: 3, amino acids 1-445 of SEQ ID NO: 4, amino acids 1-422 of SEQ ID NO: 5, amino acids 1-439 of SEQ ID NO: 6, amino acids 1-446 of SEQ ID NO: 7, amino acids 1-457 of SEQ ID NO: 8, amino acids 1-431 of SEQ ID NO: 9, and amino acids 1-422 of SEQ ID NO: 10.

A Clostridial toxin enzymatic domain includes, without limitation, naturally occurring Clostridial toxin enzymatic domain variants, such as, e.g., Clostridial toxin enzymatic domain isoforms and Clostridial toxin enzymatic domain subtypes; non-naturally occurring Clostridial toxin enzymatic domain variants, such as, e.g., conservative Clostridial toxin enzymatic domain variants, non-conservative Clostridial toxin enzymatic domain variants, Clostridial toxin enzymatic domain chimerics, active Clostridial toxin enzymatic domain fragments thereof, or any combination thereof.

As used herein, the term "Clostridial toxin enzymatic domain variant," whether naturally-occurring or non-naturally-occurring, means a Clostridial toxin enzymatic domain that has at least one amino acid change from the corresponding region of the disclosed reference sequences (Table 1) and can be described in percent identity to the corresponding region of that reference sequence. Unless expressly indicated, all Clostridial toxin enzymatic domain variants disclosed in the present specification are capable of executing the enzymatic target modification step of the intoxication process. As non-limiting examples, a BoNT/A enzymatic domain variant comprising amino acids 1-448 of SEQ ID NO: 1 will have at least one amino acid difference, such as, e.g., an amino acid substitution, deletion or addition, as compared to the amino acid region 1-448 of SEQ ID NO: 1; a BoNT/B enzymatic domain variant comprising amino acids 1-441 of SEQ ID NO: 2 will have at least one amino acid difference, such as, e.g., an amino acid substitution, deletion or addition, as compared to the amino acid region 1-441 of SEQ ID NO: 2; a BoNT/C1 enzymatic domain variant comprising amino acids 1-449 of SEQ ID NO: 3 will have at least one amino acid difference, such as, e.g., an amino acid substitution, deletion or addition, as compared to the amino acid region 1-449 of SEQ ID NO: 3; a BoNT/D enzymatic domain variant comprising amino acids 1-445 of SEQ ID NO: 4 will have at least one amino acid difference, such as, e.g., an amino acid substitution, deletion or addition, as compared to the amino acid region 1-445 of SEQ ID NO: 4; a BoNT/E enzymatic domain variant comprising amino acids 1-422 of SEQ ID NO: 5 will have at least one amino acid difference, such as, e.g., an amino acid substitution, deletion or addition, as compared to the amino acid region 1-422 of SEQ ID NO: 5; a BoNT/F enzymatic domain variant comprising amino acids 1-439 of SEQ ID NO: 6 will have at least one amino acid difference, such as, e.g., an amino acid substitution, deletion or addition, as compared to the amino acid region 1-439 of SEQ ID NO: 6; a BoNT/G enzymatic domain variant comprising amino acids 1-446 of SEQ ID NO: 7 will have at least one amino acid difference, such as, e.g., an amino acid substitution, deletion or addition, as compared to the amino acid region 1-446 of SEQ ID NO: 7; and a TeNT enzymatic domain variant comprising amino acids 1-457 of SEQ ID NO: 8 will have at least one amino acid difference, such as, e.g., an amino acid substitution, deletion or addition, as compared to the amino acid region 1-457 of SEQ ID NO: 8.

It is recognized by those of skill in the art that within each serotype of Clostridial toxin there can be naturally occurring Clostridial toxin enzymatic domain variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific enzymatic domain subtypes showing approximately 95% amino acid identity when compared to another BoNT/A enzymatic domain subtype. As used herein, the term "naturally occurring Clostridial toxin enzymatic domain variant" means any Clostridial toxin enzymatic domain produced by a naturally-occurring process, including, without limitation, Clostridial toxin enzymatic domain isoforms produced from alternatively-spliced transcripts, Clostridial toxin enzymatic domain isoforms produced by spontaneous mutation and Clostridial toxin enzymatic domain subtypes. A naturally occurring Clostridial toxin enzymatic domain variant can function in substantially the same manner as the reference Clostridial toxin enzymatic domain on which the naturally occurring Clostridial toxin enzymatic domain variant is based, and can be substituted for the reference Clostridial toxin enzymatic domain in any aspect of the present invention. A naturally occurring Clostridial toxin enzymatic domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin enzymatic domain on which the naturally occurring Clostridial toxin enzymatic domain variant is based. A naturally occurring Clostridial toxin enzymatic domain variant can also substitute at least 10 contiguous amino acids, at least 15 contiguous amino acids, at least 20 contiguous amino acids, or at least 25 contiguous amino acids from the reference Clostridial toxin enzymatic domain on which the naturally occurring Clostridial toxin enzymatic domain variant is based, that possess at least 50% amino acid identity, 65% amino acid identity, 75% amino acid identity, 85% amino acid identity or 95% amino acid identity to the reference Clostridial toxin enzymatic domain on which the naturally occurring Clostridial toxin enzymatic domain variant is based.

A non-limiting examples of a naturally occurring Clostridial toxin enzymatic domain variant is a Clostridial toxin enzymatic domain isoform such as, e.g., a BoNT/A enzymatic domain isoform, a BoNT/B enzymatic domain isoform, a BoNT/C1 enzymatic domain isoform, a BoNT/D enzymatic domain isoform, a BoNT/E enzymatic domain isoform, a BoNT/F enzymatic domain isoform, a BoNT/G enzymatic domain isoform, and a TeNT enzymatic domain isoform. A Clostridial toxin enzymatic domain isoform can function in substantially the same manner as the reference Clostridial toxin enzymatic domain on which the Clostridial toxin enzymatic domain isoform is based, and can be substituted for the reference Clostridial toxin enzymatic domain in any aspect of the present invention.

Another non-limiting examples of a naturally occurring Clostridial toxin enzymatic domain variant is a Clostridial toxin enzymatic domain subtype such as, e.g., a enzymatic domain from subtype BoNT/A1, BoNT/A2, BoNT/A3 and BoNT/A4; a enzymatic domain from subtype BoNT/B1, BoNT/B2, BoNT/B bivalent and BoNT/B nonproteolytic; a enzymatic domain from subtype BoNT/C1-1 and BoNT/C1-2; a enzymatic domain from subtype BoNT/E1, BoNT/E2 and BoNT/E3; and a enzymatic domain from subtype BoNT/F1, BoNT/F2, BoNT/F3 and BoNT/F4. A Clostridial toxin enzymatic domain subtype can function in substantially the same manner as the reference Clostridial toxin enzymatic domain on which the Clostridial toxin enzymatic domain subtype is based, and can be substituted for the reference Clostridial toxin enzymatic domain in any aspect of the present invention.

As used herein, the term "non-naturally occurring Clostridial toxin enzymatic domain variant" means any Clostridial toxin enzymatic domain produced with the aid of human manipulation, including, without limitation, Clostridial toxin enzymatic domains produced by genetic engineering using random mutagenesis or rational design and Clostridial toxin enzymatic domains produced by chemical synthesis. Non-limiting examples of non-naturally occurring Clostridial toxin enzymatic domain variants include, e.g., conservative Clostridial toxin enzymatic domain variants, non-conservative Clostridial toxin enzymatic domain variants, Clostridial toxin enzymatic domain chimeric variants and active Clostridial toxin enzymatic domain fragments.

As used herein, the term "conservative Clostridial toxin enzymatic domain variant" means a Clostridial toxin enzymatic domain that has at least one amino acid substituted by another amino acid or an amino acid analog that has at least one property similar to that of the original amino acid from the reference Clostridial toxin enzymatic domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin enzymatic domain variant can function in substantially the same manner as the reference Clostridial toxin enzymatic domain on which the conservative Clostridial toxin enzymatic domain variant is based, and can be substituted for the reference Clostridial toxin enzymatic domain in any aspect of the present invention. A conservative Clostridial toxin enzymatic domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin enzymatic domain on which the conservative Clostridial toxin enzymatic domain variant is based. A conservative Clostridial toxin enzymatic domain variant can also substitute at least 10 contiguous amino acids, at least 15 contiguous amino acids, at least 20 contiguous amino acids, or at least 25 contiguous amino acids from the reference Clostridial toxin enzymatic domain on which the conservative Clostridial toxin enzymatic domain variant is based, that possess at least 50% amino acid identity, 65% amino acid identity, 75% amino acid identity, 85% amino acid identity or 95% amino acid identity to the reference Clostridial toxin enzymatic domain on which the conservative Clostridial toxin enzymatic domain variant is based. Non-limiting examples of a conservative Clostridial toxin enzymatic domain variant include, e.g., conservative BoNT/A enzymatic domain variants, conservative BoNT/B enzymatic domain variants, conservative BoNT/C1 enzymatic domain variants, conservative BoNT/D enzymatic domain variants, conservative BoNT/E enzymatic domain variants, conservative BoNT/F enzymatic domain variants, conservative BoNT/G enzymatic domain variants, and conservative TeNT enzymatic domain variants.

As used herein, the term "non-conservative Clostridial toxin enzymatic domain variant" means a Clostridial toxin enzymatic domain in which 1) at least one amino acid is deleted from the reference Clostridial toxin enzymatic domain on which the non-conservative Clostridial toxin enzymatic domain variant is based; 2) at least one amino acid added to the reference Clostridial toxin enzymatic domain on which the non-conservative Clostridial toxin enzymatic domain is based; or 3) at least one amino acid is substituted by another amino acid or an amino acid analog that does not share any property similar to that of the original amino acid from the reference Clostridial toxin enzymatic domain sequence (Table 1). A non-conservative Clostridial toxin enzymatic domain variant can function in substantially the same manner as the reference Clostridial toxin enzymatic domain on which the non-conservative Clostridial toxin enzymatic domain variant is based, and can be substituted for the reference Clostridial toxin enzymatic domain in any aspect of the present invention. A non-conservative Clostridial toxin enzymatic domain variant can delete one or more amino acids, two or more amino acids, three or more amino acids, four or more amino acids, five or more amino acids, and ten or more amino acids from the reference Clostridial toxin enzymatic domain on which the non-conservative Clostridial toxin enzymatic domain variant is based. A non-conservative Clostridial toxin enzymatic domain variant can add one or more amino acids, two or more amino acids, three or more amino acids, four or more amino acids, five or more amino acids, and ten or more amino acids to the reference Clostridial toxin enzymatic domain on which the non-conservative Clostridial toxin enzymatic domain variant is based. A non-conservative Clostridial toxin enzymatic domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin enzymatic domain on which the non-conservative Clostridial toxin enzymatic domain variant is based. A non-conservative Clostridial toxin enzymatic domain variant can also substitute at least 10 contiguous amino acids, at least 15 contiguous amino acids, at least 20 contiguous amino acids, or at least 25 contiguous amino acids from the reference Clostridial toxin enzymatic domain on which the non-conservative Clostridial toxin enzymatic domain variant is based, that possess at least 50% amino acid identity, 65% amino acid identity, 75% amino acid identity, 85% amino acid identity or 95% amino acid identity to the reference Clostridial toxin enzymatic domain on which the non-conservative Clostridial toxin enzymatic domain variant is based. Non-limiting examples of a non-conservative Clostridial toxin enzymatic domain variant include, e.g., non-conservative BoNT/A enzymatic domain variants, non-conservative BoNT/B enzymatic domain variants, non-conservative BoNT/C1 enzymatic domain variants, non-conservative BoNT/D enzymatic domain variants, non-conservative BoNT/E enzymatic domain variants, non-conservative BoNT/F enzymatic domain variants, non-conservative BoNT/G enzymatic domain variants, and non-conservative TeNT enzymatic domain variants.

As used herein, the term "Clostridial toxin enzymatic domain chimeric" means a polypeptide comprising at least a portion of a Clostridial toxin enzymatic domain and at least a portion of at least one other polypeptide to form a toxin enzymatic domain with at least one property different from the reference Clostridial toxin enzymatic domains of Table 1, with the proviso that this Clostridial toxin enzymatic domain chimeric is still capable of specifically targeting the core components of the neurotransmitter release apparatus and thus participate in executing the overall cellular mechanism whereby a Clostridial toxin proteolytically cleaves a substrate. Such Clostridial toxin enzymatic domain chimerics are described in, e.g., Lance E. Steward et al., Leucine-based Motif and Clostridial Toxins, U.S. Patent Publication 2003/0027752 (Feb. 6, 2003); Lance E. Steward et al., Clostridial Neurotoxin Compositions and Modified Clostridial Neurotoxins, U.S. Patent Publication 2003/0219462 (Nov. 27, 2003); and Lance E. Steward et al., Clostridial Neurotoxin Compositions and Modified Clostridial Neurotoxins, U.S. Patent Publication 2004/0220386 (Nov. 4, 2004), each of which is incorporated by reference in its entirety.

As used herein, the term "active Clostridial toxin enzymatic domain fragment" means any of a variety of Clostridial toxin fragments comprising the enzymatic domain can be useful in aspects of the present invention with the proviso that these enzymatic domain fragments can specifically target the core components of the neurotransmitter release apparatus and thus participate in executing the overall cellular mechanism whereby a Clostridial toxin proteolytically cleaves a substrate. The enzymatic domains of Clostridial toxins are approximately 420-460 amino acids in length and comprise an enzymatic domain (Table 1). Research has shown that the entire length of a Clostridial toxin enzymatic domain is not necessary for the enzymatic activity of the enzymatic domain. As a non-limiting example, the first eight amino acids of the BoNT/A enzymatic domain (residues 1-8 of SEQ ID NO: 1) are not required for enzymatic activity. As another non-limiting example, the first eight amino acids of the TeNT enzymatic domain (residues 1-8 of SEQ ID NO: 8) are not required for enzymatic activity. Likewise, the carboxyl-terminus of the enzymatic domain is not necessary for activity. As a non-limiting example, the last 32 amino acids of the BoNT/A enzymatic domain (residues 417-448 of SEQ ID NO: 1) are not required for enzymatic activity. As another non-limiting example, the last 31 amino acids of the TeNT enzymatic domain (residues 427-457 of SEQ ID NO: 8) are not required for enzymatic activity. Thus, aspects of this embodiment can include Clostridial toxin enzymatic domains comprising an enzymatic domain having a length of, e.g., at least 350 amino acids, at least 375 amino acids, at least 400 amino acids, at least 425 amino acids and at least 450 amino acids. Other aspects of this embodiment can include Clostridial toxin enzymatic domains comprising an enzymatic domain having a length of, e.g., at most 350 amino acids, at most 375 amino acids, at most 400 amino acids, at most 425 amino acids and at most 450 amino acids.

Any of a variety of sequence alignment methods can be used to determine percent identity of naturally-occurring Clostridial toxin enzymatic domain variants and non-naturally-occurring Clostridial toxin enzymatic domain variants, including, without limitation, global methods, local methods and hybrid methods, such as, e.g., segment approach methods. Protocols to determine percent identity are routine procedures within the scope of one skilled in the art and from the teaching herein.

Global methods align sequences from the beginning to the end of the molecule and determine the best alignment by adding up scores of individual residue pairs and by imposing gap penalties. Non-limiting methods include, e.g., CLUSTAL W, see, e.g., Julie D. Thompson et al., *CLUSTAL W: Improving the Sensitivity of Progressive Multiple Sequence Alignment Through Sequence Weighting, Position-Specific Gap Penalties and Weight Matrix Choice,* 22(22) Nucleic Acids Research 4673-4680 (1994); and iterative refinement, see, e.g., Osamu Gotoh, *Significant Improvement in Accuracy of Multiple Protein Sequence Alignments by Iterative Refinement as Assessed by Reference to Structural Alignments,* 264(4) J. Mol. Biol. 823-838 (1996).

Local methods align sequences by identifying one or more conserved motifs shared by all of the input sequences. Non-limiting methods include, e.g., Match-box, see, e.g., Eric Depiereux and Ernest Feytmans, *Match-Box: A Fundamentally New Algorithm for the Simultaneous Alignment of Several Protein Sequences,* 8(5) CABIOS 501-509 (1992); Gibbs sampling, see, e.g., C. E. Lawrence et al., *Detecting Subtle Sequence Signals: A Gibbs Sampling Strategy for Multiple Alignment,* 262(5131) Science 208-214 (1993); Align-M, see, e.g., Ivo Van Walle et al., *Align-M—A New Algorithm for Multiple Alignment of Highly Divergent Sequences,* 20(9) Bioinformatics: 1428-1435 (2004).

Hybrid methods combine functional aspects of both global and local alignment methods. Non-limiting methods include, e.g., segment-to-segment comparison, see, e.g., Burkhard Morgenstern et al., *Multiple DNA and Protein Sequence Alignment Based On Segment-To-Segment Comparison,* 93(22) Proc. Natl. Acad. Sci. U.S.A. 12098-12103 (1996); T-Coffee, see, e.g., Cédric Notredame et al., *T-Coffee: A Novel Algorithm for Multiple Sequence Alignment,* 302(1) J. Mol. Biol. 205-217 (2000); MUSCLE, see, e.g., Robert C. Edgar, *MUSCLE: Multiple Sequence Alignment With High Score Accuracy and High Throughput,* 32(5) Nucleic Acids Res. 1792-1797 (2004); and DIALIGN-T, see, e.g., Amarendran R Subramanian et al., *DIALIGN-T: An Improved Algorithm for Segment-Based Multiple Sequence Alignment,* 6(1) BMC Bioinformatics 66 (2005).

Thus, in an embodiment, a modified Clostridial toxin disclosed in the present specification comprises a Clostridial toxin enzymatic domain. In an aspect of this embodiment, a Clostridial toxin enzymatic domain comprises a naturally occurring Clostridial toxin enzymatic domain variant, such as, e.g., a Clostridial toxin enzymatic domain isoform or a Clostridial toxin enzymatic domain subtype. In another aspect of this embodiment, a Clostridial toxin enzymatic domain comprises a non-naturally occurring Clostridial toxin enzymatic domain variant, such as, e.g., a conservative Clostridial toxin enzymatic domain variant, a non-conservative Clostridial toxin enzymatic domain variant, a Clostridial toxin chimeric enzymatic domain, an active Clostridial toxin enzymatic domain fragment, or any combination thereof.

In another embodiment, a Clostridial toxin enzymatic domain comprises a BoNT/A enzymatic domain. In an aspect of this embodiment, a BoNT/A enzymatic domain comprises amino acids 1-448 of SEQ ID NO: 1. In another aspect of this embodiment, a BoNT/A enzymatic domain comprises a naturally occurring BoNT/A enzymatic domain variant, such as, e.g., a enzymatic domain from a BoNT/A isoform or a enzymatic domain from a BoNT/A subtype. In another aspect of this embodiment, a BoNT/A enzymatic domain comprises amino acids 1-448 of a naturally occurring BoNT/A enzymatic domain variant of SEQ ID NO: 1, such as, e.g., amino acids 1-448 of a BoNT/A isoform of SEQ ID NO: 1 or amino acids 1-448 of a BoNT/A subtype of SEQ ID NO: 1. In still another aspect of this embodiment, a BoNT/A enzymatic domain comprises a non-naturally occurring BoNT/A enzymatic domain variant, such as, e.g., a conservative BoNT/A enzymatic domain variant, a non-conservative BoNT/A enzymatic domain variant, a BoNT/A chimeric enzymatic domain, an active BoNT/A enzymatic domain fragment, or any combination thereof. In still another aspect of this embodiment, a BoNT/A enzymatic domain comprises amino acids 1-448 of a non-naturally occurring BoNT/A enzymatic domain variant of SEQ ID NO: 1, such as, e.g., amino acids 1-448 of a conservative BoNT/A enzymatic domain variant of SEQ ID NO: 1, amino acids 1-448 of a non-conservative BoNT/A enzymatic domain variant of SEQ ID NO: 1, amino acids 1-448 of an active BoNT/A enzymatic domain fragment of SEQ ID NO: 1, or any combination thereof.

In other aspects of this embodiment, a BoNT/A enzymatic domain comprises a polypeptide having, e.g., at least 70% amino acid identity with amino acids 1-448 of SEQ ID NO: 1, at least 75% amino acid identity with amino acids 1-448 of SEQ ID NO: 1, at least 80% amino acid identity with amino acids 1-448 of SEQ ID NO: 1, at least 85% amino acid identity with amino acids 1-448 of SEQ ID NO: 1, at least 90% amino acid identity with amino acids 1-448 of SEQ ID NO: 1 or at least 95% amino acid identity with amino acids 1-448 of SEQ ID NO: 1. In yet other aspects of this embodiment, a BoNT/A enzymatic domain comprises a polypeptide having, e.g., at most 70% amino acid identity with amino acids 1-448 of SEQ ID NO: 1, at most 75% amino acid identity with amino acids 1-448 of SEQ ID NO: 1, at most 80% amino acid identity with amino acids 1-448 of SEQ ID NO: 1, at most 85% amino acid identity with amino acids 1-448 of SEQ ID NO: 1, at most 90% amino acid identity with amino acids 1-448 of SEQ ID NO: 1 or at most 95% amino acid identity with amino acids 1-448 of SEQ ID NO: 1.

In other aspects of this embodiment, a BoNT/A enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-448 of SEQ ID NO: 1. In other aspects of this embodiment, a BoNT/A enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-448 of SEQ ID NO: 1. In yet other aspects of this embodiment, a BoNT/A enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-448 of SEQ ID NO: 1. In other aspects of this embodiment, a BoNT/A enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-448 of SEQ ID NO: 1. In still other aspects of this embodiment, a BoNT/A enzymatic domain comprises a polypeptide having, e.g., at most one, two, three, four, five, six, seven, eight, nine, 10, 20, 30, 40, 50, 100 or 200 non-contiguous amino acid additions relative to amino acids 1-448 of SEQ ID NO: 1. In other aspects of this embodiment, a BoNT/A enzymatic domain comprises a polypeptide having, e.g., at least one, two, three, four, five, six, seven, eight, nine, 10, 20, 30, 40, 50, 100 or 200 non-contiguous amino acid additions relative to amino acids 1-448 of SEQ ID NO: 1.

In other aspects of this embodiment, a BoNT/A enzymatic domain comprises a polypeptide having, e.g., at most one, two, three, four, five, six, seven, eight, nine, 10, 20, 30, 40, 50, 100 or 200 contiguous amino acid substitutions relative to amino acids 1-448 of SEQ ID NO: 1. In other aspects of this embodiment, a BoNT/A enzymatic domain comprises a polypeptide having, e.g., at least one, two, three, four, five, six, seven, eight, nine, 10, 20, 30, 40, 50, 100 or 200 contiguous amino acid substitutions relative to amino acids 1-448 of SEQ ID NO: 1. In yet other aspects of this embodiment, a BoNT/A enzymatic domain comprises a polypeptide having, e.g., at most one, two, three, four, five, six, seven, eight, nine, 10, 20, 30, 40, 50, 100 or 200 contiguous amino acid deletions relative to amino acids 1-448 of SEQ ID NO: 1. In other aspects of this embodiment, a BoNT/A enzymatic domain comprises a polypeptide having, e.g., at least one, two, three, four, five, six, seven, eight, nine, 10, 20, 30, 40, 50, 100 or 200 contiguous amino acid deletions relative to amino acids 1-448 of SEQ ID NO: 1. In still other aspects of this embodiment, a BoNT/A enzymatic domain comprises a polypeptide having, e.g., at most one, two, three, four, five, six, seven, eight, nine, 10, 20, 30, 40, 50, 100 or 200 contiguous amino acid additions relative to amino acids 1-448 of SEQ ID NO: 1. In other aspects of this embodiment, a BoNT/A enzymatic domain comprises a polypeptide having, e.g., at least one, two, three, four, five, six, seven, eight, nine, 10, 20, 30, 40, 50, 100 or 200 contiguous amino acid additions relative to amino acids 1-448 of SEQ ID NO: 1.

In another embodiment, a Clostridial toxin enzymatic domain comprises a BoNT/B enzymatic domain. In an aspect of this embodiment, a BoNT/B enzymatic domain comprises amino acids 1-441 of SEQ ID NO: 2. In another aspect of this embodiment, a BoNT/B enzymatic domain comprises a naturally occurring BoNT/B enzymatic domain variant, such as, e.g., a enzymatic domain from a BoNT/B isoform or a enzymatic domain from a BoNT/B subtype. In another aspect of this embodiment, a BoNT/B enzymatic domain comprises amino acids 1-441 of a naturally occurring BoNT/B enzymatic domain variant of SEQ ID NO: 2, such as, e.g., amino acids 1-441 of a BoNT/B isoform of SEQ ID NO: 2 or amino acids 1-441 of a BoNT/B subtype of SEQ ID NO: 2. In still another aspect of this embodiment, a BoNT/B enzymatic domain comprises a non-naturally occurring BoNT/B enzymatic domain variant, such as, e.g., a conservative BoNT/B enzymatic domain variant, a non-conservative BoNT/B enzymatic domain variant, a BoNT/B chimeric enzymatic domain, an active BoNT/B enzymatic domain fragment, or any combination thereof. In still another aspect of this embodiment, a BoNT/B enzymatic domain comprises amino acids 1-441 of a non-naturally occurring BoNT/B enzymatic domain variant of SEQ ID NO: 2, such as, e.g., amino acids 1-441 of a conservative BoNT/B enzymatic domain variant of SEQ ID NO: 2, amino acids 1-441 of a non-conservative BoNT/B enzymatic domain variant of SEQ ID NO: 2, amino acids 1-441 of an active BoNT/B enzymatic domain fragment of SEQ ID NO: 2, or any combination thereof.

In other aspects of this embodiment, a BoNT/B enzymatic domain comprises a polypeptide having, e.g., at least 70% amino acid identity with amino acids 1-441 of SEQ ID NO: 2, at least 75% amino acid identity with amino acids 1-441 of SEQ ID NO: 2, at least 80% amino acid identity with amino acids 1-441 of SEQ ID NO: 2, at least 85% amino acid identity with amino acids 1-441 of SEQ ID NO: 2, at least 90% amino acid identity with amino acids 1-441 of SEQ ID NO: 2 or at least 95% amino acid identity with amino acids 1-441 of SEQ ID NO: 2. In yet other aspects of this embodiment, a BoNT/B enzymatic domain comprises a polypeptide having, e.g., at most 70% amino acid identity with amino acids 1-441 of SEQ ID NO: 2, at most 75% amino acid identity with amino acids 1-441 of SEQ ID NO: 2, at most 80% amino acid identity with amino acids 1-441 of SEQ ID NO: 2, at most 85% amino acid identity with amino acids 1-441 of SEQ ID NO: 2, at most 90% amino acid identity with amino acids 1-441 of SEQ ID NO: 2 or at most 95% amino acid identity with amino acids 1-441 of SEQ ID NO: 2.

In other aspects of this embodiment, a BoNT/B enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-441 of SEQ ID NO: 2. In other aspects of this embodiment, a BoNT/B enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-441 of SEQ ID NO: 2. In yet other aspects of this embodiment, a BoNT/B enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-441 of SEQ ID NO: 2. In other aspects of this embodiment, a BoNT/B enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-441 of SEQ ID NO: 2. In still other aspects of this embodiment, a BoNT/B enzymatic domain comprises a polypeptide having, e.g., at most one, two, three, four, five, six, seven, eight, nine, 10, 20, 30, 40, 50, 100 or 200 non-contiguous amino acid additions relative to amino acids 1-441 of SEQ ID NO: 2. In other aspects of this embodiment, a BoNT/B enzymatic domain comprises a polypeptide having, e.g., at least one, two, three, four, five, six, seven, eight, nine, 10, 20, 30, 40, 50, 100 or 200 non-contiguous amino acid additions relative to amino acids 1-441 of SEQ ID NO: 2.

In other aspects of this embodiment, a BoNT/B enzymatic domain comprises a polypeptide having, e.g., at most one, two, three, four, five, six, seven, eight, nine, 10, 20, 30, 40, 50, 100 or 200 contiguous amino acid substitutions relative to amino acids 1-441 of SEQ ID NO: 2. In other aspects of this embodiment, a BoNT/B enzymatic domain comprises a polypeptide having, e.g., at least one, two, three, four, five, six, seven, eight, nine, 10, 20, 30, 40, 50, 100 or 200 contiguous amino acid substitutions relative to amino acids 1-441 of SEQ ID NO: 2. In yet other aspects of this embodiment, a BoNT/B enzymatic domain comprises a polypeptide having, e.g., at most one, two, three, four, five, six, seven, eight, nine, 10, 20, 30, 40, 50, 100 or 200 contiguous amino acid deletions relative to amino acids 1-441 of SEQ ID NO: 2. In other aspects of this embodiment, a BoNT/B enzymatic domain comprises a polypeptide having, e.g., at least one, two, three, four, five, six, seven, eight, nine, 10, 20, 30, 40, 50, 100 or 200 contiguous amino acid deletions relative to amino acids 1-441 of SEQ ID NO: 2. In still other aspects of this embodiment, a BoNT/B enzymatic domain comprises a polypeptide having, e.g., at most one, two, three, four, five, six, seven, eight, nine, 10, 20, 30, 40, 50, 100 or 200 contiguous amino acid additions relative to amino acids 1-441 of SEQ ID NO: 2. In other aspects of this embodiment, a BoNT/B enzymatic domain comprises a polypeptide having, e.g., at least one, two, three, four, five, six, seven, eight, nine, 10, 20, 30, 40, 50, 100 or 200 contiguous amino acid additions relative to amino acids 1-441 of SEQ ID NO: 2.

In another embodiment, a Clostridial toxin enzymatic domain comprises a BoNT/C1 enzymatic domain. In an aspect of this embodiment, a BoNT/C1 enzymatic domain comprises amino acids 1-449 of SEQ ID NO: 3. In another aspect of this embodiment, a BoNT/C1 enzymatic domain comprises a naturally occurring BoNT/C1 enzymatic domain variant, such as, e.g., a enzymatic domain from a BoNT/C1 isoform or a enzymatic domain from a BoNT/C1 subtype. In another aspect of this embodiment, a BoNT/C1 enzymatic domain comprises amino acids 1-449 of a naturally occurring BoNT/C1 enzymatic domain variant of SEQ ID NO: 3, such as, e.g., amino acids 1-449 of a BoNT/C1 isoform of SEQ ID NO: 3 or amino acids 1-449 of a BoNT/C1 subtype of SEQ ID NO: 3. In still another aspect of this embodiment, a BoNT/C1 enzymatic domain comprises a non-naturally occurring BoNT/C1 enzymatic domain variant, such as, e.g., a conservative BoNT/C1 enzymatic domain variant, a non-conservative BoNT/C1 enzymatic domain variant, a BoNT/C1 chimeric enzymatic domain, an active BoNT/C1 enzymatic domain fragment, or any combination thereof. In still another aspect of this embodiment, a BoNT/C1 enzymatic domain comprises amino acids 1-449 of a non-naturally occurring BoNT/C1 enzymatic domain variant of SEQ ID NO: 3, such as, e.g., amino acids 1-449 of a conservative BoNT/C1 enzymatic domain variant of SEQ ID NO: 3, amino acids 1-449 of a non-conservative BoNT/C1 enzymatic domain variant of SEQ ID NO: 3, amino acids 1-449 of an active BoNT/C1 enzymatic domain fragment of SEQ ID NO: 3, or any combination thereof.

In other aspects of this embodiment, a BoNT/C1 enzymatic domain comprises a polypeptide having, e.g., at least 70% amino acid identity with amino acids 1-449 of SEQ ID NO: 3, at least 75% amino acid identity with amino acids 1-449 of SEQ ID NO: 3, at least 80% amino acid identity with amino acids 1-449 of SEQ ID NO: 3, at least 85% amino acid identity with amino acids 1-449 of SEQ ID NO: 3, at least 90% amino acid identity with amino acids 1-449 of SEQ ID NO: 3 or at least 95% amino acid identity with amino acids 1-449 of SEQ ID NO: 3. In yet other aspects of this embodiment, a BoNT/C1 enzymatic domain comprises a polypeptide having, e.g., at most 70% amino acid identity with amino acids 1-449 of SEQ ID NO: 3, at most 75% amino acid identity with amino acids 1-449 of SEQ ID NO: 3, at most 80% amino acid identity with amino acids 1-449 of SEQ ID NO: 3, at most 85% amino acid identity with amino acids 1-449 of SEQ ID NO: 3, at most 90% amino acid identity with amino acids 1-449 of SEQ ID NO: 3 or at most 95% amino acid identity with amino acids 1-449 of SEQ ID NO: 3.

In other aspects of this embodiment, a BoNT/C1 enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-449 of SEQ ID NO: 3. In other aspects of this embodiment, a BoNT/C1 enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-449 of SEQ ID NO: 3. In yet other aspects of this embodiment, a BoNT/C1 enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-449 of SEQ ID NO: 3. In other aspects of this embodiment, a BoNT/C1 enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-449 of SEQ ID NO: 3. In still other aspects of this embodiment, a BoNT/C1 enzymatic domain comprises a polypeptide having, e.g., at most one, two, three, four, five, six, seven, eight, nine, 10, 20, 30, 40, 50, 100 or 200 non-contiguous amino acid additions relative to amino acids 1-449 of SEQ ID NO: 3. In other aspects of this embodiment, a BoNT/C1 enzymatic domain comprises a polypeptide having, e.g., at least one, two, three, four, five, six, seven, eight, nine, 10, 20, 30, 40, 50, 100 or 200 non-contiguous amino acid additions relative to amino acids 1-449 of SEQ ID NO: 3.

In other aspects of this embodiment, a BoNT/C1 enzymatic domain comprises a polypeptide having, e.g., at most one, two, three, four, five, six, seven, eight, nine, 10, 20, 30, 40, 50, 100 or 200 contiguous amino acid substitutions relative to amino acids 1-449 of SEQ ID NO: 3. In other aspects of this embodiment, a BoNT/C1 enzymatic domain comprises a polypeptide having, e.g., at least one, two, three, four, five, six, seven, eight, nine, 10, 20, 30, 40, 50, 100 or 200 contiguous amino acid substitutions relative to amino acids 1-449 of SEQ ID NO: 3. In yet other aspects of this embodiment, a BoNT/C1 enzymatic domain comprises a polypeptide having, e.g., at most one, two, three, four, five, six, seven, eight, nine, 10, 20, 30, 40, 50, 100 or 200 contiguous amino acid deletions relative to amino acids 1-449 of SEQ ID NO: 3. In other aspects of this embodiment, a BoNT/C1 enzymatic domain comprises a polypeptide having, e.g., at least one, two, three, four, five, six, seven, eight, nine, 10, 20, 30, 40, 50, 100 or 200 contiguous amino acid deletions relative to amino acids 1-449 of SEQ ID NO: 3. In still other aspects of this embodiment, a BoNT/C1 enzymatic domain comprises a polypeptide having, e.g., at most one, two, three, four, five, six, seven, eight, nine, 10, 20, 30, 40, 50, 100 or 200 contiguous amino acid additions relative to amino acids 1-449 of SEQ ID NO: 3. In other aspects of this embodiment, a BoNT/C1 enzymatic domain comprises a polypeptide having, e.g., at least one, two, three, four, five, six, seven, eight, nine, 10, 20, 30, 40, 50, 100 or 200 contiguous amino acid additions relative to amino acids 1-449 of SEQ ID NO: 3.

In another embodiment, a Clostridial toxin enzymatic domain comprises a BoNT/D enzymatic domain. In an aspect of this embodiment, a BoNT/D enzymatic domain comprises amino acids 1-445 of SEQ ID NO: 4. In another aspect of this embodiment, a BoNT/D enzymatic domain comprises a naturally occurring BoNT/D enzymatic domain variant, such as, e.g., a enzymatic domain from a BoNT/D isoform or a enzymatic domain from a BoNT/D subtype. In another aspect of this embodiment, a BoNT/D enzymatic domain comprises amino acids 1-445 of a naturally occurring BoNT/D enzymatic domain variant of SEQ ID NO: 4, such as, e.g., amino acids 1-445 of a BoNT/D isoform of SEQ ID NO: 4 or amino acids 1-445 of a BoNT/D subtype of SEQ ID NO: 4. In still another aspect of this embodiment, a BoNT/D enzymatic domain comprises a non-naturally occurring BoNT/D enzymatic domain variant, such as, e.g., a conservative BoNT/D enzymatic domain variant, a non-conservative BoNT/D enzymatic domain variant, a BoNT/D chimeric enzymatic domain, an active BoNT/D enzymatic domain fragment, or any combination thereof. In still another aspect of this embodiment, a BoNT/D enzymatic domain comprises amino acids 1-445 of a non-naturally occurring BoNT/D enzymatic domain variant of SEQ ID NO: 4, such as, e.g., amino acids 1-445 of a conservative BoNT/D enzymatic domain variant of SEQ ID NO: 4, amino acids 1-445 of a non-conservative BoNT/D enzymatic domain variant of SEQ ID NO: 4, amino acids 1-445 of an active BoNT/D enzymatic domain fragment of SEQ ID NO: 4, or any combination thereof.

In other aspects of this embodiment, a BoNT/D enzymatic domain comprises a polypeptide having, e.g., at least 70% amino acid identity with amino acids 1-445 of SEQ ID NO: 4, at least 75% amino acid identity with amino acids 1-445 of SEQ ID NO: 4, at least 80% amino acid identity with amino acids 1-445 of SEQ ID NO: 4, at least 85% amino acid identity with amino acids 1-445 of SEQ ID NO: 4, at least 90% amino acid identity with amino acids 1-445 of SEQ ID NO: 4 or at least 95% amino acid identity with amino acids 1-445 of SEQ ID NO: 4. In yet other aspects of this embodiment, a BoNT/D enzymatic domain comprises a polypeptide having, e.g., at most 70% amino acid identity with amino acids 1-445 of SEQ ID NO: 4, at most 75% amino acid identity with amino acids 1-445 of SEQ ID NO: 4, at most 80% amino acid identity with amino acids 1-445 of SEQ ID NO: 4, at most 85% amino acid identity with amino acids 1-445 of SEQ ID NO: 4, at most 90% amino acid identity with amino acids 1-445 of SEQ ID NO: 4 or at most 95% amino acid identity with amino acids 1-445 of SEQ ID NO: 4.

In other aspects of this embodiment, a BoNT/D enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-445 of SEQ ID NO: 4. In other aspects of this embodiment, a BoNT/D enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-445 of SEQ ID NO: 4. In yet other aspects of this embodiment, a BoNT/D enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-445 of SEQ ID NO: 4. In other aspects of this embodiment, a BoNT/D enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-445 of SEQ ID NO: 4. In still other aspects of this embodiment, a BoNT/D enzymatic domain comprises a polypeptide having, e.g., at most one, two, three, four, five, six, seven, eight, nine, 10, 20, 30, 40, 50, 100 or 200 non-contiguous amino acid additions relative to amino acids 1-445 of SEQ ID NO: 4. In other aspects of this embodiment, a BoNT/D enzymatic domain comprises a polypeptide having, e.g., at least one, two, three, four, five, six, seven, eight, nine, 10, 20, 30, 40, 50, 100 or 200 non-contiguous amino acid additions relative to amino acids 1-445 of SEQ ID NO: 4.

In other aspects of this embodiment, a BoNT/D enzymatic domain comprises a polypeptide having, e.g., at most one, two, three, four, five, six, seven, eight, nine, 10, 20, 30, 40, 50, 100 or 200 contiguous amino acid substitutions relative to amino acids 1-445 of SEQ ID NO: 4. In other aspects of this embodiment, a BoNT/D enzymatic domain comprises a polypeptide having, e.g., at least one, two, three, four, five, six, seven, eight, nine, 10, 20, 30, 40, 50, 100 or 200 contiguous amino acid substitutions relative to amino acids 1-445 of SEQ ID NO: 4. In yet other aspects of this embodiment, a BoNT/D enzymatic domain comprises a polypeptide having, e.g., at most one, two, three, four, five, six, seven, eight, nine, 10, 20, 30, 40, 50, 100 or 200 contiguous amino acid deletions relative to amino acids 1-445 of SEQ ID NO: 4. In other aspects of this embodiment, a BoNT/D enzymatic domain comprises a polypeptide having, e.g., at least one, two, three, four, five, six, seven, eight, nine, 10, 20, 30, 40, 50, 100 or 200 contiguous amino acid deletions relative to amino acids 1-445 of SEQ ID NO: 4. In still other aspects of this embodiment, a BoNT/D enzymatic domain comprises a polypeptide having, e.g., at most one, two, three, four, five, six, seven, eight, nine, 10, 20, 30, 40, 50, 100 or 200 contiguous amino acid additions relative to amino acids 1-445 of SEQ ID NO: 4. In other aspects of this embodiment, a BoNT/D enzymatic domain comprises a polypeptide having, e.g., at least one, two, three, four, five, six, seven, eight, nine, 10, 20, 30, 40, 50, 100 or 200 contiguous amino acid additions relative to amino acids 1-445 of SEQ ID NO: 4.

In another embodiment, a Clostridial toxin enzymatic domain comprises a BoNT/E enzymatic domain. In an aspect of this embodiment, a BoNT/E enzymatic domain comprises amino acids 1-422 of SEQ ID NO: 5. In another aspect of this embodiment, a BoNT/E enzymatic domain comprises a naturally occurring BoNT/E enzymatic domain variant, such as, e.g., a enzymatic domain from a BoNT/E isoform or a enzymatic domain from a BoNT/E subtype. In another aspect of this embodiment, a BoNT/E enzymatic domain comprises amino acids 1-422 of a naturally occurring BoNT/E enzymatic domain variant of SEQ ID NO: 5, such as, e.g., amino acids 1-422 of a BoNT/E isoform of SEQ ID NO: 5 or amino acids 1-422 of a BoNT/E subtype of SEQ ID NO: 5. In still another aspect of this embodiment, a BoNT/E enzymatic domain comprises a non-naturally occurring BoNT/E enzymatic domain variant, such as, e.g., a conservative BoNT/E enzymatic domain variant, a non-conservative BoNT/E enzymatic domain variant, a BoNT/E chimeric enzymatic domain, an active BoNT/E enzymatic domain fragment, or any combination thereof. In still another aspect of this embodiment, a BoNT/E enzymatic domain comprises amino acids 1-422 of a non-naturally occurring BoNT/E enzymatic domain variant of SEQ ID NO: 5, such as, e.g., amino acids 1-422 of a conservative BoNT/E enzymatic domain variant of SEQ ID NO: 5, amino acids 1-422 of a non-conservative BoNT/E enzymatic domain variant of SEQ ID NO: 5, amino acids 1-422 of an active BoNT/E enzymatic domain fragment of SEQ ID NO: 5, or any combination thereof.

In other aspects of this embodiment, a BoNT/E enzymatic domain comprises a polypeptide having, e.g., at least 70% amino acid identity with amino acids 1-422 of SEQ ID NO: 5, at least 75% amino acid identity with amino acids 1-422 of SEQ ID NO: 5, at least 80% amino acid identity with amino acids 1-422 of SEQ ID NO: 5, at least 85% amino acid identity with amino acids 1-422 of SEQ ID NO: 5, at least 90% amino acid identity with amino acids 1-422 of SEQ ID NO: 5 or at least 95% amino acid identity with amino acids 1-422 of SEQ ID NO: 5. In yet other aspects of this embodiment, a BoNT/E enzymatic domain comprises a polypeptide having, e.g., at most 70% amino acid identity with amino acids 1-422 of SEQ ID NO: 5, at most 75% amino acid identity with amino acids 1-422 of SEQ ID NO: 5, at most 80% amino acid identity with amino acids 1-422 of SEQ ID NO: 5, at most 85% amino acid identity with amino acids 1-422 of SEQ ID NO: 5, at most 90% amino acid identity with amino acids 1-422 of SEQ ID NO: 5 or at most 95% amino acid identity with amino acids 1-422 of SEQ ID NO: 5.

In other aspects of this embodiment, a BoNT/E enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-422 of SEQ ID NO: 5. In other aspects of this embodiment, a BoNT/E enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-422 of SEQ ID NO: 5. In yet other aspects of this embodiment, a BoNT/E enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-422 of SEQ ID NO: 5. In other aspects of this embodiment, a BoNT/E enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-422 of SEQ ID NO: 5. In still other aspects of this embodiment, a BoNT/E enzymatic domain comprises a polypeptide having, e.g., at most one, two, three, four, five, six, seven, eight, nine, 10, 20, 30, 40, 50, 100 or 200 non-contiguous amino acid additions relative to amino acids 1-422 of SEQ ID NO: 5. In other aspects of this embodiment, a BoNT/E enzymatic domain comprises a polypeptide having, e.g., at least one, two, three, four, five, six, seven, eight, nine, 10, 20, 30, 40, 50, 100 or 200 non-contiguous amino acid additions relative to amino acids 1-422 of SEQ ID NO: 5.

In other aspects of this embodiment, a BoNT/E enzymatic domain comprises a polypeptide having, e.g., at most one, two, three, four, five, six, seven, eight, nine, 10, 20, 30, 40, 50, 100 or 200 contiguous amino acid substitutions relative to amino acids 1-422 of SEQ ID NO: 5. In other aspects of this embodiment, a BoNT/E enzymatic domain comprises a polypeptide having, e.g., at least one, two, three, four, five, six, seven, eight, nine, 10, 20, 30, 40, 50, 100 or 200 contiguous amino acid substitutions relative to amino acids 1-422 of SEQ ID NO: 5. In yet other aspects of this embodiment, a BoNT/E enzymatic domain comprises a polypeptide having, e.g., at most one, two, three, four, five, six, seven, eight, nine, 10, 20, 30, 40, 50, 100 or 200 contiguous amino acid deletions relative to amino acids 1-422 of SEQ ID NO: 5. In other aspects of this embodiment, a BoNT/E enzymatic domain comprises a polypeptide having, e.g., at least one, two, three, four, five, six, seven, eight, nine, 10, 20, 30, 40, 50, 100 or 200 contiguous amino acid deletions relative to amino acids 1-422 of SEQ ID NO: 5. In still other aspects of this embodiment, a BoNT/E enzymatic domain comprises a polypeptide having, e.g., at most one, two, three, four, five, six, seven, eight, nine, 10, 20, 30, 40, 50, 100 or 200 contiguous amino acid additions relative to amino acids 1-422 of SEQ ID NO: 5. In other aspects of this embodiment, a BoNT/E enzymatic domain comprises a polypeptide having, e.g., at least one, two, three, four, five, six, seven, eight, nine, 10, 20, 30, 40, 50, 100 or 200 contiguous amino acid additions relative to amino acids 1-422 of SEQ ID NO: 5.

In another embodiment, a Clostridial toxin enzymatic domain comprises a BoNT/F enzymatic domain. In an aspect of this embodiment, a BoNT/F enzymatic domain comprises amino acids 1-439 of SEQ ID NO: 6. In another aspect of this embodiment, a BoNT/F enzymatic domain comprises a naturally occurring BoNT/F enzymatic domain variant, such as, e.g., a enzymatic domain from a BoNT/F isoform or a enzymatic domain from a BoNT/F subtype. In another aspect of this embodiment, a BoNT/F enzymatic domain comprises amino acids 1-439 of a naturally occurring BoNT/F enzymatic domain variant of SEQ ID NO: 6, such as, e.g., amino acids 1-439 of a BoNT/F isoform of SEQ ID NO: 6 or amino acids 1-439 of a BoNT/F subtype of SEQ ID NO: 6. In still another aspect of this embodiment, a BoNT/F enzymatic domain comprises a non-naturally occurring BoNT/F enzymatic domain variant, such as, e.g., a conservative BoNT/F enzymatic domain variant, a non-conservative BoNT/F enzymatic domain variant, a BoNT/F chimeric enzymatic domain, an active BoNT/F enzymatic domain fragment, or any combination thereof. In still another aspect of this embodiment, a BoNT/F enzymatic domain comprises amino acids 1-439 of a non-naturally occurring BoNT/F enzymatic domain variant of SEQ ID NO: 6, such as, e.g., amino acids 1-439 of a conservative BoNT/F enzymatic domain variant of SEQ ID NO: 6, amino acids 1-439 of a non-conservative BoNT/F enzymatic domain variant of SEQ ID NO: 6, amino acids 1-439 of an active BoNT/F enzymatic domain fragment of SEQ ID NO: 6, or any combination thereof.

In other aspects of this embodiment, a BoNT/F enzymatic domain comprises a polypeptide having, e.g., at least 70% amino acid identity with amino acids 1-439 of SEQ ID NO: 6, at least 75% amino acid identity with amino acids 1-439 of SEQ ID NO: 6, at least 80% amino acid identity with amino acids 1-439 of SEQ ID NO: 6, at least 85% amino acid identity with amino acids 1-439 of SEQ ID NO: 6, at least 90% amino acid identity with amino acids 1-439 of SEQ ID NO: 6 or at least 95% amino acid identity with amino acids 1-439 of SEQ ID NO: 6. In yet other aspects of this embodiment, a BoNT/F enzymatic domain comprises a polypeptide having, e.g., at most 70% amino acid identity with amino acids 1-439 of SEQ ID NO: 6, at most 75% amino acid identity with amino acids 1-439 of SEQ ID NO: 6, at most 80% amino acid identity with amino acids 1-439 of SEQ ID NO: 6, at most 85% amino acid identity with amino acids 1-439 of SEQ ID NO: 6, at most 90% amino acid identity with amino acids 1-439 of SEQ ID NO: 6 or at most 95% amino acid identity with amino acids 1-439 of SEQ ID NO: 6.

In other aspects of this embodiment, a BoNT/F enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-439 of SEQ ID NO: 6. In other aspects of this embodiment, a BoNT/F enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-439 of SEQ ID NO: 6. In yet other aspects of this embodiment, a BoNT/F enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-439 of SEQ ID NO: 6. In other aspects of this embodiment, a BoNT/F enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-439 of SEQ ID NO: 6. In still other aspects of this embodiment, a BoNT/F enzymatic domain comprises a polypeptide having, e.g., at most one, two, three, four, five, six, seven, eight, nine, 10, 20, 30, 40, 50, 100 or 200 non-contiguous amino acid additions relative to amino acids 1-439 of SEQ ID NO: 6. In other aspects of this embodiment, a BoNT/F enzymatic domain comprises a polypeptide having, e.g., at least one, two, three, four, five, six, seven, eight, nine, 10, 20, 30, 40, 50, 100 or 200 non-contiguous amino acid additions relative to amino acids 1-439 of SEQ ID NO: 6.

In other aspects of this embodiment, a BoNT/F enzymatic domain comprises a polypeptide having, e.g., at most one, two, three, four, five, six, seven, eight, nine, 10, 20, 30, 40, 50, 100 or 200 contiguous amino acid substitutions relative to amino acids 1-439 of SEQ ID NO: 6. In other aspects of this embodiment, a BoNT/F enzymatic domain comprises a polypeptide having, e.g., at least one, two, three, four, five, six, seven, eight, nine, 10, 20, 30, 40, 50, 100 or 200 contiguous amino acid substitutions relative to amino acids 1-439 of SEQ ID NO: 6. In yet other aspects of this embodiment, a BoNT/F enzymatic domain comprises a polypeptide having, e.g., at most one, two, three, four, five, six, seven, eight, nine, 10, 20, 30, 40, 50, 100 or 200 contiguous amino acid deletions relative to amino acids 1-439 of SEQ ID NO: 6. In other aspects of this embodiment, a BoNT/F enzymatic domain comprises a polypeptide having, e.g., at least one, two, three, four, five, six, seven, eight, nine, 10, 20, 30, 40, 50, 100 or 200 contiguous amino acid deletions relative to amino acids 1-439 of SEQ ID NO: 6. In still other aspects of this embodiment, a BoNT/F enzymatic domain comprises a polypeptide having, e.g., at most one, two, three, four, five, six, seven, eight, nine, 10, 20, 30, 40, 50, 100 or 200 contiguous amino acid additions relative to amino acids 1-439 of SEQ ID NO: 6. In other aspects of this embodiment, a BoNT/F enzymatic domain comprises a polypeptide having, e.g., at least one, two, three, four, five, six, seven, eight, nine, 10, 20, 30, 40, 50, 100 or 200 contiguous amino acid additions relative to amino acids 1-439 of SEQ ID NO: 6.

In another embodiment, a Clostridial toxin enzymatic domain comprises a BoNT/G enzymatic domain. In an aspect of this embodiment, a BoNT/G enzymatic domain comprises amino acids 1-446 of SEQ ID NO: 7. In another aspect of this embodiment, a BoNT/G enzymatic domain comprises a naturally occurring BoNT/G enzymatic domain variant, such as, e.g., a enzymatic domain from a BoNT/G isoform or a enzymatic domain from a BoNT/G subtype. In another aspect of this embodiment, a BoNT/G enzymatic domain comprises amino acids 1-446 of a naturally occurring BoNT/G enzymatic domain variant of SEQ ID NO: 7, such as, e.g., amino acids 1-446 of a BoNT/G isoform of SEQ ID NO: 7 or amino acids 1-446 of a BoNT/G subtype of SEQ ID NO: 7. In still another aspect of this embodiment, a BoNT/G enzymatic domain comprises a non-naturally occurring BoNT/G enzymatic domain variant, such as, e.g., a conservative BoNT/G enzymatic domain variant, a non-conservative BoNT/G enzymatic domain variant, a BoNT/G chimeric enzymatic domain, an active BoNT/G enzymatic domain fragment, or any combination thereof. In still another aspect of this embodiment, a BoNT/G enzymatic domain comprises amino acids 1-446 of a non-naturally occurring BoNT/G enzymatic domain variant of SEQ ID NO: 7, such as, e.g., amino acids 1-446 of a conservative BoNT/G enzymatic domain variant of SEQ ID NO: 7, amino acids 1-446 of a non-conservative BoNT/G enzymatic domain variant of SEQ ID NO: 7, amino acids 1-446 of an active BoNT/G enzymatic domain fragment of SEQ ID NO: 7, or any combination thereof.

In other aspects of this embodiment, a BoNT/G enzymatic domain comprises a polypeptide having, e.g., at least 70% amino acid identity with amino acids 1-446 of SEQ ID NO: 7, at least 75% amino acid identity with amino acids 1-446 of SEQ ID NO: 7, at least 80% amino acid identity with amino acids 1-446 of SEQ ID NO: 7, at least 85% amino acid identity with amino acids 1-446 of SEQ ID NO: 7, at least 90% amino acid identity with amino acids 1-446 of SEQ ID NO: 7 or at least 95% amino acid identity with amino acids 1-446 of SEQ ID NO: 7. In yet other aspects of this embodiment, a BoNT/G enzymatic domain comprises a polypeptide having, e.g., at most 70% amino acid identity with amino acids 1-446 of SEQ ID NO: 7, at most 75% amino acid identity with amino acids 1-446 of SEQ ID NO: 7, at most 80% amino acid identity with amino acids 1-446 of SEQ ID NO: 7, at most 85% amino acid identity with amino acids 1-446 of SEQ ID NO: 7, at most 90% amino acid identity with amino acids 1-446 of SEQ ID NO: 7 or at most 95% amino acid identity with amino acids 1-446 of SEQ ID NO: 7.

In other aspects of this embodiment, a BoNT/G enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-446 of SEQ ID NO: 7. In other aspects of this embodiment, a BoNT/G enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-446 of SEQ ID NO: 7. In yet other aspects of this embodiment, a BoNT/G enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-446 of SEQ ID NO: 7. In other aspects of this embodiment, a BoNT/G enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-446 of SEQ ID NO: 7. In still other aspects of this embodiment, a BoNT/G enzymatic domain comprises a polypeptide having, e.g., at most one, two, three, four, five, six, seven, eight, nine, 10, 20, 30, 40, 50, 100 or 200 non-contiguous amino acid additions relative to amino acids 1-446 of SEQ ID NO: 7. In other aspects of this embodiment, a BoNT/G enzymatic domain comprises a polypeptide having, e.g., at least one, two, three, four, five, six, seven, eight, nine, 10, 20, 30, 40, 50, 100 or 200 non-contiguous amino acid additions relative to amino acids 1-446 of SEQ ID NO: 7.

In other aspects of this embodiment, a BoNT/G enzymatic domain comprises a polypeptide having, e.g., at most one, two, three, four, five, six, seven, eight, nine, 10, 20, 30, 40, 50, 100 or 200 contiguous amino acid substitutions relative to amino acids 1-446 of SEQ ID NO: 7. In other aspects of this embodiment, a BoNT/G enzymatic domain comprises a polypeptide having, e.g., at least one, two, three, four, five, six, seven, eight, nine, 10, 20, 30, 40, 50, 100 or 200 contiguous amino acid substitutions relative to amino acids 1-446 of SEQ ID NO: 7. In yet other aspects of this embodiment, a BoNT/G enzymatic domain comprises a polypeptide having, e.g., at most one, two, three, four, five, six, seven, eight, nine, 10, 20, 30, 40, 50, 100 or 200 contiguous amino acid deletions relative to amino acids 1-446 of SEQ ID NO: 7. In other aspects of this embodiment, a BoNT/G enzymatic domain comprises a polypeptide having, e.g., at least one, two, three, four, five, six, seven, eight, nine, 10, 20, 30, 40, 50, 100 or 200 contiguous amino acid deletions relative to amino acids 1-446 of SEQ ID NO: 7. In still other aspects of this embodiment, a BoNT/G enzymatic domain comprises a polypeptide having, e.g., at most one, two, three, four, five, six, seven, eight, nine, 10, 20, 30, 40, 50, 100 or 200 contiguous amino acid additions relative to amino acids 1-446 of SEQ ID NO: 7. In other aspects of this embodiment, a BoNT/G enzymatic domain comprises a polypeptide having, e.g., at least one, two, three, four, five, six, seven, eight, nine, 10, 20, 30, 40, 50, 100 or 200 contiguous amino acid additions relative to amino acids 1-446 of SEQ ID NO: 7.

In another embodiment, a Clostridial toxin enzymatic domain comprises a TeNT enzymatic domain. In an aspect of this embodiment, a TeNT enzymatic domain comprises amino acids 1-457 of SEQ ID NO: 8. In another aspect of this embodiment, a TeNT enzymatic domain comprises a naturally occurring TeNT enzymatic domain variant, such as, e.g., a enzymatic domain from a TeNT isoform or a enzymatic domain from a TeNT subtype. In another aspect of this embodiment, a TeNT enzymatic domain comprises amino acids 1-457 of a naturally occurring TeNT enzymatic domain variant of SEQ ID NO: 8, such as, e.g., amino acids 1-457 of a TeNT isoform of SEQ ID NO: 8 or amino acids 1-457 of a TeNT subtype of SEQ ID NO: 8. In still another aspect of this embodiment, a TeNT enzymatic domain comprises a non-naturally occurring TeNT enzymatic domain variant, such as, e.g., a conservative TeNT enzymatic domain variant, a non-conservative TeNT enzymatic domain variant, a TeNT chimeric enzymatic domain, an active TeNT enzymatic domain fragment, or any combination thereof. In still another aspect of this embodiment, a TeNT enzymatic domain comprises amino acids 1-457 of a non-naturally occurring TeNT enzymatic domain variant of SEQ ID NO: 8, such as, e.g., amino acids 1-457 of a conservative TeNT enzymatic domain variant of SEQ ID NO: 8, amino acids 1-457 of a non-conservative TeNT enzymatic domain variant of SEQ ID NO: 8, amino acids 1-457 of an active TeNT enzymatic domain fragment of SEQ ID NO: 8, or any combination thereof.

In other aspects of this embodiment, a TeNT enzymatic domain comprises a polypeptide having, e.g., at least 70% amino acid identity with amino acids 1-457 of SEQ ID NO: 8, at least 75% amino acid identity with amino acids 1-457 of SEQ ID NO: 8, at least 80% amino acid identity with amino acids 1-457 of SEQ ID NO: 8, at least 85% amino acid identity with amino acids 1-457 of SEQ ID NO: 8, at least 90% amino acid identity with amino acids 1-457 of SEQ ID NO: 8 or at least 95% amino acid identity with amino acids 1-457 of SEQ ID NO: 8. In yet other aspects of this embodiment, a TeNT enzymatic domain comprises a polypeptide having, e.g., at most 70% amino acid identity with amino acids 1-457 of SEQ ID NO: 8, at most 75% amino acid identity with amino acids 1-457 of SEQ ID NO: 8, at most 80% amino acid identity with amino acids 1-457 of SEQ ID NO: 8, at most 85% amino acid identity with amino acids 1-457 of SEQ ID NO: 8, at most 90% amino acid identity with amino acids 1-457 of SEQ ID NO: 8 or at most 95% amino acid identity with amino acids 1-457 of SEQ ID NO: 8.

In other aspects of this embodiment, a TeNT enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-457 of SEQ ID NO: 8. In other aspects of this embodiment, a TeNT enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-457 of SEQ ID NO: 8. In yet other aspects of this embodiment, a TeNT enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-457 of SEQ ID NO: 8. In other aspects of this embodiment, a TeNT enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-457 of SEQ ID NO: 8. In still other aspects of this embodiment, a TeNT enzymatic domain comprises a polypeptide having, e.g., at most one, two, three, four, five, six, seven, eight, nine, 10, 20, 30, 40, 50, 100 or 200 non-contiguous amino acid additions relative to amino acids 1-457 of SEQ ID NO: 8. In other aspects of this embodiment, a TeNT enzymatic domain comprises a polypeptide having, e.g., at least one, two, three, four, five, six, seven, eight, nine, 10, 20, 30, 40, 50, 100 or 200 non-contiguous amino acid additions relative to amino acids 1-457 of SEQ ID NO: 8.

In other aspects of this embodiment, a TeNT enzymatic domain comprises a polypeptide having, e.g., at most one, two, three, four, five, six, seven, eight, nine, 10, 20, 30, 40, 50, 100 or 200 contiguous amino acid substitutions relative to amino acids 1-457 of SEQ ID NO: 8. In other aspects of this embodiment, a TeNT enzymatic domain comprises a polypeptide having, e.g., at least one, two, three, four, five, six, seven, eight, nine, 10, 20, 30, 40, 50, 100 or 200 contiguous amino acid substitutions relative to amino acids 1-457 of SEQ ID NO: 8. In yet other aspects of this embodiment, a TeNT enzymatic domain comprises a polypeptide having, e.g., at most one, two, three, four, five, six, seven, eight, nine, 10, 20, 30, 40, 50, 100 or 200 contiguous amino acid deletions relative to amino acids 1-457 of SEQ ID NO: 8. In other aspects of this embodiment, a TeNT enzymatic domain comprises a polypeptide having, e.g., at least one, two, three, four, five, six, seven, eight, nine, 10, 20, 30, 40, 50, 100 or 200 contiguous amino acid deletions relative to amino acids 1-457 of SEQ ID NO: 8. In still other aspects of this embodiment, a TeNT enzymatic domain comprises a polypeptide having, e.g., at most one, two, three, four, five, six, seven, eight, nine, 10, 20, 30, 40, 50, 100 or 200 contiguous amino acid additions relative to amino acids 1-457 of SEQ ID NO: 8. In other aspects of this embodiment, a TeNT enzymatic domain comprises a polypeptide having, e.g., at least one, two, three, four, five, six, seven, eight, nine, 10, 20, 30, 40, 50, 100 or 200 contiguous amino acid additions relative to amino acids 1-457 of SEQ ID NO: 8.

In another embodiment, a Clostridial toxin enzymatic domain comprises a BaNT enzymatic domain. In an aspect of this embodiment, a BaNT enzymatic domain comprises amino acids 1-431 of SEQ ID NO: 9. In another aspect of this embodiment, a BaNT enzymatic domain comprises a naturally occurring BaNT enzymatic domain variant, such as, e.g., a enzymatic domain from a BaNT isoform or a enzymatic domain from a BaNT subtype. In another aspect of this embodiment, a BaNT enzymatic domain comprises amino acids 1-431 of a naturally occurring BaNT enzymatic domain variant of SEQ ID NO: 9, such as, e.g., amino acids 1-431 of a BaNT isoform of SEQ ID NO: 9 or amino acids 1-431 of a BaNT subtype of SEQ ID NO: 9. In still another aspect of this embodiment, a BaNT enzymatic domain comprises a non-naturally occurring BaNT enzymatic domain variant, such as, e.g., a conservative BaNT enzymatic domain variant, a non-conservative BaNT enzymatic domain variant, a BaNT chimeric enzymatic domain, an active BaNT enzymatic domain fragment, or any combination thereof. In still another aspect of this embodiment, a BaNT enzymatic domain comprises amino acids 1-431 of a non-naturally occurring BaNT enzymatic domain variant of SEQ ID NO: 9, such as, e.g., amino acids 1-431 of a conservative BaNT enzymatic domain variant of SEQ ID NO: 9, amino acids 1-431 of a non-conservative BaNT enzymatic domain variant of SEQ ID NO: 9, amino acids 1-431 of an active BaNT enzymatic domain fragment of SEQ ID NO: 9, or any combination thereof.

In other aspects of this embodiment, a BaNT enzymatic domain comprises a polypeptide having, e.g., at least 70% amino acid identity with amino acids 1-431 of SEQ ID NO: 9, at least 75% amino acid identity with amino acids 1-431 of SEQ ID NO: 9, at least 80% amino acid identity with amino acids 1-431 of SEQ ID NO: 9, at least 85% amino acid identity with amino acids 1-431 of SEQ ID NO: 9, at least 90% amino acid identity with amino acids 1-431 of SEQ ID NO: 9 or at least 95% amino acid identity with amino acids 1-431 of SEQ ID NO: 9. In yet other aspects of this embodiment, a BaNT enzymatic domain comprises a polypeptide having, e.g., at most 70% amino acid identity with amino acids 1-431 of SEQ ID NO: 9, at most 75% amino acid identity with amino acids 1-431 of SEQ ID NO: 9, at most 80% amino acid identity with amino acids 1-431 of SEQ ID NO: 9, at most 85% amino acid identity with amino acids 1-431 of SEQ ID NO: 9, at most 90% amino acid identity with amino acids 1-431 of SEQ ID NO: 9 or at most 95% amino acid identity with amino acids 1-431 of SEQ ID NO: 9.

In other aspects of this embodiment, a BaNT enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-431 of SEQ ID NO: 9. In other aspects of this embodiment, a BaNT enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-431 of SEQ ID NO: 9. In yet other aspects of this embodiment, a BaNT enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-431 of SEQ ID NO: 9. In other aspects of this embodiment, a BaNT enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-431 of SEQ ID NO: 9. In still other aspects of this embodiment, a BaNT enzymatic domain comprises a polypeptide having, e.g., at most one, two, three, four, five, six, seven, eight, nine, 10, 20, 30, 40, 50, 100 or 200 non-contiguous amino acid additions relative to amino acids 1-431 of SEQ ID NO: 9. In other aspects of this embodiment, a BaNT enzymatic domain comprises a polypeptide having, e.g., at least one, two, three, four, five, six, seven, eight, nine, 10, 20, 30, 40, 50, 100 or 200 non-contiguous amino acid additions relative to amino acids 1-431 of SEQ ID NO: 9.

In other aspects of this embodiment, a BaNT enzymatic domain comprises a polypeptide having, e.g., at most one, two, three, four, five, six, seven, eight, nine, 10, 20, 30, 40, 50, 100 or 200 contiguous amino acid substitutions relative to amino acids 1-431 of SEQ ID NO: 9. In other aspects of this embodiment, a BaNT enzymatic domain comprises a polypeptide having, e.g., at least one, two, three, four, five, six, seven, eight, nine, 10, 20, 30, 40, 50, 100 or 200 contiguous amino acid substitutions relative to amino acids 1-431 of SEQ ID NO: 9. In yet other aspects of this embodiment, a BaNT enzymatic domain comprises a polypeptide having, e.g., at most one, two, three, four, five, six, seven, eight, nine, 10, 20, 30, 40, 50, 100 or 200 contiguous amino acid deletions relative to amino acids 1-431 of SEQ ID NO: 9. In other aspects of this embodiment, a BaNT enzymatic domain comprises a polypeptide having, e.g., at least one, two, three, four, five, six, seven, eight, nine, 10, 20, 30, 40, 50, 100 or 200 contiguous amino acid deletions relative to amino acids 1-431 of SEQ ID NO: 9. In still other aspects of this embodiment, a BaNT enzymatic domain comprises a polypeptide having, e.g., at most one, two, three, four, five, six, seven, eight, nine, 10, 20, 30, 40, 50, 100 or 200 contiguous amino acid additions relative to amino acids 1-431 of SEQ ID NO: 9. In other aspects of this embodiment, a BaNT enzymatic domain comprises a polypeptide having, e.g., at least one, two, three, four, five, six, seven, eight, nine, 10, 20, 30, 40, 50, 100 or 200 contiguous amino acid additions relative to amino acids 1-431 of SEQ ID NO: 9.

In another embodiment, a Clostridial toxin enzymatic domain comprises a BuNT enzymatic domain. In an aspect of this embodiment, a BuNT enzymatic domain comprises amino acids 1-422 of SEQ ID NO: 10. In another aspect of this embodiment, a BuNT enzymatic domain comprises a naturally occurring BuNT enzymatic domain variant, such as, e.g., a enzymatic domain from a BuNT isoform or a enzymatic domain from a BuNT subtype. In another aspect of this embodiment, a BuNT enzymatic domain comprises amino acids 1-422 of a naturally occurring BuNT enzymatic domain variant of SEQ ID NO: 10, such as, e.g., amino acids 1-422 of a BuNT isoform of SEQ ID NO: 10 or amino acids 1-422 of a BuNT subtype of SEQ ID NO: 10. In still another aspect of this embodiment, a BuNT enzymatic domain comprises a non-naturally occurring BuNT enzymatic domain variant, such as, e.g., a conservative BuNT enzymatic domain variant, a non-conservative BuNT enzymatic domain variant, a BuNT chimeric enzymatic domain, an active BuNT enzymatic domain fragment, or any combination thereof. In still another aspect of this embodiment, a BuNT enzymatic domain comprises amino acids 1-422 of a non-naturally occurring BuNT enzymatic domain variant of SEQ ID NO: 10, such as, e.g., amino acids 1-422 of a conservative BuNT enzymatic domain variant of SEQ ID NO: 10, amino acids 1-422 of a non-conservative BuNT enzymatic domain variant of SEQ ID NO: 10, amino acids 1-422 of an active BuNT enzymatic domain fragment of SEQ ID NO: 10, or any combination thereof.

In other aspects of this embodiment, a BuNT enzymatic domain comprises a polypeptide having, e.g., at least 70% amino acid identity with amino acids 1-422 of SEQ ID NO: 10, at least 75% amino acid identity with amino acids 1-422 of SEQ ID NO: 10, at least 80% amino acid identity with amino acids 1-422 of SEQ ID NO: 10, at least 85% amino acid identity with amino acids 1-422 of SEQ ID NO: 10, at least 90% amino acid identity with amino acids 1-422 of SEQ ID NO: 10 or at least 95% amino acid identity with amino acids 1-422 of SEQ ID NO: 10. In yet other aspects of this embodiment, a BuNT enzymatic domain comprises a polypeptide having, e.g., at most 70% amino acid identity with amino acids 1-422 of SEQ ID NO: 10, at most 75% amino acid identity with amino acids 1-422 of SEQ ID NO: 10, at most 80% amino acid identity with amino acids 1-422 of SEQ ID NO: 10, at most 85% amino acid identity with amino acids 1-422 of SEQ ID NO: 10, at most 90% amino acid identity with amino acids 1-422 of SEQ ID NO: 10 or at most 95% amino acid identity with amino acids 1-422 of SEQ ID NO: 10.

In other aspects of this embodiment, a BuNT enzymatic domain comprises a polypeptide having, e.g., at most one, two, three, four, five, six, seven, eight, nine, 10, 20, 30, 40, 50, 100, or 200 non-contiguous amino acid substitutions relative to amino acids 1-422 of SEQ ID NO: 10. In other aspects of this embodiment, a BuNT enzymatic domain comprises a polypeptide having, e.g., at least one, two, three, four, five, six, seven, eight, nine, 10, 20, 30, 40, 50, 100 or 200 non-contiguous amino acid substitutions relative to amino acids 1-422 of SEQ ID NO: 10. In yet other aspects of this embodiment, a BuNT enzymatic domain comprises a polypeptide having, e.g., at most one, two, three, four, five, six, seven, eight, nine, 10, 20, 30, 40, 50, 100 or 200 non-contiguous amino acid deletions relative to amino acids 1-422 of SEQ ID NO: 10. In other aspects of this embodiment, a BuNT enzymatic domain comprises a polypeptide having, e.g., at least one, two, three, four, five, six, seven, eight, nine, 10, 20, 30, 40, 50, 100 or 200 non-contiguous amino acid deletions relative to amino acids 1-422 of SEQ ID NO: 10. In still other aspects of this embodiment, a BuNT enzymatic domain comprises a polypeptide having, e.g., at most one, two, three, four, five, six, seven, eight, nine, 10, 20, 30, 40, 50, 100 or 200 non-contiguous amino acid additions relative to amino acids 1-422 of SEQ ID NO: 10. In other aspects of this embodiment, a BuNT enzymatic domain comprises a polypeptide having, e.g., at least one, two, three, four, five, six, seven, eight, nine, 10, 20, 30, 40, 50, 100 or 200 non-contiguous amino acid additions relative to amino acids 1-422 of SEQ ID NO: 10.

In other aspects of this embodiment, a BuNT enzymatic domain comprises a polypeptide having, e.g., at most one, two, three, four, five, six, seven, eight, nine, 10, 20, 30, 40, 50, 100 or 200 contiguous amino acid substitutions relative to amino acids 1-422 of SEQ ID NO: 10. In other aspects of this embodiment, a BuNT enzymatic domain comprises a polypeptide having, e.g., at least one, two, three, four, five, six, seven, eight, nine, 10, 20, 30, 40, 50, 100 or 200 contiguous amino acid substitutions relative to amino acids 1-422 of SEQ ID NO: 10. In yet other aspects of this embodiment, a BuNT enzymatic domain comprises a polypeptide having, e.g., at most one, two, three, four, five, six, seven, eight, nine, 10, 20, 30, 40, 50, 100 or 200 contiguous amino acid deletions relative to amino acids 1-422 of SEQ ID NO: 10. In other aspects of this embodiment, a BuNT enzymatic domain comprises a polypeptide having, e.g., at least one, two, three, four, five, six, seven, eight, nine, 10, 20, 30, 40, 50, 100 or 200 contiguous amino acid deletions relative to amino acids 1-422 of SEQ ID NO: 10. In still other aspects of this embodiment, a BuNT enzymatic domain comprises a polypeptide having, e.g., at most one, two, three, four, five, six, seven, eight, nine, 10, 20, 30, 40, 50, 100 or 200 contiguous amino acid additions relative to amino acids 1-422 of SEQ ID NO: 10. In other aspects of this embodiment, a BuNT enzymatic domain comprises a polypeptide having, e.g., at least one, two, three, four, five, six, seven, eight, nine, 10, 20, 30, 40, 50, 100 or 200 contiguous amino acid additions relative to amino acids 1-422 of SEQ ID NO: 10.

The "translocation element" comprises a portion of a clostridial neurotoxin heavy chain having a translocation activity. By "translocation" is meant the ability to facilitate the transport of a polypeptide through a vesicular membrane, thereby exposing some or all of the polypeptide to the cytoplasm. In the various botulinum neurotoxins translocation is thought to involve an allosteric conformational change of the heavy chain caused by a decrease in pH within the endosome. This conformational change appears to involve and be mediated by the N terminal half of the heavy chain and to result in the formation of pores in the vesicular membrane; this change permits the movement of the proteolytic light chain from within the endosomal vesicle into the cytoplasm. See e.g., Lacy, et al., *Nature Struct. Biol.* 5:898-902 (October 1998).

The amino acid sequence of the translocation-mediating portion of the botulinum neurotoxin heavy chain is known to those of skill in the art; additionally, those amino acid residues within this portion that are known to be essential for conferring the translocation activity are also known. It would therefore be well within the ability of one of ordinary skill in the art, for example, to employ the naturally occurring N-terminal peptide half of the heavy chain of any of the various *Clostridium tetanus* or *Clostridium botulinum* neurotoxin subtypes as a translocation element, or to design an analogous translocation element by aligning the primary sequences of the N-terminal halves of the various heavy chains and selecting a consensus primary translocation sequence based on conserved amino acid, polarity, steric and hydrophobicity characteristics between the sequences.

Aspects of the present invention provide, in part, a Clostridial toxin translocation domain. As used herein, the term "Clostridial toxin translocation domain" means any Clostridial toxin polypeptide that can execute the translocation step of the intoxication process that mediates Clostridial toxin light chain translocation. Thus, a Clostridial toxin translocation domain facilitates the movement of a Clostridial toxin light chain across a membrane and encompasses the movement of a Clostridial toxin light chain through the membrane an intracellular vesicle into the cytoplasm of a cell. Non-limiting examples of a Clostridial toxin translocation domain include, e.g., a BoNT/A translocation domain, a BoNT/B translocation domain, a BoNT/C1 translocation domain, a BoNT/D translocation domain, a BoNT/E translocation domain, a BoNT/F translocation domain, a BoNT/G translocation domain, a TeNT translocation domain, a BaNT translocation domain, and a BuNT translocation domain. Other non-limiting examples of a Clostridial toxin translocation domain include, e.g., amino acids 449-873 of SEQ ID NO: 1, amino acids 442-860 of SEQ ID NO: 2, amino acids 450-868 of SEQ ID NO: 3, amino acids 446-864 of SEQ ID NO: 4, amino acids 423-847 of SEQ ID NO: 5, amino acids 440-866 of SEQ ID NO: 6, amino acids 447-865 of SEQ ID NO: 7, amino acids 458-881 of SEQ ID NO: 8, amino acids 432-857 of SEQ ID NO: 9, and amino acids 423-847 of SEQ ID NO: 10.

A Clostridial toxin translocation domain includes, without limitation, naturally occurring Clostridial toxin translocation domain variants, such as, e.g., Clostridial toxin translocation domain isoforms and Clostridial toxin translocation domain subtypes; non-naturally occurring Clostridial toxin translocation domain variants, such as, e.g., conservative Clostridial toxin translocation domain variants, non-conservative Clostridial toxin translocation domain variants, Clostridial toxin translocation domain chimerics, active Clostridial toxin translocation domain fragments thereof, or any combination thereof.

As used herein, the term "Clostridial toxin translocation domain variant," whether naturally-occurring or non-naturally-occurring, means a Clostridial toxin translocation domain that has at least one amino acid change from the corresponding region of the disclosed reference sequences (Table 1) and can be described in percent identity to the corresponding region of that reference sequence. Unless expressly indicated, all Clostridial toxin translocation domain variants disclosed in the present specification are capable of executing the translocation step of the intoxication process that mediates Clostridial toxin light chain translocation. As non-limiting examples, a BoNT/A translocation domain variant comprising amino acids 449-873 of SEQ ID NO: 1 will have at least one amino acid difference, such as, e.g., an amino acid substitution, deletion or addition, as compared to the amino acid region 449-873 of SEQ ID NO: 1; a BoNT/B translocation domain variant comprising amino acids 442-860 of SEQ ID NO: 2 will have at least one amino acid difference, such as, e.g., an amino acid substitution, deletion or addition, as compared to the amino acid region 442-860 of SEQ ID NO: 2; a BoNT/C1 translocation domain variant comprising amino acids 450-868 of SEQ ID NO: 3 will have at least one amino acid difference, such as, e.g., an amino acid substitution, deletion or addition, as compared to the amino acid region 450-868 of SEQ ID NO: 3; a BoNT/D translocation domain variant comprising amino acids 446-864 of SEQ ID NO: 4 will have at least one amino acid difference, such as, e.g., an amino acid substitution, deletion or addition, as compared to the amino acid region 446-864 of SEQ ID NO: 4; a BoNT/E translocation domain variant comprising amino acids 423-847 of SEQ ID NO: 5 will have at least one amino acid difference, such as, e.g., an amino acid substitution, deletion or addition, as compared to the amino acid region 423-847 of SEQ ID NO: 5; a BoNT/F translocation domain variant comprising amino acids 440-866 of SEQ ID NO: 6 will have at least one amino acid difference, such as, e.g., an amino acid substitution, deletion or addition, as compared to the amino acid region 440-866 of SEQ ID NO: 6; a BoNT/G translocation domain variant comprising amino acids 447-865 of SEQ ID NO: 7 will have at least one amino acid difference, such as, e.g., an amino acid substitution, deletion or addition, as compared to the amino acid region 447-865 of SEQ ID NO: 7; a TeNT translocation domain variant comprising amino acids 458-881 of SEQ ID NO: 8 will have at least one amino acid difference, such as, e.g., an amino acid substitution, deletion or addition, as compared to the amino acid region 458-881 of SEQ ID NO: 8; a BaNT translocation domain variant comprising amino acids 432-857 of SEQ ID NO: 9 will have at least one amino acid difference, such as, e.g., an amino acid substitution, deletion or addition, as compared to the amino acid region 432-857 of SEQ ID NO: 9; and a BuNT translocation domain variant comprising amino acids 423-847 of SEQ ID NO: 10 will have at least one amino acid difference, such as, e.g., an amino acid substitution, deletion or addition, as compared to the amino acid region 423-847 of SEQ ID NO: 10.

It is recognized by those of skill in the art that within each serotype of Clostridial toxin there can be naturally occurring Clostridial toxin translocation domain variants that differ somewhat in their amino acid sequence, and also in the nucleic acids encoding these proteins. For example, there are presently four BoNT/A subtypes, BoNT/A1, BoNT/A2, BoNT/A3 and BoNT/A4, with specific translocation domain subtypes showing approximately 87% amino acid identity when compared to another BoNT/A translocation domain subtype. As used herein, the term "naturally occurring Clostridial toxin translocation domain variant" means any Clostridial toxin translocation domain produced by a naturally-occurring process, including, without limitation, Clostridial toxin translocation domain isoforms produced from alternatively-spliced transcripts, Clostridial toxin translocation domain isoforms produced by spontaneous mutation and Clostridial toxin translocation domain subtypes. A naturally occurring Clostridial toxin translocation domain variant can function in substantially the same manner as the reference Clostridial toxin translocation domain on which the naturally occurring Clostridial toxin translocation domain variant is based, and can be substituted for the reference Clostridial toxin translocation domain in any aspect of the present invention. A naturally occurring Clostridial toxin translocation domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids or 100 or more amino acids from the reference Clostridial toxin translocation domain on which the naturally occurring Clostridial toxin translocation domain variant is based. A naturally occurring Clostridial toxin translocation domain variant can also substitute at least 10 contiguous amino acids, at least 15 contiguous amino acids, at least 20 contiguous amino acids, or at least 25 contiguous amino acids from the reference Clostridial toxin translocation domain on which the naturally occurring Clostridial toxin translocation domain variant is based, that possess at least 50% amino acid identity, 65% amino acid identity, 75% amino acid identity, 85% amino acid identity or 95% amino acid identity to the reference Clostridial toxin translocation domain on which the naturally occurring Clostridial toxin translocation domain variant is based.

A non-limiting examples of a naturally occurring Clostridial toxin translocation domain variant is a Clostridial toxin translocation domain isoform such as, e.g., a BoNT/A translocation domain isoform, a BoNT/B translocation domain isoform, a BoNT/C1 translocation domain isoform, a BoNT/D translocation domain isoform, a BoNT/E translocation domain isoform, a BoNT/F translocation domain isoform, a BoNT/G translocation domain isoform, a TeNT translocation domain isoform, a BaNT translocation domain isoform, and a BuNT translocation domain isoform. A Clostridial toxin translocation domain isoform can function in substantially the same manner as the reference Clostridial toxin translocation domain on which the Clostridial toxin translocation domain isoform is based, and can be substituted for the reference Clostridial toxin translocation domain in any aspect of the present invention.

Another non-limiting examples of a naturally occurring Clostridial toxin translocation domain variant is a Clostridial toxin translocation domain subtype such as, e.g., a translocation domain from subtype BoNT/A1, BoNT/A2, BoNT/A3 and BoNT/A4; a translocation domain from subtype BoNT/B1, BoNT/B2, BoNT/B bivalent and BoNT/B nonproteolytic; a translocation domain from subtype BoNT/C1-1 and BoNT/C1-2; a translocation domain from subtype BoNT/E1, BoNT/E2 and BoNT/E3; and a translocation domain from subtype BoNT/F1, BoNT/F2, BoNT/F3 and BoNT/F4. A Clostridial toxin translocation domain subtype can function in substantially the same manner as the reference Clostridial toxin translocation domain on which the Clostridial toxin translocation domain subtype is based, and can be substituted for the reference Clostridial toxin translocation domain in any aspect of the present invention.

As used herein, the term "non-naturally occurring Clostridial toxin translocation domain variant" means any Clostridial toxin translocation domain produced with the aid of human manipulation, including, without limitation, Clostridial toxin translocation domains produced by genetic engineering using random mutagenesis or rational design and Clostridial toxin translocation domains produced by chemical synthesis. Non-limiting examples of non-naturally occurring Clostridial toxin translocation domain variants include, e.g., conservative Clostridial toxin translocation domain variants, non-conservative Clostridial toxin translocation domain variants, Clostridial toxin translocation domain chimeric variants and active Clostridial toxin translocation domain fragments.

As used herein, the term "conservative Clostridial toxin translocation domain variant" means a Clostridial toxin translocation domain that has at least one amino acid substituted by another amino acid or an amino acid analog that has at least one property similar to that of the original amino acid from the reference Clostridial toxin translocation domain sequence (Table 1). Examples of properties include, without limitation, similar size, topography, charge, hydrophobicity, hydrophilicity, lipophilicity, covalent-bonding capacity, hydrogen-bonding capacity, a physicochemical property, of the like, or any combination thereof. A conservative Clostridial toxin translocation domain variant can function in substantially the same manner as the reference Clostridial toxin translocation domain on which the conservative Clostridial toxin translocation domain variant is based, and can be substituted for the reference Clostridial toxin translocation domain in any aspect of the present invention. A conservative Clostridial toxin translocation domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin translocation domain on which the conservative Clostridial toxin translocation domain variant is based. A conservative Clostridial toxin translocation domain variant can also substitute at least 10 contiguous amino acids, at least 15 contiguous amino acids, at least 20 contiguous amino acids, or at least 25 contiguous amino acids from the reference Clostridial toxin translocation domain on which the conservative Clostridial toxin translocation domain variant is based, that possess at least 50% amino acid identity, 65% amino acid identity, 75% amino acid identity, 85% amino acid identity or 95% amino acid identity to the reference Clostridial toxin translocation domain on which the conservative Clostridial toxin translocation domain variant is based. Non-limiting examples of a conservative Clostridial toxin translocation domain variant include, e.g., conservative BoNT/A translocation domain variants, conservative BoNT/B translocation domain variants, conservative BoNT/C1 translocation domain variants, conservative BoNT/D translocation domain variants, conservative BoNT/E translocation domain variants, conservative BoNT/F translocation domain variants, conservative BoNT/G translocation domain variants, conservative TeNT translocation domain variants, conservative BaNT translocation domain variants, and conservative BuNT translocation domain variants.

As used herein, the term "non-conservative Clostridial toxin translocation domain variant" means a Clostridial toxin translocation domain in which 1) at least one amino acid is deleted from the reference Clostridial toxin translocation domain on which the non-conservative Clostridial toxin translocation domain variant is based; 2) at least one amino acid added to the reference Clostridial toxin translocation domain on which the non-conservative Clostridial toxin translocation domain is based; or 3) at least one amino acid is substituted by another amino acid or an amino acid analog that does not share any property similar to that of the original amino acid from the reference Clostridial toxin translocation domain sequence (Table 1). A non-conservative Clostridial toxin translocation domain variant can function in substantially the same manner as the reference Clostridial toxin translocation domain on which the non-conservative Clostridial toxin translocation domain variant is based, and can be substituted for the reference Clostridial toxin translocation domain in any aspect of the present invention. A non-conservative Clostridial toxin translocation domain variant can delete one or more amino acids, two or more amino acids, three or more amino acids, four or more amino acids, five or more amino acids, and ten or more amino acids from the reference Clostridial toxin translocation domain on which the non-conservative Clostridial toxin translocation domain variant is based. A non-conservative Clostridial toxin translocation domain variant can add one or more amino acids, two or more amino acids, three or more amino acids, four or more amino acids, five or more amino acids, and ten or more amino acids to the reference Clostridial toxin translocation domain on which the non-conservative Clostridial toxin translocation domain variant is based. A non-conservative Clostridial toxin translocation domain variant may substitute one or more amino acids, two or more amino acids, three or more amino acids, four or more amino acids, five or more amino acids, ten or more amino acids, 20 or more amino acids, 30 or more amino acids, 40 or more amino acids, 50 or more amino acids, 100 or more amino acids, 200 or more amino acids, 300 or more amino acids, 400 or more amino acids, or 500 or more amino acids from the reference Clostridial toxin translocation domain on which the non-conservative Clostridial toxin translocation domain variant is based. A non-conservative Clostridial toxin translocation domain variant can also substitute at least 10 contiguous amino acids, at least 15 contiguous amino acids, at least 20 contiguous amino acids, or at least 25 contiguous amino acids from the reference Clostridial toxin translocation domain on which the non-conservative Clostridial toxin translocation domain variant is based, that possess at least 50% amino acid identity, 65% amino acid identity, 75% amino acid identity, 85% amino acid identity or 95% amino acid identity to the reference Clostridial toxin translocation domain on which the non-conservative Clostridial toxin translocation domain variant is based. Non-limiting examples of a non-conservative Clostridial toxin translocation domain variant include, e.g., non-conservative BoNT/A translocation domain variants, non-conservative BoNT/B translocation domain variants, non-conservative BoNT/C1 translocation domain variants, non-conservative BoNT/D translocation domain variants, non-conservative BoNT/E translocation domain variants, non-conservative BoNT/F translocation domain variants, non-conservative BoNT/G translocation domain variants, and non-conservative TeNT translocation domain variants, non-conservative BaNT translocation domain variants, and non-conservative BuNT translocation domain variants.

As used herein, the term "Clostridial toxin translocation domain chimeric" means a polypeptide comprising at least a portion of a Clostridial toxin translocation domain and at least a portion of at least one other polypeptide to form a toxin translocation domain with at least one property different from the reference Clostridial toxin translocation domains of Table 1, with the proviso that this Clostridial toxin translocation domain chimeric is still capable of specifically targeting the core components of the neurotransmitter release apparatus and thus participate in executing the overall cellular mechanism whereby a Clostridial toxin proteolytically cleaves a substrate.

As used herein, the term "active Clostridial toxin translocation domain fragment" means any of a variety of Clostridial toxin fragments comprising the translocation domain can be useful in aspects of the present invention with the proviso that these active fragments can facilitate the release of the LC from intracellular vesicles into the cytoplasm of the target cell and thus participate in executing the overall cellular mechanism whereby a Clostridial toxin proteolytically cleaves a substrate. The translocation domains from the heavy chains of Clostridial toxins are approximately 410-430 amino acids in length and comprise a translocation domain (Table 1). Research has shown that the entire length of a translocation domain from a Clostridial toxin heavy chain is not necessary for the translocating activity of the translocation domain. Thus, aspects of this embodiment can include Clostridial toxin translocation domains comprising a translocation domain having a length of, e.g., at least 350 amino acids, at least 375 amino acids, at least 400 amino acids and at least 425 amino acids. Other aspects of this embodiment can include Clostridial toxin translocation domains comprising translocation domain having a length of, e.g., at most 350 amino acids, at most 375 amino acids, at most 400 amino acids and at most 425 amino acids.

Any of a variety of sequence alignment methods can be used to determine percent identity of naturally-occurring Clostridial toxin translocation domain variants and non-naturally-occurring Clostridial toxin translocation domain variants, including, without limitation, global methods, local methods and hybrid methods, such as, e.g., segment approach methods. Protocols to determine percent identity are routine procedures within the scope of one skilled in the art and from the teaching herein.

Thus, in an embodiment, a modified Clostridial toxin disclosed in the present specification comprises a Clostridial toxin translocation domain. In an aspect of this embodiment, a Clostridial toxin translocation domain comprises a naturally occurring Clostridial toxin translocation domain variant, such as, e.g., a Clostridial toxin translocation domain isoform or a Clostridial toxin translocation domain subtype. In another aspect of this embodiment, a Clostridial toxin translocation domain comprises a non-naturally occurring Clostridial toxin translocation domain variant, such as, e.g., a conservative Clostridial toxin translocation domain variant, a non-conservative Clostridial toxin translocation domain variant, a Clostridial toxin chimeric translocation domain, an active Clostridial toxin translocation domain fragment, or any combination thereof.

In another embodiment, a Clostridial toxin translocation domain comprises a BoNT/A translocation domain. In an aspect of this embodiment, a BoNT/A translocation domain comprises amino acids 449-873 of SEQ ID NO: 1. In another aspect of this embodiment, a BoNT/A translocation domain comprises a naturally occurring BoNT/A translocation domain variant, such as, e.g., a translocation domain from a BoNT/A isoform or a translocation domain from a BoNT/A subtype. In another aspect of this embodiment, a BoNT/A translocation domain comprises amino acids 449-873 of a naturally occurring BoNT/A translocation domain variant of SEQ ID NO: 1, such as, e.g., amino acids 449-873 of a BoNT/A isoform of SEQ ID NO: 1 or amino acids 449-873 of a BoNT/A subtype of SEQ ID NO: 1. In still another aspect of this embodiment, a BoNT/A translocation domain comprises a non-naturally occurring BoNT/A translocation domain variant, such as, e.g., a conservative BoNT/A translocation domain variant, a non-conservative BoNT/A translocation domain variant, a BoNT/A chimeric translocation domain, an active BoNT/A translocation domain fragment, or any combination thereof. In still another aspect of this embodiment, a BoNT/A translocation domain comprises amino acids 449-873 of a non-naturally occurring BoNT/A translocation domain variant of SEQ ID NO: 1, such as, e.g., amino acids 449-873 of a conservative BoNT/A translocation domain variant of SEQ ID NO: 1, amino acids 449-873 of a non-conservative BoNT/A translocation domain variant of SEQ ID NO: 1, amino acids 449-873 of an active BoNT/A translocation domain fragment of SEQ ID NO: 1, or any combination thereof.

In other aspects of this embodiment, a BoNT/A translocation domain comprises a polypeptide having, e.g., at least 70% amino acid identity with amino acids 449-873 of SEQ ID NO: 1, at least 75% amino acid identity with amino acids 449-873 of SEQ ID NO: 1, at least 80% amino acid identity with amino acids 449-873 of SEQ ID NO: 1, at least 85% amino acid identity with amino acids 449-873 of SEQ ID NO: 1, at least 90% amino acid identity with amino acids 449-873 of SEQ ID NO: 1 or at least 95% amino acid identity with amino acids 449-873 of SEQ ID NO: 1. In yet other aspects of this embodiment, a BoNT/A translocation domain comprises a polypeptide having, e.g., at most 70% amino acid identity with amino acids 449-873 of SEQ ID NO: 1, at most 75% amino acid identity with amino acids 449-873 of SEQ ID NO: 1, at most 80% amino acid identity with amino acids 449-873 of SEQ ID NO: 1, at most 85% amino acid identity with amino acids 449-873 of SEQ ID NO: 1, at most 90% amino acid identity with amino acids 449-873 of SEQ ID NO: 1 or at most 95% amino acid identity with amino acids 449-873 of SEQ ID NO: 1.

In other aspects of this embodiment, a BoNT/A translocation domain comprises a polypeptide having, e.g., at most one, two, three, four, five, six, seven, eight, nine, 10, 20, 30, 40, 50, 100, or 200 non-contiguous amino acid substitutions relative to amino acids 449-873 of SEQ ID NO: 1. In other aspects of this embodiment, a BoNT/A translocation domain comprises a polypeptide having, e.g., at least one, two, three, four, five, six, seven, eight, nine, 10, 20, 30, 40, 50, 100 or 200 non-contiguous amino acid substitutions relative to amino acids 449-873 of SEQ ID NO: 1. In yet other aspects of this embodiment, a BoNT/A translocation domain comprises a polypeptide having, e.g., at most one, two, three, four, five, six, seven, eight, nine, 10, 20, 30, 40, 50, 100 or 200 non-contiguous amino acid deletions relative to amino acids 449-873 of SEQ ID NO: 1. In other aspects of this embodiment, a BoNT/A translocation domain comprises a polypeptide having, e.g., at least one, two, three, four, five, six, seven, eight, nine, 10, 20, 30, 40, 50, 100 or 200 non-contiguous amino acid deletions relative to amino acids 449-873 of SEQ ID NO: 1. In still other aspects of this embodiment, a BoNT/A translocation domain comprises a polypeptide having, e.g., at most one, two, three, four, five, six, seven, eight, nine, 10, 20, 30, 40, 50, 100 or 200 non-contiguous amino acid additions relative to amino acids 449-873 of SEQ ID NO: 1. In other aspects of this embodiment, a BoNT/A translocation domain comprises a polypeptide having, e.g., at least one, two, three, four, five, six, seven, eight, nine, 10, 20, 30, 40, 50, 100 or 200 non-contiguous amino acid additions relative to amino acids 449-873 of SEQ ID NO: 1.

In other aspects of this embodiment, a BoNT/A translocation domain comprises a polypeptide having, e.g., at most one, two, three, four, five, six, seven, eight, nine, 10, 20, 30, 40, 50, 100 or 200 contiguous amino acid substitutions relative to amino acids 449-873 of SEQ ID NO: 1. In other aspects of this embodiment, a BoNT/A translocation domain comprises a polypeptide having, e.g., at least one, two, three, four, five, six, seven, eight, nine, 10, 20, 30, 40, 50, 100 or 200 contiguous amino acid substitutions relative to amino acids 449-873 of SEQ ID NO: 1. In yet other aspects of this embodiment, a BoNT/A translocation domain comprises a polypeptide having, e.g., at most one, two, three, four, five, six, seven, eight, nine, 10, 20, 30, 40, 50, 100 or 200 contiguous amino acid deletions relative to amino acids 449-873 of SEQ ID NO: 1. In other aspects of this embodiment, a BoNT/A translocation domain comprises a polypeptide having, e.g., at least one, two, three, four, five, six, seven, eight, nine, 10, 20, 30, 40, 50, 100 or 200 contiguous amino acid deletions relative to amino acids 449-873 of SEQ ID NO: 1. In still other aspects of this embodiment, a BoNT/A translocation domain comprises a polypeptide having, e.g., at most one, two, three, four, five, six, seven, eight, nine, 10, 20, 30, 40, 50, 100 or 200 contiguous amino acid additions relative to amino acids 449-873 of SEQ ID NO: 1. In other aspects of this embodiment, a BoNT/A translocation domain comprises a polypeptide having, e.g., at least one, two, three, four, five, six, seven, eight, nine, 10, 20, 30, 40, 50, 100 or 200 contiguous amino acid additions relative to amino acids 449-873 of SEQ ID NO: 1.

In another embodiment, a Clostridial toxin translocation domain comprises a BoNT/B translocation domain. In an aspect of this embodiment, a BoNT/B translocation domain comprises amino acids 442-860 of SEQ ID NO: 2. In another aspect of this embodiment, a BoNT/B translocation domain comprises a naturally occurring BoNT/B translocation domain variant, such as, e.g., a translocation domain from a BoNT/B isoform or a translocation domain from a BoNT/B subtype. In another aspect of this embodiment, a BoNT/B translocation domain comprises amino acids 442-860 of a naturally occurring BoNT/B translocation domain variant of SEQ ID NO: 2, such as, e.g., amino acids 442-860 of a BoNT/B isoform of SEQ ID NO: 2 or amino acids 442-860 of a BoNT/B subtype of SEQ ID NO: 2. In still another aspect of this embodiment, a BoNT/B translocation domain comprises a non-naturally occurring BoNT/B translocation domain variant, such as, e.g., a conservative BoNT/B translocation domain variant, a non-conservative BoNT/B translocation domain variant, a BoNT/B chimeric translocation domain, an active BoNT/B translocation domain fragment, or any combination thereof. In still another aspect of this embodiment, a BoNT/B translocation domain comprises amino acids 442-860 of a non-naturally occurring BoNT/B translocation domain variant of SEQ ID NO: 2, such as, e.g., amino acids 442-860 of a conservative BoNT/B translocation domain variant of SEQ ID NO: 2, amino acids 442-860 of a non-conservative BoNT/B translocation domain variant of SEQ ID NO: 2, amino acids 442-860 of an active BoNT/B translocation domain fragment of SEQ ID NO: 2, or any combination thereof.

In other aspects of this embodiment, a BoNT/B translocation domain comprises a polypeptide having, e.g., at least 70% amino acid identity with amino acids 442-860 of SEQ ID NO: 2, at least 75% amino acid identity with amino acids 442-860 of SEQ ID NO: 2, at least 80% amino acid identity with amino acids 442-860 of SEQ ID NO: 2, at least 85% amino acid identity with amino acids 442-860 of SEQ ID NO: 2, at least 90% amino acid identity with amino acids 442-860 of SEQ ID NO: 2 or at least 95% amino acid identity with amino acids 442-860 of SEQ ID NO: 2. In yet other aspects of this embodiment, a BoNT/B translocation domain comprises a polypeptide having, e.g., at most 70% amino acid identity with amino acids 442-860 of SEQ ID NO: 2, at most 75% amino acid identity with amino acids 442-860 of SEQ ID NO: 2, at most 80% amino acid identity with amino acids 442-860 of SEQ ID NO: 2, at most 85% amino acid identity with amino acids 442-860 of SEQ ID NO: 2, at most 90% amino acid identity with amino acids 442-860 of SEQ ID NO: 2 or at most 95% amino acid identity with amino acids 442-860 of SEQ ID NO: 2.

In other aspects of this embodiment, a BoNT/B translocation domain comprises a polypeptide having, e.g., at most one, two, three, four, five, six, seven, eight, nine, 10, 20, 30, 40, 50, 100, or 200 non-contiguous amino acid substitutions relative to amino acids 442-860 of SEQ ID NO: 2. In other aspects of this embodiment, a BoNT/B translocation domain comprises a polypeptide having, e.g., at least one, two, three, four, five, six, seven, eight, nine, 10, 20, 30, 40, 50, 100 or 200 non-contiguous amino acid substitutions relative to amino acids 442-860 of SEQ ID NO: 2. In yet other aspects of this embodiment, a BoNT/B translocation domain comprises a polypeptide having, e.g., at most one, two, three, four, five, six, seven, eight, nine, 10, 20, 30, 40, 50, 100 or 200 non-contiguous amino acid deletions relative to amino acids 442-860 of SEQ ID NO: 2. In other aspects of this embodiment, a BoNT/B translocation domain comprises a polypeptide having, e.g., at least one, two, three, four, five, six, seven, eight, nine, 10, 20, 30, 40, 50, 100 or 200 non-contiguous amino acid deletions relative to amino acids 442-860 of SEQ ID NO: 2. In still other aspects of this embodiment, a BoNT/B translocation domain comprises a polypeptide having, e.g., at most one, two, three, four, five, six, seven, eight, nine, 10, 20, 30, 40, 50, 100 or 200 non-contiguous amino acid additions relative to amino acids 442-860 of SEQ ID NO: 2. In other aspects of this embodiment, a BoNT/B translocation domain comprises a polypeptide having, e.g., at least one, two, three, four, five, six, seven, eight, nine, 10, 20, 30, 40, 50, 100 or 200 non-contiguous amino acid additions relative to amino acids 442-860 of SEQ ID NO: 2.

In other aspects of this embodiment, a BoNT/B translocation domain comprises a polypeptide having, e.g., at most one, two, three, four, five, six, seven, eight, nine, 10, 20, 30, 40, 50, 100 or 200 contiguous amino acid substitutions relative to amino acids 442-860 of SEQ ID NO: 2. In other aspects of this embodiment, a BoNT/B translocation domain comprises a polypeptide having, e.g., at least one, two, three, four, five, six, seven, eight, nine, 10, 20, 30, 40, 50, 100 or 200 contiguous amino acid substitutions relative to amino acids 442-860 of SEQ ID NO: 2. In yet other aspects of this embodiment, a BoNT/B translocation domain comprises a polypeptide having, e.g., at most one, two, three, four, five, six, seven, eight, nine, 10, 20, 30, 40, 50, 100 or 200 contiguous amino acid deletions relative to amino acids 442-860 of SEQ ID NO: 2. In other aspects of this embodiment, a BoNT/B translocation domain comprises a polypeptide having, e.g., at least one, two, three, four, five, six, seven, eight, nine, 10, 20, 30, 40, 50, 100 or 200 contiguous amino acid deletions relative to amino acids 442-860 of SEQ ID NO: 2. In still other aspects of this embodiment, a BoNT/B translocation domain comprises a polypeptide having, e.g., at most one, two, three, four, five, six, seven, eight, nine, 10, 20, 30, 40, 50, 100 or 200 contiguous amino acid additions relative to amino acids 442-860 of SEQ ID NO: 2. In other aspects of this embodiment, a BoNT/B translocation domain comprises a polypeptide having, e.g., at least one, two, three, four, five, six, seven, eight, nine, 10, 20, 30, 40, 50, 100 or 200 contiguous amino acid additions relative to amino acids 442-860 of SEQ ID NO: 2.

In another embodiment, a Clostridial toxin translocation domain comprises a BoNT/C1 translocation domain. In an aspect of this embodiment, a BoNT/C1 translocation domain comprises amino acids 450-868 of SEQ ID NO: 3. In another aspect of this embodiment, a BoNT/C1 translocation domain comprises a naturally occurring BoNT/C1 translocation domain variant, such as, e.g., a translocation domain from a BoNT/C1 isoform or a translocation domain from a BoNT/C1 subtype. In another aspect of this embodiment, a BoNT/C1 translocation domain comprises amino acids 450-868 of a naturally occurring BoNT/C1 translocation domain variant of SEQ ID NO: 3, such as, e.g., amino acids 450-868 of a BoNT/C1 isoform of SEQ ID NO: 3 or amino acids 450-868 of a BoNT/C1 subtype of SEQ ID NO: 3. In still another aspect of this embodiment, a BoNT/C1 translocation domain comprises a non-naturally occurring BoNT/C1 translocation domain variant, such as, e.g., a conservative BoNT/C1 translocation domain variant, a non-conservative BoNT/C1 translocation domain variant, a BoNT/C1 chimeric translocation domain, an active BoNT/C1 translocation domain fragment, or any combination thereof. In still another aspect of this embodiment, a BoNT/C1 translocation domain comprises amino acids 450-868 of a non-naturally occurring BoNT/C1 translocation domain variant of SEQ ID NO: 3, such as, e.g., amino acids 450-868 of a conservative BoNT/C1 translocation domain variant of SEQ ID NO: 3, amino acids 450-868 of a non-conservative BoNT/C1 translocation domain variant of SEQ ID NO: 3, amino acids 450-868 of an active BoNT/C1 translocation domain fragment of SEQ ID NO: 3, or any combination thereof.

In other aspects of this embodiment, a BoNT/C1 translocation domain comprises a polypeptide having, e.g., at least 70% amino acid identity with amino acids 450-868 of SEQ ID NO: 3, at least 75% amino acid identity with amino acids 450-868 of SEQ ID NO: 3, at least 80% amino acid identity with amino acids 450-868 of SEQ ID NO: 3, at least 85% amino acid identity with amino acids 450-868 of SEQ ID NO: 3, at least 90% amino acid identity with amino acids 450-868 of SEQ ID NO: 3 or at least 95% amino acid identity with amino acids 450-868 of SEQ ID NO: 3. In yet other aspects of this embodiment, a BoNT/C1 translocation domain comprises a polypeptide having, e.g., at most 70% amino acid identity with amino acids 450-868 of SEQ ID NO: 3, at most 75% amino acid identity with amino acids 450-868 of SEQ ID NO: 3, at most 80% amino acid identity with amino acids 450-868 of SEQ ID NO: 3, at most 85% amino acid identity with amino acids 450-868 of SEQ ID NO: 3, at most 90% amino acid identity with amino acids 450-868 of SEQ ID NO: 3 or at most 95% amino acid identity with amino acids 450-868 of SEQ ID NO: 3.

In other aspects of this embodiment, a BoNT/C1 translocation domain comprises a polypeptide having, e.g., at most one, two, three, four, five, six, seven, eight, nine, 10, 20, 30, 40, 50, 100, or 200 non-contiguous amino acid substitutions relative to amino acids 450-868 of SEQ ID NO: 3. In other aspects of this embodiment, a BoNT/C1 translocation domain comprises a polypeptide having, e.g., at least one, two, three, four, five, six, seven, eight, nine, 10, 20, 30, 40, 50, 100 or 200 non-contiguous amino acid substitutions relative to amino acids 450-868 of SEQ ID NO: 3. In yet other aspects of this embodiment, a BoNT/C1 translocation domain comprises a polypeptide having, e.g., at most one, two, three, four, five, six, seven, eight, nine, 10, 20, 30, 40, 50, 100 or 200 non-contiguous amino acid deletions relative to amino acids 450-868 of SEQ ID NO: 3. In other aspects of this embodiment, a BoNT/C1 translocation domain comprises a polypeptide having, e.g., at least one, two, three, four, five, six, seven, eight, nine, 10, 20, 30, 40, 50, 100 or 200 non-contiguous amino acid deletions relative to amino acids 450-868 of SEQ ID NO: 3. In still other aspects of this embodiment, a BoNT/C1 translocation domain comprises a polypeptide having, e.g., at most one, two, three, four, five, six, seven, eight, nine, 10, 20, 30, 40, 50, 100 or 200 non-contiguous amino acid additions relative to amino acids 450-868 of SEQ ID NO: 3. In other aspects of this embodiment, a BoNT/C1 translocation domain comprises a polypeptide having, e.g., at least one, two, three, four, five, six, seven, eight, nine, 10, 20, 30, 40, 50, 100 or 200 non-contiguous amino acid additions relative to amino acids 450-868 of SEQ ID NO: 3.

In other aspects of this embodiment, a BoNT/C1 translocation domain comprises a polypeptide having, e.g., at most one, two, three, four, five, six, seven, eight, nine, 10, 20, 30, 40, 50, 100 or 200 contiguous amino acid substitutions relative to amino acids 450-868 of SEQ ID NO: 3. In other aspects of this embodiment, a BoNT/C1 translocation domain comprises a polypeptide having, e.g., at least one, two, three, four, five, six, seven, eight, nine, 10, 20, 30, 40, 50, 100 or 200 contiguous amino acid substitutions relative to amino acids 450-868 of SEQ ID NO: 3. In yet other aspects of this embodiment, a BoNT/C1 translocation domain comprises a polypeptide having, e.g., at most one, two, three, four, five, six, seven, eight, nine, 10, 20, 30, 40, 50, 100 or 200 contiguous amino acid deletions relative to amino acids 450-868 of SEQ ID NO: 3. In other aspects of this embodiment, a BoNT/C1 translocation domain comprises a polypeptide having, e.g., at least one, two, three, four, five, six, seven, eight, nine, 10, 20, 30, 40, 50, 100 or 200 contiguous amino acid deletions relative to amino acids 450-868 of SEQ ID NO: 3. In still other aspects of this embodiment, a BoNT/C1 translocation domain comprises a polypeptide having, e.g., at most one, two, three, four, five, six, seven, eight, nine, 10, 20, 30, 40, 50, 100 or 200 contiguous amino acid additions relative to amino acids 450-868 of SEQ ID NO: 3. In other aspects of this embodiment, a BoNT/C1 translocation domain comprises a polypeptide having, e.g., at least one, two, three, four, five, six, seven, eight, nine, 10, 20, 30, 40, 50, 100 or 200 contiguous amino acid additions relative to amino acids 450-868 of SEQ ID NO: 3.

In another embodiment, a Clostridial toxin translocation domain comprises a BoNT/D translocation domain. In an aspect of this embodiment, a BoNT/D translocation domain comprises amino acids 446-864 of SEQ ID NO: 4. In another aspect of this embodiment, a BoNT/D translocation domain comprises a naturally occurring BoNT/D translocation domain variant, such as, e.g., a translocation domain from a BoNT/D isoform or a translocation domain from a BoNT/D subtype. In another aspect of this embodiment, a BoNT/D translocation domain comprises amino acids 446-864 of a naturally occurring BoNT/D translocation domain variant of SEQ ID NO: 4, such as, e.g., amino acids 446-864 of a BoNT/D isoform of SEQ ID NO: 4 or amino acids 446-864 of a BoNT/D subtype of SEQ ID NO: 4. In still another aspect of this embodiment, a BoNT/D translocation domain comprises a non-naturally occurring BoNT/D translocation domain variant, such as, e.g., a conservative BoNT/D translocation domain variant, a non-conservative BoNT/D translocation domain variant, a BoNT/D chimeric translocation domain, an active BoNT/D translocation domain fragment, or any combination thereof. In still another aspect of this embodiment, a BoNT/D translocation domain comprises amino acids 446-864 of a non-naturally occurring BoNT/D translocation domain variant of SEQ ID NO: 4, such as, e.g., amino acids 446-864 of a conservative BoNT/D translocation domain variant of SEQ ID NO: 4, amino acids 446-864 of a non-conservative BoNT/D translocation domain variant of SEQ ID NO: 4, amino acids 446-864 of an active BoNT/D translocation domain fragment of SEQ ID NO: 4, or any combination thereof.

In other aspects of this embodiment, a BoNT/D translocation domain comprises a polypeptide having, e.g., at least 70% amino acid identity with amino acids 446-864 of SEQ ID NO: 4, at least 75% amino acid identity with amino acids 446-864 of SEQ ID NO: 4, at least 80% amino acid identity with amino acids 446-864 of SEQ ID NO: 4, at least 85% amino acid identity with amino acids 446-864 of SEQ ID NO: 4, at least 90% amino acid identity with amino acids 446-864 of SEQ ID NO: 4 or at least 95% amino acid identity with amino acids 446-864 of SEQ ID NO: 4. In yet other aspects of this embodiment, a BoNT/D translocation domain comprises a polypeptide having, e.g., at most 70% amino acid identity with amino acids 446-864 of SEQ ID NO: 4, at most 75% amino acid identity with amino acids 446-864 of SEQ ID NO:

4, at most 80% amino acid identity with amino acids 446-864 of SEQ ID NO: 4, at most 85% amino acid identity with amino acids 446-864 of SEQ ID NO: 4, at most 90% amino acid identity with amino acids 446-864 of SEQ ID NO: 4 or at most 95% amino acid identity with amino acids 446-864 of SEQ ID NO: 4.

In other aspects of this embodiment, a BoNT/D translocation domain comprises a polypeptide having, e.g., at most one, two, three, four, five, six, seven, eight, nine, 10, 20, 30, 40, 50, 100, or 200 non-contiguous amino acid substitutions relative to amino acids 446-864 of SEQ ID NO: 4. In other aspects of this embodiment, a BoNT/D translocation domain comprises a polypeptide having, e.g., at least one, two, three, four, five, six, seven, eight, nine, 10, 20, 30, 40, 50, 100 or 200 non-contiguous amino acid substitutions relative to amino acids 446-864 of SEQ ID NO: 4. In yet other aspects of this embodiment, a BoNT/D translocation domain comprises a polypeptide having, e.g., at most one, two, three, four, five, six, seven, eight, nine, 10, 20, 30, 40, 50, 100 or 200 non-contiguous amino acid deletions relative to amino acids 446-864 of SEQ ID NO: 4. In other aspects of this embodiment, a BoNT/D translocation domain comprises a polypeptide having, e.g., at least one, two, three, four, five, six, seven, eight, nine, 10, 20, 30, 40, 50, 100 or 200 non-contiguous amino acid deletions relative to amino acids 446-864 of SEQ ID NO: 4. In still other aspects of this embodiment, a BoNT/D translocation domain comprises a polypeptide having, e.g., at most one, two, three, four, five, six, seven, eight, nine, 10, 20, 30, 40, 50, 100 or 200 non-contiguous amino acid additions relative to amino acids 446-864 of SEQ ID NO: 4. In other aspects of this embodiment, a BoNT/D translocation domain comprises a polypeptide having, e.g., at least one, two, three, four, five, six, seven, eight, nine, 10, 20, 30, 40, 50, 100 or 200 non-contiguous amino acid additions relative to amino acids 446-864 of SEQ ID NO: 4.

In other aspects of this embodiment, a BoNT/D translocation domain comprises a polypeptide having, e.g., at most one, two, three, four, five, six, seven, eight, nine, 10, 20, 30, 40, 50, 100 or 200 contiguous amino acid substitutions relative to amino acids 446-864 of SEQ ID NO: 4. In other aspects of this embodiment, a BoNT/D translocation domain comprises a polypeptide having, e.g., at least one, two, three, four, five, six, seven, eight, nine, 10, 20, 30, 40, 50, 100 or 200 contiguous amino acid substitutions relative to amino acids 446-864 of SEQ ID NO: 4. In yet other aspects of this embodiment, a BoNT/D translocation domain comprises a polypeptide having, e.g., at most one, two, three, four, five, six, seven, eight, nine, 10, 20, 30, 40, 50, 100 or 200 contiguous amino acid deletions relative to amino acids 446-864 of SEQ ID NO: 4. In other aspects of this embodiment, a BoNT/D translocation domain comprises a polypeptide having, e.g., at least one, two, three, four, five, six, seven, eight, nine, 10, 20, 30, 40, 50, 100 or 200 contiguous amino acid deletions relative to amino acids 446-864 of SEQ ID NO: 4. In still other aspects of this embodiment, a BoNT/D translocation domain comprises a polypeptide having, e.g., at most one, two, three, four, five, six, seven, eight, nine, 10, 20, 30, 40, 50, 100 or 200 contiguous amino acid additions relative to amino acids 446-864 of SEQ ID NO: 4. In other aspects of this embodiment, a BoNT/D translocation domain comprises a polypeptide having, e.g., at least one, two, three, four, five, six, seven, eight, nine, 10, 20, 30, 40, 50, 100 or 200 contiguous amino acid additions relative to amino acids 446-864 of SEQ ID NO: 4.

In another embodiment, a Clostridial toxin translocation domain comprises a BoNT/E translocation domain. In an aspect of this embodiment, a BoNT/E translocation domain comprises amino acids 423-847 of SEQ ID NO: 5. In another aspect of this embodiment, a BoNT/E translocation domain comprises a naturally occurring BoNT/E translocation domain variant, such as, e.g., a translocation domain from a BoNT/E isoform or a translocation domain from a BoNT/E subtype. In another aspect of this embodiment, a BoNT/E translocation domain comprises amino acids 423-847 of a naturally occurring BoNT/E translocation domain variant of SEQ ID NO: 5, such as, e.g., amino acids 423-847 of a BoNT/E isoform of SEQ ID NO: 5 or amino acids 423-847 of a BoNT/E subtype of SEQ ID NO: 5. In still another aspect of this embodiment, a BoNT/E translocation domain comprises a non-naturally occurring BoNT/E translocation domain variant, such as, e.g., a conservative BoNT/E translocation domain variant, a non-conservative BoNT/E translocation domain variant, a BoNT/E chimeric translocation domain, an active BoNT/E translocation domain fragment, or any combination thereof. In still another aspect of this embodiment, a BoNT/E translocation domain comprises amino acids 423-847 of a non-naturally occurring BoNT/E translocation domain variant of SEQ ID NO: 5, such as, e.g., amino acids 423-847 of a conservative BoNT/E translocation domain variant of SEQ ID NO: 5, amino acids 423-847 of a non-conservative BoNT/E translocation domain variant of SEQ ID NO: 5, amino acids 423-847 of an active BoNT/E translocation domain fragment of SEQ ID NO: 5, or any combination thereof.

In other aspects of this embodiment, a BoNT/E translocation domain comprises a polypeptide having, e.g., at least 70% amino acid identity with amino acids 423-847 of SEQ ID NO: 5, at least 75% amino acid identity with amino acids 423-847 of SEQ ID NO: 5, at least 80% amino acid identity with amino acids 423-847 of SEQ ID NO: 5, at least 85% amino acid identity with amino acids 423-847 of SEQ ID NO: 5, at least 90% amino acid identity with amino acids 423-847 of SEQ ID NO: 5 or at least 95% amino acid identity with amino acids 423-847 of SEQ ID NO: 5. In yet other aspects of this embodiment, a BoNT/E translocation domain comprises a polypeptide having, e.g., at most 70% amino acid identity with amino acids 423-847 of SEQ ID NO: 5, at most 75% amino acid identity with amino acids 423-847 of SEQ ID NO: 5, at most 80% amino acid identity with amino acids 423-847 of SEQ ID NO: 5, at most 85% amino acid identity with amino acids 423-847 of SEQ ID NO: 5, at most 90% amino acid identity with amino acids 423-847 of SEQ ID NO: 5 or at most 95% amino acid identity with amino acids 423-847 of SEQ ID NO: 5.

In other aspects of this embodiment, a BoNT/E translocation domain comprises a polypeptide having, e.g., at most one, two, three, four, five, six, seven, eight, nine, 10, 20, 30, 40, 50, 100, or 200 non-contiguous amino acid substitutions relative to amino acids 423-847 of SEQ ID NO: 5. In other aspects of this embodiment, a BoNT/E translocation domain comprises a polypeptide having, e.g., at least one, two, three, four, five, six, seven, eight, nine, 10, 20, 30, 40, 50, 100 or 200 non-contiguous amino acid substitutions relative to amino acids 423-847 of SEQ ID NO: 5. In yet other aspects of this embodiment, a BoNT/E translocation domain comprises a polypeptide having, e.g., at most one, two, three, four, five, six, seven, eight, nine, 10, 20, 30, 40, 50, 100 or 200 non-contiguous amino acid deletions relative to amino acids 423-847 of SEQ ID NO: 5. In other aspects of this embodiment, a BoNT/E translocation domain comprises a polypeptide having, e.g., at least one, two, three, four, five, six, seven, eight, nine, 10, 20, 30, 40, 50, 100 or 200 non-contiguous amino acid deletions relative to amino acids 423-847 of SEQ ID NO: 5. In still other aspects of this embodiment, a BoNT/E translocation domain comprises a polypeptide having, e.g., at most one, two, three, four, five, six, seven, eight, nine, 10, 20, 30, 40, 50, 100 or 200 non-contiguous amino acid additions relative to amino acids 423-847 of SEQ ID NO: 5. In other aspects of this embodiment, a BoNT/E translocation domain comprises a polypeptide having, e.g., at least one, two, three, four, five, six, seven, eight, nine, 10, 20, 30, 40, 50, 100 or 200 non-contiguous amino acid additions relative to amino acids 423-847 of SEQ ID NO: 5.

In other aspects of this embodiment, a BoNT/E translocation domain comprises a polypeptide having, e.g., at most one, two, three, four, five, six, seven, eight, nine, 10, 20, 30, 40, 50, 100 or 200 contiguous amino acid substitutions relative to amino acids 423-847 of SEQ ID NO: 5. In other aspects of this embodiment, a BoNT/E translocation domain comprises a polypeptide having, e.g., at least one, two, three, four, five, six, seven, eight, nine, 10, 20, 30, 40, 50, 100 or 200 contiguous amino acid substitutions relative to amino acids 423-847 of SEQ ID NO: 5. In yet other aspects of this embodiment, a BoNT/E translocation domain comprises a polypeptide having, e.g., at most one, two, three, four, five, six, seven, eight, nine, 10, 20, 30, 40, 50, 100 or 200 contiguous amino acid deletions relative to amino acids 423-847 of SEQ ID NO: 5. In other aspects of this embodiment, a BoNT/E translocation domain comprises a polypeptide having, e.g., at least one, two, three, four, five, six, seven, eight, nine, 10, 20, 30, 40, 50, 100 or 200 contiguous amino acid deletions relative to amino acids 423-847 of SEQ ID NO: 5. In still other aspects of this embodiment, a BoNT/E translocation domain comprises a polypeptide having, e.g., at most one, two, three, four, five, six, seven, eight, nine, 10, 20, 30, 40, 50, 100 or 200 contiguous amino acid additions relative to amino acids 423-847 of SEQ ID NO: 5. In other aspects of this embodiment, a BoNT/E translocation domain comprises a polypeptide having, e.g., at least one, two, three, four, five, six, seven, eight, nine, 10, 20, 30, 40, 50, 100 or 200 contiguous amino acid additions relative to amino acids 423-847 of SEQ ID NO: 5.

In another embodiment, a Clostridial toxin translocation domain comprises a BoNT/F translocation domain. In an aspect of this embodiment, a BoNT/F translocation domain comprises amino acids 440-866 of SEQ ID NO: 6. In another aspect of this embodiment, a BoNT/F translocation domain comprises a naturally occurring BoNT/F translocation domain variant, such as, e.g., a translocation domain from a BoNT/F isoform or a translocation domain from a BoNT/F subtype. In another aspect of this embodiment, a BoNT/F translocation domain comprises amino acids 440-866 of a naturally occurring BoNT/F translocation domain variant of SEQ ID NO: 6, such as, e.g., amino acids 440-866 of a BoNT/F isoform of SEQ ID NO: 6 or amino acids 440-866 of a BoNT/F subtype of SEQ ID NO: 6. In still another aspect of this embodiment, a BoNT/F translocation domain comprises a non-naturally occurring BoNT/F translocation domain variant, such as, e.g., a conservative BoNT/F translocation domain variant, a non-conservative BoNT/F translocation domain variant, a BoNT/F chimeric translocation domain, an active BoNT/F translocation domain fragment, or any combination thereof. In still another aspect of this embodiment, a BoNT/F translocation domain comprises amino acids 440-866 of a non-naturally occurring BoNT/F translocation domain variant of SEQ ID NO: 6, such as, e.g., amino acids 440-866 of a conservative BoNT/F translocation domain variant of SEQ ID NO: 6, amino acids 440-866 of a non-conservative BoNT/F translocation domain variant of SEQ ID NO: 6, amino acids 440-866 of an active BoNT/F translocation domain fragment of SEQ ID NO: 6, or any combination thereof.

In other aspects of this embodiment, a BoNT/F translocation domain comprises a polypeptide having, e.g., at least 70% amino acid identity with amino acids 440-866 of SEQ ID NO: 6, at least 75% amino acid identity with amino acids 440-866 of SEQ ID NO: 6, at least 80% amino acid identity with amino acids 440-866 of SEQ ID NO: 6, at least 85% amino acid identity with amino acids 440-866 of SEQ ID NO: 6, at least 90% amino acid identity with amino acids 440-866 of SEQ ID NO: 6 or at least 95% amino acid identity with amino acids 440-866 of SEQ ID NO: 6. In yet other aspects of this embodiment, a BoNT/F translocation domain comprises a polypeptide having, e.g., at most 70% amino acid identity with amino acids 440-866 of SEQ ID NO: 6, at most 75% amino acid identity with amino acids 440-866 of SEQ ID NO: 6, at most 80% amino acid identity with amino acids 440-866 of SEQ ID NO: 6, at most 85% amino acid identity with amino acids 440-866 of SEQ ID NO: 6, at most 90% amino acid identity with amino acids 440-866 of SEQ ID NO: 6 or at most 95% amino acid identity with amino acids 440-866 of SEQ ID NO: 6.

In other aspects of this embodiment, a BoNT/F translocation domain comprises a polypeptide having, e.g., at most one, two, three, four, five, six, seven, eight, nine, 10, 20, 30, 40, 50, 100, or 200 non-contiguous amino acid substitutions relative to amino acids 440-866 of SEQ ID NO: 6. In other aspects of this embodiment, a BoNT/F translocation domain comprises a polypeptide having, e.g., at least one, two, three, four, five, six, seven, eight, nine, 10, 20, 30, 40, 50, 100 or 200 non-contiguous amino acid substitutions relative to amino acids 440-866 of SEQ ID NO: 6. In yet other aspects of this embodiment, a BoNT/F translocation domain comprises a polypeptide having, e.g., at most one, two, three, four, five, six, seven, eight, nine, 10, 20, 30, 40, 50, 100 or 200 non-contiguous amino acid deletions relative to amino acids 440-866 of SEQ ID NO: 6. In other aspects of this embodiment, a BoNT/F translocation domain comprises a polypeptide having, e.g., at least one, two, three, four, five, six, seven, eight, nine, 10, 20, 30, 40, 50, 100 or 200 non-contiguous amino acid deletions relative to amino acids 440-866 of SEQ ID NO: 6. In still other aspects of this embodiment, a BoNT/F translocation domain comprises a polypeptide having, e.g., at most one, two, three, four, five, six, seven, eight, nine, 10, 20, 30, 40, 50, 100 or 200 non-contiguous amino acid additions relative to amino acids 440-866 of SEQ ID NO: 6. In other aspects of this embodiment, a BoNT/F translocation domain comprises a polypeptide having, e.g., at least one, two, three, four, five, six, seven, eight, nine, 10, 20, 30, 40, 50, 100 or 200 non-contiguous amino acid additions relative to amino acids 440-866 of SEQ ID NO: 6.

In other aspects of this embodiment, a BoNT/F translocation domain comprises a polypeptide having, e.g., at most one, two, three, four, five, six, seven, eight, nine, 10, 20, 30, 40, 50, 100 or 200 contiguous amino acid substitutions relative to amino acids 440-866 of SEQ ID NO: 6. In other aspects of this embodiment, a BoNT/F translocation domain comprises a polypeptide having, e.g., at least one, two, three, four, five, six, seven, eight, nine, 10, 20, 30, 40, 50, 100 or 200 contiguous amino acid substitutions relative to amino acids 440-866 of SEQ ID NO: 6. In yet other aspects of this embodiment, a BoNT/F translocation domain comprises a polypeptide having, e.g., at most one, two, three, four, five, six, seven, eight, nine, 10, 20, 30, 40, 50, 100 or 200 contiguous amino acid deletions relative to amino acids 440-866 of SEQ ID NO: 6. In other aspects of this embodiment, a BoNT/F translocation domain comprises a polypeptide having, e.g., at least one, two, three, four, five, six, seven, eight, nine, 10, 20, 30, 40, 50, 100 or 200 contiguous amino acid deletions relative to amino acids 440-866 of SEQ ID NO: 6. In still other aspects of this embodiment, a BoNT/F translocation domain comprises a polypeptide having, e.g., at most one, two, three, four, five, six, seven, eight, nine, 10, 20, 30, 40, 50, 100 or 200 contiguous amino acid additions relative to amino acids 440-866 of SEQ ID NO: 6. In other aspects of this embodiment, a BoNT/F translocation domain comprises a polypeptide having, e.g., at least one, two, three, four, five, six, seven, eight, nine, 10, 20, 30, 40, 50, 100 or 200 contiguous amino acid additions relative to amino acids 440-866 of SEQ ID NO: 6.

In another embodiment, a Clostridial toxin translocation domain comprises a BoNT/G translocation domain. In an aspect of this embodiment, a BoNT/G translocation domain comprises amino acids 447-865 of SEQ ID NO: 7. In another aspect of this embodiment, a BoNT/G translocation domain comprises a naturally occurring BoNT/G translocation domain variant, such as, e.g., a translocation domain from a BoNT/G isoform or a translocation domain from a BoNT/G subtype. In another aspect of this embodiment, a BoNT/G translocation domain comprises amino acids 447-865 of a naturally occurring BoNT/G translocation domain variant of SEQ ID NO: 7, such as, e.g., amino acids 447-865 of a BoNT/G isoform of SEQ ID NO: 7 or amino acids 447-865 of a BoNT/G subtype of SEQ ID NO: 7. In still another aspect of this embodiment, a BoNT/G translocation domain comprises a non-naturally occurring BoNT/G translocation domain variant, such as, e.g., a conservative BoNT/G translocation domain variant, a non-conservative BoNT/G translocation domain variant, a BoNT/G chimeric translocation domain, an active BoNT/G translocation domain fragment, or any combination thereof. In still another aspect of this embodiment, a BoNT/G translocation domain comprises amino acids 447-865 of a non-naturally occurring BoNT/G translocation domain variant of SEQ ID NO: 7, such as, e.g., amino acids 447-865 of a conservative BoNT/G translocation domain variant of SEQ ID NO: 7, amino acids 447-865 of a non-conservative BoNT/G translocation domain variant of SEQ ID NO: 7, amino acids 447-865 of an active BoNT/G translocation domain fragment of SEQ ID NO: 7, or any combination thereof.

In other aspects of this embodiment, a BoNT/G translocation domain comprises a polypeptide having, e.g., at least 70% amino acid identity with amino acids 447-865 of SEQ ID NO: 7, at least 75% amino acid identity with amino acids 447-865 of SEQ ID NO: 7, at least 80% amino acid identity with amino acids 447-865 of SEQ ID NO: 7, at least 85% amino acid identity with amino acids 447-865 of SEQ ID NO: 7, at least 90% amino acid identity with amino acids 447-865 of SEQ ID NO: 7 or at least 95% amino acid identity with amino acids 447-865 of SEQ ID NO: 7. In yet other aspects of this embodiment, a BoNT/G translocation domain comprises a polypeptide having, e.g., at most 70% amino acid identity with amino acids 447-865 of SEQ ID NO: 7, at most 75% amino acid identity with amino acids 447-865 of SEQ ID NO: 7, at most 80% amino acid identity with amino acids 447-865 of SEQ ID NO: 7, at most 85% amino acid identity with amino acids 447-865 of SEQ ID NO: 7, at most 90% amino acid identity with amino acids 447-865 of SEQ ID NO: 7 or at most 95% amino acid identity with amino acids 447-865 of SEQ ID NO: 7.

In other aspects of this embodiment, a BoNT/G translocation domain comprises a polypeptide having, e.g., at most one, two, three, four, five, six, seven, eight, nine, 10, 20, 30, 40, 50, 100, or 200 non-contiguous amino acid substitutions relative to amino acids 447-865 of SEQ ID NO: 7. In other aspects of this embodiment, a BoNT/G translocation domain comprises a polypeptide having, e.g., at least one, two, three, four, five, six, seven, eight, nine, 10, 20, 30, 40, 50, 100 or 200 non-contiguous amino acid substitutions relative to amino acids 447-865 of SEQ ID NO: 7. In yet other aspects of this embodiment, a BoNT/G translocation domain comprises a polypeptide having, e.g., at most one, two, three, four, five, six, seven, eight, nine, 10, 20, 30, 40, 50, 100 or 200 non-contiguous amino acid deletions relative to amino acids 447-865 of SEQ ID NO: 7. In other aspects of this embodiment, a BoNT/G translocation domain comprises a polypeptide having, e.g., at least one, two, three, four, five, six, seven, eight, nine, 10, 20, 30, 40, 50, 100 or 200 non-contiguous amino acid deletions relative to amino acids 447-865 of SEQ ID NO: 7. In still other aspects of this embodiment, a BoNT/G translocation domain comprises a polypeptide having, e.g., at most one, two, three, four, five, six, seven, eight, nine, 10, 20, 30, 40, 50, 100 or 200 non-contiguous amino acid additions relative to amino acids 447-865 of SEQ ID NO: 7. In other aspects of this embodiment, a BoNT/G translocation domain comprises a polypeptide having, e.g., at least one, two, three, four, five, six, seven, eight, nine, 10, 20, 30, 40, 50, 100 or 200 non-contiguous amino acid additions relative to amino acids 447-865 of SEQ ID NO: 7.

In other aspects of this embodiment, a BoNT/G translocation domain comprises a polypeptide having, e.g., at most one, two, three, four, five, six, seven, eight, nine, 10, 20, 30, 40, 50, 100 or 200 contiguous amino acid substitutions relative to amino acids 447-865 of SEQ ID NO: 7. In other aspects of this embodiment, a BoNT/G translocation domain comprises a polypeptide having, e.g., at least one, two, three, four, five, six, seven, eight, nine, 10, 20, 30, 40, 50, 100 or 200 contiguous amino acid substitutions relative to amino acids 447-865 of SEQ ID NO: 7. In yet other aspects of this embodiment, a BoNT/G translocation domain comprises a polypeptide having, e.g., at most one, two, three, four, five, six, seven, eight, nine, 10, 20, 30, 40, 50, 100 or 200 contiguous amino acid deletions relative to amino acids 447-865 of SEQ ID NO: 7. In other aspects of this embodiment, a BoNT/G translocation domain comprises a polypeptide having, e.g., at least one, two, three, four, five, six, seven, eight, nine, 10, 20, 30, 40, 50, 100 or 200 contiguous amino acid deletions relative to amino acids 447-865 of SEQ ID NO: 7. In still other aspects of this embodiment, a BoNT/G translocation domain comprises a polypeptide having, e.g., at most one, two, three, four, five, six, seven, eight, nine, 10, 20, 30, 40, 50, 100 or 200 contiguous amino acid additions relative to amino acids 447-865 of SEQ ID NO: 7. In other aspects of this embodiment, a BoNT/G translocation domain comprises a polypeptide having, e.g., at least one, two, three, four, five, six, seven, eight, nine, 10, 20, 30, 40, 50, 100 or 200 contiguous amino acid additions relative to amino acids 447-865 of SEQ ID NO: 7.

In another embodiment, a Clostridial toxin translocation domain comprises a TeNT translocation domain. In an aspect of this embodiment, a TeNT translocation domain comprises amino acids 458-881 of SEQ ID NO: 8. In another aspect of this embodiment, a TeNT translocation domain comprises a naturally occurring TeNT translocation domain variant, such as, e.g., a translocation domain from a TeNT isoform or a translocation domain from a TeNT subtype. In another aspect of this embodiment, a TeNT translocation domain comprises amino acids 458-881 of a naturally occurring TeNT translocation domain variant of SEQ ID NO: 8, such as, e.g., amino acids 458-881 of a TeNT isoform of SEQ ID NO: 8 or amino acids 458-881 of a TeNT subtype of SEQ ID NO: 8. In still another aspect of this embodiment, a TeNT translocation domain comprises a non-naturally occurring TeNT translocation domain variant, such as, e.g., a conservative TeNT translocation domain variant, a non-conservative TeNT translocation domain variant, a TeNT chimeric translocation domain, an active TeNT translocation domain fragment, or any combination thereof. In still another aspect of this embodiment, a TeNT translocation domain comprises amino acids 458-881 of a non-naturally occurring TeNT translocation domain variant of SEQ ID NO: 8, such as, e.g., amino acids 458-881 of a conservative TeNT translocation domain variant of SEQ ID NO: 8, amino acids 458-881 of a non-conservative TeNT translocation domain variant of SEQ ID NO: 8, amino acids 458-881 of an active TeNT translocation domain fragment of SEQ ID NO: 8, or any combination thereof.

In other aspects of this embodiment, a TeNT translocation domain comprises a polypeptide having, e.g., at least 70% amino acid identity with amino acids 458-881 of SEQ ID NO: 8, at least 75% amino acid identity with amino acids 458-881 of SEQ ID NO: 8, at least 80% amino acid identity with amino acids 458-881 of SEQ ID NO: 8, at least 85% amino acid identity with amino acids 458-881 of SEQ ID NO: 8, at least 90% amino acid identity with amino acids 458-881 of SEQ ID NO: 8 or at least 95% amino acid identity with amino acids 458-881 of SEQ ID NO: 8. In yet other aspects of this embodiment, a TeNT translocation domain comprises a polypeptide having, e.g., at most 70% amino acid identity with amino acids 458-881 of SEQ ID NO: 8, at most 75% amino acid identity with amino acids 458-881 of SEQ ID NO: 8, at most 80% amino acid identity with amino acids 458-881 of SEQ ID NO: 8, at most 85% amino acid identity with amino acids 458-881 of SEQ ID NO: 8, at most 90% amino acid identity with amino acids 458-881 of SEQ ID NO: 8 or at most 95% amino acid identity with amino acids 458-881 of SEQ ID NO: 8.

In other aspects of this embodiment, a TeNT translocation domain comprises a polypeptide having, e.g., at most one, two, three, four, five, six, seven, eight, nine, 10, 20, 30, 40, 50, 100, or 200 non-contiguous amino acid substitutions relative to amino acids 458-881 of SEQ ID NO: 8. In other aspects of this embodiment, a TeNT translocation domain comprises a polypeptide having, e.g., at least one, two, three, four, five, six, seven, eight, nine, 10, 20, 30, 40, 50, 100 or 200 non-contiguous amino acid substitutions relative to amino acids 458-881 of SEQ ID NO: 8. In yet other aspects of this embodiment, a TeNT translocation domain comprises a polypeptide having, e.g., at most one, two, three, four, five, six, seven, eight, nine, 10, 20, 30, 40, 50, 100 or 200 non-contiguous amino acid deletions relative to amino acids 458-881 of SEQ ID NO: 8. In other aspects of this embodiment, a TeNT translocation domain comprises a polypeptide having, e.g., at least one, two, three, four, five, six, seven, eight, nine, 10, 20, 30, 40, 50, 100 or 200 non-contiguous amino acid deletions relative to amino acids 458-881 of SEQ ID NO: 8. In still other aspects of this embodiment, a TeNT translocation domain comprises a polypeptide having, e.g., at most one, two, three, four, five, six, seven, eight, nine, 10, 20, 30, 40, 50, 100 or 200 non-contiguous amino acid additions relative to amino acids 458-881 of SEQ ID NO: 8. In other aspects of this embodiment, a TeNT translocation domain comprises a polypeptide having, e.g., at least one, two, three, four, five, six, seven, eight, nine, 10, 20, 30, 40, 50, 100 or 200 non-contiguous amino acid additions relative to amino acids 458-881 of SEQ ID NO: 8.

In other aspects of this embodiment, a TeNT translocation domain comprises a polypeptide having, e.g., at most one, two, three, four, five, six, seven, eight, nine, 10, 20, 30, 40, 50, 100 or 200 contiguous amino acid substitutions relative to amino acids 458-881 of SEQ ID NO: 8. In other aspects of this embodiment, a TeNT translocation domain comprises a polypeptide having, e.g., at least one, two, three, four, five, six, seven, eight, nine, 10, 20, 30, 40, 50, 100 or 200 contiguous amino acid substitutions relative to amino acids 458-881 of SEQ ID NO: 8. In yet other aspects of this embodiment, a TeNT translocation domain comprises a polypeptide having, e.g., at most one, two, three, four, five, six, seven, eight, nine, 10, 20, 30, 40, 50, 100 or 200 contiguous amino acid deletions relative to amino acids 458-881 of SEQ ID NO: 8. In other aspects of this embodiment, a TeNT translocation domain comprises a polypeptide having, e.g., at least one, two, three, four, five, six, seven, eight, nine, 10, 20, 30, 40, 50, 100 or 200 contiguous amino acid deletions relative to amino acids 458-881 of SEQ ID NO: 8. In still other aspects of this embodiment, a TeNT translocation domain comprises a polypeptide having, e.g., at most one, two, three, four, five, six, seven, eight, nine, 10, 20, 30, 40, 50, 100 or 200 contiguous amino acid additions relative to amino acids 458-881 of SEQ ID NO: 8. In other aspects of this embodiment, a TeNT translocation domain comprises a polypeptide having, e.g., at least one, two, three, four, five, six, seven, eight, nine, 10, 20, 30, 40, 50, 100 or 200 contiguous amino acid additions relative to amino acids 458-881 of SEQ ID NO: 8.

In another embodiment, a Clostridial toxin translocation domain comprises a BaNT translocation domain. In an aspect of this embodiment, a BaNT translocation domain comprises amino acids 432-857 of SEQ ID NO: 9. In another aspect of this embodiment, a BaNT translocation domain comprises a naturally occurring BaNT translocation domain variant, such as, e.g., a translocation domain from a BaNT isoform or a translocation domain from a BaNT subtype. In another aspect of this embodiment, a BaNT translocation domain comprises amino acids 432-857 of a naturally occurring BaNT translocation domain variant of SEQ ID NO: 9, such as, e.g., amino acids 432-857 of a BaNT isoform of SEQ ID NO: 9 or amino acids 432-857 of a BaNT subtype of SEQ ID NO: 9. In still another aspect of this embodiment, a BaNT translocation domain comprises a non-naturally occurring BaNT translocation domain variant, such as, e.g., a conservative BaNT translocation domain variant, a non-conservative BaNT translocation domain variant, a BaNT chimeric translocation domain, an active BaNT translocation domain fragment, or any combination thereof. In still another aspect of this embodiment, a BaNT translocation domain comprises amino acids 432-857 of a non-naturally occurring BaNT translocation domain variant of SEQ ID NO: 9, such as, e.g., amino acids 432-857 of a conservative BaNT translocation domain variant of SEQ ID NO: 9, amino acids 432-857 of a non-conservative BaNT translocation domain variant of SEQ ID NO: 9, amino acids 432-857 of an active BaNT translocation domain fragment of SEQ ID NO: 9, or any combination thereof.

In other aspects of this embodiment, a BaNT translocation domain comprises a polypeptide having, e.g., at least 70% amino acid identity with amino acids 432-857 of SEQ ID NO: 9, at least 75% amino acid identity with amino acids 432-857 of SEQ ID NO: 9, at least 80% amino acid identity with amino acids 432-857 of SEQ ID NO: 9, at least 85% amino acid identity with amino acids 432-857 of SEQ ID NO: 9, at least 90% amino acid identity with amino acids 432-857 of SEQ ID NO: 9 or at least 95% amino acid identity with amino acids 432-857 of SEQ ID NO: 9. In yet other aspects of this embodiment, a BaNT translocation domain comprises a polypeptide having, e.g., at most 70% amino acid identity with amino acids 432-857 of SEQ ID NO: 9, at most 75% amino acid identity with amino acids 432-857 of SEQ ID NO: 9, at most 80% amino acid identity with amino acids 432-857 of SEQ ID NO: 9, at most 85% amino acid identity with amino acids 432-857 of SEQ ID NO: 9, at most 90% amino acid identity with amino acids 432-857 of SEQ ID NO: 9 or at most 95% amino acid identity with amino acids 432-857 of SEQ ID NO: 9.

In other aspects of this embodiment, a BaNT translocation domain comprises a polypeptide having, e.g., at most one, two, three, four, five, six, seven, eight, nine, 10, 20, 30, 40, 50, 100, or 200 non-contiguous amino acid substitutions relative to amino acids 432-857 of SEQ ID NO: 9. In other aspects of this embodiment, a BaNT translocation domain comprises a polypeptide having, e.g., at least one, two, three, four, five, six, seven, eight, nine, 10, 20, 30, 40, 50, 100 or 200 non-contiguous amino acid substitutions relative to amino acids 432-857 of SEQ ID NO: 9. In yet other aspects of this embodiment, a BaNT translocation domain comprises a polypeptide having, e.g., at most one, two, three, four, five, six, seven, eight, nine, 10, 20, 30, 40, 50, 100 or 200 non-contiguous amino acid deletions relative to amino acids 432-857 of SEQ ID NO: 9. In other aspects of this embodiment, a BaNT translocation domain comprises a polypeptide having, e.g., at least one, two, three, four, five, six, seven, eight, nine, 10, 20, 30, 40, 50, 100 or 200 non-contiguous amino acid deletions relative to amino acids 432-857 of SEQ ID NO: 9. In still other aspects of this embodiment, a BaNT translocation domain comprises a polypeptide having, e.g., at most one, two, three, four, five, six, seven, eight, nine, 10, 20, 30, 40, 50, 100 or 200 non-contiguous amino acid additions relative to amino acids 432-857 of SEQ ID NO: 9. In other aspects of this embodiment, a BaNT translocation domain comprises a polypeptide having, e.g., at least one, two, three, four, five, six, seven, eight, nine, 10, 20, 30, 40, 50, 100 or 200 non-contiguous amino acid additions relative to amino acids 432-857 of SEQ ID NO: 9.

In other aspects of this embodiment, a BaNT translocation domain comprises a polypeptide having, e.g., at most one, two, three, four, five, six, seven, eight, nine, 10, 20, 30, 40, 50, 100 or 200 contiguous amino acid substitutions relative to amino acids 432-857 of SEQ ID NO: 9. In other aspects of this embodiment, a BaNT translocation domain comprises a polypeptide having, e.g., at least one, two, three, four, five, six, seven, eight, nine, 10, 20, 30, 40, 50, 100 or 200 contiguous amino acid substitutions relative to amino acids 432-857 of SEQ ID NO: 9. In yet other aspects of this embodiment, a BaNT translocation domain comprises a polypeptide having, e.g., at most one, two, three, four, five, six, seven, eight, nine, 10, 20, 30, 40, 50, 100 or 200 contiguous amino acid deletions relative to amino acids 432-857 of SEQ ID NO: 9. In other aspects of this embodiment, a BaNT translocation domain comprises a polypeptide having, e.g., at least one, two, three, four, five, six, seven, eight, nine, 10, 20, 30, 40, 50, 100 or 200 contiguous amino acid deletions relative to amino acids 432-857 of SEQ ID NO: 9. In still other aspects of this embodiment, a BaNT translocation domain comprises a polypeptide having, e.g., at most one, two, three, four, five, six, seven, eight, nine, 10, 20, 30, 40, 50, 100 or 200 contiguous amino acid additions relative to amino acids 432-857 of SEQ ID NO: 9. In other aspects of this embodiment, a BaNT translocation domain comprises a polypeptide having, e.g., at least one, two, three, four, five, six, seven, eight, nine, 10, 20, 30, 40, 50, 100 or 200 contiguous amino acid additions relative to amino acids 432-857 of SEQ ID NO: 9.

In another embodiment, a Clostridial toxin translocation domain comprises a BuNT translocation domain. In an aspect of this embodiment, a BuNT translocation domain comprises amino acids 423-847 of SEQ ID NO: 10. In another aspect of this embodiment, a BuNT translocation domain comprises a naturally occurring BuNT translocation domain variant, such as, e.g., a translocation domain from a BuNT isoform or a translocation domain from a BuNT subtype. In another aspect of this embodiment, a BuNT translocation domain comprises amino acids 423-847 of a naturally occurring BuNT translocation domain variant of SEQ ID NO: 10, such as, e.g., amino acids 423-847 of a BuNT isoform of SEQ ID NO: 10 or amino acids 423-847 of a BuNT subtype of SEQ ID NO: 10. In still another aspect of this embodiment, a BuNT translocation domain comprises a non-naturally occurring BuNT translocation domain variant, such as, e.g., a conservative BuNT translocation domain variant, a non-conservative BuNT translocation domain variant, a BuNT chimeric translocation domain, an active BuNT translocation domain fragment, or any combination thereof. In still another aspect of this embodiment, a BuNT translocation domain comprises amino acids 423-847 of a non-naturally occurring BuNT translocation domain variant of SEQ ID NO: 10, such as, e.g., amino acids 423-847 of a conservative BuNT translocation domain variant of SEQ ID NO: 10, amino acids 423-847 of a non-conservative BuNT translocation domain variant of SEQ ID NO: 10, amino acids 423-847 of an active BuNT translocation domain fragment of SEQ ID NO: 10, or any combination thereof.

In other aspects of this embodiment, a BuNT translocation domain comprises a polypeptide having, e.g., at least 70% amino acid identity with amino acids 423-847 of SEQ ID NO: 10, at least 75% amino acid identity with amino acids 423-847 of SEQ ID NO: 10, at least 80% amino acid identity with amino acids 423-847 of SEQ ID NO: 10, at least 85% amino acid identity with amino acids 423-847 of SEQ ID NO: 10, at least 90% amino acid identity with amino acids 423-847 of SEQ ID NO: 10 or at least 95% amino acid identity with amino acids 423-847 of SEQ ID NO: 10. In yet other aspects of this embodiment, a BuNT translocation domain comprises a polypeptide having, e.g., at most 70% amino acid identity with amino acids 423-847 of SEQ ID NO: 10, at most 75% amino acid identity with amino acids 423-847 of SEQ ID NO: 10, at most 80% amino acid identity with amino acids 423-847 of SEQ ID NO: 10, at most 85% amino acid identity with amino acids 423-847 of SEQ ID NO: 10, at most 90% amino acid identity with amino acids 423-847 of SEQ ID NO: 10 or at most 95% amino acid identity with amino acids 423-847 of SEQ ID NO: 10.

In other aspects of this embodiment, a BuNT translocation domain comprises a polypeptide having, e.g., at most one, two, three, four, five, six, seven, eight, nine, 10, 20, 30, 40, 50, 100, or 200 non-contiguous amino acid substitutions relative to amino acids 423-847 of SEQ ID NO: 10. In other aspects of this embodiment, a BuNT translocation domain comprises a polypeptide having, e.g., at least one, two, three, four, five, six, seven, eight, nine, 10, 20, 30, 40, 50, 100 or 200 non-contiguous amino acid substitutions relative to amino acids 423-847 of SEQ ID NO: 10. In yet other aspects of this embodiment, a BuNT translocation domain comprises a polypeptide having, e.g., at most one, two, three, four, five, six, seven, eight, nine, 10, 20, 30, 40, 50, 100 or 200 non-contiguous amino acid deletions relative to amino acids 423-847 of SEQ ID NO: 10. In other aspects of this embodiment, a BuNT translocation domain comprises a polypeptide having, e.g., at least one, two, three, four, five, six, seven, eight, nine, 10, 20, 30, 40, 50, 100 or 200 non-contiguous amino acid deletions relative to amino acids 423-847 of SEQ ID NO: 10. In still other aspects of this embodiment, a BuNT translocation domain comprises a polypeptide having, e.g., at most one, two, three, four, five, six, seven, eight, nine, 10, 20, 30, 40, 50, 100 or 200 non-contiguous amino acid additions relative to amino acids 423-847 of SEQ ID NO: 10. In other aspects of this embodiment, a BuNT translocation domain comprises a polypeptide having, e.g., at least one, two, three, four, five, six, seven, eight, nine, 10, 20, 30, 40, 50, 100 or 200 non-contiguous amino acid additions relative to amino acids 423-847 of SEQ ID NO: 10.

In other aspects of this embodiment, a BuNT translocation domain comprises a polypeptide having, e.g., at most one, two, three, four, five, six, seven, eight, nine, 10, 20, 30, 40, 50, 100 or 200 contiguous amino acid substitutions relative to amino acids 423-847 of SEQ ID NO: 10. In other aspects of this embodiment, a BuNT translocation domain comprises a polypeptide having, e.g., at least one, two, three, four, five, six, seven, eight, nine, 10, 20, 30, 40, 50, 100 or 200 contiguous amino acid substitutions relative to amino acids 423-847 of SEQ ID NO: 10. In yet other aspects of this embodiment, a BuNT translocation domain comprises a polypeptide having, e.g., at most one, two, three, four, five, six, seven, eight, nine, 10, 20, 30, 40, 50, 100 or 200 contiguous amino acid deletions relative to amino acids 423-847 of SEQ ID NO: 10. In other aspects of this embodiment, a BuNT translocation domain comprises a polypeptide having, e.g., at least one, two, three, four, five, six, seven, eight, nine, 10, 20, 30, 40, 50, 100 or 200 contiguous amino acid deletions relative to amino acids 423-847 of SEQ ID NO: 10. In still other aspects of this embodiment, a BuNT translocation domain comprises a polypeptide having, e.g., at most one, two, three, four, five, six, seven, eight, nine, 10, 20, 30, 40, 50, 100 or 200 contiguous amino acid additions relative to amino acids 423-847 of SEQ ID NO: 10. In other aspects of this embodiment, a BuNT translocation domain comprises a polypeptide having, e.g., at least one, two, three, four, five, six, seven, eight, nine, 10, 20, 30, 40, 50, 100 or 200 contiguous amino acid additions relative to amino acids 423-847 of SEQ ID NO: 10.

By "binding element" is meant an amino acid sequence region able to preferentially bind to a cell surface marker characteristic of the target cell under physiological conditions. The cell surface marker may comprise a polypeptide, a polysaccharide, a lipid, a glycoprotein, a lipoprotein, or may have structural characteristics of more than one of these. By "preferentially interact" is meant that the disassociation constant ($K_d$) of the binding element for the cell surface marker is at least one order of magnitude less than that of the binding element for any other cell surface marker. Preferably, the disassociation constant is at least 2 orders of magnitude less, even more preferably the disassociation constant is at least 3 orders of magnitude less than that of the binding element for any other cell surface marker to which the neurotoxin or modified neurotoxin is exposed. Examples of binding elements are described in, e.g., Steward, L. E. et al., Modified Clostridial Toxins with Enhanced Translocation Capability and Enhanced Targeting Activity, U.S. patent application Ser. No. 11/776,043 (Jul. 11, 2007); Steward, L. E. et al., Modified Clostridial Toxins with Enhanced Translocation Capabilities and Altered Targeting Activity For Clostridial Toxin Target Cells, U.S. patent application Ser. No. 11/776,052 (Jul. 11, 2007); and Steward, L. E. et al., Modified Clostridial Toxins with Enhanced Translocation Capabilities and Altered Targeting Activity For Non-Clostridial Toxin Target Cells, U.S. patent application Ser. No. 11/776,075 (Jul. 11, 2007), each of which is incorporated by reference in its entirety.

A non-limiting example of a binding element disclosed in the present specification is, e.g., a melanocortin peptide, such as, e.g., an α-melanocyte stimulating hormones (α-MSH), a β-melanocyte stimulating hormones (β-MSH), a γ-melanocyte stimulating hormones (γ-MSH). Thus, in an embodiment, a binding element is derived from a melanocortin peptide.

In another embodiment, a binding element comprises a melanocyte stimulating hormone. In aspects of this embodiment, a binding element comprises a melanocyte stimulating hormone is derived from an α-melanocyte stimulating hormones (α-MSH), a β-melanocyte stimulating hormones (β-MSH), a γ-melanocyte stimulating hormones (γ-MSH). In other aspects of this embodiment, a binding element comprises a melanocyte stimulating hormone comprises SEQ ID NO: 81, SEQ ID NO: 82 or SEQ ID NO: 83.

In other aspects of this embodiment, a binding element comprises a melanocyte stimulating hormone has, e.g., at least 70% amino acid identity with SEQ ID NO: 81, SEQ ID NO: 82 or SEQ ID NO: 83, at least 75% amino acid identity with SEQ ID NO: 81, SEQ ID NO: 82 or SEQ ID NO: 83, at least 80% amino acid identity with SEQ ID NO: 81, SEQ ID NO: 82 or SEQ ID NO: 83, at least 85% amino acid identity with SEQ ID NO: 81, SEQ ID NO: 82 or SEQ ID NO: 83, at least 90% amino acid identity with SEQ ID NO: 81, SEQ ID NO: 82 or SEQ ID NO: 83 or at least 95% amino acid identity with SEQ ID NO: 81, SEQ ID NO: 82 or SEQ ID NO: 83. In yet other aspects of this embodiment, a binding element comprises a melanocyte stimulating hormone has, e.g., at most 70% amino acid identity with SEQ ID NO: 81, SEQ ID NO: 82 or SEQ ID NO: 83, at most 75% amino acid identity with SEQ ID NO: 81, SEQ ID NO: 82 or SEQ ID NO: 83, at most 80% amino acid identity with SEQ ID NO: 81, SEQ ID NO: 82 or SEQ ID NO: 83, at most 85% amino acid identity with SEQ ID NO: 81, SEQ ID NO: 82 or SEQ ID NO: 83, at most 90% amino acid identity with SEQ ID NO: 81, SEQ ID NO: 82 or SEQ ID NO: 83 or at most 95% amino acid identity with SEQ ID NO: 81, SEQ ID NO: 82 or SEQ ID NO: 83.

In other aspects of this embodiment, a binding element comprises a melanocyte stimulating hormone has, e.g., at least one, two, three, four or five non-contiguous amino acid substitutions relative to SEQ ID NO: 81, SEQ ID NO: 82 or SEQ ID NO: 83. In other aspects of this embodiment, a binding element comprises a melanocyte stimulating hormone has, e.g., at most one, two, three, four or five non-contiguous amino acid substitutions relative to SEQ ID NO: 81, SEQ ID NO: 82 or SEQ ID NO: 83. In yet other aspects of this embodiment, a binding element comprises a melanocyte stimulating hormone has, e.g., at least one, two, three, four or five non-contiguous amino acid deletions relative to SEQ ID NO: 81, SEQ ID NO: 82 or SEQ ID NO: 83. In yet other aspects of this embodiment, a binding element comprises a melanocyte stimulating hormone has, e.g., at most one, two, three, four or five non-contiguous amino acid deletions relative to SEQ ID NO: 81, SEQ ID NO: 82 or SEQ ID NO: 83. In still other aspects of this embodiment, a binding element comprises a melanocyte stimulating hormone has, e.g., at least one, two, three, four or five non-contiguous amino acid additions relative to SEQ ID NO: 81, SEQ ID NO: 82 or SEQ ID NO: 83. In yet other aspects of this embodiment, a binding element comprises a melanocyte stimulating hormone has, e.g., at most one, two, three, four or five non-contiguous amino acid additions relative to SEQ ID NO: 81, SEQ ID NO: 82 or SEQ ID NO: 83.

In other aspects of this embodiment, a binding element comprises a melanocyte stimulating hormone has, e.g., at least one, two, three, four or five contiguous amino acid substitutions relative to SEQ ID NO: 81, SEQ ID NO: 82 or SEQ ID NO: 83. In other aspects of this embodiment, a binding element comprises a melanocyte stimulating hormone has, e.g., at most one, two, three, four or five contiguous amino acid substitutions relative to SEQ ID NO: 81, SEQ ID NO: 82 or SEQ ID NO: 83. In yet other aspects of this embodiment, a binding element comprises a melanocyte stimulating hormone has, e.g., at least one, two, three, four or five contiguous amino acid deletions relative to SEQ ID NO: 81, SEQ ID NO: 82 or SEQ ID NO: 83. In yet other aspects of this embodiment, a binding element comprises a melanocyte stimulating hormone has, e.g., at most one, two, three, four or five contiguous amino acid deletions relative to SEQ ID NO: 81, SEQ ID NO: 82 or SEQ ID NO: 83. In still other aspects of this embodiment, a binding element comprises a melanocyte stimulating hormone has, e.g., at least one, two, three, four or five contiguous amino acid additions relative to SEQ ID NO: 81, SEQ ID NO: 82 or SEQ ID NO: 83. In yet other aspects of this embodiment, a binding element comprises a melanocyte stimulating hormone has, e.g., at most one, two, three, four or five contiguous amino acid additions relative to SEQ ID NO: 81, SEQ ID NO: 82 or SEQ ID NO: 83.

In another embodiment, a binding element comprises an adrenocorticotropin. In aspects of this embodiment, a binding element comprising an adrenocorticotropin is derived from an adrenocorticotropin (ACTH) or a Corticotropin-like intermediary peptide (CLIP). In other aspects of this embodiment, a binding element comprising an adrenocorticotropin comprises SEQ ID NO: 84 or SEQ ID NO: 85.

In other aspects of this embodiment, a binding element comprising an adrenocorticotropin has, e.g., at least 70% amino acid identity with SEQ ID NO: 84 or SEQ ID NO: 85, at least 75% amino acid identity with SEQ ID NO: 84 or SEQ ID NO: 85, at least 80% amino acid identity with SEQ ID NO: 84 or SEQ ID NO: 85, at least 85% amino acid identity with SEQ ID NO: 84 or SEQ ID NO: 85, at least 90% amino acid identity with SEQ ID NO: 84 or SEQ ID NO: 85 or at least 95% amino acid identity with SEQ ID NO: 84 or SEQ ID NO: 85. In yet other aspects of this embodiment, a binding element comprising an adrenocorticotropin has, e.g., at most 70% amino acid identity with SEQ ID NO: 84 or SEQ ID NO: 85, at most 75% amino acid identity with SEQ ID NO: 84 or SEQ ID NO: 85, at most 80% amino acid identity with SEQ ID NO: 84 or SEQ ID NO: 85, at most 85% amino acid identity with SEQ ID NO: 84 or SEQ ID NO: 85, at most 90% amino acid identity with SEQ ID NO: 84 or SEQ ID NO: 85 or at most 95% amino acid identity with SEQ ID NO: 84 or SEQ ID NO: 85.

In other aspects of this embodiment, a binding element comprising an adrenocorticotropin has, e.g., at least one, two, three, four or five non-contiguous amino acid substitutions relative to SEQ ID NO: 84 or SEQ ID NO: 85. In other aspects of this embodiment, a binding element comprising an adrenocorticotropin has, e.g., at most one, two, three, four or five non-contiguous amino acid substitutions relative to SEQ ID NO: 84 or SEQ ID NO: 85. In yet other aspects of this embodiment, a binding element comprising an adrenocorticotropin has, e.g., at least one, two, three, four or five non-contiguous amino acid deletions relative to SEQ ID NO: 84 or SEQ ID NO: 85. In yet other aspects of this embodiment, a binding element comprising an adrenocorticotropin has, e.g., at most one, two, three, four or five non-contiguous amino acid deletions relative to SEQ ID NO: 84 or SEQ ID NO: 85. In still other aspects of this embodiment, a binding element comprising an adrenocorticotropin has, e.g., at least one, two, three, four or five non-contiguous amino acid additions relative to SEQ ID NO: 84 or SEQ ID NO: 85. In yet other aspects of this embodiment, a binding element comprising an adrenocorticotropin has, e.g., at most one, two, three, four or five non-contiguous amino acid additions relative to SEQ ID NO: 84 or SEQ ID NO: 85.

In other aspects of this embodiment, a binding element comprising an adrenocorticotropin has, e.g., at least one, two, three, four or five contiguous amino acid substitutions relative to SEQ ID NO: 84 or SEQ ID NO: 85. In other aspects of this embodiment, a binding element comprising an adrenocorticotropin has, e.g., at most one, two, three, four or five contiguous amino acid substitutions relative to SEQ ID NO: 84 or SEQ ID NO: 85. In yet other aspects of this embodiment, a binding element comprising an adrenocorticotropin has, e.g., at least one, two, three, four or five contiguous amino acid deletions relative to SEQ ID NO: 84 or SEQ ID NO: 85. In yet other aspects of this embodiment, a binding element comprising an adrenocorticotropin has, e.g., at most one, two, three, four or five contiguous amino acid deletions relative to SEQ ID NO: 84 or SEQ ID NO: 85. In still other aspects of this embodiment, a binding element comprising an adrenocorticotropin has, e.g., at least one, two, three, four or five contiguous amino acid additions relative to SEQ ID NO: 84 or SEQ ID NO: 85. In yet other aspects of this embodiment, a binding element comprising an adrenocorticotropin has, e.g., at most one, two, three, four or five contiguous amino acid additions relative to SEQ ID NO: 84 or SEQ ID NO: 85.

In another embodiment, a binding element comprises a lipotropin. In aspects of this embodiment, a binding element comprising a lipotropin is derived from a β-lipotropin (β-LPH) or a γ-lipotropin (γ-LPH). In other aspects of this embodiment, a binding element comprising a lipotropin comprises SEQ ID NO: 86 or SEQ ID NO: 87.

In other aspects of this embodiment, a binding element comprising a lipotropin has, e.g., at least 70% amino acid identity with SEQ ID NO: 86 or SEQ ID NO: 87, at least 75% amino acid identity with SEQ ID NO: 86 or SEQ ID NO: 87, at least 80% amino acid identity with SEQ ID NO: 86 or SEQ ID NO: 87, at least 85% amino acid identity with SEQ ID NO: 86 or SEQ ID NO: 87, at least 90% amino acid identity with SEQ ID NO: 86 or SEQ ID NO: 87 or at least 95% amino acid identity with SEQ ID NO: 86 or SEQ ID NO: 87. In yet other aspects of this embodiment, a binding element comprising a lipotropin has, e.g., at most 70% amino acid identity with SEQ ID NO: 86 or SEQ ID NO: 87, at most 75% amino acid identity with SEQ ID NO: 86 or SEQ ID NO: 87, at most 80% amino acid identity with SEQ ID NO: 86 or SEQ ID NO: 87, at most 85% amino acid identity with SEQ ID NO: 86 or SEQ ID NO: 87, at most 90% amino acid identity with SEQ ID NO: 86 or SEQ ID NO: 87 or at most 95% amino acid identity with SEQ ID NO: 86 or SEQ ID NO: 87.

In other aspects of this embodiment, a binding element comprising a lipotropin has, e.g., at least one, two, three, four, five, six, seven, eight, nine or ten non-contiguous amino acid substitutions relative to SEQ ID NO: 86 or SEQ ID NO: 87. In other aspects of this embodiment, a binding element comprising a lipotropin has, e.g., at most one, two, three, four, five, six, seven, eight, nine or ten non-contiguous amino acid substitutions relative to SEQ ID NO: 86 or SEQ ID NO: 87. In yet other aspects of this embodiment, a binding element comprising a lipotropin has, e.g., at least one, two, three, four, five, six, seven, eight, nine or ten non-contiguous amino acid deletions relative to SEQ ID NO: 86 or SEQ ID NO: 87. In yet other aspects of this embodiment, a binding element comprising a lipotropin has, e.g., at most one, two, three, four, five, six, seven, eight, nine or ten non-contiguous amino acid deletions relative to SEQ ID NO: 86 or SEQ ID NO: 87. In still other aspects of this embodiment, a binding element comprising a lipotropin has, e.g., at least one, two, three, four, five, six, seven, eight, nine or ten non-contiguous amino acid additions relative to SEQ ID NO: 86 or SEQ ID NO: 87. In yet other aspects of this embodiment, a binding element comprising a lipotropin has, e.g., at most one, two, three, four, five, six, seven, eight, nine or ten non-contiguous amino acid additions relative to SEQ ID NO: 86 or SEQ ID NO: 87.

In other aspects of this embodiment, a binding element comprising a lipotropin has, e.g., at least one, two, three, four, five, six, seven, eight, nine or ten contiguous amino acid substitutions relative to SEQ ID NO: 86 or SEQ ID NO: 87. In other aspects of this embodiment, a binding element comprising a lipotropin has, e.g., at most one, two, three, four, five, six, seven, eight, nine or ten contiguous amino acid substitutions relative to SEQ ID NO: 86 or SEQ ID NO: 87. In yet other aspects of this embodiment, a binding element comprising a lipotropin has, e.g., at least one, two, three, four, five, six, seven, eight, nine or ten contiguous amino acid deletions relative to SEQ ID NO: 86 or SEQ ID NO: 87. In yet other aspects of this embodiment, a binding element comprising a lipotropin has, e.g., at most one, two, three, four, five, six, seven, eight, nine or ten contiguous amino acid deletions relative to SEQ ID NO: 86 or SEQ ID NO: 87. In still other aspects of this embodiment, a binding element comprising a lipotropin has, e.g., at least one, two, three, four, five, six, seven, eight, nine or ten contiguous amino acid additions relative to SEQ ID NO: 86 or SEQ ID NO: 87. In yet other aspects of this embodiment, a binding element comprising a lipotropin has, e.g., at most one, two, three, four, five, six, seven, eight, nine or ten contiguous amino acid additions relative to SEQ ID NO: 86 or SEQ ID NO: 87.

In another embodiment, a binding element comprising a neuropeptide derived from a melanocortin peptide. In aspects of this embodiment, a binding element comprising a neuropeptide derived from a melanocortin peptide comprises SEQ ID NO: 88, SEQ ID NO: 89 or SEQ ID NO: 90.

In other aspects of this embodiment, a binding element comprising a neuropeptide derived from a melanocortin peptide has, e.g., at least 70% amino acid identity with SEQ ID NO: 88, SEQ ID NO: 89 or SEQ ID NO: 90, at least 75% amino acid identity with SEQ ID NO: 88, SEQ ID NO: 89 or SEQ ID NO: 90, at least 80% amino acid identity with SEQ ID NO: 88, SEQ ID NO: 89 or SEQ ID NO: 90, at least 85% amino acid identity with SEQ ID NO: 88, SEQ ID NO: 89 or SEQ ID NO: 90, at least 90% amino acid identity with SEQ ID NO: 88, SEQ ID NO: 89 or SEQ ID NO: 90 or at least 95% amino acid identity with SEQ ID NO: 88, SEQ ID NO: 89 or SEQ ID NO: 90. In yet other aspects of this embodiment, a binding element comprising a neuropeptide derived from a melanocortin peptide has, e.g., at most 70% amino acid identity with SEQ ID NO: 88, SEQ ID NO: 89 or SEQ ID NO: 90, at most 75% amino acid identity with SEQ ID NO: 88, SEQ ID NO: 89 or SEQ ID NO: 90, at most 80% amino acid identity with SEQ ID NO: 88, SEQ ID NO: 89 or SEQ ID NO: 90, at most 85% amino acid identity with SEQ ID NO: 88, SEQ ID NO: 89 or SEQ ID NO: 90, at most 90% amino acid identity with SEQ ID NO: 88, SEQ ID NO: 89 or SEQ ID NO: 90 or at most 95% amino acid identity with SEQ ID NO: 88, SEQ ID NO: 89 or SEQ ID NO: 90.

In other aspects of this embodiment, a binding element comprising a neuropeptide derived from a melanocortin peptide has, e.g., at least one, two, three, four, five, six, seven, eight, nine or ten non-contiguous amino acid substitutions relative to SEQ ID NO: 88, SEQ ID NO: 89 or SEQ ID NO: 90. In other aspects of this embodiment, a binding element comprising a neuropeptide derived from a melanocortin peptide has, e.g., at most one, two, three, four, five, six, seven, eight, nine or ten non-contiguous amino acid substitutions relative to SEQ ID NO: 88, SEQ ID NO: 89 or SEQ ID NO: 90. In yet other aspects of this embodiment, a binding element comprising a neuropeptide derived from a melanocortin peptide has, e.g., at least one, two, three, four, five, six, seven, eight, nine or ten non-contiguous amino acid deletions relative to SEQ ID NO: 88, SEQ ID NO: 89 or SEQ ID NO: 90. In yet other aspects of this embodiment, a binding element comprising a neuropeptide derived from a melanocortin peptide has, e.g., at most one, two, three, four, five, six, seven, eight, nine or ten non-contiguous amino acid deletions relative to SEQ ID NO: 88, SEQ ID NO: 89 or SEQ ID NO: 90. In still other aspects of this embodiment, a binding element comprising a neuropeptide derived from a melanocortin peptide has, e.g., at least one, two, three, four, five, six, seven, eight, nine or ten non-contiguous amino acid additions relative to SEQ ID NO: 88, SEQ ID NO: 89 or SEQ ID NO: 90. In yet other aspects of this embodiment, a binding element comprising a neuropeptide derived from a melanocortin peptide has, e.g., at most one, two, three, four, five, six, seven, eight, nine or ten non-contiguous amino acid additions relative to SEQ ID NO: 88, SEQ ID NO: 89 or SEQ ID NO: 90.

In other aspects of this embodiment, a binding element comprising a neuropeptide derived from a melanocortin peptide has, e.g., at least one, two, three, four, five, six, seven, eight, nine or ten contiguous amino acid substitutions relative to SEQ ID NO: 88, SEQ ID NO: 89 or SEQ ID NO: 90. In other aspects of this embodiment, a binding element comprising a neuropeptide derived from a melanocortin peptide has, e.g., at most one, two, three, four, five, six, seven, eight, nine or ten contiguous amino acid substitutions relative to SEQ ID NO: 88, SEQ ID NO: 89 or SEQ ID NO: 90. In yet other aspects of this embodiment, a binding element comprising a neuropeptide derived from a melanocortin peptide has, e.g., at least one, two, three, four, five, six, seven, eight, nine or ten contiguous amino acid deletions relative to SEQ ID NO: 88, SEQ ID NO: 89 or SEQ ID NO: 90. In yet other aspects of this embodiment, a binding element comprising a neuropeptide derived from a melanocortin peptide has, e.g., at most one, two, three, four, five, six, seven, eight, nine or ten contiguous amino acid deletions relative to SEQ ID NO: 88, SEQ ID NO: 89 or SEQ ID NO: 90. In still other aspects of this embodiment, a binding element comprising a neuropeptide derived from a melanocortin peptide has, e.g., at least one, two, three, four, five, six, seven, eight, nine or ten contiguous amino acid additions relative to SEQ ID NO: 88, SEQ ID NO: 89 or SEQ ID NO: 90. In yet other aspects of this embodiment, a binding element comprising a neuropeptide derived from a melanocortin peptide has, e.g., at most one, two, three, four, five, six, seven, eight, nine or ten contiguous amino acid additions relative to SEQ ID NO: 88, SEQ ID NO: 89 or SEQ ID NO: 90.

In another embodiment, a binding element comprises a galanin. In aspects of this embodiment, a binding element comprising a galanin is derived from a galanin or a galanin message-associated peptide (GMAP). In other aspects of this embodiment, a binding element comprising a galanin comprises SEQ ID NO: 91 or SEQ ID NO: 92.

In other aspects of this embodiment, a binding element comprising a galanin has, e.g., at least 70% amino acid identity with SEQ ID NO: 91 or SEQ ID NO: 92, at least 75% amino acid identity with SEQ ID NO: 91 or SEQ ID NO: 92, at least 80% amino acid identity with SEQ ID NO: 91 or SEQ ID NO: 92, at least 85% amino acid identity with SEQ ID NO: 91 or SEQ ID NO: 92, at least 90% amino acid identity with SEQ ID NO: 91 or SEQ ID NO: 92 or at least 95% amino acid identity with SEQ ID NO: 91 or SEQ ID NO: 92. In yet other aspects of this embodiment, a binding element comprising a galanin has, e.g., at most 70% amino acid identity with SEQ ID NO: 91 or SEQ ID NO: 92, at most 75% amino acid identity with SEQ ID NO: 91 or SEQ ID NO: 92, at most 80% amino acid identity with SEQ ID NO: 91 or SEQ ID NO: 92, at most 85% amino acid identity with SEQ ID NO: 91 or SEQ ID NO: 92, at most 90% amino acid identity with SEQ ID NO:

91 or SEQ ID NO: 92 or at most 95% amino acid identity with SEQ ID NO: 91 or SEQ ID NO: 92.

In other aspects of this embodiment, a binding element comprising a galanin has, e.g., at least one, two, three, four, five, six, seven, eight, nine or ten non-contiguous amino acid substitutions relative to SEQ ID NO: 91 or SEQ ID NO: 92. In other aspects of this embodiment, a binding element comprising a galanin has, e.g., at most one, two, three, four, five, six, seven, eight, nine or ten non-contiguous amino acid substitutions relative to SEQ ID NO: 91 or SEQ ID NO: 92. In yet other aspects of this embodiment, a binding element comprising a galanin has, e.g., at least one, two, three, four, five, six, seven, eight, nine or ten non-contiguous amino acid deletions relative to SEQ ID NO: 91 or SEQ ID NO: 92. In yet other aspects of this embodiment, a binding element comprising a galanin has, e.g., at most one, two, three, four, five, six, seven, eight, nine or ten non-contiguous amino acid deletions relative to SEQ ID NO: 91 or SEQ ID NO: 92. In still other aspects of this embodiment, a binding element comprising a galanin has, e.g., at least one, two, three, four, five, six, seven, eight, nine or ten non-contiguous amino acid additions relative to SEQ ID NO: 91 or SEQ ID NO: 92. In yet other aspects of this embodiment, a binding element comprising a galanin has, e.g., at most one, two, three, four, five, six, seven, eight, nine or ten non-contiguous amino acid additions relative to SEQ ID NO: 91 or SEQ ID NO: 92.

In other aspects of this embodiment, a binding element comprising a galanin has, e.g., at least one, two, three, four, five, six, seven, eight, nine or ten contiguous amino acid substitutions relative to SEQ ID NO: 91 or SEQ ID NO: 92. In other aspects of this embodiment, a binding element comprising a galanin has, e.g., at most one, two, three, four, five, six, seven, eight, nine or ten contiguous amino acid substitutions relative to SEQ ID NO: 91 or SEQ ID NO: 92. In yet other aspects of this embodiment, a binding element comprising a galanin has, e.g., at least one, two, three, four, five, six, seven, eight, nine or ten contiguous amino acid deletions relative to SEQ ID NO: 91 or SEQ ID NO: 92. In yet other aspects of this embodiment, a binding element comprising a galanin has, e.g., at most one, two, three, four, five, six, seven, eight, nine or ten contiguous amino acid deletions relative to SEQ ID NO: 91 or SEQ ID NO: 92. In still other aspects of this embodiment, a binding element comprising a galanin has, e.g., at least one, two, three, four, five, six, seven, eight, nine or ten contiguous amino acid additions relative to SEQ ID NO: 91 or SEQ ID NO: 92. In yet other aspects of this embodiment, a binding element comprising a galanin has, e.g., at most one, two, three, four, five, six, seven, eight, nine or ten contiguous amino acid additions relative to SEQ ID NO: 91 or SEQ ID NO: 92.

Another example of a binding element disclosed in the present specification is, e.g., a granin peptide, such as, e.g., a chromogranin A, a chromogranin B (secretogranin I) or a chromogranin C (secretogranin II). Thus, in an embodiment, a binding element is derived from a granin peptide.

In another embodiment, a binding element comprising a granin peptide comprises a chromogranin A peptide. In aspects of this embodiment, a binding element comprising a chromogranin A peptide is derived from a β-granin, a vasostatin, a chromostatin, a pancreastatin, a WE-14, a catestatin, a parastatin or a GE-25. In other aspects of this embodiment, a binding element comprising a chromogranin A peptide comprises SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100.

In other aspects of this embodiment, a binding element comprising a chromogranin A peptide has, e.g., at least 70% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at least 75% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at least 80% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at least 85% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at least 90% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100 or at least 95% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In yet other aspects of this embodiment, a binding element comprising a chromogranin A peptide has, e.g., at most 70% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at most 75% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at most 80% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at most 85% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100, at most 90% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100 or at most 95% amino acid identity with SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100.

In other aspects of this embodiment, a binding element comprising a chromogranin A peptide has, e.g., at least one, two, three, four, five, six, seven, eight, nine or ten non-contiguous amino acid substitutions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In other aspects of this embodiment, a binding element comprising a chromogranin A peptide has, e.g., at most one, two, three, four, five, six, seven, eight, nine or ten non-contiguous amino acid substitutions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In yet other aspects of this embodiment, a binding element comprising a chromogranin A peptide has, e.g., at least one, two, three, four, five, six, seven, eight, nine or ten non-contiguous amino acid deletions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In yet other aspects of this embodiment, a binding element comprising a chromogranin A peptide has, e.g., at most one, two, three, four, five, six, seven, eight, nine or ten non-contiguous amino acid deletions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In still other aspects of this embodiment, a binding element comprising a chromogranin A peptide has, e.g., at least one, two, three, four, five, six, seven, eight, nine or ten non-contiguous amino acid additions relative to SEQ ID NO: 93, SEQ ID NO: 94, SEQ ID NO: 95, SEQ ID NO: 96, SEQ ID NO: 97, SEQ ID NO: 98, SEQ ID NO:99 or SEQ ID NO:100. In yet other aspects of this embodiment, a binding element comprising a chromogranin A peptide has, e.g., at most one, two, three, four, five, six, seven, eight, nine or ten non-contiguous amino acid additions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100.

In other aspects of this embodiment, a binding element comprising a chromogranin A peptide has, e.g., at least one, two, three, four, five, six, seven, eight, nine or ten contiguous amino acid substitutions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In other aspects of this embodiment, a binding element comprising a chromogranin A peptide has, e.g., at most one, two, three, four, five, six, seven, eight, nine or ten contiguous amino acid substitutions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In yet other aspects of this embodiment, a binding element comprising a chromogranin A peptide has, e.g., at least one, two, three, four, five, six, seven, eight, nine or ten contiguous amino acid deletions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In yet other aspects of this embodiment, a binding element comprising a chromogranin A peptide has, e.g., at most one, two, three, four, five, six, seven, eight, nine or ten contiguous amino acid deletions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In still other aspects of this embodiment, a binding element comprising a chromogranin A peptide has, e.g., at least one, two, three, four, five, six, seven, eight, nine or ten contiguous amino acid additions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100. In yet other aspects of this embodiment, a binding element comprising a chromogranin A peptide has, e.g., at most one, two, three, four, five, six, seven, eight, nine or ten contiguous amino acid additions relative to SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100.

In another embodiment, a binding element comprising a chromogranin B peptide. In aspects of this embodiment, a binding element comprising a chromogranin B peptide is derived from a GAWK peptide, an adrenomedullary peptide or a secretolytin. In other aspects of this embodiment, a binding element comprising a chromogranin B peptide comprises SEQ ID NO: 101, SEQ ID NO: 102, SEQ ID NO: 103, SEQ ID NO: 104 or SEQ ID NO: 105.

In other aspects of this embodiment, a binding element comprising a chromogranin B peptide has, e.g., at least 70% amino acid identity with SEQ ID NO: 101, SEQ ID NO: 102, SEQ ID NO: 103, SEQ ID NO: 104 or SEQ ID NO: 105, at least 75% amino acid identity with SEQ ID NO: 101, SEQ ID NO: 102, SEQ ID NO: 103, SEQ ID NO: 104 or SEQ ID NO: 105, at least 80% amino acid identity with SEQ ID NO: 101, SEQ ID NO: 102, SEQ ID NO: 103, SEQ ID NO: 104 or SEQ ID NO: 105, at least 85% amino acid identity with SEQ ID NO: 101, SEQ ID NO: 102, SEQ ID NO: 103, SEQ ID NO: 104 or SEQ ID NO: 105, at least 90% amino acid identity with SEQ ID NO: 101, SEQ ID NO: 102, SEQ ID NO: 103, SEQ ID NO: 104 or SEQ ID NO: 105 or at least 95% amino acid identity with SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at most 70% amino acid identity with SEQ ID NO: 101, SEQ ID NO: 102, SEQ ID NO: 103, SEQ ID NO: 104 or SEQ ID NO: 105, at most 75% amino acid identity with SEQ ID NO: 101, SEQ ID NO: 102, SEQ ID NO: 103, SEQ ID NO: 104 or SEQ ID NO: 105, at most 80% amino acid identity with SEQ ID NO: 101, SEQ ID NO: 102, SEQ ID NO: 103, SEQ ID NO: 104 or SEQ ID NO: 105, at most 85% amino acid identity with SEQ ID NO: 101, SEQ ID NO: 102, SEQ ID NO: 103, SEQ ID NO: 104 or SEQ ID NO: 105, at most 90% amino acid identity with SEQ ID NO: 101, SEQ ID NO: 102, SEQ ID NO: 103, SEQ ID NO: 104 or SEQ ID NO: 105 or at most 95% amino acid identity with SEQ ID NO: 101, SEQ ID NO: 102, SEQ ID NO: 103, SEQ ID NO: 104 or SEQ ID NO: 105.

In other aspects of this embodiment, a binding element comprising a chromogranin B peptide has, e.g., at least one, two, three, four, five, six, seven, eight, nine or ten non-contiguous amino acid substitutions relative to SEQ ID NO: 101, SEQ ID NO: 102, SEQ ID NO: 103, SEQ ID NO: 104 or SEQ ID NO: 105. In other aspects of this embodiment, a binding element comprising a chromogranin B peptide has, e.g., at most one, two, three, four, five, six, seven, eight, nine or ten non-contiguous amino acid substitutions relative to SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at least one, two, three, four, five, six, seven, eight, nine or ten non-contiguous amino acid deletions relative to SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at most one, two, three, four, five, six, seven, eight, nine or ten non-contiguous amino acid deletions relative to SEQ ID NO: 101, SEQ ID NO: 102, SEQ ID NO: 103, SEQ ID NO: 104 or SEQ ID NO: 105. In still other aspects of this embodiment, a binding element comprising a chromogranin B peptide has, e.g., at least one, two, three, four, five, six, seven, eight, nine or ten non-contiguous amino acid additions relative to SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at most one, two, three, four, five, six, seven, eight, nine or ten non-contiguous amino acid additions relative to SEQ ID NO: 101, SEQ ID NO: 102, SEQ ID NO: 103, SEQ ID NO: 104 or SEQ ID NO: 105.

In other aspects of this embodiment, a binding element comprising a chromogranin B peptide has, e.g., at least one, two, three, four, five, six, seven, eight, nine or ten contiguous amino acid substitutions relative to SEQ ID NO: 101, SEQ ID NO: 102, SEQ ID NO: 103, SEQ ID NO: 104 or SEQ ID NO: 105. In other aspects of this embodiment, a binding element comprising a chromogranin B peptide has, e.g., at most one, two, three, four, five, six, seven, eight, nine or ten contiguous amino acid substitutions relative to SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at least one, two, three, four, five, six, seven, eight, nine or ten contiguous amino acid deletions relative to SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at most one, two, three, four, five, six, seven, eight, nine or ten contiguous amino acid deletions relative to SEQ ID NO: 101, SEQ ID NO: 102, SEQ ID NO: 103, SEQ ID NO: 104 or SEQ ID NO: 105. In still other aspects of this embodiment, a binding element comprising a chromogranin B peptide has, e.g., at least one, two, three, four, five, six, seven, eight, nine or ten contiguous amino acid additions relative to SEQ ID NO: 101, SEQ ID NO: 102, SEQ ID NO: 103, SEQ ID NO: 104 or SEQ ID NO: 105. In yet other aspects of this embodiment, a binding element comprising a chromogranin B peptide has, e.g., at most one, two, three, four, five, six, seven, eight, nine or ten contiguous amino acid additions relative to SEQ ID NO: 101, SEQ ID NO: 102, SEQ ID NO: 103, SEQ ID NO: 104 or SEQ ID NO: 105.

In another embodiment, a binding element comprising a chromogranin C peptide. In aspects of this embodiment, a binding element comprising a chromogranin C peptide is derived from a secretoneurin. In other aspects of this embodiment, a binding element comprising a chromogranin C peptide comprises SEQ ID NO: 106.

In other aspects of this embodiment, a binding element comprising a chromogranin C peptide has, e.g., at least 70% amino acid identity with SEQ ID NO: 106, at least 75% amino acid identity with SEQ ID NO: 106, at least 80% amino acid identity with SEQ ID NO: 106, at least 85% amino acid identity with SEQ ID NO: 106, at least 90% amino acid identity with SEQ ID NO: 106 or at least 95% amino acid identity with SEQ ID NO: 106. In yet other aspects of this embodiment, a binding element comprising a chromogranin C peptide has, e.g., at most 70% amino acid identity with SEQ ID NO: 106, at most 75% amino acid identity with SEQ ID NO: 106, at most 80% amino acid identity with SEQ ID NO: 106, at most 85% amino acid identity with SEQ ID NO: 106, at most 90% amino acid identity with SEQ ID NO: 106 or at most 95% amino acid identity with SEQ ID NO: 106.

In other aspects of this embodiment, a binding element comprising a chromogranin C peptide has, e.g., at least one, two, three, four, five, six, seven, eight, nine or ten non-contiguous amino acid substitutions relative to SEQ ID NO: 106. In other aspects of this embodiment, a binding element comprising a chromogranin C peptide has, e.g., at most one, two, three, four, five, six, seven, eight, nine or ten non-contiguous amino acid substitutions relative to SEQ ID NO: 106. In yet other aspects of this embodiment, a binding element comprising a chromogranin C peptide has, e.g., at least one, two, three, four, five, six, seven, eight, nine or ten non-contiguous amino acid deletions relative to SEQ ID NO: 106. In yet other aspects of this embodiment, a binding element comprising a chromogranin C peptide has, e.g., at most one, two, three, four, five, six, seven, eight, nine or ten non-contiguous amino acid deletions relative to SEQ ID NO: 106. In still other aspects of this embodiment, a binding element comprising a chromogranin C peptide has, e.g., at least one, two, three, four, five, six, seven, eight, nine or ten non-contiguous amino acid additions relative to SEQ ID NO: 106. In yet other aspects of this embodiment, a binding element comprising a chromogranin C peptide has, e.g., at most one, two, three, four, five, six, seven, eight, nine or ten non-contiguous amino acid additions relative to SEQ ID NO: 106.

In other aspects of this embodiment, a binding element comprising a chromogranin C peptide has, e.g., at least one, two, three, four, five, six, seven, eight, nine or ten contiguous amino acid substitutions relative to SEQ ID NO: 106. In other aspects of this embodiment, a binding element comprising a chromogranin C peptide has, e.g., at most one, two, three, four, five, six, seven, eight, nine or ten contiguous amino acid substitutions relative to SEQ ID NO: 106. In yet other aspects of this embodiment, a binding element comprising a chromogranin C peptide has, e.g., at least one, two, three, four, five, six, seven, eight, nine or ten contiguous amino acid deletions relative to SEQ ID NO: 106. In yet other aspects of this embodiment, a binding element comprising a chromogranin C peptide has, e.g., at most one, two, three, four, five, six, seven, eight, nine or ten contiguous amino acid deletions relative to SEQ ID NO: 106. In still other aspects of this embodiment, a binding element comprising a chromogranin C peptide has, e.g., at least one, two, three, four, five, six, seven, eight, nine or ten contiguous amino acid additions relative to SEQ ID NO: 106. In yet other aspects of this embodiment, a binding element comprising a chromogranin C peptide has, e.g., at most one, two, three, four, five, six, seven, eight, nine or ten contiguous amino acid additions relative to SEQ ID NO: 106.

Another example of a binding element disclosed in the present specification is, e.g., a tachykinin peptide, such as, e.g., a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. Thus, in an embodiment, a binding element is derived from a tachykinin peptide.

In aspects of this embodiment, a binding element comprising a tachykinin peptide is derived from a Substance P, a neuropeptide K (NPK), a neuropeptide gamma (NP gamma), a neurokinin A (NKA; Substance K, neurokinin alpha, neuromedin L), a neurokinin B (NKB), a hemokinin or a endokinin. In other aspects of this embodiment, a binding element comprising a tachykinin peptide comprises SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118.

In other aspects of this embodiment, a binding element comprising a tachykinin peptide has, e.g., at least 70% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at least 75% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at least 80% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at least 85% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at least 90% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118 or at least 95% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at most 70% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at most 75% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at most 80% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at most 85% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118, at most 90% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118 or at most 95% amino acid identity with SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118.

In other aspects of this embodiment, a binding element comprising a tachykinin peptide has, e.g., at least one, two, three, four or five non-contiguous amino acid substitutions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In other aspects of this embodiment, a binding element comprising a tachykinin peptide has, e.g., at most one, two, three, four or five non-contiguous amino acid substitutions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at least one, two, three, four or five non-contiguous amino acid deletions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at most one, two, three, four or five non-contiguous amino acid deletions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In still other aspects of this embodiment, a binding element comprising a tachykinin peptide has, e.g., at least one, two, three, four or five non-contiguous amino acid additions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at most one, two, three, four or five non-contiguous amino acid additions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118.

In other aspects of this embodiment, a binding element comprising a tachykinin peptide has, e.g., at least one, two, three, four or five contiguous amino acid substitutions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In other aspects of this embodiment, a binding element comprising a tachykinin peptide has, e.g., at most one, two, three, four or five contiguous amino acid substitutions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at least one, two, three, four or five contiguous amino acid deletions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at most one, two, three, four or five contiguous amino acid deletions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In still other aspects of this embodiment, a binding element comprising a tachykinin peptide has, e.g., at least one, two, three, four or five contiguous amino acid additions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118. In yet other aspects of this embodiment, a binding element comprising a tachykinin peptide has, e.g., at most one, two, three, four or five contiguous amino acid additions relative to SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 OR SEQ ID NO: 118.

Another example of a binding element disclosed in the present specification is, e.g., a Neuropeptide Y related peptide, such as, e.g., a Neuropeptide Y (NPY), a Peptide YY (PYY), Pancreatic peptide (PP) or a Pancreatic icosapeptide (PIP). Thus, in an embodiment, a binding element is derived from a Neuropeptide Y related peptide.

In aspects of this embodiment, a binding element comprising a Neuropeptide Y related peptide is derived from a Neuropeptide Y (NPY), a Peptide YY (PYY), Pancreatic peptide (PP) or a Pancreatic icosapeptide (PIP). In other aspects of this embodiment, a binding element comprising a Neuropeptide Y related peptide comprises SEQ ID NO: 119, SEQ ID NO: 120, SEQ ID NO: 121, SEQ ID NO: 122 or SEQ ID NO: 123.

In other aspects of this embodiment, a binding element comprising a Neuropeptide Y related peptide has, e.g., at least 70% amino acid identity with SEQ ID NO: 119, SEQ ID NO: 120, SEQ ID NO: 121, SEQ ID NO: 122 or SEQ ID NO: 123, at least 75% amino acid identity with SEQ ID NO: 119, SEQ ID NO: 120, SEQ ID NO: 121, SEQ ID NO: 122 or SEQ ID NO: 123, at least 80% amino acid identity with SEQ ID NO: 119, SEQ ID NO: 120, SEQ ID NO: 121, SEQ ID NO: 122 or SEQ ID NO: 123, at least 85% amino acid identity with SEQ ID NO: 119, SEQ ID NO: 120, SEQ ID NO: 121, SEQ ID NO: 122 or SEQ ID NO: 123, at least 90% amino acid identity with SEQ ID NO: 119, SEQ ID NO: 120, SEQ ID NO: 121, SEQ ID NO: 122 or SEQ ID NO: 123 or at least 95% amino acid identity with SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at most 70% amino acid identity with SEQ ID NO: 119, SEQ ID NO: 120, SEQ ID NO: 121, SEQ ID NO: 122 or SEQ ID NO: 123, at most 75% amino acid identity with SEQ ID NO: 119, SEQ ID NO:

120, SEQ ID NO: 121, SEQ ID NO: 122 or SEQ ID NO: 123, at most 80% amino acid identity with SEQ ID NO: 119, SEQ ID NO: 120, SEQ ID NO: 121, SEQ ID NO: 122 or SEQ ID NO: 123, at most 85% amino acid identity with SEQ ID NO: 119, SEQ ID NO: 120, SEQ ID NO: 121, SEQ ID NO: 122 or SEQ ID NO: 123, at most 90% amino acid identity with SEQ ID NO: 119, SEQ ID NO: 120, SEQ ID NO: 121, SEQ ID NO: 122 or SEQ ID NO: 123 or at most 95% amino acid identity with SEQ ID NO: 119, SEQ ID NO: 120, SEQ ID NO: 121, SEQ ID NO: 122 or SEQ ID NO: 123.

In other aspects of this embodiment, a binding element comprising a Neuropeptide Y related peptide has, e.g., at least one, two, three, four, five, six, seven, eight, nine or ten non-contiguous amino acid substitutions relative to SEQ ID NO: 119, SEQ ID NO: 120, SEQ ID NO: 121, SEQ ID NO: 122 or SEQ ID NO: 123. In other aspects of this embodiment, a binding element comprising a Neuropeptide Y related peptide has, e.g., at most one, two, three, four, five, six, seven, eight, nine or ten non-contiguous amino acid substitutions relative to SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at least one, two, three, four, five, six, seven, eight, nine or ten non-contiguous amino acid deletions relative to SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at most one, two, three, four, five, six, seven, eight, nine or ten non-contiguous amino acid deletions relative to SEQ ID NO: 119, SEQ ID NO: 120, SEQ ID NO: 121, SEQ ID NO: 122 or SEQ ID NO: 123. In still other aspects of this embodiment, a binding element comprising a Neuropeptide Y related peptide has, e.g., at least one, two, three, four, five, six, seven, eight, nine or ten non-contiguous amino acid additions relative to SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at most one, two, three, four, five, six, seven, eight, nine or ten non-contiguous amino acid additions relative to SEQ ID NO: 119, SEQ ID NO: 120, SEQ ID NO: 121, SEQ ID NO: 122 or SEQ ID NO: 123.

In other aspects of this embodiment, a binding element comprising a Neuropeptide Y related peptide has, e.g., at least one, two, three, four, five, six, seven, eight, nine or ten contiguous amino acid substitutions relative to SEQ ID NO: 119, SEQ ID NO: 120, SEQ ID NO: 121, SEQ ID NO: 122 or SEQ ID NO: 123. In other aspects of this embodiment, a binding element comprising a Neuropeptide Y related peptide has, e.g., at most one, two, three, four, five, six, seven, eight, nine or ten contiguous amino acid substitutions relative to SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at least one, two, three, four, five, six, seven, eight, nine or ten contiguous amino acid deletions relative to SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at most one, two, three, four, five, six, seven, eight, nine or ten contiguous amino acid deletions relative to SEQ ID NO: 119, SEQ ID NO: 120, SEQ ID NO: 121, SEQ ID NO: 122 or SEQ ID NO: 123. In still other aspects of this embodiment, a binding element comprising a Neuropeptide Y related peptide has, e.g., at least one, two, three, four, five, six, seven, eight, nine or ten contiguous amino acid additions relative to SEQ ID NO: 119, SEQ ID NO: 120, SEQ ID NO: 121, SEQ ID NO: 122 or SEQ ID NO: 123. In yet other aspects of this embodiment, a binding element comprising a Neuropeptide Y related peptide has, e.g., at most one, two, three, four, five, six, seven, eight, nine or ten contiguous amino acid additions relative to SEQ ID NO: 119, SEQ ID NO: 120, SEQ ID NO: 121, SEQ ID NO: 122 or SEQ ID NO: 123.

It is envisioned that a modified Clostridial toxin disclosed in the present specification can comprise a binding element in any and all locations with the proviso that modified Clostridial toxin is capable of performing the intoxication process. Non-limiting examples include, locating a binding element at the amino terminus of a modified Clostridial toxin; locating a binding element between a Clostridial toxin therapeutic element and a translocation element of a modified Clostridial toxin; and locating a binding element at the carboxyl terminus of a modified Clostridial toxin. Other non-limiting examples include, locating a binding element between a Clostridial toxin enzymatic domain and a Clostridial toxin translocation domain of a modified Clostridial toxin. The enzymatic domain of naturally-occurring Clostridial toxins contains the native start methionine. Thus, in domain organizations where the enzymatic domain is not in the amino-terminal location an amino acid sequence comprising the start methionine should be placed in front of the amino-terminal domain. Likewise, where a binding element is in the amino-terminal position, an amino acid sequence comprising a start methionine and a protease cleavage site may be operably-linked in situations in which a binding element requires a free amino terminus, see, e.g., Shengwen Li et al., Degradable Clostridial Toxins, U.S. patent application Ser. No. 11/572,512 (Jan. 23, 2007), which is hereby incorporated by reference in its entirety. In addition, it is known in the art that when adding a polypeptide that is operably-linked to the amino terminus of another polypeptide comprising the start methionine that the original methionine residue can be deleted.

Figure 20A:
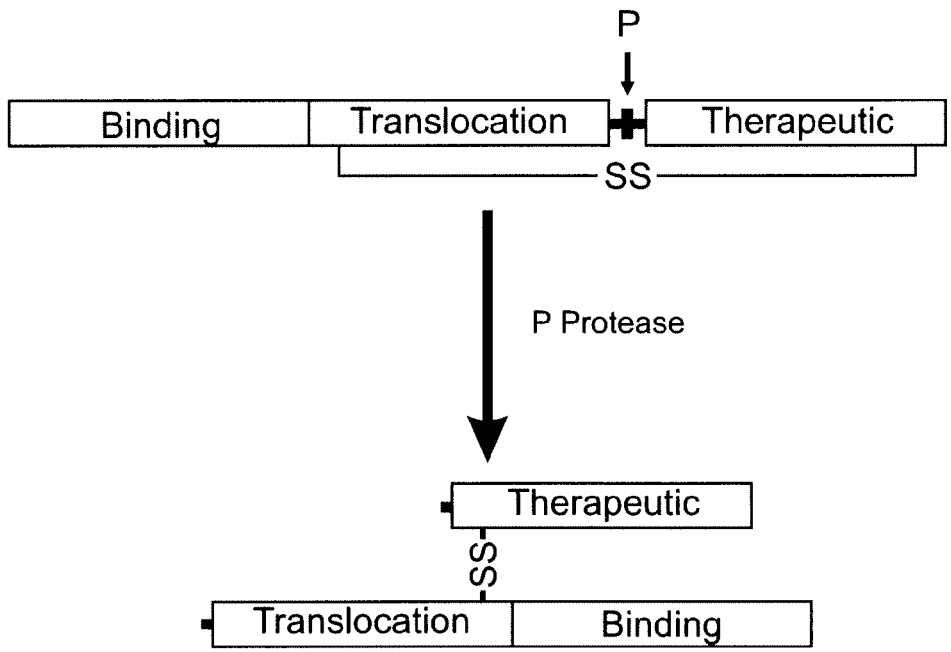
FIG. 20A depicts the single-chain polypeptide form of a modified Clostridial toxin with an amino to carboxyl linear organization comprising a binding element, a translocation element, a di-chain loop region comprising an exogenous protease cleavage site (P), and a therapeutic element. Upon proteolytic cleavage with a P protease, the single-chain form of the toxin is converted to the di-chain form.

Thus, in an embodiment, a modified Clostridial toxin can comprise an amino to carboxyl single polypeptide linear order comprising a binding element, a translocation element, an exogenous protease cleavage site and a therapeutic element (FIG. 20A). In an aspect of this embodiment, a modified Clostridial toxin can comprise an amino to carboxyl single polypeptide linear order comprising a binding element, a Clostridial toxin translocation domain, an exogenous protease cleavage site and a Clostridial toxin enzymatic domain.

Figure 20B:
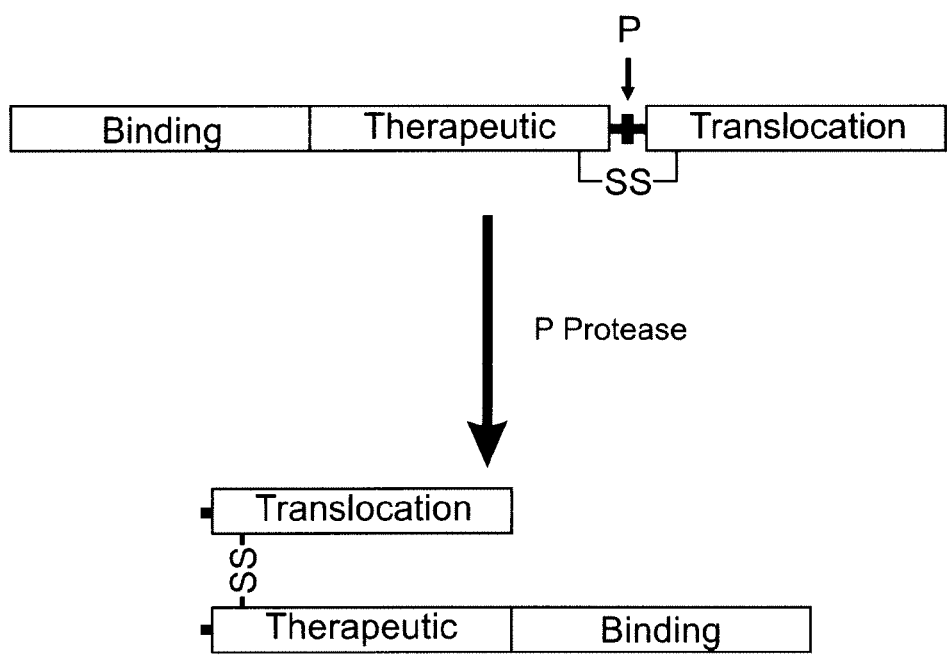
FIG. 20B depicts the single polypeptide form of a modified Clostridial toxin with an amino to carboxyl linear organization comprising a binding element, a therapeutic element, a di-chain loop region comprising an exogenous protease cleavage site (P), and a translocation element. Upon proteolytic cleavage with a P protease, the single-chain form of the toxin is converted to the di-chain form.

In another embodiment, a modified Clostridial toxin can comprise an amino to carboxyl single polypeptide linear order comprising a binding element, a therapeutic element, an exogenous protease cleavage site, and a translocation element (FIG. 20B). In an aspect of this embodiment, a modified Clostridial toxin can comprise an amino to carboxyl single polypeptide linear order comprising a binding element, a Clostridial toxin enzymatic domain, an exogenous protease cleavage site, a Clostridial toxin translocation domain.

Figure 21A:
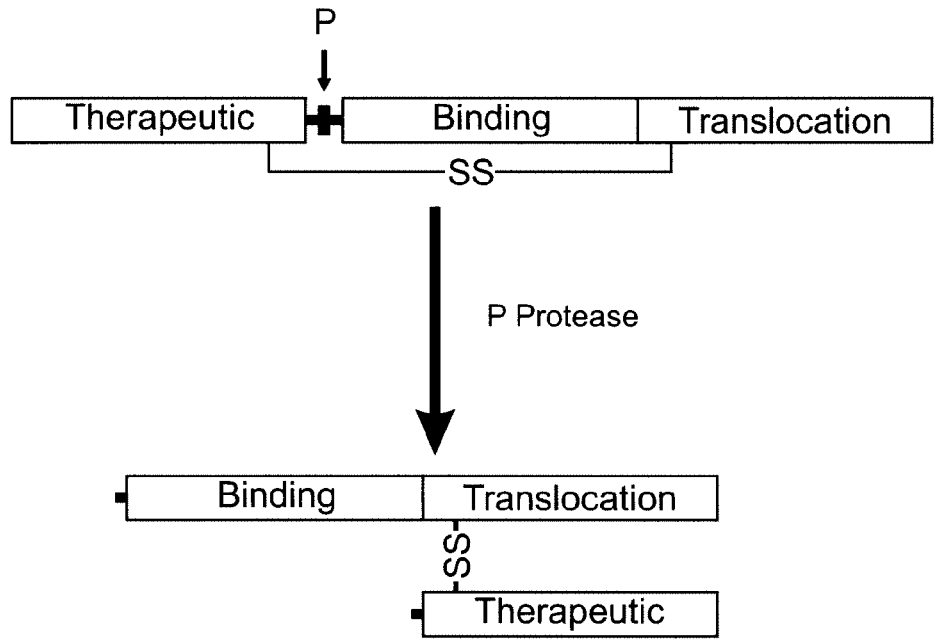
FIG. 21A depicts the single polypeptide form of a modified Clostridial toxin with an amino to carboxyl linear organization comprising a therapeutic element, a di-chain loop region comprising an exogenous protease cleavage site (P), a binding element, and a translocation element. Upon proteolytic cleavage with a P protease, the single-chain form of the toxin is converted to the di-chain form.

In yet another embodiment, a modified Clostridial toxin can comprise an amino to carboxyl single polypeptide linear order comprising a therapeutic element, an exogenous protease cleavage site, a binding element, and a translocation element (FIG. 21A). In an aspect of this embodiment, a modified Clostridial toxin can comprise an amino to carboxyl single polypeptide linear order comprising a Clostridial toxin enzymatic domain, an exogenous protease cleavage site, a binding element, and a Clostridial toxin translocation domain.

Figure 21B:
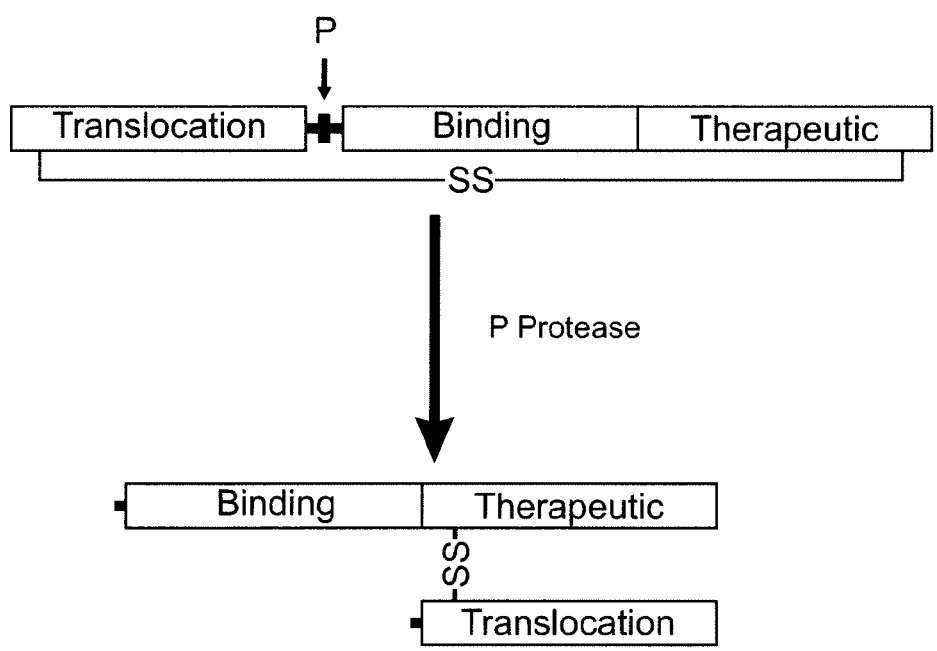
FIG. 21B depicts the single polypeptide form of a modified Clostridial toxin with an amino to carboxyl linear organization comprising a translocation element, a di-chain loop region comprising an exogenous protease cleavage site (P), a binding element, and a therapeutic element. Upon proteolytic cleavage with a P protease, the single-chain form of the toxin is converted to the di-chain form.

In yet another embodiment, a modified Clostridial toxin can comprise an amino to carboxyl single polypeptide linear order comprising a translocation element, an exogenous protease cleavage site, a binding element, and a therapeutic element (FIG. 21B). In an aspect of this embodiment, a modified Clostridial toxin can comprise an amino to carboxyl single polypeptide linear order comprising a Clostridial toxin translocation domain, a binding element, an exogenous protease cleavage site and a Clostridial toxin enzymatic domain.

Figure 21C:
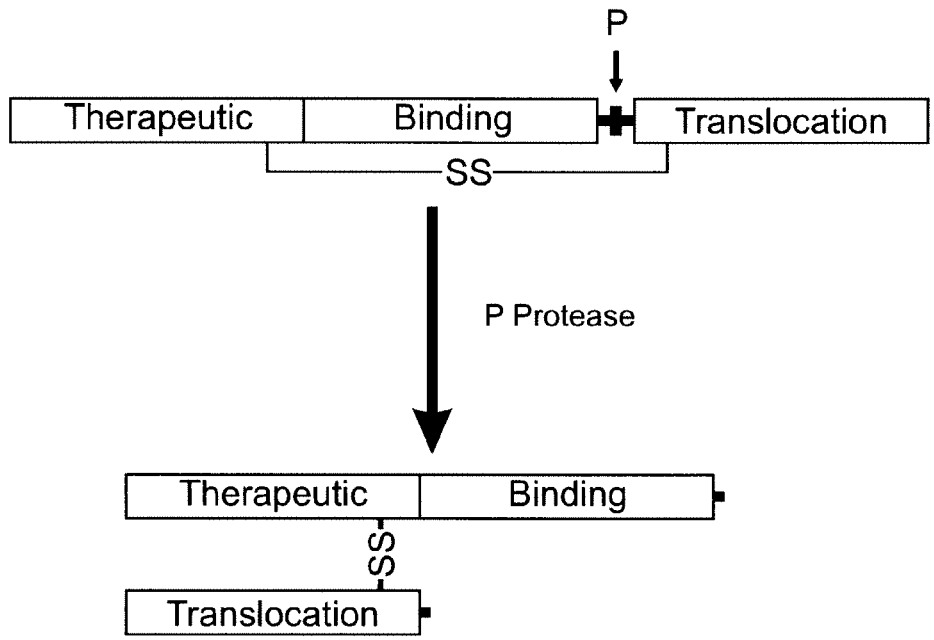
FIG. 21C depicts the single polypeptide form of a modified Clostridial toxin with an amino to carboxyl linear organization comprising a therapeutic element, a binding element, a di-chain loop region comprising an exogenous protease cleavage site (P), and a translocation element. Upon proteolytic cleavage with a P protease, the single-chain form of the toxin is converted to the di-chain form.

In another embodiment, a modified Clostridial toxin can comprise an amino to carboxyl single polypeptide linear order comprising a therapeutic element, a binding element, an exogenous protease cleavage site, and a translocation element (FIG. 21C). In an aspect of this embodiment, a modified Clostridial toxin can comprise an amino to carboxyl single polypeptide linear order comprising a Clostridial toxin enzymatic domain, a binding element, an exogenous protease cleavage site, a Clostridial toxin translocation domain.

Figure 21D:
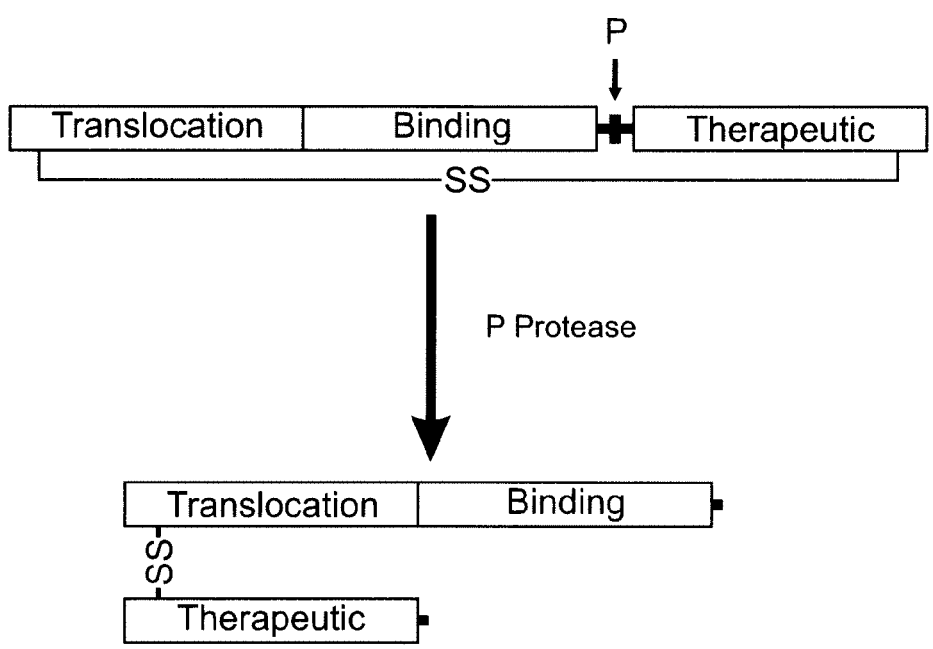
FIG. 21D depicts the single polypeptide form of a modified Clostridial toxin with an amino to carboxyl linear organization comprising a translocation element, a binding element, a di-chain loop region comprising an exogenous protease cleavage site (P), and a therapeutic element. Upon proteolytic cleavage with a P protease, the single-chain form of the toxin is converted to the di-chain form.

In yet another embodiment, a modified Clostridial toxin can comprise an amino to carboxyl single polypeptide linear order comprising a translocation element, a binding element, an exogenous protease cleavage site and a therapeutic element (FIG. 21D). In an aspect of this embodiment, a modified Clostridial toxin can comprise an amino to carboxyl single polypeptide linear order comprising a Clostridial toxin translocation domain, a binding element, an exogenous protease cleavage site and a Clostridial toxin enzymatic domain.

Figure 22A:
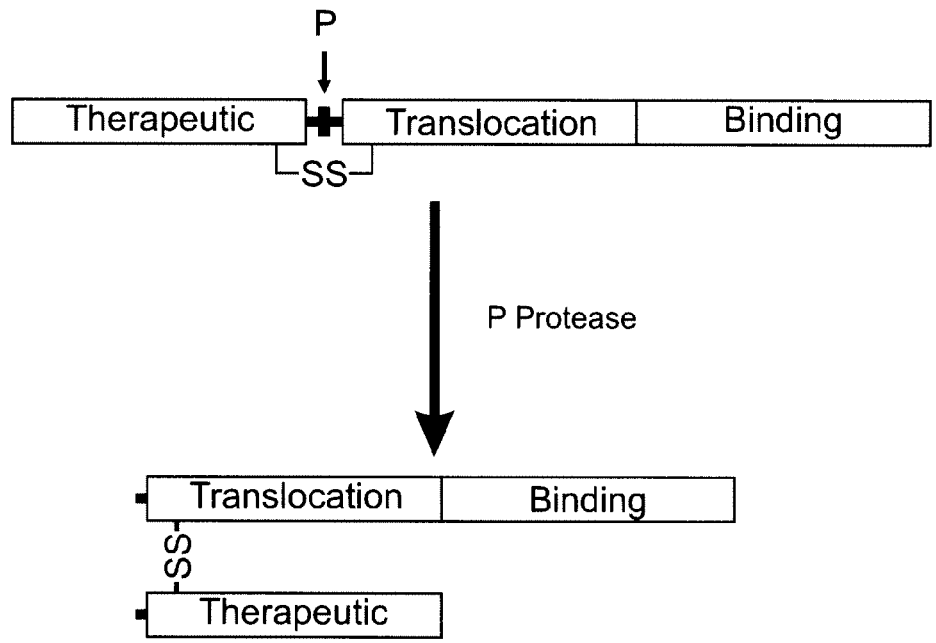
FIG. 22A depicts the single polypeptide form of a modified Clostridial toxin with an amino to carboxyl linear organization comprising a therapeutic element, a di-chain loop region comprising an exogenous protease cleavage site (P), a translocation element, and a binding element. Upon proteolytic cleavage with a P protease, the single-chain form of the toxin is converted to the di-chain form.

In still another embodiment, a modified Clostridial toxin can comprise an amino to carboxyl single polypeptide linear order comprising a therapeutic element, an exogenous protease cleavage site, a translocation element, and a binding element (FIG. 22A). In an aspect of this embodiment, a modified Clostridial toxin can comprise an amino to carboxyl single polypeptide linear order comprising a Clostridial toxin enzymatic domain, an exogenous protease cleavage site, a Clostridial toxin translocation domain, and a binding element.

Figure 22B:
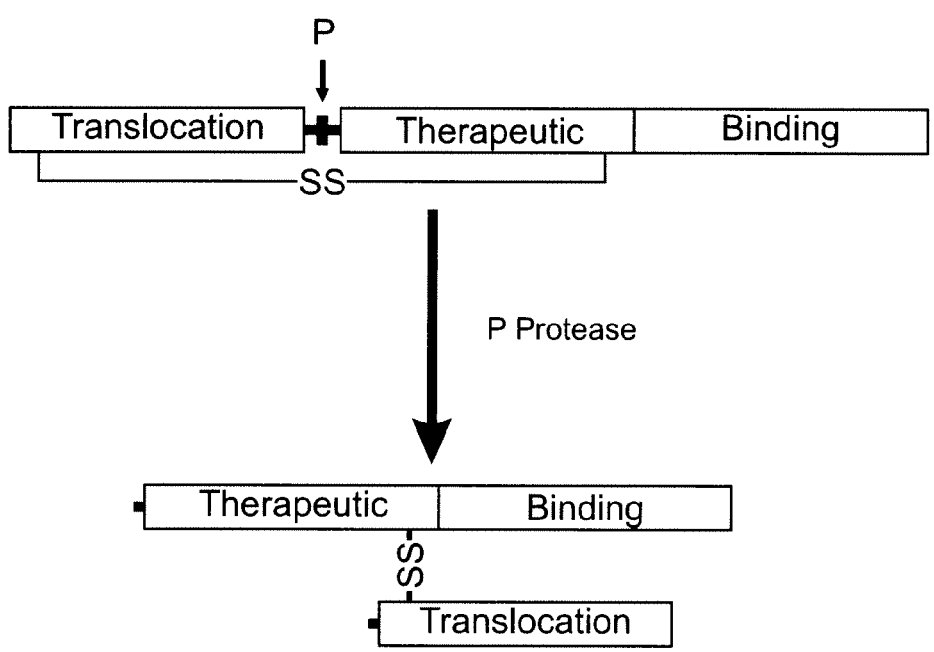
FIG. 22B depicts the single polypeptide form of a modified Clostridial toxin with an amino to carboxyl linear organization comprising a translocation element, a di-chain loop region comprising an exogenous protease cleavage site (P), a therapeutic element, and a binding element. Upon proteolytic cleavage with a P protease, the single-chain form of the toxin is converted to the di-chain form.

In still another embodiment, a modified Clostridial toxin can comprise an amino to carboxyl single polypeptide linear order comprising a translocation element, an exogenous protease cleavage site, a therapeutic element and a binding element, (FIG. 22B). In an aspect of this embodiment, a modified Clostridial toxin can comprise an amino to carboxyl single polypeptide linear order comprising a Clostridial toxin translocation domain, a binding element, an exogenous protease cleavage site and a Clostridial toxin enzymatic domain.

In a particularly preferred embodiment, the single-chain neurotoxin or neurotoxin derivative of the invention, altered as indicated above, is further modified to remove other incidental endogenous proteolytic sites such as those cleaved by trypsin, Arg C protease, chymotrypsin, or host cell proteases. As indicated below, modification of the primary amino acid sequences in these regions to confer protease resistance can increase the yield of the neurotoxin and reduce the toxicity of the single-chain neurotoxin prior to cleavage and activation.

In another preferred embodiment, the recombinant modified single-chain neurotoxin is further modified by joining the chain to a binding tag comprising one member of a specific binding complex. By "specific binding complex" is meant two or more chemical or biochemical entities that will bind each other under defined environmental conditions and which will not significantly bind other chemical or biochemical entities present in the environment under the same conditions. Examples of members of a specific binding complex include, without limitation, an antibody and its antigen, a lectin and its target carbohydrate, a nucleic acid strand and its complementary nucleic acid strand, a cell surface receptor and its ligand, a metal and a compound able to form a coordination or chelation complex with that metal, and the like.

In this embodiment, the binding tag may be joined to the single-chain toxin through a linker, preferably a cleavable linker. Examples of possible linkers, while not an exhaustive list, include 1) aliphatic dicarboxylic acids of the formula HOOC—$(CH_2)_n$—COOH, where n=1-12 (may be linked at a free amino group); 2) HO—$(CH_2)_n$—COOH, where n>10 (suitable for attachment at the amino terminus of the polypeptide), 3) substituted polybenzene structures, and 4) a N-hydroxysuccinimide (NHS) ester linker. The use of an linker containing an ester permits cleavage of the ester linker following use in the purification of the single-chain neurotoxin under relatively mild acidic conditions.

Alternatively, and most preferably, the binding tag may comprise some or all of the amino acid sequence of an appropriately chosen polypeptide coexpressed with the single-chain toxin as a fusion protein; such polypeptides may comprise, without limitation, the maltose binding domain of maltose binding protein (MBP), a polyhistidine peptide like $HIS_6$, the calmodilin binding domain of calmodulin binding protein, the glutathione binding domain of glutathione-S-transferase, FLAG, human Influenza virus hemaglutinin (HA), human p62c-Myc protein (c MYC), Vesicular Stomatitis Virus Glycoprotein (VSV-G), Substance P, glycoprotein-D precursor of Herpes simplex virus (HSV), V5, AU1 and AU5, streptavidin binding peptide (strep), and biotin or a biotinylation sequence. Non-limiting examples of specific protocols for selecting, making and using an appropriate binding peptide are described in, e.g., Epitope Tagging, pp. 17.90-17.93 (Sambrook and Russell, eds., Molecular Cloning A Laboratory Manual, Vol. 3, 3rd ed. 2001); Antibodies: A Laboratory Manual (Edward Harlow & David Lane, eds., Cold Spring Harbor Laboratory Press, 2nd ed. 1998); and Using Antibodies: A Laboratory Manual Portable Protocol No. I (Edward Harlow & David Lane, Cold Spring Harbor Laboratory Press, 1998). In addition, non-limiting examples of binding tags as well as well-characterized reagents, conditions and protocols are readily available from commercial vendors that include, without limitation, BD Biosciences-Clontech, Palo Alto, Calif.; BD Biosciences Pharmingen, San Diego, Calif.; Invitrogen, Inc, Carlsbad, Calif.; QIAGEN, Inc., Valencia, Calif.; and Stratagene, La Jolla, Calif. These protocols are routine procedures well within the scope of one skilled in the art and from the teaching herein.

Thus, in an embodiment, a modified Clostridial toxin disclosed in the present specification can further comprise a binding tag. In another embodiment, a modified Clostridial toxin disclosed in the present specification can further comprises a plurality of binding tags. In aspects of this embodiment, a modified Clostridial toxin can comprise, e.g., at least 1 binding tag, at least 2 binding tags, at least 3 binding tags, at least 4 binding tags or at least 5 binding tags. In other aspects of this embodiment, a modified Clostridial toxin can comprise, e.g., at most 1 binding tag, at most 2 binding tags, at most 3 binding tags, at most 4 binding tags or at most 5 binding tags. In another aspect of this embodiment, a modified Clostridial toxin can comprise one or more copies of the same binding tag, one or more copies of different binding tag, or any combination thereof.

The location of a binding tag can be in various positions, including, without limitation, at the amino terminus of a modified Clostridial toxin, within a modified Clostridial toxin, or at the carboxyl terminus of a modified Clostridial toxin. Thus, in an embodiment, a binding tag is located at the amino-terminus of a modified Clostridial toxin. In such a location, a start methionine should be placed in front of the binding tag. In addition, it is known in the art that when adding a polypeptide that is operably-linked to the amino terminus of another polypeptide comprising the start methionine that the original methionine residue can be deleted. This is due to the fact that the added polypeptide will contain a new start methionine and that the original start methionine may reduce optimal expression of the fusion protein. In aspects of this embodiment, a binding tag located at the amino-terminus of a modified Clostridial toxin disclosed in the present specification can be, e.g., a FLAG Express™ binding tag, a human Influenza virus hemaglutinin (HA) binding tag, a human p62c-Myc protein (c MYC) binding tag, a Vesicular Stomatitis Virus Glycoprotein (VSV-G) binding tag, a Substance P binding tag, a glycoprotein-D precursor of Herpes simplex virus (HSV) binding tag, a V5 binding tag, a AU1 binding tag, a AU5 binding tag, a polyhistidine binding tag, a streptavidin binding peptide binding tag, a biotin binding tag, a biotinylation binding tag, a glutathione binding domain of glutathione-S-transferase, a calmodulin binding domain of the calmodulin binding protein or a maltose binding domain of the maltose binding protein.

In another embodiment, an epitope-binding region is located at the carboxyl-terminus of a modified Clostridial toxin. In aspects of this embodiment, an epitope-binding region located at the carboxyl-terminus of a modified Clostridial toxin disclosed in the present specification can be, e.g., a FLAG Express™ binding tag, a human Influenza virus hemaglutinin (HA) binding tag, a human p62c-Myc protein (c MYC) binding tag, a Vesicular Stomatitis Virus Glycoprotein (VSV-G) binding tag, a Substance P binding tag, a glycoprotein-D precursor of Herpes simplex virus (HSV) binding tag, a V5 binding tag, a AU1 binding tag, a AU5 binding tag, a polyhistidine binding tag, a streptavidin binding peptide binding tag, a biotin binding tag, a biotinylation binding tag, a glutathione binding domain of glutathione-S-transferase, a calmodulin binding domain of the calmodulin binding protein or a maltose binding domain of the maltose binding protein.

Additionally, the binding tag may be constructed to have a protease cleavage site between itself and either the amino terminus or the carboxyl terminus of the single-chain toxin so as be removable following purification of the peptide. The proteolytic cleavage site may be designed to be cleaved by the same activator protease chosen to nick the single-chain toxin between the H and L chains.

It is therefore an object of the invention to provide a recombinant activatable single-chain neurotoxin molecule that has reduced toxicity compared to the native neurotoxin until activated by reaction with a non-clostridial protease. The single-chain neurotoxin is more easily purified, is less dangerous to handle in the purification process, and can be optionally modified to give the toxin more desirable properties.

It is also an object of the invention to provide an method of making a recombinant activatable single-chain neurotoxin by modifying the nucleotide sequence encoding the neurotoxin to replace the native amino acid proteolytic cleavage sequence separating the H and L chain with an amino acid sequence stable to indigenous clostridial or host cell proteases but susceptible to cleavage by chosen protease in vitro.

It is further an object of the present invention to provide more stable neurotoxin polypeptides through modification of the nucleotide sequence of the coding region of the H and L chains thereof, removing incidental proteolytic cleavage sites by causing the replacement of labile amino acids with other amino acid residues which confer upon the toxin resistance to undesired proteolytic degradation.

Additionally, it is an object of the invention to provide methods of purifying recombinant neurotoxins as a single-chain by joining the expressed single-chain neurotoxin to a binding moiety comprising partner of a specific binding complex which can be used in the affinity purification with the binding partner comprising the other half of the binding complex. Purification can be performed batch-wise or in a chromatography column. The binding moiety may then be removed following the affinity step, and separated from the neurotoxin.

It is also an object of the invention to provide single-chain recombinant modified neurotoxin molecules for use as therapeutic agents. The modified neurotoxin molecules may have an altered target specificity or an altered activity compared to the native neurotoxin from which it is derived, or both.

Another aspect of the present invention provides a method of activating an activatable polypeptide disclosed in the present specification, such method comprising the step of incubating the activatable polypeptide with an exogenous protease, wherein the exogenous protease can cleave the exogenous protease cleavage site present in the polypeptide and wherein cleavage of the activatable polypeptide by the exogenous protease converts the activatable polypeptide from its single-chain polypeptide form into its di-chain form, thereby activating the polypeptide.

Aspects of the present invention provide, in part, an exogenous protease. As used herein, the term "exogenous protease" means any protease capable of selectively cleaving the P1-P1' scissile bond comprising the exogenous protease cleavage site, with the proviso that the exogenous protease is not a human protease or a protease being expressed by the host cell expressing a construct encoding an activatable polypeptide disclosed in the present specification. As used herein, the term "selectively" means having a highly preferred activity or effect. Thus, with reference to an exogenous protease, there is a discriminatory proteolytic cleavage of the P1-P1' scissile bond comprising the exogenous protease cleavage site. It is envisioned that any and all proteases capable of selectively cleaving the P1-P1' scissile bond comprising the exogenous protease cleavage site can be useful in the disclosed methods. As a non-limiting example, a bovine enterokinse can selectively cleave a bovine enterokinse cleavage site, a tobacco etch virus protease can selectively cleave a tobacco etch virus protease cleavage site, a human rhinovirus 3C protease can selectively cleave a human rhinovirus 3C protease cleavage site, a subtilisin can selectively cleave a subtilisin cleavage site, a hydroxylamine can selectively cleave a hydroxylamine cleavage site, and a SUMO/ULP-1 protease can selectively cleave a SUMO/ULP-1 protease cleavage site.

A therapeutic agent useful in the invention generally is administered as a pharmaceutical acceptable composition comprising a modified neurotoxin as disclosed in the present specification. As used herein, the term "pharmaceutically acceptable" means any molecular entity or composition that does not produce an adverse, allergic or other untoward or unwanted reaction when administered to an individual. As used herein, the term "pharmaceutically acceptable composition" is synonymous with "pharmaceutical composition" and means a therapeutically effective concentration of an active ingredient, such as, e.g., any of the modified neurotoxins disclosed in the present specification. A pharmaceutical composition comprising a modified neurotoxin is useful for medical and veterinary applications. A pharmaceutical composition may be administered to a patient alone, or in combination with other supplementary active ingredients, agents, drugs or hormones. The pharmaceutical compositions may be manufactured using any of a variety of processes, including, without limitation, conventional mixing, dissolving, granulating, dragee-making, levigating, emulsifying, encapsulating, entrapping, and lyophilizing. The pharmaceutical composition can take any of a variety of forms including, without limitation, a sterile solution, suspension, emulsion, lyophilizate, tablet, pill, pellet, capsule, powder, syrup, elixir or any other dosage form suitable for administration.

It is also envisioned that a pharmaceutical composition comprising a modified neurotoxin can optionally include a pharmaceutically acceptable carriers that facilitate processing of an active ingredient into pharmaceutically acceptable compositions. As used herein, the term "pharmacologically acceptable carrier" is synonymous with "pharmacological carrier" and means any carrier that has substantially no long term or permanent detrimental effect when administered and encompasses terms such as "pharmacologically acceptable vehicle, stabilizer, diluent, additive, auxiliary or excipient." Such a carrier generally is mixed with an active compound, or permitted to dilute or enclose the active compound and can be a solid, semi-solid, or liquid agent. It is understood that the active ingredients can be soluble or can be delivered as a suspension in the desired carrier or diluent. Any of a variety of pharmaceutically acceptable carriers can be used including, without limitation, aqueous media such as, e.g., water, saline, glycine, hyaluronic acid and the like; solid carriers such as, e.g., mannitol, lactose, starch, magnesium stearate, sodium saccharin, talcum, cellulose, glucose, sucrose, magnesium carbonate, and the like; solvents; dispersion media; coatings; antibacterial and antifungal agents; isotonic and absorption delaying agents; or any other inactive ingredient. Selection of a pharmacologically acceptable carrier can depend on the mode of administration. Except insofar as any pharmacologically acceptable carrier is incompatible with the active ingredient, its use in pharmaceutically acceptable compositions is contemplated. Non-limiting examples of specific uses of such pharmaceutical carriers can be found in PHARMACEUTICAL DOSAGE FORMS AND DRUG DELIVERY SYSTEMS (Howard C. Ansel et al., eds., Lippincott Williams & Wilkins Publishers, 7$^{th}$ ed. 1999); REMINGTON: THE SCIENCE AND PRACTICE OF PHARMACY (Alfonso R. Gennaro ed., Lippincott, Williams & Wilkins, 20 ed. 2000); GOODMAN & GILMAN'S THE PHARMACOLOGICAL BASIS OF THERAPEUTICS (Joel G. Hardman et al., eds., McGraw-Hill Professional, 10$^{th}$ ed. 2001); and HANDBOOK OF PHARMACEUTICAL EXCIPIENTS (Raymond C. Rowe et al., APhA Publications, 4$^{th}$ edition 2003). These protocols are routine procedures and any modifications are well within the scope of one skilled in the art and from the teaching herein.

It is further envisioned that a pharmaceutical composition disclosed in the present specification can optionally include, without limitation, other pharmaceutically acceptable components (or pharmaceutical components), including, without limitation, buffers, preservatives, tonicity adjusters, salts, antioxidants, osmolality adjusting agents, physiological substances, pharmacological substances, bulking agents, emulsifying agents, wetting agents, sweetening or flavoring agents, and the like. Various buffers and means for adjusting pH can be used to prepare a pharmaceutical composition disclosed in the present specification, provided that the resulting preparation is pharmaceutically acceptable. Such buffers include, without limitation, acetate buffers, citrate buffers, phosphate buffers, neutral buffered saline, phosphate buffered saline and borate buffers. It is understood that acids or bases can be used to adjust the pH of a composition as needed. Pharmaceutically acceptable antioxidants include, without limitation, sodium metabisulfite, sodium thiosulfate, acetylcysteine, butylated hydroxyanisole and butylated hydroxytoluene. Useful preservatives include, without limitation, benzalkonium chloride, chlorobutanol, thimerosal, phenylmercuric acetate, phenylmercuric nitrate, a stabilized oxy chloro composition, such as, e.g., PURITE® and chelants, such as, e.g., DTPA or DTPA-bisamide, calcium DTPA, and CaNaDTPA-bisamide. Tonicity adjustors useful in a pharmaceutical composition include, without limitation, salts such as, e.g., sodium chloride, potassium chloride, mannitol or glycerin and other pharmaceutically acceptable tonicity adjustor. The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. It is understood that these and other substances known in the art of pharmacology can be included in a pharmaceutical composition useful in the invention.

In an embodiment, a therapeutic agent is a pharmaceutical composition comprising a modified neurotoxin. In an aspect of this embodiment, a pharmaceutical composition comprises an unactivated, single-chain for of the modified toxin. In another aspect of this embodiment, a pharmaceutical composition comprises an activated di-chain form of the modified toxin. In other aspects of this embodiment, a pharmaceutical composition comprising a modified neurotoxin further comprises a pharmacological carrier, a pharmaceutical component, or both a pharmacological carrier and a pharmaceutical component. In other aspects of this embodiment, a pharmaceutical composition comprising a modified neurotoxin further comprises at least one pharmacological carrier, at least one pharmaceutical component, or at least one pharmacological carrier and at least one pharmaceutical component.

It is also an object of the invention to provide a single-chain activatable recombinant neurotoxin that may be more easily purified than the wild type neurotoxin. Such a neurotoxin permits the large scale preparation of properly folded highly pure toxin for clinical use.

EXAMPLES

The following Examples serve to illustrate particular embodiments of the invention, and do not limit the scope of the invention defined in the claims in any way.

Example 1

Construction of an Expression Vector Containing a Single-Chain TeNT Coding Region The present invention can be exemplified describing the construction of a plasmid that will express TeNT in *E. coli* as a single protein that is readily purified, i.e., by affinity chromatography. TeNT can be chosen as a pilot system because (i) the availability of an excellent vaccine greatly reduces the risk of its handling and (ii) it is the most comprehensively studied of the toxins in terms of expressing HC and LC domains. However, those of skill in the art will understand that the same or similar strategies may be employed using any di-chain or binary toxin or other bioactive molecule expressed as a single polypeptide and activated by proteolytic cleavage. Single chain molecules were constructed containing the wild type TeNT L chain and a mutated version of the TeNT light chain wherein a glutamic acid residue at position 234 is changed to an alanine (termed "E234A", Ala$^{234}$, or "the E234A mutant light chain"), respectively. This latter mutation results in an inactive TeNT light chain, and a plasmid encoding the E234A mutant light chain (pMAL-E234A) was constructed as described in Li et al., Biochemistry 33:7014-7020 (1994)

(hereby incorporated by reference herein). The following protocol is used for the construction of each single-chain toxin.

The vector pTrcHisA, purchased from Invitrogen, is modified using a Stratagene QuickChange® site-directed mutagenesis kit (for site-directed mutagenesis techniques, see e.g., Smith et al., *J. Biol. Chem.* 253:6651-6560 (1979); incorporated by reference herein in its entirety) to create two extra restriction sites (SalI and HindIII) upstream of the nucleotides encoding a pre-existing enterokinase (EK) cleavage site. The plasmid also contains a translational start codon (ATG) followed by a run of codons encoding 6 histidine residues immediately upstream of the enterokinase cleavage site. A multiple cloning site containing Bam HI, XhoI, Bgl II, Pst I, Kpn I, Eco RI BstB I and Hind III cleavage sites is located immediately downstream of the EK site; the Hind III site is removed by site-directed mutagenesis. The following primers are employed to insert the restriction sites (underlined) upstream of the EK cleavage site:

```
                                            (SEQ ID NO: 67)
GACTGGTGGACAGCAAGTCGACCGGAAGCTTTACGACGATGACG,
               Sal I   Hind III
and
                                            (SEQ ID NO: 68)
CGTCATCGTCGTAAAGCTTCCGGTCGACTTGCTGTCCACCAGTC
              Hind III  Sal I
```

The resulting plasmid contains both Sal I and Hind III sites located at the 5' side of the nucleotide sequence encoding the bovine enterokinase (EK) cleavage site.

The nucleotide sequence encoding the wild-type TeNT L chain is obtained from plasmid pMAL-LC, described in Li et al., *Biochemistry* 33, 7014-7020 (1994), incorporated by reference herein. The plasmid encodes the TeNT light chain as a fusion protein with maltose binding protein (MBP) located immediately upstream of the coding sequence for the L chain. The MBP and L chain portions of the fusion protein are designed to contain the cleavage site for human blood coagulation factor Xa (Ile-Glu-Gly-Arg) to facilitate removal of the MBP once affinity purification has been performed.

The DNA fragment containing the coding sequence of the L chain is excised from plasmid pMAL-LC by digesting the plasmid with Sal I and Hind III, gel purifying the resulting DNA fragment containing the L chain, and ligating this fragment into plasmid pTrcHisA at the newly created Sal I and Hind III sites upstream of the EK site. This fragment results in the excision of the maltose binding protein sequences from the N terminus of the L chain.

An identical procedure is used to subclone the DNA fragment containing a mutant L chain from plasmid pMAL-LC-$Ala^{234}$, in which a single amino acid change is made at amino acid 234 of the L chain, substituting the native glutamic acid with alanine. This change is sufficient to abrogate the zinc endopeptidase activity of the L chain, and to render non-toxic a reconstituted tetanus toxin containing native H chain and the $Ala^{234}$ L chain.

The DNA fragment containing the H chain is obtained from plasmid pMAL-HC; construction of this vector is described in Li et al., *J. Biochem.* 125:1200-1208 (1999), hereby incorporated by reference herein. Briefly, the gene encoding the H chain is constructed by assembling three DNA fragments containing different portions of the H chain coding sequence which had been cloned into separate plasmids. The fragments comprising the amino terminal half of the H are first amplified using standard polymerase chain reaction methods (see, e.g., Mullis, U.S. Pat. No. 4,683,202 and Mullis et al., U.S. Pat. No. 4,800,159, both incorporated by reference herein in their entirety) and the following primers: PCR primers a (containing a Xba I cleavage site) and b (containing a Bgl II cleavage site) (SEQ ID NO: 113 and 114, respectively) are used to amplify the H chain fragment contained in a plasmid termed pTet8; PCR primers c (containing a Bgl II cleavage site) and d (containing both a Hind III and a Sal I cleavage site) (SEQ ID NO: 115 and 116, respectively) are used to amplify the H chain fragment contained in a plasmid termed pTet14. The nucleotide sequences of these primer are provided below, with restriction sites underlined.

```
                                          (SEQ ID NO: 69)
AATAGATCTAGATCATTAACAGATTTAGGA                 (a)

(SEQ ID NO: 70)
TTCTAAAGATCTATACATTTGATAACT                    (b)

(SEQ ID NO: 71)
ATGTATAGATCTTTAGAATATCAAGTA                    (c)

(SEQ ID NO: 72)
ATCGATAAGCTTTTATCAGTCGACCCAACAATCCAGATTTTTAGA  (d)
```

Following PCR amplification and gel purification of the amplified H chain fragments, each fragment is digested with Bgl II and ligated to yield the complete N terminal half of the H chain coding region. This ligation product is then digested with Xba I and Hind III and subcloned into the multiple cloning site of pMAL-c2-T (the plasmid being also cut with Xba I and Hind III), which is located downstream of the coding region for MBP and the factor Xa site. pMAL-c2 is a commercially available vector well known to those of skill in the art. The resulting plasmid is pMAL-$H_N$.

The entire H chain coding region is assembled as follows. The pMAL-$H_N$ plasmid is digested with Sac I and Sal I to yield the DNA fragment encoding the N-terminus of the H chain. Plasmid pTet215 is digested with Sal I and Bam HI to yield the DNA fragment encoding the H chain carboxyl terminus. The vector pMAL-c2-T is digested with Sac I and Bam HI, and ligated to the digested H chain fragments, which will assemble in the proper orientation due to the use of distinct endonucleases. The resulting plasmid is pMAL-HC.

The DNA fragments encoding the H and L chains (including $Ala^{234}$ L chain) are cut and purified directly from pMAL-LC or pMALE234A and pMAL-HC constructs and subcloned into the modified pTrcHisA vector described above. The H chain was first ligated into the modified vector at the Bam HI site immediately downstream of the EK site, and the resulting plasmid was gel purified. Following digestion of this plasmid with Hind III and Sal I, the L chain was ligated at a position just upstream of the EK cleavage site.

The resulting plasmid construct contains the nucleotide sequence encoding the single-chain toxin protein, comprising (from amino to carboxyl terminus): six histidine residues (the His tag), followed by the L chain, an enterokinase cleavage site, and the H chain. The translated junction between the L and H chains containing the EK cleavage site (SEQ ID NO: 21) is shown below (in the direction from N-terminus to C-terminus) and in FIG. 1.

```
                                                      SEQ ID NO: 73
                          ER site
SKLIGLCKKIIPPTNIRENLYNRTA-GEKLYDDDDKDRWGSSR-SLTDLGGELCIKNEDLTFIAEKN
      L chain              interchain loop          H chain
```

To allow expression of the two chains as a single unit, a nucleotide sequence comprising a stop codon present at the 3' end of the L chain coding sequence in the pMAL-LC is removed by site-directed mutagenesis using two primers (SEQ ID NO: 74 and 75), resulting in a single reading frame containing both H and L chains.

```
                                          (SEQ ID NO: 74)
  AATAGAACTGCAGGAGAAAAGCTTTACGACGATGAC,
  and TGATAA (deleted stop codon; coding strand)

(SEQ ID. NO: 75)
  GTCATCGTCGTAAAGCTTTTCTCCTGCAGTTCTATT

TTATCA (deleted stop codon; non-coding strand)
```

The resulting pTrcHisA-based construct is transformed into *E. coli* strain JM109 by heat shock using the method of Hanahan, and transformant colonies are isolated on Luria agar plates containing 100 μg/ml ampicillin. Plasmids are purified from these transformants and the insertions are confirmed by analytical restriction endonuclease digestion and agarose gel electrophoresis.

Example 2

Expression and Physical Characterization of Single-Chain TeNT

Expression of the pTrcHisA-based single-chain TeNT construct (under control of a hybrid trp/lac promoter) is induced by addition of 1 mM IPTG (isopropyl thio-galactopyranoside) to a confluent culture of a representative transformant clone in 200 ml Luria broth containing 100 μg/ml ampicillin and incubating further at 37° C. for 16 hours before cell harvest by centrifugation.

The cell pellets are resuspended in 30 ml Buffer A (20 mM $Na_2PO_4$, 500 mM NaCl (pH 7.8)), then lysed by ultrasonication at 4° C., using 10-second bursts at a medium setting. Insoluble debris is removed by centrifugation at 9,000×g for 30 min at 4° C., and the supernatant recovered by centrifugation.

The supernatant containing each single-chain construct is incubated for 20 minutes at 22° C. with 2 ml of nickel-ion resin (Invitrogen Corp.) for affinity purification by means of chelation between the histidine residues at the amino terminus of the single-chain toxin molecule and the nickel. The resins were then load onto mini columns and washed with 200 ml of washing buffer (20 mM $Na_2PO_4$, 500 mM NaCl (pH 6.0)) to remove any non-specifically bound material, the recombinant single-chain proteins are eluted on 0.5 ml fractions with 8-15 ml of 100 mM imidazole in Buffer A. The concentration of the eluted single-chains was measured by Bradford's protein assay (Bio-Rad Laboratories); approximately 1 milligram of the fusion protein was recovered.

Example 3

SDS-PAGE and Western Blot Analysis of Recombinant Single-Chain TeNT

The single-chain TeNT constructs are grown in Luria broth containing ampicillin at 37° C., and aliquots taken both before and after induction of protein expression with IPTG. Crude cell extracts are prepared for SDS-PAGE by dilution in sample buffer under reducing conditions in the presence of β-mercaptoethanol (BME). Following SDS-PAGE electrophoresis, the separated proteins are Western-blotted as follows: the proteins are electrophoretically transferred to a polyvinylidenedifluoride (PVDF) membrane using standard methods (see, e.g., Sambrook et al., *Molecular Cloning, A Laboratory Manual* (2d ed. Cold Spring Harbor Laboratory Press 1989), hereby incorporated by reference in its entirety), the membrane treated to reduce background Ig binding, and then probed using an anti-$His_6$ antibody, followed by detection using an alkaline phosphatase-conjugated secondary antibody and development with a 5-bromo-4-chloro-3-indolyl-phosphate/nitro blue tetrazolium substrate.

As shown in lanes 1 and 2 of FIG. 2A, the Western blot revealed no detectable TeNT expression before induction of protein synthesis; by contrast, a single band of approximate molecular weight 150 kDa was revealed in the aliquots taken following protein induction (See lanes 3 and 4.) In FIG. 2A, lanes 1 and 3 are the WT light chain construct and lanes 2 and 4 contain the E234A mutant construct.

FIG. 2B is a Western blot of IPTG-induced cell extracts from cells transformed with the E234A construct. Significantly, no discernable lower molecular weight proteolytic cleavage products of the light chain were observed, providing evidence for the relative stability of the single-chain toxin following expression and purification.

FIG. 3 shows the results of a second experiment, in which affinity purified recombinant single-chain (SC) TeNT is nicked with enterokinase as follows. Thirty micrograms of purified single-chain toxin are incubated with 1 unit of enterokinase in a solution containing 50 mM Tris-HCl (pH 8.0), 1 mM $CaCl_2$ and 0.1% Tween-20(v/v). As a control, the recombinant protein is incubated in the same reaction mixture containing no EK. These samples, plus an aliquot of native (non-recombinant) TeNT are subjected to SDS-PAGE in an 8% polyacrylamide gel under either reducing (+BME) or non-reducing (−BME) conditions. The resulting gel is used both for a Western blot and subsequent detection using anti-H claim antibodies (FIG. 3B), and direct staining with Coomassie Blue (FIG. 3A).

As indicated by FIG. 3, under non-reducing conditions all three samples (Native TeNT (Lane 1), unnicked recombinant toxin (Lane 2), and enterokinase nicked recombinant toxin (Lane 3)) will migrate as doublets (apparently different conformers that resolve into a single band upon reduction) with essentially indistinguishable apparent molecular weights of about 150 kDa. The non-reducing gel confirms that 1) high levels of expression are obtained, 2) the disulfide bonds linking the light and heavy chains are fully formed, and 3) the recombinant single-chain toxin is not subject to observable proteolytic degradation.

By contrast, under reducing conditions wild-type and nicked recombinant toxin yield an H chain having a molecular weight of about 100 kDa by both Western blot and Coomassie staining. Additionally, in the Coomassie stained gel, both of these samples also show a lower molecular weight species of about 50 kDa, corresponding to the L chain. The wild-type L chain will migrate with a lower apparent molecular weight than that of the recombinant L chain, which has 22 additional amino acid residues due to the presence of the His$_6$ moiety and a modified EK cleavage site-containing interchain junction region. The unnicked recombinant toxin (Lane 2) migrates as a single band with an apparent molecular weight of about 150 kDa. Notably, no trace of the unnicked toxin is seen in lane 3, indicating the effectiveness of enterokinase treatment.

Example 4

In Vitro Toxin-Induced Paralysis by Recombinant Single-Chain TeNT

The biological activity of the recombinant TeNT is also examined and compared to wild-type toxin using mouse phrenic nerve hemi-diaphragm, since the native toxin is known to cause neuromuscular paralysis, albeit at higher concentrations than act in the CNS. For this experiment, mouse left phrenic nerve-hemidiaphragm is dissected from mice (T/O strain, 4-week old and ~20 g in weight) and immediately transferred into a closed circulatory superfusion system containing 10 ml of Krebs-Ringer solution (118 mM NaCl, 4.7 mM KCl, 1.2 mM MgSO$_4$, 2.5 mM CaCl$_2$, 23.8 mM NaHCO$_4$, 1.2 mM KH$_2$PO$_4$, 11.7 mM glucose (pH 7.4)), bubbled with 95% O$_2$ and 5% CO$_2$ and supplemented with 0.1% (w/v) bovine serum albumin to diminish non-specific adsorption of the toxins (Li et al., Biochemistry 33:7014-7020 (1994)). The hemidiaphragms are kept in a bath containing 10 ml Krebs-Ringer buffer at 37° C. for 10 minutes before being exposed to 4 or 10 nM native TeNT (▼ and ∇, respectively) or 10 nM nicked recombinant TeNT (●) or 10 nM un-nicked recombinant TeNT (○), respectively. (See FIG. 4).

Muscle twitch is evoked by supra-maximal stimulation of the phrenic nerve with bipolar electrodes and recorded via a force-displacement transducer (Lectromed, UK) connected to an amplifier and computer system (MacLab, AD Instruments, UK). Parameters of nerve stimulation are 0.2 Hz square waves of 0.1 msec duration with 1.5-2.5 V amplitude. Toxin-induced paralysis of neuromuscular transmission is quantified as the time required for nerve-evoked muscle contraction to decrease to 10% (90% reduction) of the original value.

Figure 4:
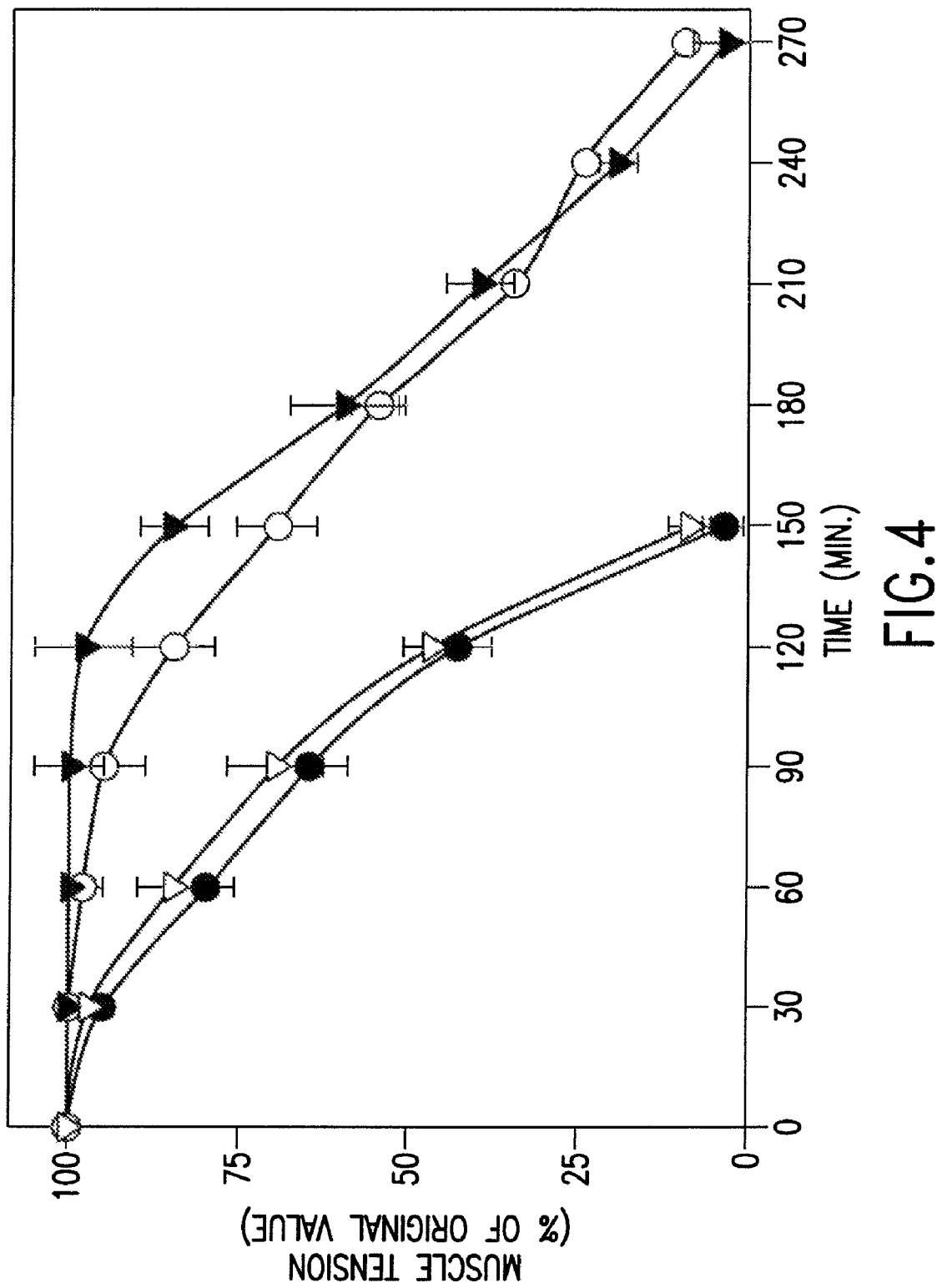
FIG. 4 is a plot of the degree of paralysis induced in a nerve/muscle preparation in vitro using native TeNT, and recombinant single-chain neurotoxin before, and after nicking as a function of time.

As shown in FIG. 4, 10 nM recombinant nicked TeNT was found to be as potent as 10 nM native toxin in blocking nerve-induced muscle twitch, with the preparations yielding a 90% reduction in muscle tension in approximately 170 minutes. Thus, this novel preparation of TeNT expressed in *E. coli* at high level as a single-chain, activatable polypeptide and purified by a simple affinity chromatography step proved to be fully active by all the criteria examined.

By contrast, 10 nM of the unnicked TeNT preparation require approximately twice as long to reduce muscle tension, and was approximately as active as 4 nM of the wild-type TeNT. As a control, hemidiaphragms incubated with KR buffer and the trace amount of enterokinase present in the experimental samples were found to show negligible decrease in muscle tension over 5 hrs.

Thus, this experiment indicates that the unnicked TeNT is considerably less toxic that either the wild type or recombinant nicked protein in vitro.

Example 5

Further Modification of Single-Chain TeNT to Remove Proteolytic Cleavage Sites Reduces Toxicity of Unnicked Recombinant Toxin While the unnicked recombinant single-chain form of TeNT displays reduced toxicity as compared to the nicked form, the residual toxin activity probably arises from activation of the toxin by additional proteases in vivo. To test this possibility, sites in the single-chain toxin molecule susceptible to proteolytic cleavage by trypsin and Arg C protease are identified by incubation of single-chain TeNT with these enzymes as follows. Fifty micrograms μg of recombinant single-chain TeNT is incubated with 4 μg of Arg-C at 37° C. for 4 h; 0.1 μg of trypsin at 37° C. for 0.5 h; or buffer without protease as a control. These reactions are terminated by the addition of SDS-PAGE sample buffer containing 0.1% SDS followed by boiling for 5 minutes; then the samples are subjected to SDS-PAGE, followed by a Western electrophoretic transfer to a polyvinylidenedifluoride (PVDF) membrane. The membrane is blotted with IgG specific for the His$_6$-tag and detected using a horseradish peroxidase staining system.

As shown in FIG. 5, the Western blot reveals that trypsin and Arg C protease yielded a L chain (and thus a H chain) fragment of the same size. Additionally, the transfer of a duplicate gel was stained for protein with Ponceau red and the H chain band of approximate molecular weight 100 kDa was excised from each lane and analysed by N-terminal sequencing.

Figure 1B:
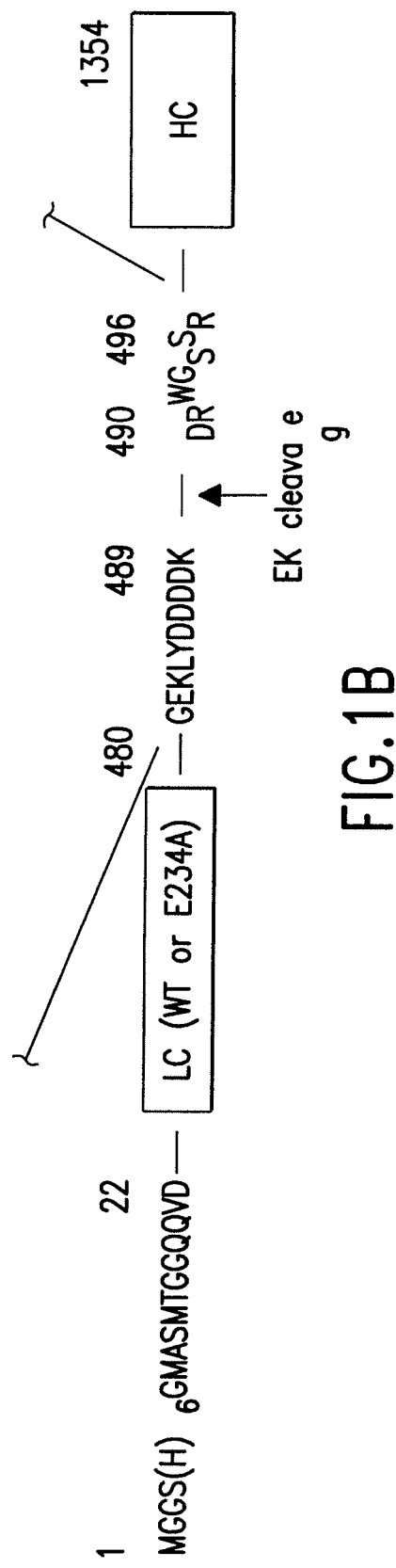
FIG. 1B shows the and amino acid sequence connecting the carboxyl terminus of the L chain and the amino terminus of the H chain and an engineered loop region containing an enterokinase cleavage site.

In the recombinant single-chain TeNT, the LC and HC are linked by 17 amino acids (GEKLYDDDDKDRWGSSR SEQ ID NO: 130), followed by the beginning of the H chain sequence (SLTDLGGEL . . . i.e., amino acids 458 to 466 of SEQ ID NO: 8). N-terminal amino acid sequencing of the larger fragment produced by both trypsin and Arg C protease reveal that first 5 amino acids of the 100 kDa trypsin and Arg C protease cleavage product protein are SLTDL (amino acids 458 to 462 of SEQ ID NO: 8); thus, these proteases appear to cleave the single-chain toxin between the R—S bond (see FIG. 1) so as to liberate the H chain and the L chain containing the EK linker at its C terminus, with this variant therefore yielding a di-chain toxin essentially identical to the EK nicked toxin.

The arginine at the carboxy terminus of the EK linker sequence is mutated by site-directed mutagenesis to a glycine (R496G), and the resulting single-chain toxin polypeptide is expressed and purified as above.

Figure 6:
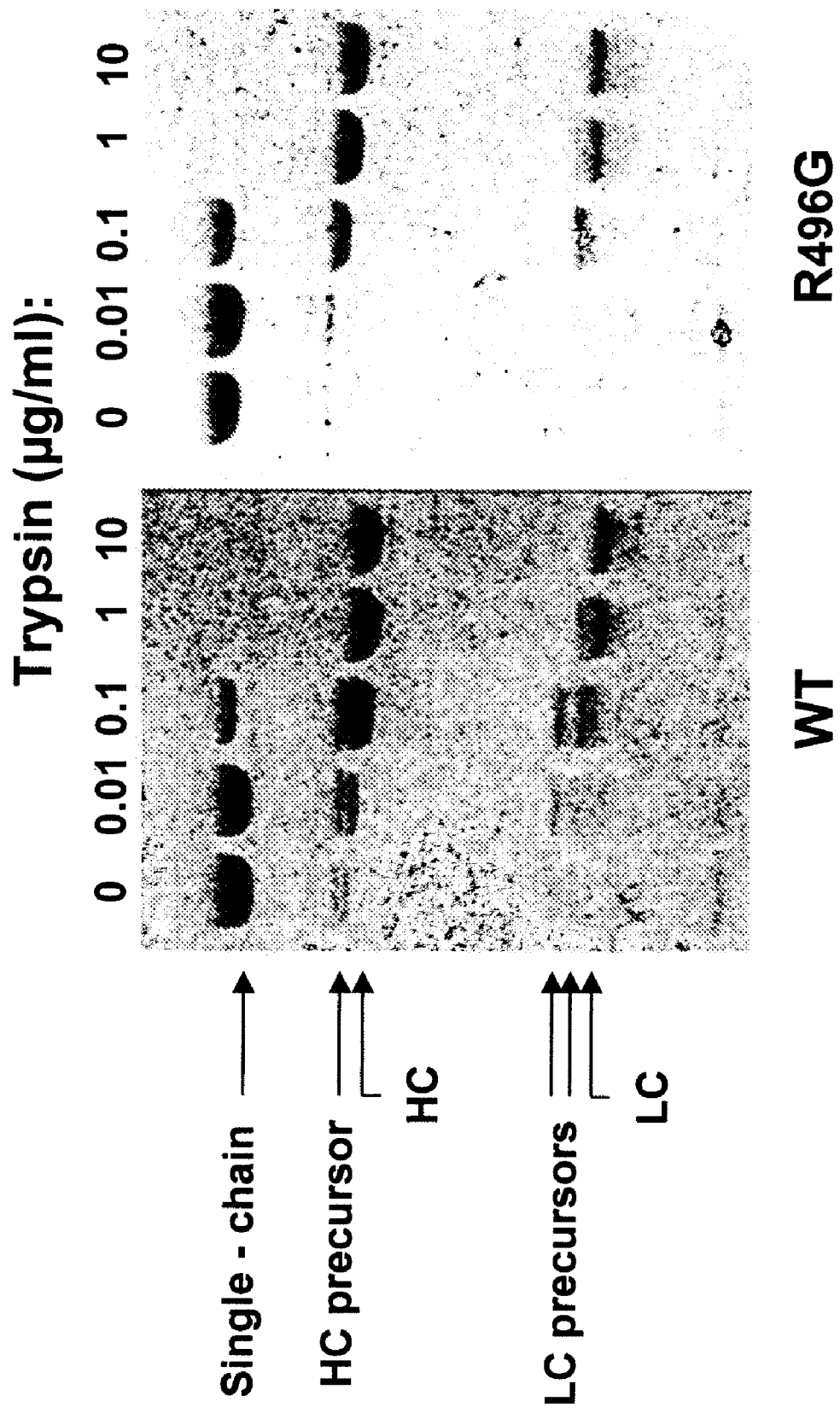
FIG. 6 shows the digestion of unnicked SC WT TeNT and SC R496G TeNT with various concentrations of trypsin.

Titration of the 6 micrograms of the R496G mutated single-chain (WT LC) toxin and the SC TeNT lacking such a mutation against 0, 0.01, 0.1, 1, 10 μg/ml of trypsin, followed by SDS-PAGE and staining with Coomassie Brilliant Blue, yields the cleavage pattern seen in FIG. 6. As can be seen, both single-chain molecules are susceptible to typsin cleavage; however the R496G mutant yields fewer fragments than the SC toxin not containing a mutation in the loop region between the chains. For example, while three trypsin peptide bands can clearly be seen near the light chain band upon trypsin cleavage of the SC WT toxin, only two such bands are seen in the R496G digests.

The fact that there exist remaining trypsin sites in the R496G mutant SC toxin probably accounts for the fact that this mutant does not cause the lowering of toxicity as compared to the un-nicked SC toxin; both preparations give similar values in the mouse lethality and neuromuscular paralysis assays described above.

A different assay system is used to measure neurotoxin activity toward CNS neurons, the cells naturally affected by TeNT. The cells used are cerebellar neurons; these cells are disassociated from the cerebella of 7 day old rats. Neurons are suspended at 1-2×10$^6$/mL in medium consisting of 3 parts Basal Eagle Medium and 1 part of a buffer consisting of 40 mM HEPES-NaOH (pH 7.3), 78.4 mM KCl, 37.6 mM D-glucose, 2.8 mM CaCl$_2$, 1.6 mM MgSO$_4$ and 1.0 mM NaH$_2$PO$_4$, as well as 1×N2 supplement, 1.0 mM L-glutamine, 60 units/ mL penicillin, 60 μg/mL streptomycin and 5% (v/v) dialysed horse serum. One milliliter of this cell suspension is added to 22 mm diameter poly-D-lysine coated wells. Cytosine β-D-arabinofuranoside (Ara-C, 40 μM) is added after 20-24 hours in 5% (v/v) $CO_2$ culture, and neurons are maintained by weekly replacement of the above-noted medium containing 40 μM Ara-C.

For each assay, neurons are cultured for at least 10 days in vitro are washed four times with $O_2$-gassed Krebs-Ringer HEPES buffer (KRH, mM: 20 HEPES.NaOH pH7.4, 128 NaCl, 5 KCl, 1 $NaH_2PO_4$, 1.4 $CaCl_2$, 1.2 mM $MgSO_4$, 10 D-glucose and 0.05 mg/mL BSA), and 0.5 mL of the latter buffer containing 0.25 μCi/mL [14C]-glutamine (i.e. the glutamate precursor) is added. All steps are performed at 37° C. After a 45 minute labeling period, the medium is removed and the neurons washed four times as before. Control and toxin-treated neurons are incubated for 5 minutes at 37° C. in KRH buffer containing either 1.4 mM $Ca^{2+}$ or 0.5 mM EGTA (i.e. to assess $C^{2+}$-independent release); aliquots are then removed and retained for assessment of [$^{14}C$]-glutamate content by scintillation counting. Immediately after removal of the above basal medium, a modified KRH buffer containing 50 mM KCl (containing a lowered 83 mM NaCl content in order to maintain a normal osmotic potential) and either 1.4 $Ca^{2+}$ or 0.5 mM EGTA are added for a 5 minute stimulation period. Finally, neurons were solubilized with 20 mM EGTA.NaOH pH 7.5 containing 1% (w/v) SDS, and aliquots subjected to scintillation counting in order to calculate their remaining radioactive contents. The amounts of $^{14}C$-glutamate in basal and stimulated samples are expressed as percentages relative to the calculated total cell content. The percentage [$^{14}C$]-glutamate contents in EGTA-containing buffer are subtracted from the values recorded in $C^{2+}$-containing samples in order to calculate the relevant $Ca^{2+}$-dependent component of release and in turn the latter basal readings are subtracted from values obtained for 50 mM KCl samples to yield the $K^+$-evoked $Ca^{2+}$-dependent glutamate release component.

Figure 8:
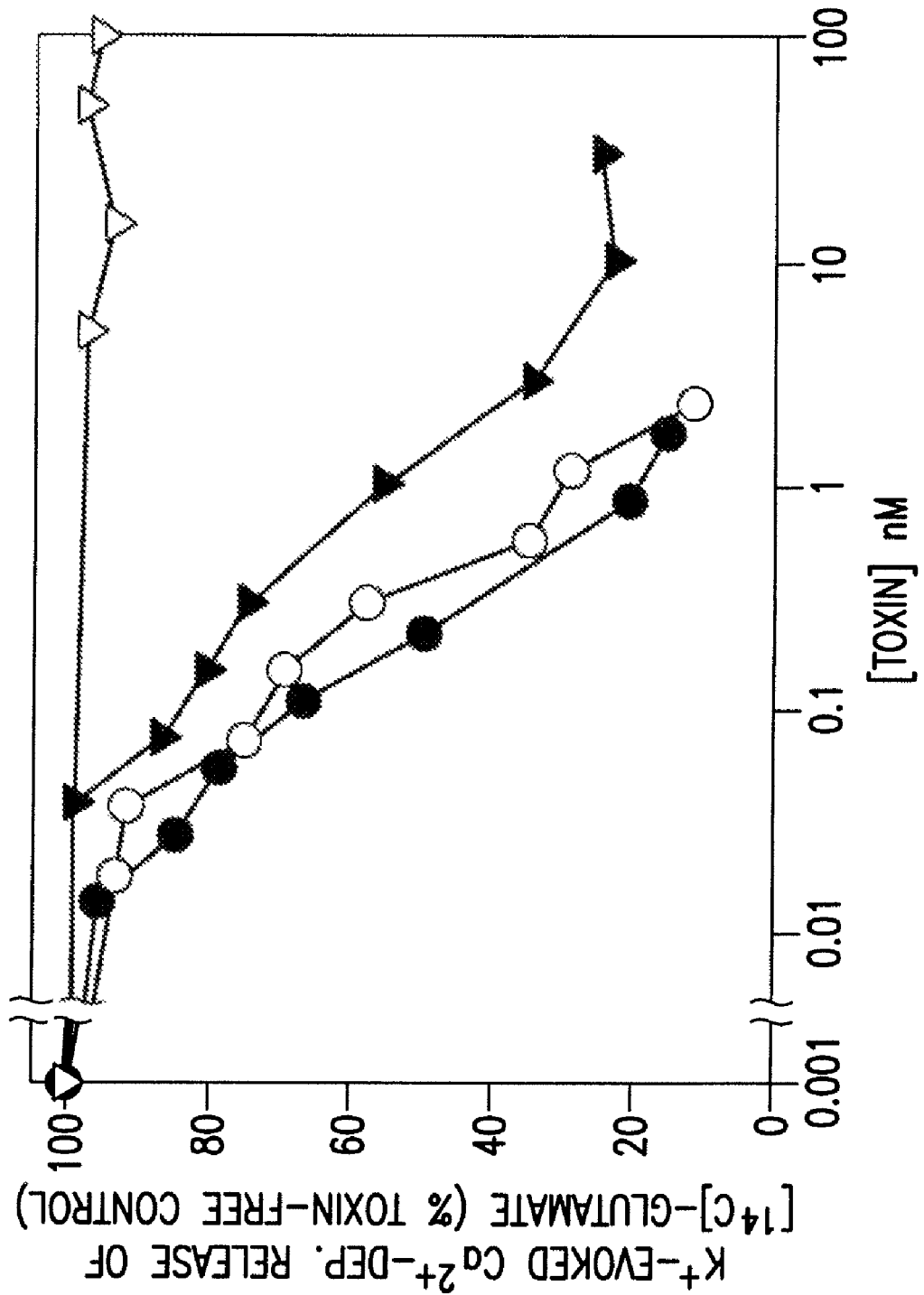
FIG. 8 shows the effect upon $Ca^{++}$-dependent neurotransmitter release of cerebellar neurons upon exposure to native, recombinant E234A mutant single-chain, and the recombinant R496G mutant single-chain TeNT.

FIG. 8 demonstrates the ability of the recombinant toxin to inhibit neurotransmitter release. Cerebellar neurons, maintained for 10 days in vitro, were washed twice with ice-cold KRH buffer containing 5 mM $Mg^{2+}$ and 0.5 mM $Ca^{2+}$, then exposed in this buffer to the specified concentrations of (●) native TeNT, (○) EK-nicked TeNT R496G, (▼) single-chain unnicked TeNT, or (▽) EK-nicked TeNT E234A for 60 min at 4° C. (see FIG. 8). Native TeNT (0.2 nM) was then added to the wells specified and, after an additional 30 min, the neurons were washed three times with ice-cold KRH buffer and incubated for 30 min at 37° C. Subsequent assessment of $K^+$-evoked $Ca^{2+}$-dependent neurotransmitter release was performed as detailed above. The results of this assay are shown in FIG. 8.

When cerebellar neurons are exposed to nicked recombinant TeNT, a dose-dependent inhibition of $Ca^{++}$ dependent transmitter release is seen with a potency similar to the native toxin. Nicked recombinant SC TeNT, both WT and R496G, gave similar values in this assay. Thus, while toxin activity in the unnicked single-chain molecule is not abrogated through the removal of a single trypsin cleavage site, the removal of additional such sites is feasible in regions of the single-chain toxin to achieve an activatable single-chain proform of the toxin that exhibits even lower toxicity unless activated in vitro, when its full activity can be achieved.

Example 6

Protease-Deficient TeNT Mutant Antagonises the Actions of TeNT on Peripheral and Central Neurons Table 3 shows the tabulated results of the indicated TeNT constructs tested in three assays of toxin activity: ability to cleave the HV62 peptide (which measures proteolytic activity only); neuromuscular paralysis (which is an indication of the toxin molecules' ability to enter the cell and thence to inhibit neurotransmitter release), and mouse lethality upon intraperitoneal injection of the various toxin constructs. The first two of these assays was performed as described above.

The mouse lethality assay was performed essentially as follows: Samples of recombinant purified single-chain TeNT, R496G mutant TeNT, and E234A mutant TeNT are each divided into two aliquots and one aliquot treated with enterokinase to nick the toxin. All samples are serially diluted into 50 mM phosphate buffer (pH 7.0), 150 mM NaCl and 0.25% (w/v) bovine serum albumin (BSA), and the toxin preparations are injected into mice intraperitoneally.

As shown in Table 3, the native and nicked TeNT preparations were comparably active in the mouse lethality assay, having an $LD_{50}$ of about $1 \times 10^8$/mg. The unnicked recombinant toxin and unnicked R496G mutant were both about half as active. Finally, the nicked E234A proteolytically inactive toxin was less than $5 \times 10^7$ fold less active.

TABLE 3

Biological Adivity of SC TeNT wild type and mutants (E234A and R496G) before and after nicking with enterokinase

| Purified TeNT preparations | Initial rate of cleavage[a] of HV62 (nmol · $min^{-1}mg^{-1}$) [Relative rate (%)] | Mouse lethality[b] (LD50/mg) | Time (min.) for 10 nM to cause 90% neuromuscular paralysis |
|---|---|---|---|
| Native | 20.3 ± 0.91 | $1 \times 10^8$ | 145 |
| Un-nicked SC WT | 8.0 ± 0.03 | $0.5 \times 10^8$ | 260 |
| Nicked[c] SC WT | 22.7 ± 3.37 | $1 \times 10^8$ | 150 |
| Un-nicked SC R496G | 11.7 ± 0.6 | $0.5 \times 10^8$ | 250 ± 15 |
| Nicked[c] SC R496G | 52.3 ± 4.9 | $1 \times 10^8$ | 135 ± 10 |
| Un-nicked SC E234A | ≦0.01[d] | Not tested | Not tested |
| Nicked[c] SC E234A | ≦0.01[d] | <50 | No detectable activity |

[a]Initial rates of proteolysis were measured using the RP-HPLC-based method detailed in Foran et al. (1994). Incubations with 15 μM of a synthetic peptide corresponding to residues 33 to 94 of human VAMP-2 (HV62) were performed at 37° C. in 50 mM HEPES, NaOH pH 7.5 containing 2 mM DTT 0.2 mg · $ml^{-1}$ BSA and 50 μM $ZnCl_2$, using the appropriate concentration of each reduced toxin preparation required to proteolyze 10-15% of the substrate during a 30 min period. Data are means (±S.D.; n = 4).
[b]$LD_{50}$ is the amount of toxin that killed 50% of the injected mice within 4 days.
[c]Toxin preparations were nicked with EK (1 unit/30 μg) at 22° C. for 1 h.
[d]This v° value represents the detection limits of the RP-HPLC assay; no proteolysis of HV62 was observed using prolonged incubations.

Purified SC E234A TeNT, in which the catalytic E at position 234 was replaced by an A, failed to show any detectable proteolysis of a peptide containing residues 33 to 94 of human VAMP-2 (termed HV62), either before or after nicking with EK. Accordingly, nicked TeNT E234A proved to be devoid of toxicity in mice and unable to inhibit transmitter release at the neuromuscular junction or from cerebellar neurons.

Importantly, however, this mutant toxin retained the ability to bind to the cell surface receptors on peripheral and central neurons. Pre-incubation of cerebellar neurons with nicked (10-60 nM) or unnicked (7-40 nM) TeNT E234A at 4° C. followed by the addition of 0.2 nM native toxin, antagonized the native toxin's inhibition of transmitter release at 37° C. to similar extents (FIG. 7).

Figure 9:
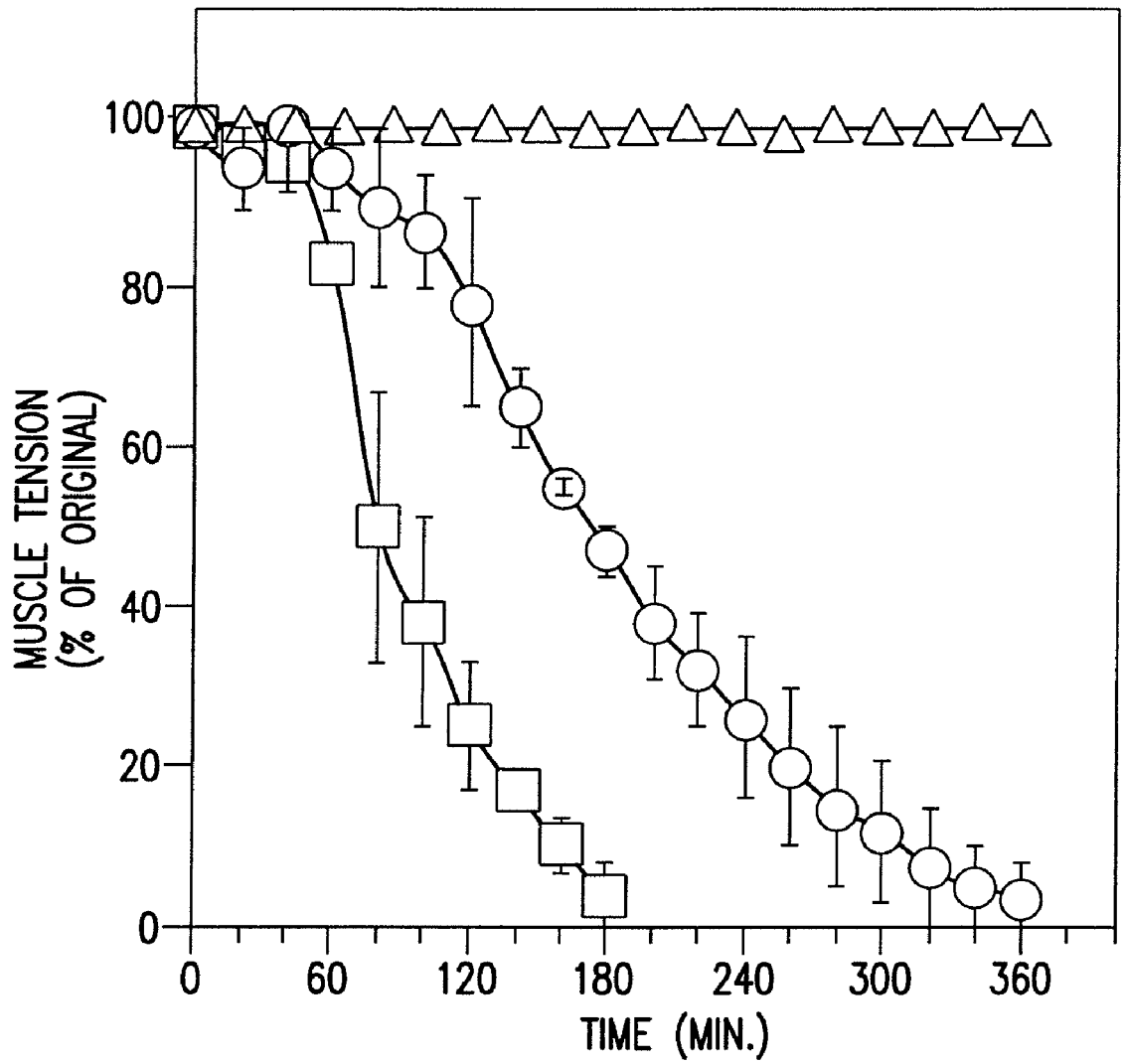
FIG. 9 shows the inhibitory effect upon TeNT-stimulated paralytic activity of preincubating mouse hemi diaphrams with the E234A mutant TeNT.

As demonstrated in FIG. 9, exposure of mouse diaphragm to 100 nM TeNT E234A at 4° C. for 60 minutes prior to adding 1 nM native toxin prolonged the time taken to cause neuromuscular paralysis.

Mouse phrenic-nerve hemi-diaphragm was incubated in KR at 37° C. with 20 nM recombinant TeNT E234A (Δ) whilst stimulating the nerve (0.2 Hz, 1.5-2.5 v) and recording muscle tension. For assessing competition, hemi-diaphragms were incubated for 60 minutes at 4° C. with MKR containing 0.1% BSA only (□), or the latter plus 100 nM nicked TeNT E234A (○), before the addition of 1 nM native TeNT. Following 30 minutes exposure to the latter, the tissues were washed three times with MKR and twice with KR. The temperature was raised to 37° C. and the nerve stimulated with recording of the evoked muscle twitch, as outlined above. This apparent competition for toxin binding by the mutant seen with both tissues demonstrates that the recombinant di-chain TeNT exhibits much higher affinity for the cell surface receptors than the heavy chain or H, of TeNT alone. These results suggest that the conformation of the recombinant di-chain TeNT has high affinity to the cell surface receptor.

Moreover, and very significantly, these data demonstrate that recombinant molecules can be made according to the inventive methods of the present patent application having specific binding for the same cellular receptor as TeNT. However, such molecules may, like the E234A mutant, be inactive as toxin molecules but will retain the ability to be taken up by the target cell; thus serving as potential transporter molecules.

Example 7

Expression of Single-Chain BoNT/A

Using methods similar to those described above, DNA fragments containing the BoNT subtype A neurotoxin H and L chains were ligated together, separated by the EK cleavage site. This single-chain toxin coding sequence was inserted into a variety of expression vectors containing different N terminal sequences and promoters, as shown in Table 4, below.

TABLE 4

| Vector | Promoter | Fusion Tag | Tag Size (amino acids) | Fusion Size (kDa) | E. coli strain |
|---|---|---|---|---|---|
| pTrcSCPHY | trc | Poly His | 18 | 150 | JM109 |
| pCalSCPHY | T7 | Calmodulin binding protein | 31 | 154 | BL21 (DE3) |
| pETSCPHY | T7 | Poly His | 32 | 154 | BL21 (DE3) |
| pGEXSCPHY | tac | Glutathione-S-tranferase | 224 | 177 | JM109 |
| pMALPHY | tac | Maltose Binding Protein | 390 | 193 | JM109 |

The "fusion tags" each comprised a member of a specific binding complex as a purification aid and to improve the solubility and stability of the expressed protein. These plasmids were transformed into the E. coli strains indicated in Table 4 and expression of the single-chain toxin was monitored.

In another experiment, the single-chain BoNT/A construct was inserted into plasmid pMAL-c2 between the Bam HI and Hind III restriction sites, resulting in a coding sequence for a fusion polypeptide containing the maltose binding protein at the N terminus, followed by a Factor Xa cleavage site. Transformant JM 109 colonies were selected in Luria broth containing ampicillin. Expression was induced by the addition of IPTG to a final concentration of 0.3 mM. As for the TeNT construct, aliquots of the cell culture were collected before and after induction, the cells in each sample lysed by sonication, and the supernatant prepared for SDS-PAGE under both reducing and non-reducing conditions. Following electrophoresis to separate the proteins according to apparent molecular weight, the gel was subjected to a Western blot using an antibody raised against the H chain of BoNT/A. The Western blot resulted in the appearance of an immunologically reactive single-chain toxin band of apparent molecular weight approximately 200 kDa. Further modifications of the single-chain BoNT molecule to eliminate fortuitous protease cleavage sites (similar to those modifications made at the TeNT site labile to trypsin and Arg C protease, described above) will result in even greater stability of the single-chain BoNT/A molecule.

Example 8

Construction of a Plasmid Vector Expressing BoNT/E

A plasmid expressing a single-chain recombinant version of the neurotoxin from Clostridium botulinum subtype E (strain Beluga) (BoNT/E) was constructed as follows. PCR primers were designed based on the EMBL database cDNA sequence of the BoNT/E neurotoxin (Genbank accession number X62089) This nucleotide sequence is represented herein as SEQ ID NO: 76.

```
gaattcaagt agtagataat aaaaataatg ccacagattt ttattattaa taatgatata tttatctcta actgtttaac tttaacttat aacaatgtaa atatatattt gtctataaaa aatcaagatt acaattgggt tatatgtgat cttaatcatg
```

-continued

```
atataccaaa aaagtcatat ctatggatat taaaaaatat
ataaatttaa aattaggaga tgctgtatat gccaaaaatt
aatagtttta attataatga tcctgttaat gatagaacaa
ttttatatat taaaccaggc ggttgtcaag aattttataa
atcatttaat attatgaaaa atatttggat aattccagag
agaaatgtaa ttggtacaac cccccaagat tttcatccgc
ctacttcatt aaaaaatgga gatagtagtt attatgaccc
taattattta caaagtgatg aagaaaagga tagatttta
aaaatagtca caaaaatatt taatagaata aataataatc
tttcaggagg gatttatta gaagaactgt caaaagctaa
tccatatta gggaatgata atactccaga taatcaattc
catattggtg atgcatcagc agttgagatt aaattctcaa
atggtagcca agacatacta ttacctaatg ttattataat
gggagcagag cctgatttat ttgaaactaa cagttccaat
atttctctaa gaataatta tatgccaagc aatcaccgtt
ttggatcaat agctatagta acattctcac ctgaatattc
ttttagattt aatgataatt gtatgaatga atttattcaa
gatcctgctc ttacattaat gcatgaatta atacattcat
tacatggact atatggggct aaagggatta ctacaaagta
tactataaca caaaacaaa atcccctaat aacaaatata
agaggtacaa atattgaaga attcttaact tttggaggta
ctgatttaaa cattattact agtgctcagt ccaatgatat
ctatactaat cttctagctg attataaaaa aatagcgtct
aaacttagca aagtacaagt atctaatcca ctacttaatc
cttataaaga tgttttgaa gcaaagtatg gattagataa
agatgctagc ggaatttatt cggtaaatat aaacaaattt
aatgatattt ttaaaaaatt atacagcttt acggaatttg
atttacgaac taaatttcaa gttaaatgta ggcaaactta
tattggacag tataaatact tcaaactttc aaacttgtta
aatgattcta tttataatat atcagaaggc tataatataa
ataatttaaa ggtaaatttt agaggacaga atgcaaattt
aaatcctaga attattacac caattacagg tagaggacta
gtaaaaaaaa tcattagatt ttgtaaaaat attgtttctg
taaaaggcat aaggaaatca atatgtatcg aaataaataa
tggtgagtta ttttttgtgg cttccgagaa tagttataat
gatgataata taaatactcc taaagaaatt gacgatacag
taacttcaaa taataattat gaaaatgatt tagatcaggt
tattttaaat tttaatagtg aatcagcacc tggactttca
gatgaaaaat taaatttaac tatccaaaat gatgcttata
taccaaaata tgattctaat ggaacaagtg atatagaaca
acatgatgtt aatgaactta atgtattttt ctatttagat
gcacagaaag tgcccgaagg tgaaaataat gtcaatctca
cctcttcaat tgatacagca ttattagaac aacctaaaat
atatacattt ttttcatcag aatttattaa taatgtcaat
aaacctgtgc aagcagcatt atttgtaagc tggatacaac
aagtgttagt agatttact actgaagcta accaaaaag
tactgttgat aaaattgcag atattctat agttgttcca
tatataggtc ttgctttaaa tataggaaat gaagcacaaa
aaggaaattt taaagatgca cttgaattat taggagcagg
tattttatta gaatttgaac ccgagctttt aattcctaca
attttagtat tcacgataaa atctttttta ggttcatctg
ataataaaaa taaagttatt aaagcaataa ataatgcatt
gaaagaaaga gatgaaaaat ggaaagaagt atatagttt
atagtatcga attggatgac taaaattaat acacaattta
ataaagaaa agaacaaatg tatcaagctt tacaaaatca
agtaaatgca attaaaacaa taatagaatc taagtataat
agttatactt tagaggaaaa aaatgagctt acaaataaat
atgatattaa gcaaatagaa aatgaactta atcaaaaggt
ttctatagca atgaataata tagacaggtt cttaactgaa
agttctatat cctatttaat gaaaataata aatgaagtaa
aaattaataa attaagagaa tatgatgaga atgtcaaaac
gtatttattg aattatatta tacaacatgg atcaatcttg
ggagagagtc agcaagaact aaattctatg gtaactgata
ccctaaataa tagtattcct tttaagcttt cttcttatac
agatgataaa atttttaattt catattttaa taaattctt
aagagaatta aaagtagttc agttttaaat atgagatata
aaaatgataa atacgtagat acttcaggat atgattcaaa
tataaatatt aatggagatg tatataaata tccaactaat
aaaaatcaat ttggaatata taatgataaa cttagtgaag
ttaatatatc tcaaaatgat tacattatat atgataataa
atataaaat tttagtatta gttttgggt aagaattcct
aactatgata ataagatagt aaatgttaat aatgaataca
ctataataaa ttgtatgaga gataataatt caggatggaa
agtatctctt aatcataatg aaataatttg gacattcgaa
gataatcgag gaattaatca aaaattagca tttaactatg
gtaacgcaaa tggtatttct gattatataa ataagtggat
ttttgtaact ataactaatg atagattagg agattctaaa
ctttatatta tgggaaattt aatagatcaa aaatcaattt
taaatttagg taatattcat gttagtgaca atatattatt
taaaatagtt aattgtagtt atacaagata tattggtatt
agatatttta atatttttga taaagaatta gatgaaacag
```

-continued

```
aaattcaaac tttatatagc aatgaaccta atacaaatat tttgaaggat ttttggggaa attatttgct ttatgacaaa gaatactatt tattaaatgt gttaaaacca aataacttta ttgataggag aaaagattct acttaagca ttaataatat aagaagcact attcttttag ctaatagatt atatagtgga ataaaagtta aaatacaaag agttaataat agtagtacta acgataatct tgttagaaag aatgatcagg tatatattaa ttttgtagcc agcaaaactc acttatttcc attatatgct gatacagcta ccacaaataa agagaaaaca ataaaaatat catcatctgg caatagattt aatcaagtag tagttatgaa ttcagtagga aattgtacaa tgaattttaa aaataataat ggaaataata ttgggttgtt aggtttcaag gcagatactg tcgttgctag tacttggtat tatacacata tgagagatca tacaaacagc aatggatgtt tttggaactt tatttctgaa gaacatggat ggcaagaaaa ataaaaatta gattaaacgg ctaaagtcat aaattc
```

The forward primer had the following nucleotide base sequence:

(SEQ ID NO: 77)
CCC<u>GGATCC</u> CCA AAA ATT AAT AGT TTT AAT TAT AAT G where the BamHI endonuclease site is underlined and the sequence of the light chain minus the start codon is in bold. The inverse primer had the sequence:

(SEQ ID NO: 78)
CCC<u>CTGCAG</u> tca TTT TTC TTG CCA TCC ATG TTC TTC where the PstI endonuclease site is underlined, the end of the coding region of the heavy chain is in bold, and the stop codon is in lower case. These primers were made using standard DNA synthesis methodology.

The two primers were used in a PCR reaction containing different amounts of *Clostridium botulinum* type E (strain beluga) chromosomal DNA. The PCR reaction employed a DNA polymerase with proofreading activity (Pfx DNA polymerase, obtained from Life Technology) in order to avoid sequence errors in the amplified gene. The amplification reaction conditions were as follows: 30 cycles of: a 45 second denaturation at 95° C., followed by a 45 second annealing step at 56° C., followed by a primer extension reaction for 3 minutes 48 seconds at 68° C.

The PCR product was digested with BamHI and HindIII, and the digest subjected to agarose gel electrophoresis. Staining of the agarose gel with ethidium bromide revealed a major DNA fragment of approximately 3.5 kilobases (see FIG. 10). The band containing this fragment was excised from the gel, and the DNA purified from the agarose and ligated to BamHI and HindIII-cut pQE30 vector (Qiagen). The resulting ligated plasmid was used to transform *E. coli* strain JM 109 as described above, and the transformants plated onto selective LB agar plates. Several clones were recovered and the presence of the correct BoNT/E DNA insert checked by restriction digest. The resultant construct contains the BoNT/E gene (minus the first methionine) fused to the $His_6$ tag of the pQE30 vector, and contains 2 extra amino acid residues (glycine, serine), which are contributed by the engineered BamHI site.

Example 9

Construction of a Proteolytically-Inactive Mutant of BoNT/E by Site Directed Mutagenesis By mutating the glutamic acid at position 212 (within the active site) of the BoNT/E polypeptide construct to glutamine, a proteolytically-inactive and non-toxic single-chain BoNT/E polypeptide was obtained.

The glutamine replacement was introduced on the forward primer using routine site directed mutagenesis methods. The mutagenic DNA primer had the sequence cagTTAATACATTCATTA CATGGACTATATG (SEQ ID NO: 79), where the codon encoding glutamine at position 212 is indicated in small letters. An inverse PCR reaction was performed using the above primer, along with the reverse primer ATGCATTAATGTAAGAGCAGGATCTT (SEQ ID NO: 80) and Pfx DNA polymerase (Life Technology) as above. The PCR template was the wild-type single-chain BoNT/E construct (termed pQEESCwt). The cycling parameters (30 cycles) were as follows: 1) a 45 second denaturation step at 95° C.; 2) a 45 second annealing step at 56° C.; and 3) a 7 minute 10 second extension step at 68° C.

Figure 11:
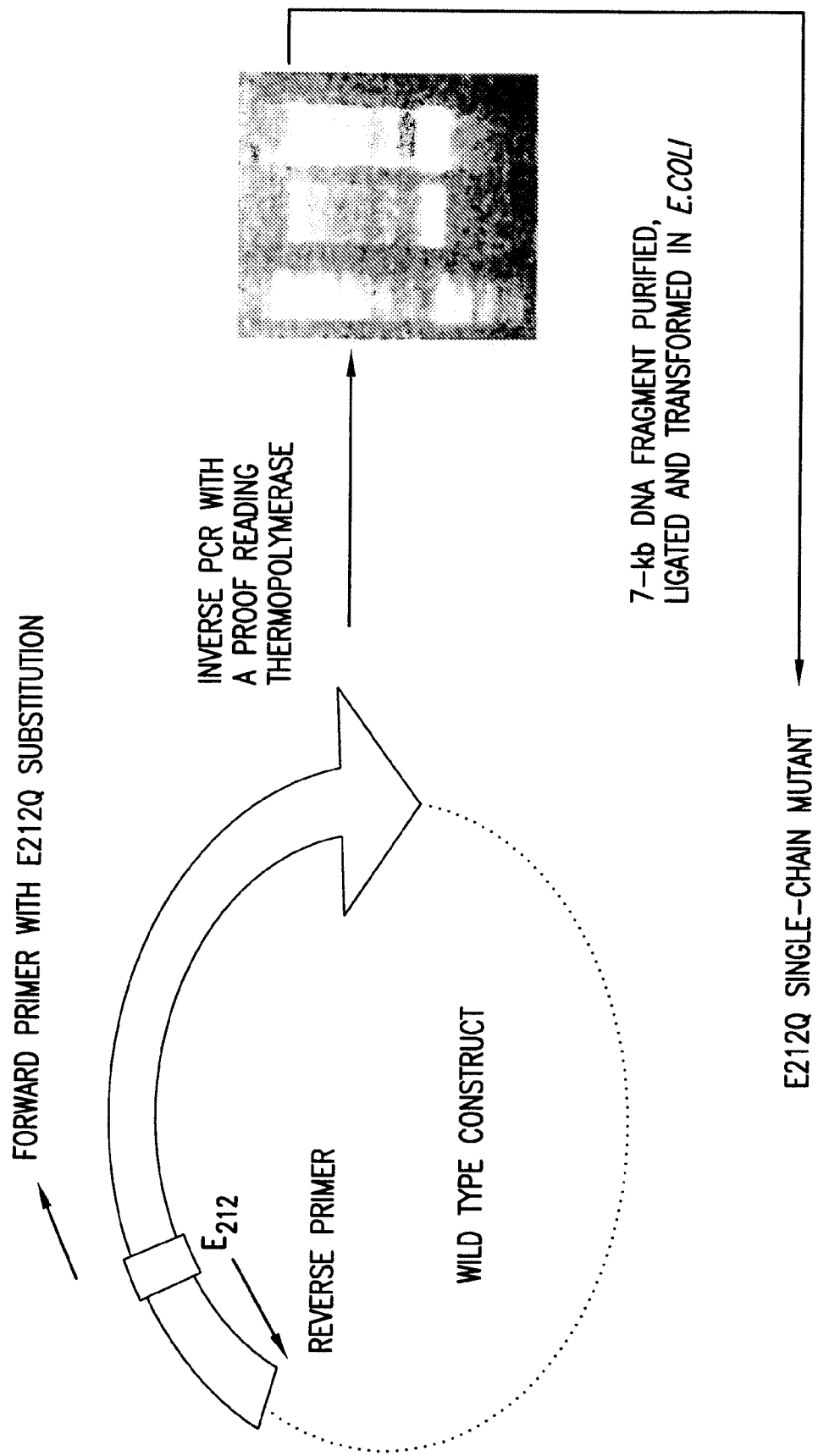
FIG. 11 shows the scheme for construction of a plasmid encoding the E212Q proteolytically inactive single-chain BoNT/E mutant, and an agarose gel electrophoretogram of the inverse PCR fragment obtained during the construction of the plasmid.

At the end of the amplification reaction, the DNA template was digested by the restriction enzyme DpnI to permit selection of mutated clones only. After subjecting the PCR product to agarose gel electrophoresis, a band of approximately 7 kilobases was removed and the DNA purified and used for self-ligation in the presence of T4 DNA ligase (Promega) and polynucleotide kinase (Promega) to permit phosphorylation of the PCR product. The ligation mixture was used to transform *E. coli* strain DH10B, and the transformants plated onto selective agar plates. The presence of the correct plasmid construct was verified in several representative transformants by restriction digest and the mutation confirmed also by DNA sequencing. FIG. 11 shows the protocol for construction of the mutant BoNT/E plasmid, and an ethidium bromide-stained agarose gel of the PCR reaction mixture (lanes 2 and 3) versus molecular weight markers (lane 1).

Example 10

Purification of Single-Chain Recombinant BoNT/E

The presence of the histidine tag at the N-terminus of the expressed protein allowed a single-step purification of the recombinant neurotoxin by metal-affinity chromatography.

The *E. coli* strain M15 (Qiagen) was used for expression of the BoNT/E single-chain construct. This strain carries an endogenous plasmid (pREP4, kanamycin resistant) containing a region encoding the lac $I^q$ repressor gene in order to prevent transcription of the neurotoxin gene prior to induction with IPTG. The pQE30 vector contain a T5 bacteriophage RNA polymerase promoter, which is also recognized by *E. coli* RNA polymerase.

A colony of M15 cells containing pQEESCwt was grown at 37° C. overnight in 5 ml of 2TY medium containing 0.1 mg/ml ampicillin; 0.025 mg/ml kanamycin and 0.2% glucose (w/v), and the resultant culture used to inoculate 500 ml of the same medium. When this second culture reached an optical density of 0.5-0.8 at 600 nm, IPTG was added to a final concentration of 0.3 mM and the culture incubated at 25° C. overnight to permit expression of the neurotoxin.

Subsequent centrifugation of the culture yielded ~2.3 g of wet cell pellet which was resuspended in 10 ml of extraction buffer (20 mM Hepes pH 7.0, 300 mM NaCl, 5 mM benzamidine, 2 µM pepstatin and 2 µM E-64). Lysozyme was added to a final concentration of 0.25 mg/ml, and the cell suspension incubated on ice for 60 minutes. Approximately 0.5 ml of glass beads (0.1 mm diameter from Biospec) was added to the cell suspension, followed by vortexing for 2 minutes to break the cells. Cell-free extracts was obtained by centrifugation at 10,000×g for 30 minutes at 4° C. The supernatant was incubated with 0.5 ml of Talone cobalt metal affinity resin (Clontech) pre-washed with extraction buffer in a rocking platform for 45 minutes at 4° C. The resin was then loaded into a disposable chromatography column and washed twice with 10 bed volumes of wash buffer (20 mM Hepes pH 7.0, 300 mM NaCl, 2 mM imidazole) before eluting the bound neurotoxin in 6 bed volumes of elution buffer (20 mM Hepes pH 7.0, 300 mM NaCl, 150 mM imidazole).

The elute was dialyzed overnight at 4° C. against 10 mM Hepes (pH 7.0) containing 150 mM NaCl and concentrated by centrifugal filtration (MW cutoff 10 KDa) to a final concentration of 1 mg/ml protein.

Figure 12:
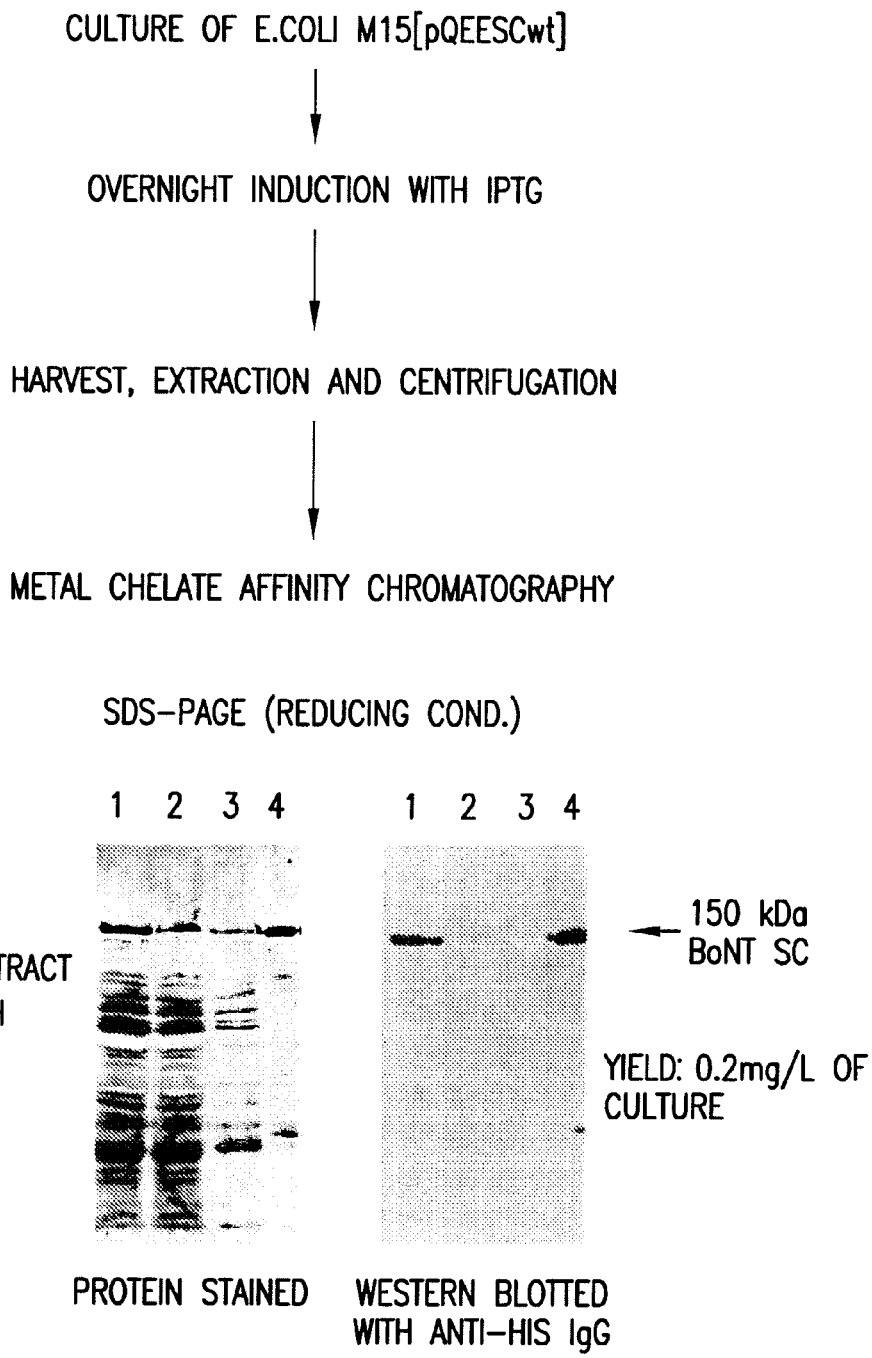
FIG. 12 shows the expression and purification scheme for recombinant single-chain BoNT/E, and a SDS-PAGE electrophoretogram and Western blot of the purification fractions.

As shown in FIG. 12, the purity of the affinity-purified toxin was demonstrated by SDS-PAGE under reducing conditions, followed by Coomassie staining and Western-blotting, detecting the N-terminus with a mouse monoclonal anti-His antibody from Quiagen (diluted 2000 fold). Enhanced Chemiluminescence solutions (Santa Cruz) and mouse secondary horseradish peroxidase (affinity purified from Sigma) were used for detection of bound antibody. Approximately 2 µg of protein samples were loaded per well.

Example 11

Trypsin Activation of Purified Recombinant BoNT/E Single-Chain Polypeptide

Figure 13:
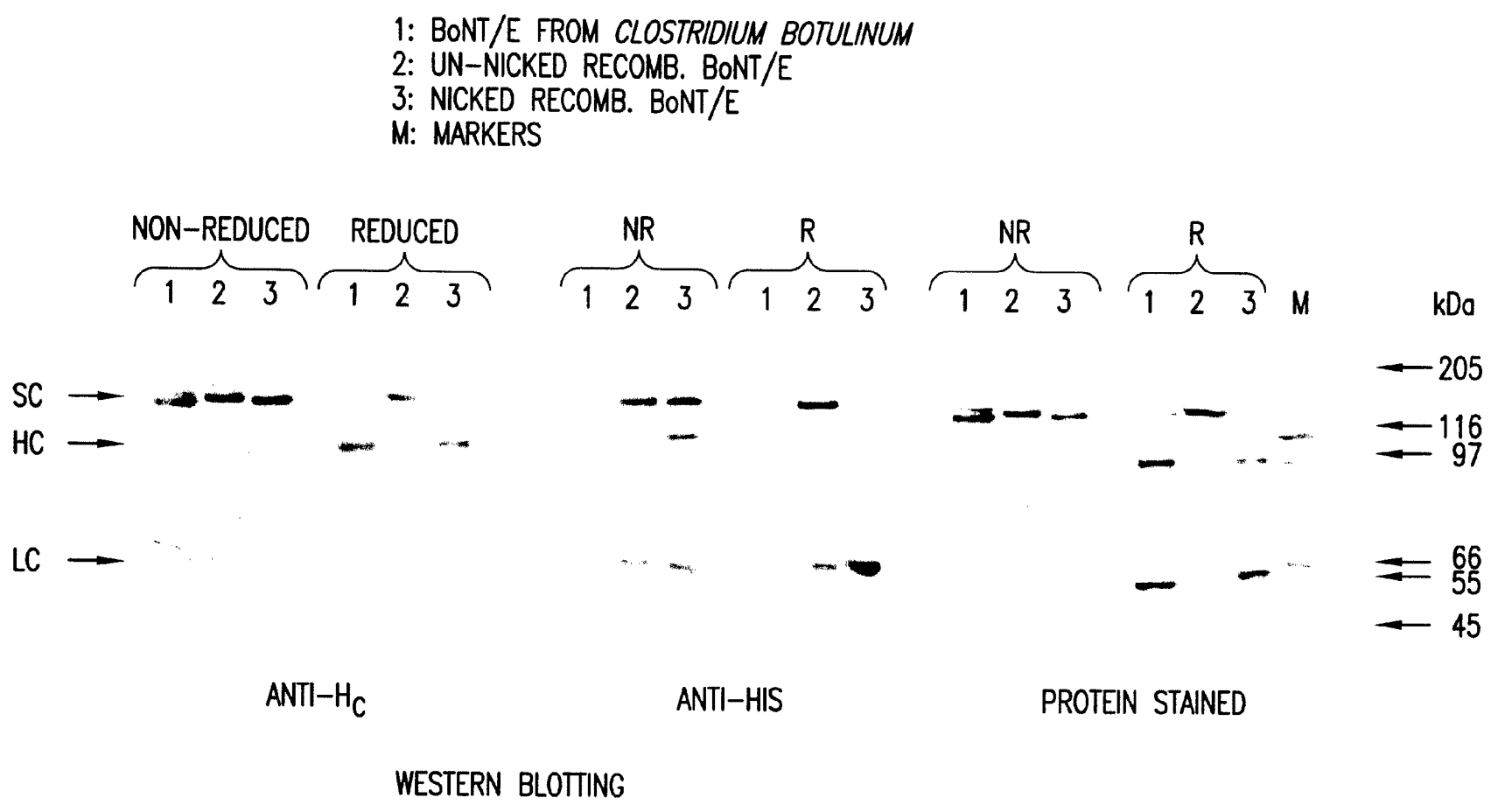

Purified BoNT/E single-chain neurotoxin polypeptide samples were activated by nicking the single-chain with trypsin (1.5 µg/ml final concentration) for 60 minutes at a concentration of 1 mg toxin/ml in 10 mm Hepes (pH 7.0), 150 mM NaCl. Following the reaction, the trypsin was inactivated using 0.5 mM PMSF and 10 µg trypsin inhibitor/ml. The quality of the trypsinization was assessed and verified by SDS-PAGE under both reducing and non-reducing conditions, then staining with Coomassie staining and Western blotting the polyacrylamide gel using a mouse monoclonal anti-His antibody (Quiagen, diluted 2000-fold) and a mouse monoclonal anti-$H_C$ IgG (diluted 26-fold). As shown in FIG. 13, the Commassie-stained nicked protein resolves into two bands under reducing conditions, while the heavy and light chains remain disulfide-linked under non-reducing conditions, similar to the native toxin. The antibody-detected recombinant heavy chain is of approximately identical size as its wild-type *Clostridium* counterpart, whereas the recombinant light chain migrates at a slightly higher molecular weight compared to the native protein. This latter characteristic is due to the extra residues provided by the $His_6$ tag at the N-terminus.

Example 12

Recombinant BoNT/E is Proteolytically Active

Stock solutions (1 µM) of native nicked BoNT/E toxin, un-nicked single-chain recombinant toxin, nicked di-chain recombinant toxin, and nicked mutant (E212Q) BoNT/E were prepared in HEPES-buffered saline (HBS, 150 mM NaCl, 10 mM HEPES, pH 7.4, 10 µg/ml BSA). These samples were incubated for 30 minutes at 37° C. in the absence or presence of 20 mM DTT, and then serially diluted in 0.02 ml of HBS to the final concentrations shown in FIG. 14.

A recombinant peptide containing amino acids 140-205 of SNAP-25 fused to glutathione-S-transferase (termed GST-SNAP-25 [140-205]) was used as a protease substrate to test the proteolytic activity of the recombinant BoNT/E polypeptides. Ten micrograms this protease substrate was incubated with the toxin samples. The digestion reaction was allowed to proceed for 30 minutes at 37° C. in the absence or presence of 2 mM DTT, and stopped by addition of SDS-PAGE sample buffer followed by boiling for 5 minutes.

Figure 14:
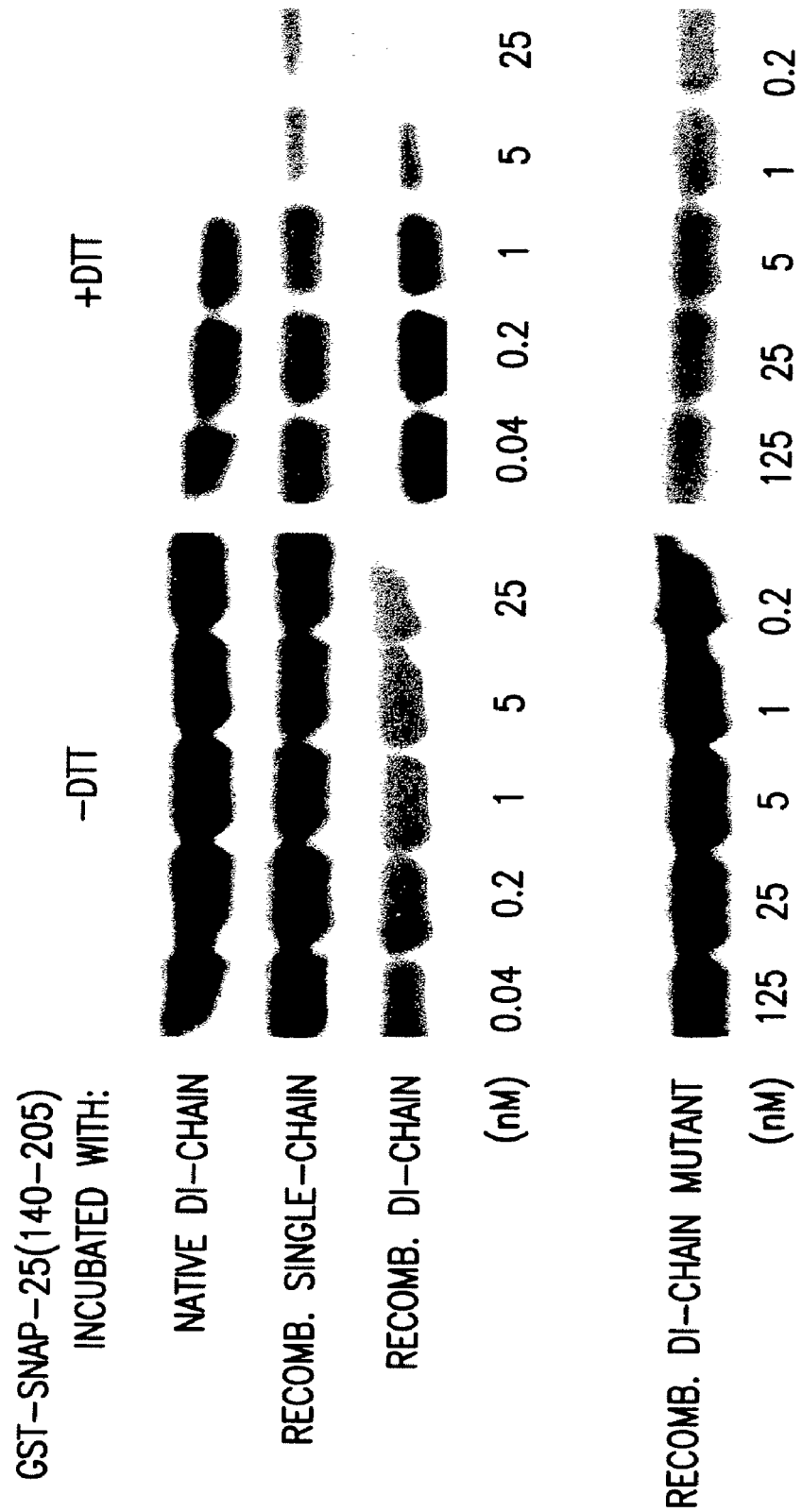
FIG. 14 shows the results of incubating native BoNT/E, recombinant nicked and un-nicked BoNT/E, and the E212Q mutant with a GST-SNAP-25[140-205] protease substrate.

The resultant samples were analyzed by SDS-PAGE (3 µg of GST-SNAP-25 [140-205] per lane) and silver staining. As FIG. 14 demonstrates, even unnicked recombinant single-chain toxin retains proteolytic activity. As expected, the mutant E212Q BoNT/E construct has no detectable proteolytic activity. FIG. 14 shows only the GST-SNAP-25[140-205] bands.

Example 13

Nicking Makes Recombinant BoNT/E Fully Functional

Cerebellar neurons maintained for 10 days in culture ($2 \times 10^6$/22 mm diameter well) were washed with Krebs-Ringer HEPES (KRH) buffer, then exposed to the specified concentrations of BoNT/E native (●), trypsin-nicked recombinant (○), or un-nicked single-chain (▼) BoNT/E. (See FIG. 15). After 60 minutes at 37° C., the toxin-containing buffer was removed and the cells were washed twice, then incubated with KRH buffer containing 0.25 µCi/ml [$^{14}$C]-labeled glutamine (i.e. the glutamate precursor). After 45 minutes, the latter medium was removed and the neurons were washed four times at 37° C. prior to assessment of transmitter glutamate release. Control and toxin-treated neurons were incubated for 5 minutes at 37° C. in KRH buffer containing either 1.4 mM $Ca^{2+}$ or 0.5 mM EGTA to assess $Ca^{2+}$-independent release; aliquots were then removed for determination of their [$^{14}$C]-glutamate content (see below).

Immediately after removal of the basal medium, KRH buffer containing 50 mM KCl and either 1.4 mM $Ca^{2+}$ or 0.5 mM EGTA was added; as before, aliquots were removed for [$^{14}$C]-glutamate assay after a 5 minute stimulation period. Finally, neurons were solubilized with 20 mM EGTA.NaOH pH 7.5 containing 1% (w/v) SDS and aliquots were removed to determine the amounts of radioactivity remaining within the cells. The amount of [$^{14}$C]-glutamate in each of the samples was assayed by scintillation counting and the levels released under basal and stimulated conditions were expressed as percentages relative to the calculated total cell content.

The percent [$^{14}$C]-glutamate content in the EGTA-containing buffer for each sample was subtracted from the values recorded in $Ca^{2+}$-containing KRH samples in order to obtain the $Ca^{2+}$-dependent component of release, and the latter basal readings were subtracted from values obtained for 50 mM KCl samples to yield $K^+$-evoked $Ca^{2+}$-dependent release. The values, thus, obtained from toxin-treated neurons are expressed relative to toxin-free controls.

Figure 15:
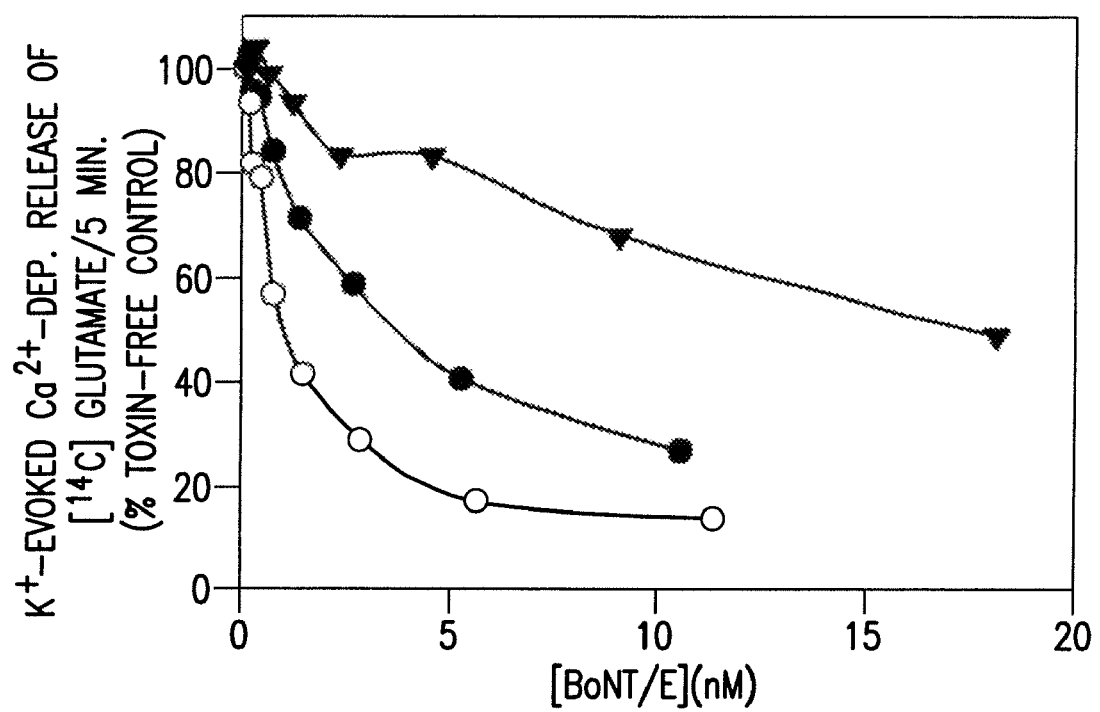
FIG. 15 shows the effect upon Ca++-dependent glutamate release of incubating cerebellar cells with native BoNT/E, un-nicked recombinant single-chain BoNT/E, and nicked recombinant single-chain BoNT/E.

FIG. 15 shows that, despite retaining proteolytic activity, the un-nicked recombinant BoNT/E has markedly less activity than either the native BoNT/E or the nicked recombinant version. This finding may reflect the inability of the un-nicked toxin to adequately enter the target cell. Additionally, the nicked recombinant version appears to be more effective in inhibiting glutamate release than the native toxin.

Example 14

Figure 16A:
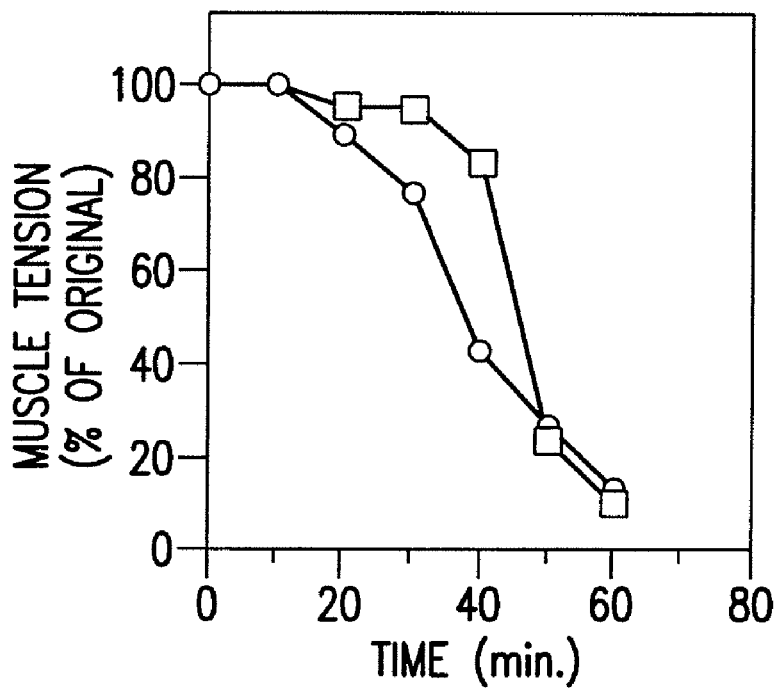
FIG. 16A shows the effects on muscle tension of incubating mouse phrenic-nerve hemi-diaphragms with 0.2 nM recombinant nicked BoNT/E (○) or 0.2 nM native BoNT/E (□).
Figure 16B:
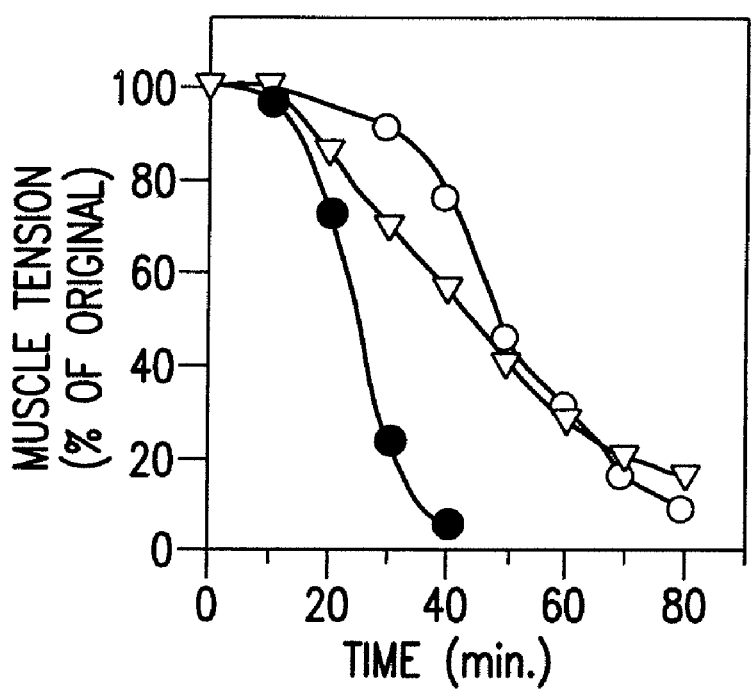
FIG. 16B shows the effects on muscle tension of incubating mouse phrenic-nerve hemi-diaphragms with 1 nM recombinant un-nicked (○), 1 nM recombinant nicked (●) or 0.05 nM recombinant nicked (∇) BoNT/E.

Recombinant BoNT/E has a Neuromuscular Paralytic Activity Equivalent to that of the Native Toxin at Mouse Neuromuscular Endplates Nicking Increases Potency Mouse phrenic-nerve hemi-diaphragms were bathed in KR supplemented with 0.1% BSA and saturated with 95% $O_2$/5% $CO_2$. The phrenic nerves were stimulated (0.2 Hz, 1.5-2.5 mV) and nerve evoked muscle tension was recorded before and after the addition of (FIG. 16A) 0.2 nM recombinant nicked BoNT/E (○) or 0.2 nM native BoNT/E (□), and (FIG. 16B) 1 nM recombinant un-nicked (○), 1 nM recombinant nicked (●) or 0.05 nM recombinant nicked (∇) BoNT/E. As shown in FIGS. 16A and 16B, the recombinant nicked BoNT/E is an effective paralytic agent, displaying greater activity in this assay that the native toxin. The un-nicked toxin displays significantly lower activity than the nicked toxin in this assay.

The neuromuscular paralytic activity of recombinant nicked BoNT/E was also demonstrated in mice by intramuscular injection into hind-limb muscles. This resulted in paralysis, as assessed by the toe spread reflex assay, with a pattern of symptoms typical of botulism.

The in vivo neurotoxicity of the nicked, recombinant neurotoxin was established, by injecting the toxin into mice, to have a specific neurotoxicity of less than $10^7$ mouse $LD_{50}$ units per mg.

Example 15

Figure 17:
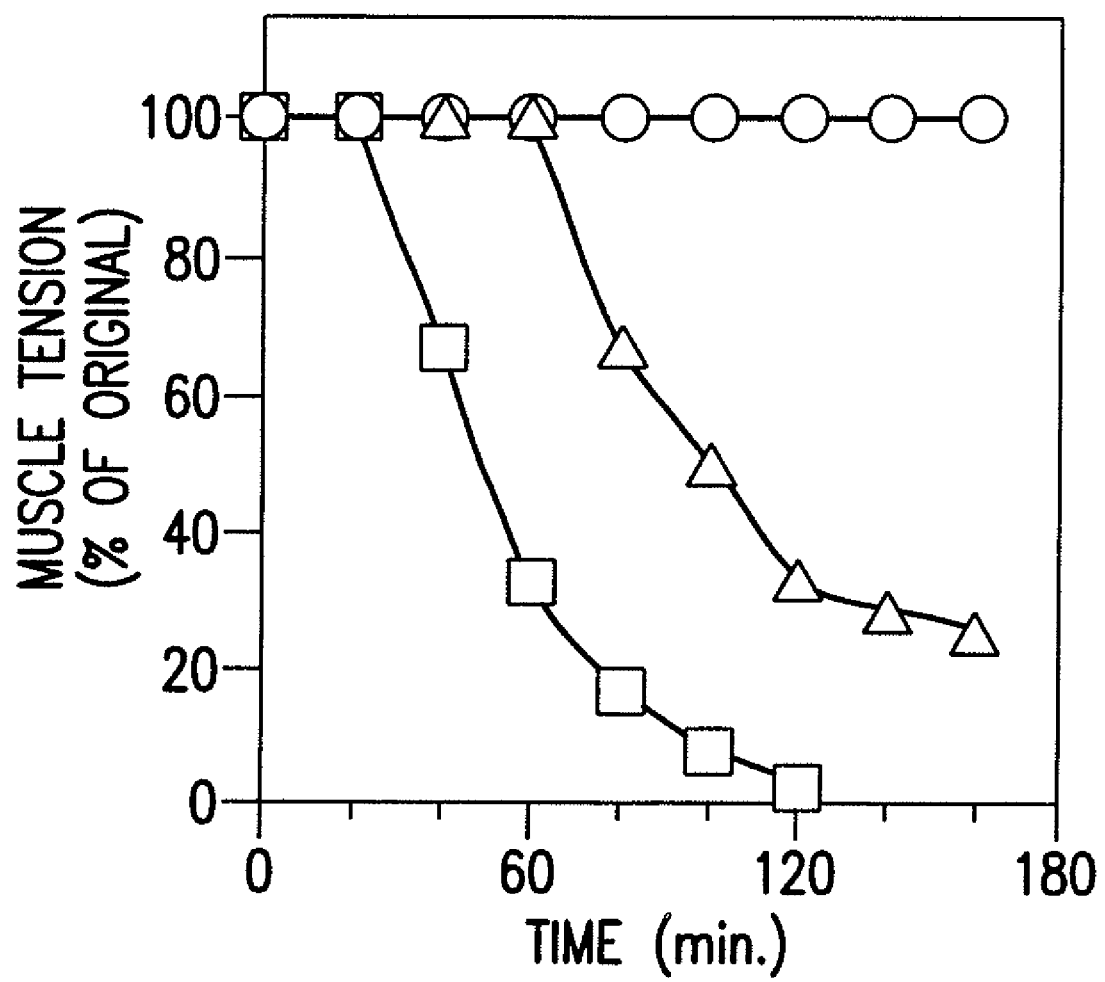
FIG. 17 shows the attenuation of paralytic activity on mouse phrenic-nerve hemi-diaphragms of preincubation with the inactive E212Q mutant prior to exposure to native nicked BoNT/E toxin.
Figure 19:
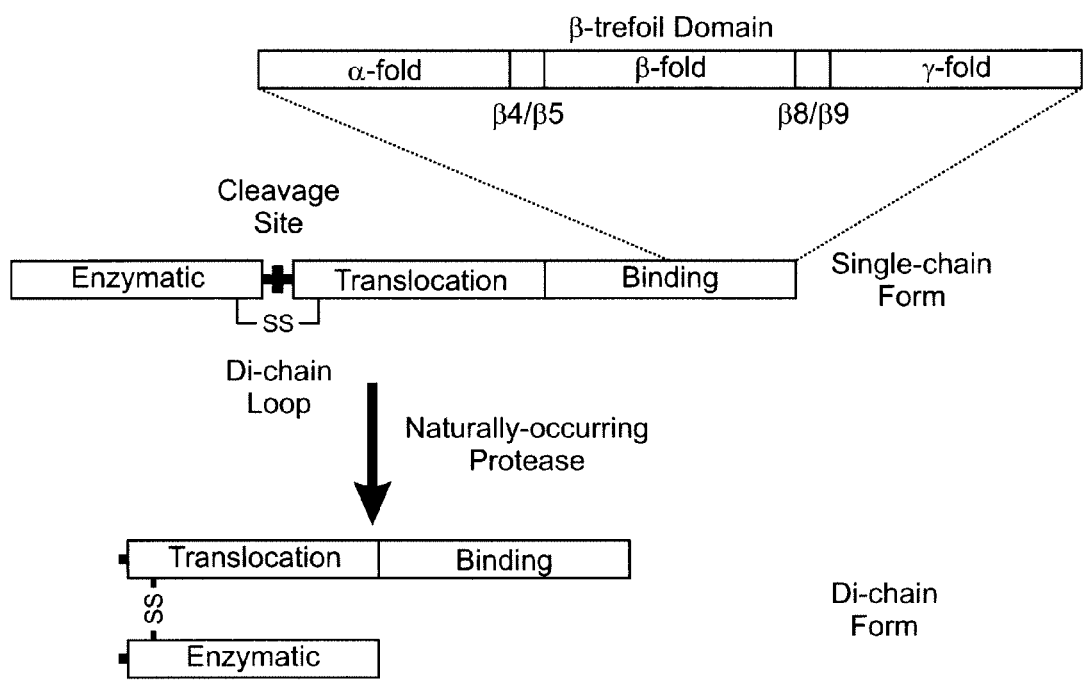
FIG. 19 shows the domain organization of naturally-occurring Clostridial toxins. The single-chain form depicts the amino to carboxyl linear organization comprising an enzymatic domain, a translocation domain, and a binding domain. The di-chain loop region located between the translocation and enzymatic domains is depicted by the double SS bracket. This region comprises an endogenous di-chain loop protease cleavage site that upon proteolytic cleavage with a naturally-occurring protease, such as, e.g., an endogenous Clostridial toxin protease or a naturally-occurring protease produced in the environment, converts the single-chain form of the toxin into the di-chain form. Above the single-chain form, the $H_{CC}$ region of the Clostridial toxin binding domain is depicted. This region comprises the β-trefoil domain which comprises in a amino to carboxyl linear organization an α-fold, a β4/β5 hairpin turn, β-fold, a β8/β9 hairpin turn and a γ-fold.

The BoNT/E E212Q Protease Inactive Mutant Antagonises BoNT/E-Induced Neuroparalysis A mouse phrenic-nerve hemi-diaphragm was exposed to 10 nM BoNT/E E212Q in KR medium, the nerve was stimulated and evoked muscle tension was recorded. As indicated by FIG. 17, the BoNT E212Q mutant does not inhibit neurotransmission, as determined by its failure to reduce nerve-evoked muscle tension (○). To assess the ability of this non-toxic mutant to antagonise the activity of the native toxin, mouse phrenic-nerve hemi-diaphragms were bathed for 60 minutes at 4° C. in MKR supplemented with 0.1% BSA and saturated with 95% $O_2$/5% $CO_2$, without (□) or with (Δ) the inclusion of 5 nM BoNT/E E212Q. Native nicked BoNT/E was added to each bath (0.05 nM final) and the tissues were incubated for a further 30 min. The nerve-muscles were then washed three times each with MKR followed by KR, before the temperature was raised to 37° C., the nerve stimulated and evoked muscle tension recorded.

As shown in FIG. 17, the onset of native BoNT/E activity in this assay was delayed and antagonized when the phrenic-nerve hemi-diaphragms are preincubated with the E212Q protease inactive mutant, thereby indicating that the recombinant mutant faithfully binds to the same cell surface receptor as does the native toxin. Thus, the methods of the present patent application can be used to produce recombinant and modified toxins having fully functional receptor binding domains, and BoNT-related transported molecules for the intracellular delivery of therapeutic agents.

Example 16

Construction of an Activatable Clostridial Toxin Comprising an Amino-Terminally Presented Binding Element This example illustrates how to make an activatable Clostridial toxin disclosed in the present specification comprising a binding element located at the amino terminus of the modified toxin.

16a. A Binding Element-Translocation Element-Exogenous Protease Cleavage Site-Therapeutic Element Organization.

A polynucleotide molecule based on BoNT/A-TEV-αMSHAP4A (SEQ ID NO: 124) will be synthesized using standard procedures (BlueHeron® Biotechnology, Bothell, Wash.). This polynucleotide molecule encodes a BoNT/A modified to replace amino acids 872-1296 of SEQ ID NO: 1, a BoNT/A $H_C$ binding element, with SEQ ID NO: 81, an αMSH peptide and to incorporate a TEV protease site of SEQ ID NO: 24 within the di-chain loop region, arranged in an amino to carboxyl linear organization as depicted in FIG. 20A. The In addition, the altered binding element further comprises at its amino terminus, a PAR 1 leader sequence ending in an enterokinse cleavage site, which, upon cleavage, results in exposing the first amino acid of the αMSH binding element. Oligonucleotides of 20 to 50 bases in length are synthesized using standard phosphoramidite synthesis. These oligonucleotides will be hybridized into double stranded duplexes that are ligated together to assemble the full-length polynucleotide molecule. This polynucleotide molecule will be cloned using standard molecular biology methods into a pUCBHB1 vector at the SmaI site to generate pUCBHB1/BoNT/A-TEV-αMSHAP4A. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.).

If desired, an expression optimized polynucleotide molecule based on BoNT/A-TEV-αMSHAP4A can be synthesized in order to improve expression in an *Escherichia coli* strain. The polynucleotide molecule encoding the BoNT/A-TEV-αMSHAP4A will be modified to 1) contain synonymous codons typically present in native polynucleotide molecules of an *Escherichia coli* strain; 2) contain a G+C content that more closely matches the average G+C content of native polynucleotide molecules found in an *Escherichia coli* strain; 3) reduce polymononucleotide regions found within the polynucleotide molecule; and/or 4) eliminate internal regulatory or structural sites found within the polynucleotide molecule, see, e.g., Lance E. Steward et al., Optimizing Expression of Active Botulinum Toxin Type E, International Patent Publication WO 2006/011966 (Feb. 2, 2006); Lance E. Steward et al., Optimizing Expression of Active Botulinum Toxin Type A, International Patent Publication WO 2006/017749 (Feb. 16, 2006). Once sequence optimization is complete, oligonucleotides of 20 to 50 bases in length are synthesized using standard phosphoramidite synthesis. These oligonucleotides are hybridized into double stranded duplexes that are ligated together to assemble the full-length polynucleotide molecule. This polynucleotide molecule is cloned using standard molecular biology methods into a pUCBHB1 vector at the SmaI site to generate pUCBHB1/BoNT/A-TEV-αMSHAP4A. The synthesized polynucleotide molecule is verified by sequencing using Big Dye Terminator™ Chemistry 3.1 (Applied Biosystems, Foster City, Calif.) and an ABI 3100 sequencer (Applied Biosystems, Foster City, Calif.). If so desired, expression optimization to a different organism, such as, e.g., a yeast strain, an insect cell-line or a mammalian cell line, can be done, see, e.g., Steward, supra, (Feb. 2, 2006); and Steward, supra, (Feb. 16, 2006).

A similar cloning strategy will be used to make pUCBHB1 cloning constructs for BoNT/B-TEV-αMSHAP4A, a modified BoNT/B where amino acids 861-1291 of SEQ ID NO: 2 are replaced with SEQ ID NO: 81; BoNT/C1-TEV-αMSHAP4A, a modified BoNT/C1 where amino acids 869-1291 of SEQ ID NO: 3 are replaced with SEQ ID NO: 81; BoNT/D-TEV-αMSHAP4A, a modified BoNT/D where amino acids 865-1276 of SEQ ID NO: 4 are replaced with SEQ ID NO: 81; BoNT/E-TEV-αMSHAP4A, a modified BoNT/E where amino acids 848-1252 of SEQ ID NO: 5 are replaced with SEQ ID NO: 81; BoNT/F-TEV-αMSHAP4A, a modified BoNT/F where amino acids 867-1274 of SEQ ID NO: 6 are replaced with SEQ ID NO: 81; BoNT/G-TEV-αMSHAP4A, a modified BoNT/G where amino acids 866-1297 of SEQ ID NO: 7 are replaced with SEQ ID NO: 81; TeNT-TEV-αMSHAP4A, a modified TeNT where amino acids 882-1315 of SEQ ID NO: 8 are replaced with SEQ ID NO: 81; BaNT-TEV-αMSHAP4A, a modified BaNT where amino acids 858-1268 of SEQ ID NO: 9 are replaced with SEQ ID NO: 81; and BuNT-TEV-αMSHAP4A, a modified BuNT where amino acids 848-1251 of SEQ ID NO: 10 are replaced with SEQ ID NO: 81.

Likewise, a similar cloning strategy will be used to make pUCBHB1 cloning constructs comprising a polynucleotide molecule encoding a modified Clostridial toxin-TEV-AP4A that will replace the $H_C$ binding element from a Clostridial toxin the with an binding element comprising, e.g., a melanocyte stimulating hormone comprising SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Likewise, a similar cloning strategy will be used to make pUCBHB1 cloning constructs comprising a polynucleotide molecule encoding a modified Clostridial toxin AP4A comprising an exogenous protease cleavage site incorporated within the di-chain loop region, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

To construct pET29/BoNT/A-TEV-αMSHAP4A, a pUCBHB1/BoNT/A-TEV-αMSHAP4A construct will be digested with restriction endonucleases that 1) will excise the polynucleotide molecule encoding the open reading frame of BoNT/A-TEV-αMSHAP4A; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-TEV-αMSHAP4A. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-TEV-αMSHAP4A operably-linked to a carboxyl terminal polyhistidine affinity binding peptide.

A similar cloning strategy will be used to make pET29 expression constructs for other modified Clostridial toxin-TEV-αMSHAP4A toxins, such as, e.g., BoNT/B-TEV-αMSHAP4A, BoNT/C1-TEV-αMSHAP4A, BoNT/D-TEV-αMSHAP4A, BoNT/E-TEV-αMSHAP4A, BoNT/F-TEV-αMSHAP4A, BoNT/G-TEV-αMSHAP4A TeNT-TEV-αMSHAP4AB, BaNT-TEV-αMSHAP4A, or BuNT-TEV-αMSHAP4A. Likewise, a similar cloning strategy will be used to make pET29 expression constructs comprising a polynucleotide molecule encoding a modified Clostridial toxin-TEV-AP4B comprising a binding element such as, e.g., a melanocyte stimulating hormone comprising SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Furthermore, a similar cloning strategy will be used to make pET29 expression constructs comprising a polynucleotide molecule encoding a modified Clostridial toxin-AP4A comprising an exogenous protease cleavage site incorporated within the di-chain loop region such as, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

16b. A Binding Element-Therapeutic Element-Exogenous Protease Cleavage Site-Translocation Element Organization.

A polynucleotide molecule based on BoNT/A-TEV-αMSHAP4B (SEQ ID NO: 125) will be synthesized and cloned into a pUCBHB1 vector as described in Example 17a. This polynucleotide molecule encodes a BoNT/A modified to replace amino acids 872-1296 of SEQ ID NO: 1, a BoNT/A $H_C$ binding element, with SEQ ID NO: 81, an αMSH peptide and to incorporate a TEV protease site of SEQ ID NO: 24 within the di-chain loop region, arranged in an amino to carboxyl linear organization as depicted in FIG. 20B. In addition, the altered binding element further comprises at its amino terminus, a PAR 1 leader sequence ending in an enterokinse cleavage site, which upon cleavage, results in exposing the first amino acid of the αMSH binding element. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

A similar cloning strategy will be used to make pUCBHB1 cloning constructs for BoNT/B-TEV-αMSHAP4B, a modified BoNT/B where amino acids 861-1291 of SEQ ID NO: 2 are replaced with SEQ ID NO: 81; BoNT/C1-TEV-αMSHAP4B, a modified BoNT/C1 where amino acids 869-1291 of SEQ ID NO: 3 are replaced with SEQ ID NO: 81; BoNT/D-TEV-αMSHAP4B, a modified BoNT/D where amino acids 865-1276 of SEQ ID NO: 4 are replaced with SEQ ID NO: 81; BoNT/E-TEV-αMSHAP4B, a modified BoNT/E where amino acids 848-1252 of SEQ ID NO: 5 are replaced with SEQ ID NO: 81; BoNT/F-TEV-αMSHAP4B, a modified BoNT/F where amino acids 867-1274 of SEQ ID NO: 6 are replaced with SEQ ID NO: 81; BoNT/G-TEV-αMSHAP4B, a modified BoNT/G where amino acids 866-1297 of SEQ ID NO: 7 are replaced with SEQ ID NO: 81; TeNT-TEV-αMSHAP4B, a modified TeNT where amino acids 882-1315 of SEQ ID NO: 8 are replaced with SEQ ID NO: 81; BaNT-TEV-αMSHAP4B, a modified BaNT where amino acids 858-1268 of SEQ ID NO: 9 are replaced with SEQ ID NO: 81; and BuNT-TEV-αMSHAP4B, a modified BuNT where amino acids 848-1251 of SEQ ID NO: 10 are replaced with SEQ ID NO: 81.

Likewise, a similar cloning strategy will be used to make pUCBHB1 cloning constructs comprising a polynucleotide molecule encoding a modified Clostridial toxin-TEV-AP4B that will replace the $H_C$ binding element from a Clostridial toxin the with an binding element comprising, e.g., a melanocyte stimulating hormone comprising SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Likewise, a similar cloning strategy will be used to make pUCBHB1 cloning constructs comprising a polynucleotide molecule encoding a modified Clostridial toxin-AP4B comprising an exogenous protease cleavage site incorporated within the di-chain loop region, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

To construct pET29/BoNT/A-TEV-αMSHAP4B, a pUCBHB1/BoNT/A-TEV-αMSHAP4B construct will be digested with restriction endonucleases that 1) will excise the polynucleotide molecule encoding the open reading frame of BoNT/A-TEV-αMSHAP4B; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-TEV-αMSHAP4B. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 μg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-TEV-αMSHAP4B operably-linked to a carboxyl terminal polyhistidine affinity binding peptide.

A similar cloning strategy will be used to make pET29 expression constructs for other modified Clostridial toxin-TEV-αMSHAP4B toxins, such as, e.g., BoNT/B-TEV-αMSHAP4B, BoNT/C1-TEV-αMSHAP4B, BoNT/D-TEV-αMSHAP4B, BoNT/E-TEV-αMSHAP4B, BoNT/F-TEV-αMSHAP4B, BoNT/G-TEV-αMSHAP4B, TeNT-TEV- αMSHAP4B, BaNT-TEV-αMSHAP4B, or BuNT-TEV-αMSHAP4B. Likewise, a similar cloning strategy will be used to make pET29 expression constructs comprising a polynucleotide molecule encoding a modified Clostridial toxin-TEV-AP4B comprising a binding element such as, e.g., a melanocyte stimulating hormone comprising SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Furthermore, a similar cloning strategy will be used to make pET29 expression constructs comprising a polynucleotide molecule encoding a modified Clostridial toxin-AP4B comprising an exogenous protease cleavage site incorporated within the di-chain loop region such as, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

Example 17

Construction of an Activatable Clostridial Toxin Comprising a Centrally Presented Altered Targeting Domain This example illustrates how to make an activatable Clostridial toxin disclosed in the present specification comprising a binding element located between two other domains of the modified toxin.

17a. A Therapeutic Element-Exogenous Protease Cleavage Site-Binding Element-Translocation Element Organization.

A polynucleotide molecule based on BoNT/A-ENT-NPYCP5A (SEQ ID NO: 126) will be synthesized and cloned into a pUCBHB1 vector as described in Example 17a. This polynucleotide molecule encodes a BoNT/A modified to replace amino acids 872-1296 of SEQ ID NO: 1, a BoNT/A $H_C$ binding element, with SEQ ID NO: 119, a NPY peptide and to incorporate a bovine enterokinse protease site of SEQ ID NO: 21 within the di-chain loop region, arranged in an amino to carboxyl linear organization as depicted in FIG. 21A. Cleavage of an enterokinse cleavage site used to form the di-chain toxin also exposes the first amino acid of the NPY binding element. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

A similar cloning strategy will be used to make pUCBHB1 cloning constructs for BoNT/B-ENT-NPYCP5A, a modified BoNT/B where amino acids 861-1291 of SEQ ID NO: 2 are replaced with SEQ ID NO: 119; BoNT/C1-ENT-NPYCP5A, a modified BoNT/C1 where amino acids 869-1291 of SEQ ID NO: 3 are replaced with SEQ ID NO: 119; BoNT/D-ENT-NPYCP5A, a modified BoNT/D where amino acids 865-1276 of SEQ ID NO: 4 are replaced with SEQ ID NO: 119; BoNT/E-ENT-NPYCP5A, a modified BoNT/E where amino acids 848-1252 of SEQ ID NO: 5 are replaced with SEQ ID NO: 119; BoNT/F-ENT-NPYCP5A, a modified BoNT/F where amino acids 867-1274 of SEQ ID NO: 6 are replaced with SEQ ID NO: 119; BoNT/G-ENT-NPYCP5A, a modified BoNT/G where amino acids 866-1297 of SEQ ID NO: 7 are replaced with SEQ ID NO: 119; TeNT-ENT-NPYCP5A, a modified TeNT where amino acids 882-1315 of SEQ ID NO: 8 are replaced with SEQ ID NO: 119; BaNT-ENT-NPYCP5A, a modified BaNT where amino acids 858-1268 of SEQ ID NO: 9 are replaced with SEQ ID NO: 119; and BuNT-ENT-NPYCP5A, a modified BuNT where amino acids 848-1251 of SEQ ID NO: 10 are replaced with SEQ ID NO: 119.

Likewise, a similar cloning strategy will be used to make pUCBHB1 cloning constructs comprising a polynucleotide molecule encoding a modified Clostridial toxin-ENT-CP5A that will replace the $H_C$ binding element from a Clostridial toxin the with an binding element comprising, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 120, SEQ ID NO: 121, SEQ ID NO: 122 or SEQ ID NO: 123.

Likewise, a similar cloning strategy will be used to make pUCBHB1 cloning constructs comprising a polynucleotide molecule encoding a modified Clostridial toxin-CP5A comprising an exogenous protease cleavage site incorporated within the di-chain loop region, e.g., a Tobacco Etch Virus protease cleavage site comprising SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63. In addition, a similar cloning strategy will be used to make pUCBHB1 cloning constructs comprising a polynucleotide molecule encoding a modified Clostridial toxin-CP5A comprising an exogenous protease cleavage site incorporated within the di-chain loop region, cleavage of which converts the single-chain polypeptide of the toxin into its di-chain form and also exposes the first amino acid of the binding element.

To construct pET29/BoNT/A-ENT-NPYCP5A, a pUCBHB1/BoNT/A-ENT-NPYCP5A construct will be digested with restriction endonucleases that 1) will excise the polynucleotide molecule encoding the open reading frame of BoNT/A-ENT-NPYCP5A; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-ENT-NPYCP5A. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 μg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-TEV-NPYCP5A operably-linked to a carboxyl terminal polyhistidine affinity binding peptide.

A similar cloning strategy will be used to make pET29 expression constructs for other modified Clostridial toxin-ENT-NPYCP5A toxins, such as, e.g., BoNT/B-ENT-NPYCP5A, BoNT/C1-ENT-NPYCP5A, BoNT/D-ENT-NPYCP5A, BoNT/E-ENT-NPYCP5A, BoNT/F-ENT-NPYCP5A, BoNT/G-ENT-NPYCP5A, TeNT-ENT-NPYCP5A, BaNT-ENT-NPYCP5A, or BuNT-ENT-NPYCP5A. Likewise, a similar cloning strategy will be used to make pET29 expression constructs comprising a polynucleotide molecule encoding a modified Clostridial toxin-ENT-CP5B comprising a binding element such as, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 120, SEQ ID NO: 121, SEQ ID NO: 122 or SEQ ID NO: 123. If required for function, the selected binding element will be engineered to expose the free amino terminal amino acid of the binding element.

Furthermore, a similar cloning strategy will be used to make pET29 expression constructs comprising a polynucleotide molecule encoding a modified Clostridial toxin-CP5A comprising an exogenous protease cleavage site incorporated within the di-chain loop region such as, e.g., a Tobacco Etch Virus protease cleavage site comprising SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63. In addition, a similar cloning strategy will be used to make pET29 expression constructs comprising a polynucleotide molecule encoding a modified Clostridial toxin-CP5A comprising an exogenous protease cleavage site incorporated within the di-chain loop region such as, e.g., an exogenous protease cleavage site which upon cleavage converts the single-chain polypeptide of the toxin into its di-chain form and also exposes the first amino acid of the binding element.

17b. A Translocation Element-Exogenous Protease Cleavage Site-Binding Element-Therapeutic Element Organization.

A polynucleotide molecule based on BoNT/A-ENT-NPYCP5B (SEQ ID NO: 127) will be synthesized and cloned into a pUCBHB1 vector as described in Example 17a. This polynucleotide molecule encodes a BoNT/A modified to replace amino acids 872-1296 of SEQ ID NO: 1, a BoNT/A $H_c$ binding element, with SEQ ID NO: 119, a NPY peptide and to incorporate a bovine enterokinse protease site of SEQ ID NO: 21 within the di-chain loop region, arranged in an amino to carboxyl linear organization as depicted in FIG. 21B. Cleavage of an enterokinse cleavage site used to form the di-chain toxin also exposes the first amino acid of the NPY binding element. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

A similar cloning strategy will be used to make pUCBHB1 cloning constructs for BoNT/B-ENT-NPYCP5B, a modified BoNT/B where amino acids 861-1291 of SEQ ID NO: 2 are replaced with SEQ ID NO: 119; BoNT/C1-ENT-NPYCP5B, a modified BoNT/C1 where amino acids 869-1291 of SEQ ID NO: 3 are replaced with SEQ ID NO: 119; BoNT/D-ENT-NPYCP5B, a modified BoNT/D where amino acids 865-1276 of SEQ ID NO: 4 are replaced with SEQ ID NO: 119; BoNT/E-ENT-NPYCP5B, a modified BoNT/E where amino acids 848-1252 of SEQ ID NO: 5 are replaced with SEQ ID NO: 119; BoNT/F-ENT-NPYCP5B, a modified BoNT/F where amino acids 867-1274 of SEQ ID NO: 6 are replaced with SEQ ID NO: 119; BoNT/G-ENT-NPYCP5B, a modified BoNT/G where amino acids 866-1297 of SEQ ID NO: 7 are replaced with SEQ ID NO: 119; TeNT-ENT-NPYCP5B, a modified TeNT where amino acids 882-1315 of SEQ ID NO: 8 are replaced with SEQ ID NO: 119; BaNT-ENT-NPYCP5B, a modified BaNT where amino acids 858-1268 of SEQ ID NO: 9 are replaced with SEQ ID NO: 119; and BuNT-ENT-NPYCP5B, a modified BuNT where amino acids 848-1251 of SEQ ID NO: 10 are replaced with SEQ ID NO: 119.

Likewise, a similar cloning strategy will be used to make pUCBHB1 cloning constructs comprising a polynucleotide molecule encoding a modified Clostridial toxin-ENT-CP5B that will replace the $H_C$ binding element from a Clostridial toxin the with an binding element comprising, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 120, SEQ ID NO: 121, SEQ ID NO: 122 or SEQ ID NO: 123.

Likewise, a similar cloning strategy will be used to make pUCBHB1 cloning constructs comprising a polynucleotide molecule encoding a modified Clostridial toxin-CP5B comprising an exogenous protease cleavage site incorporated within the di-chain loop region, e.g., a Tobacco Etch Virus protease cleavage site comprising SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63. In addition, a similar cloning strategy will be used to make pUCBHB1 cloning constructs comprising a polynucleotide molecule encoding a modified Clostridial toxin-CP5B comprising an exogenous protease cleavage site incorporated within the di-chain loop region, cleavage of which converts the single-chain polypeptide of the toxin into its di-chain form and also exposes the first amino acid of the binding element.

To construct pET29/BoNT/A-ENT-NPYCP5B, a pUCBHB1/BoNT/A-ENT-NPYCP5B construct will be digested with restriction endonucleases that 1) will excise the polynucleotide molecule encoding the open reading frame of BoNT/A-ENT-NPYCP5B; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-ENT-NPYCP5B. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-ENT-NPYCP5B operably-linked to a carboxyl terminal polyhistidine affinity binding peptide.

A similar cloning strategy will be used to make pET29 expression constructs for other modified Clostridial toxin-ENT-NPYCP5B toxins, such as, e.g., BoNT/B-ENT-NPYCP5B, BoNT/C1-ENT-NPYCP5B, BoNT/D-ENT-NPYCP5B, BoNT/E-ENT-NPYCP5B, BoNT/F-ENT-NPYCP5B, BoNT/G-ENT-NPYCP5B, TeNT-ENT-NPYCP5B, BaNT-ENT-NPYCP5B, or BuNT-ENT-NPYCP5B. Likewise, a similar cloning strategy will be used to make pET29 expression constructs comprising a polynucleotide molecule encoding a modified Clostridial toxin-ENT-CP5B comprising a binding element such as, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 91 or SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 120, SEQ ID NO: 121, SEQ ID NO: 122 or SEQ ID NO: 123. If required for function, the selected binding element will be engineered to expose the free amino terminal amino acid of the binding element.

Furthermore, a similar cloning strategy will be used to make pET29 expression constructs comprising a polynucleotide molecule encoding a modified Clostridial toxin-CP5B comprising an exogenous protease cleavage site incorporated within the di-chain loop region such as, e.g., a Tobacco Etch Virus protease cleavage site comprising SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63. In addition, a similar cloning strategy will be used to make pET29 expression constructs comprising a polynucleotide molecule encoding a modified Clostridial toxin-CP5B comprising an exogenous protease cleavage site incorporated within the di-chain loop region such as, e.g., an exogenous protease cleavage site which upon cleavage converts the single-chain polypeptide of the toxin into its di-chain form and also exposes the first amino acid of the binding element.

Example 18

Construction of an Activatable Clostridial Toxin Comprising a Carboxyl-Terminally Presented Altered Targeting Domain This example illustrates how to make an activatable Clostridial toxin disclosed in the present specification comprising a binding element located at the carboxyl terminus of the modified toxin.

18a. A Therapeutic Element-Exogenous Pro Tease Cleavage Site-Translocation Element-Binding Element Organization.

A polynucleotide molecule based on BoNT/A-TEV-GalaninXP6A (SEQ ID NO: 128) will be synthesized and cloned into a pUCBHB1 vector as described in Example 17a. This polynucleotide molecule encodes a BoNT/A modified to replace amino acids 872-1296 of SEQ ID NO: 1, a BoNT/A $H_C$ binding element, with SEQ ID NO: 91, a Galanin peptide and to incorporate a TEV protease site of SEQ ID NO: 24 within the di-chain loop region, arranged in an amino to carboxyl linear organization as depicted in FIG. 22A. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

A similar cloning strategy will be used to make pUCBHB1 cloning constructs for BoNT/B-TEV-GalaninXP6A, a modified BoNT/B where amino acids 861-1291 of SEQ ID NO: 2 are replaced with SEQ ID NO: 91; BoNT/C1-TEV-GalaninXP6A, a modified BoNT/C1 where amino acids 869-1291 of SEQ ID NO: 3 are replaced with SEQ ID NO: 91; BoNT/D-TEV-GalaninXP6A, a modified BoNT/D where amino acids 865-1276 of SEQ ID NO: 4 are replaced with SEQ ID NO: 91; BoNT/E-TEV-GalaninXP6A, a modified BoNT/E where amino acids 848-1252 of SEQ ID NO: 5 are replaced with SEQ ID NO: 91; BoNT/F-TEV-GalaninXP6A, a modified BoNT/F where amino acids 867-1274 of SEQ ID NO: 6 are replaced with SEQ ID NO: 91; BoNT/G-TEV-GalaninXP6A, a modified BoNT/G where amino acids 866-1297 of SEQ ID NO: 7 are replaced with SEQ ID NO: 91; TeNT-TEV-GalaninXP6A, a modified TeNT where amino acids 882-1315 of SEQ ID NO: 8 are replaced with SEQ ID NO: 91; BaNT-TEV-GalaninXP6A, a modified BaNT where amino acids 858-1268 of SEQ ID NO: 9 are replaced with SEQ ID NO: 91; and BuNT-TEV-GalaninXP6A, a modified BuNT where amino acids 848-1251 of SEQ ID NO: 10 are replaced with SEQ ID NO: 91.

Likewise, a similar cloning strategy will be used to make pUCBHB1 cloning constructs comprising a polynucleotide molecule encoding a modified Clostridial toxin-TEV-XP6A that will replace the $H_C$ binding element from a Clostridial toxin the with an binding element comprising, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Likewise, a similar cloning strategy will be used to make pUCBHB1 cloning constructs comprising a polynucleotide molecule encoding a modified Clostridial toxin-XP6A comprising an exogenous protease cleavage site incorporated within the di-chain loop region, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

To construct pET29/BoNT/A-TEV-GalaninXP6A, a pUCBHB1/BoNT/A-TEV-GalaninXP6A construct will be digested with restriction endonucleases that 1) will excise the polynucleotide molecule encoding the open reading frame of BoNT/A-TEV-GalaninXP6A; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-TEV-GalaninXP6A. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-TEV-GalaninXP6A operably-linked to a carboxyl terminal polyhistidine affinity binding peptide.

A similar cloning strategy will be used to make pET29 expression constructs for other modified Clostridial toxin-TEV-GalaninXP6A toxins, such as, e.g., BoNT/B-TEV-GalaninXP6A, BoNT/C1-TEV-GalaninXP6A, BoNT/D-TEV-GalaninXP6A, BoNT/E-TEV-GalaninXP6A, BoNT/F-TEV-GalaninXP6A, BoNT/G-TEV-GalaninXP6A, TeNT-TEV-GalaninXP6A, BaNT-TEV-GalaninXP6A, or BuNT-TEV-GalaninXP6A. Likewise, a similar cloning strategy will be used to make pET29 expression constructs comprising a polynucleotide molecule encoding a modified Clostridial toxin-TEV-XP6A comprising a binding element such as, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Furthermore, a similar cloning strategy will be used to make pET29 expression constructs comprising a polynucleotide molecule encoding a modified Clostridial toxin-XP6A comprising an exogenous protease cleavage site incorporated within the di-chain loop region such as, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

18b. A Translocation Element-Exogenous Protease Cleavage Site-Therapeutic Element-Binding Element Organization.

A polynucleotide molecule based on BoNT/A-TEV-GalaninXP6B (SEQ ID NO: 129) will be synthesized and cloned into a pUCBHB1 vector as described in Example 17a. This polynucleotide molecule encodes a BoNT/A modified to replace amino acids 872-1296 of SEQ ID NO: 1, a BoNT/A $H_C$ binding element, with SEQ ID NO: 91, a Galanin peptide and to incorporate a TEV protease site of SEQ ID NO: 24 within the di-chain loop region, arranged in an amino to carboxyl linear organization as depicted in FIG. 22B. If so desired, expression optimization to a different organism, such as, e.g., a bacteria, a yeast strain, an insect cell-line or a mammalian cell line, can be done as described above, see, e.g., Steward, supra, (Feb. 2, 2006); and Steward, supra, (Feb. 16, 2006).

A similar cloning strategy will be used to make pUCBHB1 cloning constructs for BoNT/B-TEV-GalaninXP6B, a modified BoNT/B where amino acids 861-1291 of SEQ ID NO: 2 are replaced with SEQ ID NO: 91; BoNT/C1-TEV-GalaninXP6B, a modified BoNT/C1 where amino acids 869-1291 of SEQ ID NO: 3 are replaced with SEQ ID NO: 91; BoNT/D-TEV-GalaninXP6B, a modified BoNT/D where amino acids 865-1276 of SEQ ID NO: 4 are replaced with SEQ ID NO: 91; BoNT/E-TEV-GalaninXP6B, a modified BoNT/E where amino acids 848-1252 of SEQ ID NO: 5 are replaced with SEQ ID NO: 91; BoNT/F-TEV-GalaninXP6B, a modified BoNT/F where amino acids 867-1274 of SEQ ID NO: 6 are replaced with SEQ ID NO: 91; BoNT/G-TEV-GalaninXP6B, a modified BoNT/G where amino acids 866-1297 of SEQ ID NO: 7 are replaced with SEQ ID NO: 91; TeNT-TEV-GalaninXP6B, a modified TeNT where amino acids 882-1315 of SEQ ID NO: 8 are replaced with SEQ ID NO: 91; BaNT-TEV-GalaninXP6B, a modified BaNT where amino acids 858-1268 of SEQ ID NO: 9 are replaced with SEQ ID NO: 91; and BuNT-TEV-GalaninXP6B, a modified BuNT where amino acids 848-1251 of SEQ ID NO: 10 are replaced with SEQ ID NO: 91.

Likewise, a similar cloning strategy will be used to make pUCBHB1 cloning constructs comprising a polynucleotide molecule encoding a modified Clostridial toxin-TEV-XP6B that will replace the $H_C$ binding element from a Clostridial toxin the with an binding element comprising, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Likewise, a similar cloning strategy will be used to make pUCBHB1 cloning constructs comprising a polynucleotide molecule encoding a modified Clostridial toxin-XP6B comprising an exogenous protease cleavage site incorporated within the di-chain loop region, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

To construct pET29/BoNT/A-TEV-αMSHAP4B, a pUCBHB1/BoNT/A-TEV-GalaninXP6B construct will be digested with restriction endonucleases that 1) will excise the polynucleotide molecule encoding the open reading frame of BoNT/A-TEV-GalaninXP6B; and 2) will enable this polynucleotide molecule to be operably-linked to a pET29 vector (EMD Biosciences-Novagen, Madison, Wis.). This insert will be subcloned using a T4 DNA ligase procedure into a pET29 vector that is digested with appropriate restriction endonucleases to yield pET29/BoNT/A-TEV-GalaninXP6B. The ligation mixture will be transformed into chemically competent E. coli DH5α cells (Invitrogen, Inc, Carlsbad, Calif.) using a heat shock method, will be plated on 1.5% Luria-Bertani agar plates (pH 7.0) containing 50 µg/mL of Kanamycin, and will be placed in a 37° C. incubator for overnight growth. Bacteria containing expression constructs will be identified as Kanamycin resistant colonies. Candidate constructs will be isolated using an alkaline lysis plasmid mini-preparation procedure and will be analyzed by restriction endonuclease digest mapping to determine the presence and orientation of the insert. This cloning strategy will yield a pET29 expression construct comprising the polynucleotide molecule encoding the BoNT/A-TEV-GalaninXP6B operably-linked to a carboxyl terminal polyhistidine affinity binding peptide.

A similar cloning strategy will be used to make pET29 expression constructs for other modified Clostridial toxin-TEV-GalaninXP6B toxins, such as, e.g., BoNT/B-TEV-GalaninXP6B, BoNT/C1-TEV-GalaninXP6B, BoNT/D-TEV-GalaninXP6B, BoNT/E-TEV-GalaninXP6B, BoNT/F-TEV-GalaninXP6B, BoNT/G-TEV-GalaninXP6B, TeNT-TEV-GalaninXP6B, BaNT-TEV-GalaninXP6B, or BuNT-TEV-GalaninXP6B. Likewise, a similar cloning strategy will be used to make pET29 expression constructs comprising a polynucleotide molecule encoding a modified Clostridial toxin-TEV-XP6B comprising a binding element such as, e.g., a melanocyte stimulating hormone comprising SEQ ID NO: 81, SEQ ID NO: 82 or SEQ ID NO: 83; an adrenocorticotropin comprising SEQ ID NO: 84 or SEQ ID NO: 85; a lipotropin comprising SEQ ID NO: 86 or SEQ ID NO: 87; a neuropeptide derived from a melanocortin peptide comprising SEQ ID NO: 88, SEQ ID NO: 89 or SEQ ID NO: 90; a galanin comprising SEQ ID NO: 92; a chromogranin A peptide comprising SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100; a chromogranin B peptide comprising SEQ ID NO: 101, SEQ ID NO: 102, SEQ ID NO: 103, SEQ ID NO: 104 or SEQ ID NO: 105; a chromogranin C peptide comprising SEQ ID NO: 106; a tachykinin peptide comprising SEQ ID NO: 107, SEQ ID NO: 108, SEQ ID NO: 109, SEQ ID NO: 110, SEQ ID NO: 111, SEQ ID NO: 112, SEQ ID NO: 113, SEQ ID NO: 114, SEQ ID NO: 115, SEQ ID NO: 116, SEQ ID NO: 117 or SEQ ID NO: 118; a Neuropeptide Y related peptide comprising SEQ ID NO: 119, SEQ ID NO: 120, SEQ ID NO: 121, SEQ ID NO: 122 or SEQ ID NO: 123.

Furthermore, a similar cloning strategy will be used to make pET29 expression constructs comprising a polynucleotide molecule encoding a modified Clostridial toxin-XP6B comprising an exogenous protease cleavage site incorporated within the di-chain loop region such as, e.g., a bovine enterokinase protease cleavage site comprising SEQ ID NO: 21; a Tobacco Etch Virus protease cleavage site comprising SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33; a Tobacco Vein Mottling Virus protease cleavage site comprising SEQ ID NO: 36, SEQ ID NO: 37, SEQ ID NO: 38, or SEQ ID NO: 39; a human rhinovirus 3C protease cleavage site comprising SEQ ID NO: 41, SEQ ID NO: 42, SEQ ID NO: 43, SEQ ID NO: 44, SEQ ID NO: 45 or SEQ ID NO: 46; a subtilisin cleavage site comprising SEQ ID NO: 49, SEQ ID NO: 50, or SEQ ID NO: 51; a hydroxylamine cleavage site comprising SEQ ID NO: 52, SEQ ID NO: 53, or SEQ ID NO: 54; a SUMO/ULP-1 protease cleavage site comprising SEQ ID NO: 56; a non-human Caspase 3 protease cleavage site comprising SEQ ID NO: 58, SEQ ID NO: 59, SEQ ID NO: 60, SEQ ID NO: 61, SEQ ID NO: 62 or SEQ ID NO: 63.

Example 19

Expression of Activatable Clostridial Toxins in a Bacterial Cell

The following example illustrates a procedure useful for expressing any of the activatable Clostridial toxins disclosed in the present specification in a bacterial cell.

An expression construct, such as, e.g., any of the expression constructs in Examples 17-19, will be introduced into chemically competent E. coli BL21 (DE3) cells (Invitrogen, Inc, Carlsbad, Calif.) using a heat-shock transformation protocol. The heat-shock reaction will be plated onto 1.5% Luria-Bertani agar plates (pH 7.0) containing 50 µg/mL of Kanamycin and will be placed in a 37° C. incubator for overnight growth. Kanamycin-resistant colonies of transformed E. coli containing the expression construct will be used to inoculate a baffled flask containing 3.0 mL of PA-0.5G media containing 50 µg/mL of Kanamycin which will then placed in a 37° C. incubator, shaking at 250 rpm, for overnight growth. The resulting overnight starter culture will be used to inoculate a 3 L baffled flask containing ZYP-5052 autoinducing media containing 50 µg/mL of Kanamycin at a dilution of 1:1000. Culture volumes will range from about 600 mL (20% flask volume) to about 750 mL (25% flask volume). These cultures will be grown in a 37° C. incubator shaking at 250 rpm for approximately 5.5 hours and will be then transferred to a 16° C. incubator shaking at 250 rpm for overnight expression. Cells will be harvested by centrifugation (4,000 rpm at 4° C. for 20-30 minutes) and will be used immediately, or will be stored dry at −80° C. until needed.

Example 20

Purification and Quantification of Activatable Clostridial Toxins

The following example illustrates methods useful for purification and quantification of any activatable Clostridial toxins disclosed in the present specification.

For immobilized metal affinity chromatography (IMAC) protein purification, E. coli BL21 (DE3) cell pellets used to express a modified Clostridial toxin, as described in Example 20, will be resuspended in Column Binding Buffer (25 mM N-(2-hydroxyethyl) piperazine-N'-(2-ethanesulfonic acid) (HEPES), pH 7.8; 500 mM sodium chloride; 10 mM imidazole; 2× Protease Inhibitor Cocktail Set III (EMD Biosciences-Calbiochem, San Diego Calif.); 5 units/mL of Benzonase (EMD Biosciences—Novagen, Madison, Wis.); 0.1% (v/v) TRITON-X® 100, 4-octylphenol polyethoxylate; 10% (v/v) glycerol), and will then be transferred to a cold Oakridge centrifuge tube. The cell suspension will be sonicated on ice (10-12 pulses of 10 seconds at 40% amplitude with 60 seconds cooling intervals on a Branson Digital Sonifier) in order to lyse the cells and then is centrifuged (16,000 rpm at 4° C. for 20 minutes) to clarify the lysate. An immobilized metal affinity chromatography column will be prepared using a 20 mL Econo-Pac column support (Bio-Rad Laboratories, Hercules, Calif.) packed with 2.5-5.0 mL of TALON™ Super-Flow Co2+ affinity resin (BD Biosciences-Clontech, Palo Alto, Calif.), which will then be equilibrated by rinsing with 5 column volumes of deionized, distilled water, followed by 5 column volumes of Column Binding Buffer. The clarified lysate will be applied slowly to the equilibrated column by gravity flow (approximately 0.25-0.3 mL/minute). The column will then be washed with 5 column volumes of Column Wash Buffer (N-(2-hydroxyethyl) piperazine-N'-(2-ethanesulfonic acid) (HEPES), pH 7.8; 500 mM sodium chloride; 10 mM imidazole; 0.1% (v/v) Triton-X® 100, 4-octylphenol polyethoxylate; 10% (v/v) glycerol). The modified Clostridial toxin will be eluted with 20-30 mL of Column Elution Buffer (25 mM N-(2-hydroxyethyl) piperazine-N'-(2-ethanesulfonic acid) (HEPES), pH 7.8; 500 mM sodium chloride; 500 mM imidazole; 0.1% (v/v) TRITON-X® 100, 4-octylphenol polyethoxylate; 10% (v/v) glycerol) and will be collected in approximately twelve 1 mL fractions. The amount of modified Clostridial toxin contained in each elution fraction will be determined by a Bradford dye assay. In this procedure, 20 µL aliquots of each 1.0 mL fraction will be combined with 200 µL of Bio-Rad Protein Reagent (Bio-Rad Laboratories, Hercules, Calif.), diluted 1 to 4 with deionized, distilled water, and then the intensity of the colorimetric signal will be measured using a spectrophotometer. The five fractions with the strongest signal will be considered the elution peak and will be combined together. Total protein yield will be determined by estimating the total protein concentration of the pooled peak elution fractions using bovine gamma globulin as a standard (Bio-Rad Laboratories, Hercules, Calif.).

For purification of a modified Clostridial toxin using a FPLC desalting column, a HiPrep™ 26/10 size exclusion column (Amersham Biosciences, Piscataway, N.J.) will be pre-equilibrated with 80 mL of 4° C. Column Buffer (50 mM sodium phosphate, pH 6.5). After the column is equilibrated, a modified Clostridial toxin sample will be applied to the size exclusion column with an isocratic mobile phase of 4° C. Column Buffer and at a flow rate of 10 mL/minute using a BioLogic DuoFlow chromatography system (Bio-Rad Laboratories, Hercules, Calif.). The desalted modified Clostridial toxin sample will be collected as a single fraction of approximately 7-12 mL.

For purification of a modified Clostridial toxin using a FPLC ion exchange column, a modified Clostridial toxin sample that has been desalted following elution from an IMAC column will be applied to a 1 mL Q1™ anion exchange column (Bio-Rad Laboratories, Hercules, Calif.) using a BioLogic DuoFlow chromatography system (Bio-Rad Laboratories, Hercules, Calif.). The sample will be applied to the column in 4° C. Column Buffer (50 mM sodium phosphate, pH 6.5) and will be eluted by linear gradient with 4° C. Elution Buffer (50 mM sodium phosphate, 1 M sodium chloride, pH 6.5) as follows: step 1, 5.0 mL of 5% Elution Buffer at a flow rate of 1 mL/minute; step 2, 20.0 mL of 5-30% Elution Buffer at a flow rate of 1 mL/minute; step 3, 2.0 mL of 50% Elution Buffer at a flow rate of 1.0 mL/minute; step 4, 4.0 mL of 100% Elution Buffer at a flow rate of 1.0 mL/minute; and step 5, 5.0 mL of 0% Elution Buffer at a flow rate of 1.0 mL/minute. Elution of modified Clostridial toxin from the column will be monitored at 280, 260, and 214 nm, and peaks absorbing above a minimum threshold (0.01 au) at 280 nm will be collected. Most of the modified Clostridial toxin will be eluted at a sodium chloride concentration of approximately 100 to 200 mM. Average total yields of modified Clostridial toxin will be determined by a Bradford assay.

Expression of a modified Clostridial toxin will be analyzed by polyacrylamide gel electrophoresis. Samples purified using the procedure described above are added to 2×LDS Sample Buffer (Invitrogen, Inc, Carlsbad, Calif.) and will be separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Gels will be stained with SYPRO® Ruby (Bio-Rad Laboratories, Hercules, Calif.) and the separated polypeptides will be imaged using a Fluor-S MAX MultiImager (Bio-Rad Laboratories, Hercules, Calif.) for quantification of modified Clostridial toxin expression levels. The size and amount of modified Clostridial toxin will be determined by comparison to MagicMark™ protein molecular weight standards (Invitrogen, Inc, Carlsbad, Calif.).

Expression of modified Clostridial toxin will also be analyzed by Western blot analysis. Protein samples purified using the procedure described above will be added to 2×LDS Sample Buffer (Invitrogen, Inc, Carlsbad, Calif.) and will be separated by MOPS polyacrylamide gel electrophoresis using NuPAGE® Novex 4-12% Bis-Tris precast polyacrylamide gels (Invitrogen, Inc, Carlsbad, Calif.) under denaturing, reducing conditions. Separated polypeptides will be transferred from the gel onto polyvinylidene fluoride (PVDF) membranes (Invitrogen, Inc, Carlsbad, Calif.) by Western blotting using a Trans-Blot® SD semi-dry electrophoretic transfer cell apparatus (Bio-Rad Laboratories, Hercules, Calif.). PVDF membranes will be blocked by incubating at room temperature for 2 hours in a solution containing 25 mM Tris-Buffered Saline (25 mM 2-amino-2-hydroxymethyl-1,3-propanediol hydrochloric acid (Tris-HCl) (pH 7.4), 137 mM sodium chloride, 2.7 mM potassium chloride), 0.1% TWEEN-20®, polyoxyethylene (20) sorbitan monolaureate, 2% bovine serum albumin, 5% nonfat dry milk. Blocked membranes will be incubated at 4° C. for overnight in Tris-Buffered Saline TWEEN-20® (25 mM Tris-Buffered Saline, 0.1% TWEEN-20®, polyoxyethylene (20) sorbitan monolaureate) containing appropriate primary antibodies as a probe. Primary antibody probed blots will be washed three times for 15 minutes each time in Tris-Buffered Saline TWEEN-20®. Washed membranes will be incubated at room temperature for 2 hours in Tris-Buffered Saline TWEEN-20® containing an appropriate immunoglobulin G antibody conjugated to horseradish peroxidase as a secondary antibody. Secondary antibody-probed blots will be washed three times for 15 minutes each time in Tris-Buffered Saline TWEEN-20®. Signal detection of the labeled modified Clostridial toxin will be visualized using the ECL Plus™ Western Blot Detection System (Amersham Biosciences, Piscataway, N.J.) and will be imaged with a Typhoon 9410 Variable Mode Imager (Amersham Biosciences, Piscataway, N.J.) for quantification of modified Clostridial toxin expression levels.

Although aspects of the present invention have been described with reference to the disclosed embodiments, one skilled in the art will readily appreciate that the specific examples disclosed are only illustrative of these aspects and in no way limit the present invention. Various modifications can be made without departing from the spirit of the present invention.

Those of skill in the art will understand that the Examples provided herein describe preferred compositions and methods, and that a variety of different cloning strategies, protease cleavage sites, and specific binding complex members may be employed in the practice and use of the present invention while remaining within the invention's scope. Additionally, different di-chain or binary toxin molecules and modified versions thereof (for example, BoNT/B-E and modified variants thereof) may be used as the basis for the methods and compositions of the present invention.

SEQUENCE LISTING

```
<160> NUMBER OF SEQ ID NOS: 130

<210> SEQ ID NO 1
<211> LENGTH: 1296
<212> TYPE: PRT
<213> ORGANISM: Clostridium botulinum Serotype A
<220> FEATURE:
<221> NAME/KEY: DOMAIN
<222> LOCATION: (1)...(448)
<223> OTHER INFORMATION: Light chain comprising the enzymatic domain.
<221> NAME/KEY: DOMAIN
<222> LOCATION: (449)...(860)
<223> OTHER INFORMATION: Amino-terminal half of heavy chain comprising
      the translocation domain.
<221> NAME/KEY: DOMAIN
<222> LOCATION: (861)...(1296)
<223> OTHER INFORMATION: Carboxyl-terminal half of heavy chain
      comprising the binding domain.

<400> SEQUENCE: 1

Met Pro Phe Val Asn Lys Gln Phe Asn Tyr Lys Asp Pro Val Asn Gly
 1               5                   10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60

Ala Lys Gln Val Pro Val Ser Tyr Tyr Asp Ser Thr Tyr Leu Ser Thr
65                  70                  75                  80

Asp Asn Glu Lys Asp Asn Tyr Leu Lys Gly Val Thr Lys Leu Phe Glu
                85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
    130                 135                 140

Arg Ser Glu Glu Leu Asn Leu Val Ile Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
    210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255
```

```
Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
            275                 280                 285

Lys Phe Lys Asp Ile Ala Ser Thr Leu Asn Lys Ala Lys Ser Ile Val
            290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
            355                 360                 365

Phe Asp Lys Ala Val Phe Lys Ile Asn Ile Val Pro Lys Val Asn Tyr
            370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Asp Lys Gly Tyr Asn Lys
            435                 440                 445

Ala Leu Asn Asp Leu Cys Ile Lys Val Asn Asn Trp Asp Leu Phe Phe
450                 455                 460

Ser Pro Ser Glu Asp Asn Phe Thr Asn Asp Leu Asn Lys Gly Glu Glu
465                 470                 475                 480

Ile Thr Ser Asp Thr Asn Ile Glu Ala Ala Glu Glu Asn Ile Ser Leu
                485                 490                 495

Asp Leu Ile Gln Gln Tyr Tyr Leu Thr Phe Asn Phe Asp Asn Glu Pro
            500                 505                 510

Glu Asn Ile Ser Ile Glu Asn Leu Ser Ser Asp Ile Ile Gly Gln Leu
            515                 520                 525

Glu Leu Met Pro Asn Ile Glu Arg Phe Pro Asn Gly Lys Lys Tyr Glu
            530                 535                 540

Leu Asp Lys Tyr Thr Met Phe His Tyr Leu Arg Ala Gln Glu Phe Glu
545                 550                 555                 560

His Gly Lys Ser Arg Ile Ala Leu Thr Asn Ser Val Asn Glu Ala Leu
                565                 570                 575

Leu Asn Pro Ser Arg Val Tyr Thr Phe Phe Ser Ser Asp Tyr Val Lys
            580                 585                 590

Lys Val Asn Lys Ala Thr Glu Ala Met Phe Leu Gly Trp Val Glu
            595                 600                 605

Gln Leu Val Tyr Asp Phe Thr Asp Glu Thr Ser Glu Val Ser Thr Thr
            610                 615                 620

Asp Lys Ile Ala Asp Ile Thr Ile Ile Pro Tyr Ile Gly Pro Ala
625                 630                 635                 640

Leu Asn Ile Gly Asn Met Leu Tyr Lys Asp Asp Phe Val Gly Ala Leu
                645                 650                 655

Ile Phe Ser Gly Ala Val Ile Leu Leu Glu Phe Ile Pro Glu Ile Ala
            660                 665                 670

Ile Pro Val Leu Gly Thr Phe Ala Leu Val Ser Tyr Ile Ala Asn Lys
```

```
                675                 680                 685
Val Leu Thr Val Gln Thr Ile Asp Asn Ala Leu Ser Lys Arg Asn Glu
690                 695                 700

Lys Trp Asp Glu Val Tyr Lys Tyr Ile Val Thr Asn Trp Leu Ala Lys
705                 710                 715                 720

Val Asn Thr Gln Ile Asp Leu Ile Arg Lys Met Lys Glu Ala Leu
            725                 730                 735

Glu Asn Gln Ala Glu Ala Thr Lys Ala Ile Ile Asn Tyr Gln Tyr Asn
            740                 745                 750

Gln Tyr Thr Glu Glu Lys Asn Asn Ile Asn Phe Asn Ile Asp Asp
            755                 760                 765

Leu Ser Ser Lys Leu Asn Glu Ser Ile Asn Lys Ala Met Ile Asn Ile
770                 775                 780

Asn Lys Phe Leu Asn Gln Cys Ser Val Ser Tyr Leu Met Asn Ser Met
785                 790                 795                 800

Ile Pro Tyr Gly Val Lys Arg Leu Glu Asp Phe Asp Ala Ser Leu Lys
                805                 810                 815

Asp Ala Leu Leu Lys Tyr Ile Tyr Asp Asn Arg Gly Thr Leu Ile Gly
            820                 825                 830

Gln Val Asp Arg Leu Lys Asp Lys Val Asn Asn Thr Leu Ser Thr Asp
            835                 840                 845

Ile Pro Phe Gln Leu Ser Lys Tyr Val Asp Asn Gln Arg Leu Leu Ser
850                 855                 860

Thr Phe Thr Glu Tyr Ile Lys Asn Ile Ile Asn Thr Ser Ile Leu Asn
865                 870                 875                 880

Leu Arg Tyr Glu Ser Asn His Leu Ile Asp Leu Ser Arg Tyr Ala Ser
                885                 890                 895

Lys Ile Asn Ile Gly Ser Lys Val Asn Phe Asp Pro Ile Asp Lys Asn
            900                 905                 910

Gln Ile Gln Leu Phe Asn Leu Glu Ser Ser Lys Ile Glu Val Ile Leu
            915                 920                 925

Lys Asn Ala Ile Val Tyr Asn Ser Met Tyr Glu Asn Phe Ser Thr Ser
930                 935                 940

Phe Trp Ile Arg Ile Pro Lys Tyr Phe Asn Ser Ile Ser Leu Asn Asn
945                 950                 955                 960

Glu Tyr Thr Ile Ile Asn Cys Met Glu Asn Asn Ser Gly Trp Lys Val
                965                 970                 975

Ser Leu Asn Tyr Gly Glu Ile Ile Trp Thr Leu Gln Asp Thr Gln Glu
            980                 985                 990

Ile Lys Gln Arg Val Val Phe Lys Tyr Ser Gln Met Ile Asn Ile Ser
            995                 1000                1005

Asp Tyr Ile Asn Arg Trp Ile Phe Val Thr Ile Thr Asn Asn Arg Leu
            1010                1015                1020

Asn Asn Ser Lys Ile Tyr Ile Asn Gly Arg Leu Ile Asp Gln Lys Pro
1025                1030                1035                1040

Ile Ser Asn Leu Gly Asn Ile His Ala Ser Asn Asn Ile Met Phe Lys
            1045                1050                1055

Leu Asp Gly Cys Arg Asp Thr His Arg Tyr Ile Trp Ile Lys Tyr Phe
            1060                1065                1070

Asn Leu Phe Asp Lys Glu Leu Asn Glu Lys Glu Ile Lys Asp Leu Tyr
            1075                1080                1085

Asp Asn Gln Ser Asn Ser Gly Ile Leu Lys Asp Phe Trp Gly Asp Tyr
            1090                1095                1100
```

-continued

```
Leu Gln Tyr Asp Lys Pro Tyr Met Leu Asn Leu Tyr Asp Pro Asn
1105                1110                1115                1120

Lys Tyr Val Asp Val Asn Asn Val Gly Ile Arg Gly Tyr Met Tyr Leu
                1125                1130                1135

Lys Gly Pro Arg Gly Ser Val Met Thr Thr Asn Ile Tyr Leu Asn Ser
            1140                1145                1150

Ser Leu Tyr Arg Gly Thr Lys Phe Ile Ile Lys Tyr Ala Ser Gly
        1155                1160                1165

Asn Lys Asp Asn Ile Val Arg Asn Asn Asp Arg Val Tyr Ile Asn Val
    1170                1175                1180

Val Val Lys Asn Lys Glu Tyr Arg Leu Ala Thr Asn Ala Ser Gln Ala
1185                1190                1195                1200

Gly Val Glu Lys Ile Leu Ser Ala Leu Glu Ile Pro Asp Val Gly Asn
                1205                1210                1215

Leu Ser Gln Val Val Val Met Lys Ser Lys Asn Asp Gln Gly Ile Thr
            1220                1225                1230

Asn Lys Cys Lys Met Asn Leu Gln Asp Asn Asn Gly Asn Asp Ile Gly
        1235                1240                1245

Phe Ile Gly Phe His Gln Phe Asn Asn Ile Ala Lys Leu Val Ala Ser
    1250                1255                1260

Asn Trp Tyr Asn Arg Gln Ile Glu Arg Ser Ser Arg Thr Leu Gly Cys
1265                1270                1275                1280

Ser Trp Glu Phe Ile Pro Val Asp Asp Gly Trp Gly Glu Arg Pro Leu
                1285                1290                1295

<210> SEQ ID NO 2
<211> LENGTH: 1291
<212> TYPE: PRT
<213> ORGANISM: Clostridium botulinum Serotype B
<220> FEATURE:
<221> NAME/KEY: DOMAIN
<222> LOCATION: (1)...(441)
<223> OTHER INFORMATION: Light chain comprising the enzymatic domain.
<221> NAME/KEY: DOMAIN
<222> LOCATION: (442)...(847)
<223> OTHER INFORMATION: Amino-terminal half of heavy chain comprising
      the translocation domain.
<221> NAME/KEY: DOMAIN
<222> LOCATION: (848)...(1291)
<223> OTHER INFORMATION: Carboxyl-terminal half of heavy chain
      comprising the binding domain.

<400> SEQUENCE: 2

Met Pro Val Thr Ile Asn Asn Phe Asn Tyr Asn Asp Pro Ile Asp Asn
  1               5                  10                  15

Asn Asn Ile Ile Met Met Glu Pro Pro Phe Ala Arg Gly Thr Gly Arg
                 20                  25                  30

Tyr Tyr Lys Ala Phe Lys Ile Thr Asp Arg Ile Trp Ile Ile Pro Glu
             35                  40                  45

Arg Tyr Thr Phe Gly Tyr Lys Pro Glu Asp Phe Asn Lys Ser Ser Gly
         50                  55                  60

Ile Phe Asn Arg Asp Val Cys Glu Tyr Tyr Asp Pro Asp Tyr Leu Asn
 65                  70                  75                  80

Thr Asn Asp Lys Lys Asn Ile Phe Leu Gln Thr Met Ile Lys Leu Phe
                 85                  90                  95

Asn Arg Ile Lys Ser Lys Pro Leu Gly Glu Lys Leu Leu Glu Met Ile
            100                 105                 110

Ile Asn Gly Ile Pro Tyr Leu Gly Asp Arg Arg Val Pro Leu Glu Glu
        115                 120                 125
```

-continued

```
Phe Asn Thr Asn Ile Ala Ser Val Thr Val Asn Lys Leu Ile Ser Asn
            130                 135                 140

Pro Gly Glu Val Glu Arg Lys Lys Gly Ile Phe Ala Asn Leu Ile Ile
145                 150                 155                 160

Phe Gly Pro Gly Pro Val Leu Asn Glu Asn Glu Thr Ile Asp Ile Gly
                165                 170                 175

Ile Gln Asn His Phe Ala Ser Arg Glu Gly Phe Gly Gly Ile Met Gln
            180                 185                 190

Met Lys Phe Cys Pro Glu Tyr Val Ser Val Phe Asn Asn Val Gln Glu
        195                 200                 205

Asn Lys Gly Ala Ser Ile Phe Asn Arg Arg Gly Tyr Phe Ser Asp Pro
    210                 215                 220

Ala Leu Ile Leu Met His Glu Leu Ile His Val Leu His Gly Leu Tyr
225                 230                 235                 240

Gly Ile Lys Val Asp Asp Leu Pro Ile Val Pro Asn Glu Lys Lys Phe
                245                 250                 255

Phe Met Gln Ser Thr Asp Ala Ile Gln Ala Glu Glu Leu Tyr Thr Phe
            260                 265                 270

Gly Gly Gln Asp Pro Ser Ile Ile Thr Pro Ser Thr Asp Lys Ser Ile
        275                 280                 285

Tyr Asp Lys Val Leu Gln Asn Phe Arg Gly Ile Val Asp Arg Leu Asn
    290                 295                 300

Lys Val Leu Val Cys Ile Ser Asp Pro Asn Ile Asn Ile Asn Ile Tyr
305                 310                 315                 320

Lys Asn Lys Phe Lys Asp Lys Tyr Lys Phe Val Glu Asp Ser Glu Gly
                325                 330                 335

Lys Tyr Ser Ile Asp Val Glu Ser Phe Asp Lys Leu Tyr Lys Ser Leu
            340                 345                 350

Met Phe Gly Phe Thr Glu Thr Asn Ile Ala Glu Asn Tyr Lys Ile Lys
        355                 360                 365

Thr Arg Ala Ser Tyr Phe Ser Asp Ser Leu Pro Pro Val Lys Ile Lys
    370                 375                 380

Asn Leu Leu Asp Asn Glu Ile Tyr Thr Ile Glu Glu Gly Phe Asn Ile
385                 390                 395                 400

Ser Asp Lys Asp Met Glu Lys Glu Tyr Arg Gly Gln Asn Lys Ala Ile
                405                 410                 415

Asn Lys Gln Ala Tyr Glu Glu Ile Ser Lys Glu His Leu Ala Val Tyr
            420                 425                 430

Lys Ile Gln Met Cys Lys Ser Val Lys Ala Pro Gly Ile Cys Ile Asp
        435                 440                 445

Val Asp Asn Glu Asp Leu Phe Phe Ile Ala Asp Lys Asn Ser Phe Ser
450                 455                 460

Asp Asp Leu Ser Lys Asn Glu Arg Ile Glu Tyr Asn Thr Gln Ser Asn
465                 470                 475                 480

Tyr Ile Glu Asn Asp Phe Pro Ile Asn Glu Leu Ile Leu Asp Thr Asp
                485                 490                 495

Leu Ile Ser Lys Ile Glu Leu Pro Ser Glu Asn Thr Glu Ser Leu Thr
            500                 505                 510

Asp Phe Asn Val Asp Val Pro Val Tyr Glu Lys Gln Pro Ala Ile Lys
        515                 520                 525

Lys Ile Phe Thr Asp Glu Asn Thr Ile Phe Gln Tyr Leu Tyr Ser Gln
    530                 535                 540

Thr Phe Pro Leu Asp Ile Arg Asp Ile Ser Leu Thr Ser Ser Phe Asp
545                 550                 555                 560
```

```
Asp Ala Leu Leu Phe Ser Asn Lys Val Tyr Ser Phe Ser Met Asp
            565                 570                 575

Tyr Ile Lys Thr Ala Asn Lys Val Val Glu Ala Gly Leu Phe Ala Gly
            580                 585                 590

Trp Val Lys Gln Ile Val Asn Asp Phe Val Ile Glu Ala Asn Lys Ser
            595                 600                 605

Asn Thr Met Asp Lys Ile Ala Asp Ile Ser Leu Ile Val Pro Tyr Ile
            610                 615                 620

Gly Leu Ala Leu Asn Val Gly Asn Glu Thr Ala Lys Gly Asn Phe Glu
625                 630                 635                 640

Asn Ala Phe Glu Ile Ala Gly Ala Ser Ile Leu Leu Glu Phe Ile Pro
            645                 650                 655

Glu Leu Leu Ile Pro Val Val Gly Ala Phe Leu Leu Glu Ser Tyr Ile
            660                 665                 670

Asp Asn Lys Asn Lys Ile Ile Lys Thr Ile Asp Asn Ala Leu Thr Lys
            675                 680                 685

Arg Asn Glu Lys Trp Ser Asp Met Tyr Gly Leu Ile Val Ala Gln Trp
            690                 695                 700

Leu Ser Thr Val Asn Thr Gln Phe Tyr Thr Ile Lys Glu Gly Met Tyr
705                 710                 715                 720

Lys Ala Leu Asn Tyr Gln Ala Gln Ala Leu Glu Glu Ile Ile Lys Tyr
            725                 730                 735

Arg Tyr Asn Ile Tyr Ser Glu Lys Glu Lys Ser Asn Ile Asn Ile Asp
            740                 745                 750

Phe Asn Asp Ile Asn Ser Lys Leu Asn Glu Gly Ile Asn Gln Ala Ile
            755                 760                 765

Asp Asn Ile Asn Asn Phe Ile Asn Gly Cys Ser Val Ser Tyr Leu Met
            770                 775                 780

Lys Lys Met Ile Pro Leu Ala Val Glu Lys Leu Leu Asp Phe Asp Asn
785                 790                 795                 800

Thr Leu Lys Lys Asn Leu Leu Asn Tyr Ile Asp Glu Asn Lys Leu Tyr
            805                 810                 815

Leu Ile Gly Ser Ala Glu Tyr Glu Lys Ser Lys Val Asn Lys Tyr Leu
            820                 825                 830

Lys Thr Ile Met Pro Phe Asp Leu Ser Ile Tyr Thr Asn Asp Thr Ile
            835                 840                 845

Leu Ile Glu Met Phe Asn Lys Tyr Asn Ser Glu Ile Leu Asn Asn Ile
850                 855                 860

Ile Leu Asn Leu Arg Tyr Lys Asp Asn Asn Leu Ile Asp Leu Ser Gly
865                 870                 875                 880

Tyr Gly Ala Lys Val Glu Val Tyr Asp Gly Val Glu Leu Asn Asp Lys
            885                 890                 895

Asn Gln Phe Lys Leu Thr Ser Ser Ala Asn Ser Lys Ile Arg Val Thr
            900                 905                 910

Gln Asn Gln Asn Ile Ile Phe Asn Ser Val Phe Leu Asp Phe Ser Val
            915                 920                 925

Ser Phe Trp Ile Arg Ile Pro Lys Tyr Lys Asn Asp Gly Ile Gln Asn
            930                 935                 940

Tyr Ile His Asn Glu Tyr Thr Ile Ile Asn Cys Met Lys Asn Asn Ser
945                 950                 955                 960

Gly Trp Lys Ile Ser Ile Arg Gly Asn Arg Ile Ile Trp Thr Leu Ile
            965                 970                 975

Asp Ile Asn Gly Lys Thr Lys Ser Val Phe Phe Glu Tyr Asn Ile Arg
```

-continued

```
                  980                 985                 990
Glu Asp Ile Ser Glu Tyr Ile Asn Arg Trp Phe Phe Val Thr Ile Thr
            995                1000                1005
Asn Asn Leu Asn Asn Ala Lys Ile Tyr Ile Asn Gly Lys Leu Glu Ser
       1010                1015                1020
Asn Thr Asp Ile Lys Asp Ile Arg Glu Val Ile Ala Asn Gly Glu Ile
1025                1030                1035                1040
Ile Phe Lys Leu Asp Gly Asp Ile Asp Arg Thr Gln Phe Ile Trp Met
                1045                1050                1055
Lys Tyr Phe Ser Ile Phe Asn Thr Glu Leu Ser Gln Ser Asn Ile Glu
            1060                1065                1070
Glu Arg Tyr Lys Ile Gln Ser Tyr Ser Glu Tyr Leu Lys Asp Phe Trp
       1075                1080                1085
Gly Asn Pro Leu Met Tyr Asn Lys Glu Tyr Tyr Met Phe Asn Ala Gly
            1090                1095                1100
Asn Lys Asn Ser Tyr Ile Lys Leu Lys Lys Asp Ser Pro Val Gly Glu
1105                1110                1115                1120
Ile Leu Thr Arg Ser Lys Tyr Asn Gln Asn Ser Lys Tyr Ile Asn Tyr
                1125                1130                1135
Arg Asp Leu Tyr Ile Gly Glu Lys Phe Ile Ile Arg Arg Lys Ser Asn
                1140                1145                1150
Ser Gln Ser Ile Asn Asp Asp Ile Val Arg Lys Glu Asp Tyr Ile Tyr
            1155                1160                1165
Leu Asp Phe Phe Asn Leu Asn Gln Glu Trp Arg Val Tyr Thr Tyr Lys
       1170                1175                1180
Tyr Phe Lys Lys Glu Glu Glu Lys Leu Phe Leu Ala Pro Ile Ser Asp
1185                1190                1195                1200
Ser Asp Glu Phe Tyr Asn Thr Ile Gln Ile Lys Glu Tyr Asp Glu Gln
                1205                1210                1215
Pro Thr Tyr Ser Cys Gln Leu Leu Phe Lys Lys Asp Glu Glu Ser Thr
            1220                1225                1230
Asp Glu Ile Gly Leu Ile Gly Ile His Arg Phe Tyr Glu Ser Gly Ile
       1235                1240                1245
Val Phe Glu Glu Tyr Lys Asp Tyr Phe Cys Ile Ser Lys Trp Tyr Leu
1250                1255                1260
Lys Glu Val Lys Arg Lys Pro Tyr Asn Leu Lys Leu Gly Cys Asn Trp
1265                1270                1275                1280
Gln Phe Ile Pro Lys Asp Glu Gly Trp Thr Glu
                1285                1290

<210> SEQ ID NO 3
<211> LENGTH: 1291
<212> TYPE: PRT
<213> ORGANISM: Clostridium botulinum Serotype C1
<220> FEATURE:
<221> NAME/KEY: DOMAIN
<222> LOCATION: (1)...(449)
<223> OTHER INFORMATION: Light chain comprising the enzymatic domain.
<221> NAME/KEY: DOMAIN
<222> LOCATION: (450)...(855)
<223> OTHER INFORMATION: Amino-terminal half of heavy chain comprising
      the translocation domain.
<221> NAME/KEY: DOMAIN
<222> LOCATION: (856)...(1291)
<223> OTHER INFORMATION: Carboxyl-terminal half of heavy chain
      comprising the binding domain.

<400> SEQUENCE: 3

Met Pro Ile Thr Ile Asn Asn Phe Asn Tyr Ser Asp Pro Val Asp Asn
```

-continued

```
  1               5                  10                 15
Lys Asn Ile Leu Tyr Leu Asp Thr His Leu Asn Thr Leu Ala Asn Glu
                20                  25                 30

Pro Glu Lys Ala Phe Arg Ile Thr Gly Asn Ile Trp Val Ile Pro Asp
                35                  40                 45

Arg Phe Ser Arg Asn Ser Asn Pro Asn Leu Asn Lys Pro Pro Arg Val
        50                  55                  60

Thr Ser Pro Lys Ser Gly Tyr Tyr Asp Pro Asn Tyr Leu Ser Thr Asp
 65                  70                  75                 80

Ser Asp Lys Asp Pro Phe Leu Lys Glu Ile Ile Lys Leu Phe Lys Arg
                85                  90                 95

Ile Asn Ser Arg Glu Ile Gly Glu Leu Ile Tyr Arg Leu Ser Thr
                100                 105                110

Asp Ile Pro Phe Pro Gly Asn Asn Thr Pro Ile Asn Thr Phe Asp
                115                 120                125

Phe Asp Val Asp Phe Asn Ser Val Asp Val Lys Thr Arg Gln Gly Asn
        130                 135                 140

Asn Trp Val Lys Thr Gly Ser Ile Asn Pro Ser Val Ile Ile Thr Gly
145                 150                 155                160

Pro Arg Glu Asn Ile Ile Asp Pro Glu Thr Ser Thr Phe Lys Leu Thr
                165                 170                 175

Asn Asn Thr Phe Ala Ala Gln Glu Gly Phe Gly Ala Leu Ser Ile Ile
                180                 185                 190

Ser Ile Ser Pro Arg Phe Met Leu Thr Tyr Ser Asn Ala Thr Asn Asp
                195                 200                 205

Val Gly Glu Gly Arg Phe Ser Lys Ser Glu Phe Cys Met Asp Pro Ile
        210                 215                 220

Leu Ile Leu Met His Glu Leu Asn His Ala Met His Asn Leu Tyr Gly
225                 230                 235                240

Ile Ala Ile Pro Asn Asp Gln Thr Ile Ser Ser Val Thr Ser Asn Ile
                245                 250                 255

Phe Tyr Ser Gln Tyr Asn Val Lys Leu Glu Tyr Ala Glu Ile Tyr Ala
                260                 265                 270

Phe Gly Gly Pro Thr Ile Asp Leu Ile Pro Lys Ser Ala Arg Lys Tyr
                275                 280                 285

Phe Glu Glu Lys Ala Leu Asp Tyr Tyr Arg Ser Ile Ala Lys Arg Leu
                290                 295                 300

Asn Ser Ile Thr Thr Ala Asn Pro Ser Ser Phe Asn Lys Tyr Ile Gly
305                 310                 315                320

Glu Tyr Lys Gln Lys Leu Ile Arg Lys Tyr Arg Phe Val Val Glu Ser
                325                 330                 335

Ser Gly Glu Val Thr Val Asn Arg Asn Lys Phe Val Glu Leu Tyr Asn
                340                 345                 350

Glu Leu Thr Gln Ile Phe Thr Glu Phe Asn Tyr Ala Lys Ile Tyr Asn
                355                 360                 365

Val Gln Asn Arg Lys Ile Tyr Leu Ser Asn Val Tyr Thr Pro Val Thr
        370                 375                 380

Ala Asn Ile Leu Asp Asp Asn Val Tyr Asp Ile Gln Asn Gly Phe Asn
385                 390                 395                400

Ile Pro Lys Ser Asn Leu Asn Val Leu Phe Met Gly Gln Asn Leu Ser
                405                 410                 415

Arg Asn Pro Ala Leu Arg Lys Val Asn Pro Glu Asn Met Leu Tyr Leu
                420                 425                 430
```

-continued

```
Phe Thr Lys Phe Cys His Lys Ala Ile Asp Gly Arg Ser Leu Tyr Asn
        435                 440                 445
Lys Thr Leu Asp Cys Arg Glu Leu Leu Val Lys Asn Thr Asp Leu Pro
    450                 455                 460
Phe Ile Gly Asp Ile Ser Asp Val Lys Thr Asp Ile Phe Leu Arg Lys
465                 470                 475                 480
Asp Ile Asn Glu Glu Thr Glu Val Ile Tyr Tyr Pro Asp Asn Val Ser
                485                 490                 495
Val Asp Gln Val Ile Leu Ser Lys Asn Thr Ser Glu His Gly Gln Leu
                500                 505                 510
Asp Leu Leu Tyr Pro Ser Ile Asp Ser Glu Ser Glu Ile Leu Pro Gly
            515                 520                 525
Glu Asn Gln Val Phe Tyr Asp Asn Arg Thr Gln Asn Val Asp Tyr Leu
        530                 535                 540
Asn Ser Tyr Tyr Tyr Leu Glu Ser Gln Lys Leu Ser Asp Asn Val Glu
545                 550                 555                 560
Asp Phe Thr Phe Thr Arg Ser Ile Glu Glu Ala Leu Asp Asn Ser Ala
                565                 570                 575
Lys Val Tyr Thr Tyr Phe Pro Thr Leu Ala Asn Lys Val Asn Ala Gly
            580                 585                 590
Val Gln Gly Gly Leu Phe Leu Met Trp Ala Asn Asp Val Val Glu Asp
        595                 600                 605
Phe Thr Thr Asn Ile Leu Arg Lys Asp Thr Leu Asp Lys Ile Ser Asp
    610                 615                 620
Val Ser Ala Ile Ile Pro Tyr Ile Gly Pro Ala Leu Asn Ile Ser Asn
625                 630                 635                 640
Ser Val Arg Arg Gly Asn Phe Thr Glu Ala Phe Ala Val Thr Gly Val
                645                 650                 655
Thr Ile Leu Leu Glu Ala Phe Pro Glu Phe Thr Ile Pro Ala Leu Gly
                660                 665                 670
Ala Phe Val Ile Tyr Ser Lys Val Gln Glu Arg Asn Glu Ile Ile Lys
            675                 680                 685
Thr Ile Asp Asn Cys Leu Glu Gln Arg Ile Lys Arg Trp Lys Asp Ser
        690                 695                 700
Tyr Glu Trp Met Met Gly Thr Trp Leu Ser Arg Ile Ile Thr Gln Phe
705                 710                 715                 720
Asn Asn Ile Ser Tyr Gln Met Tyr Asp Ser Leu Asn Tyr Gln Ala Gly
                725                 730                 735
Ala Ile Lys Ala Lys Ile Asp Leu Glu Tyr Lys Lys Tyr Ser Gly Ser
            740                 745                 750
Asp Lys Glu Asn Ile Lys Ser Gln Val Glu Asn Leu Lys Asn Ser Leu
        755                 760                 765
Asp Val Lys Ile Ser Glu Ala Met Asn Asn Ile Asn Lys Phe Ile Arg
    770                 775                 780
Glu Cys Ser Val Thr Tyr Leu Phe Lys Asn Met Leu Pro Lys Val Ile
785                 790                 795                 800
Asp Glu Leu Asn Glu Phe Asp Arg Asn Thr Lys Ala Lys Leu Ile Asn
                805                 810                 815
Leu Ile Asp Ser His Asn Ile Ile Leu Val Gly Glu Val Asp Lys Leu
            820                 825                 830
Lys Ala Lys Val Asn Asn Ser Phe Gln Asn Thr Ile Pro Phe Asn Ile
        835                 840                 845
Phe Ser Tyr Thr Asn Asn Ser Leu Leu Lys Asp Ile Ile Asn Glu Tyr
    850                 855                 860
```

```
Phe Asn Asn Ile Asn Asp Ser Lys Ile Leu Ser Leu Gln Asn Arg Lys
865                 870                 875                 880

Asn Thr Leu Val Asp Thr Ser Gly Tyr Asn Ala Glu Val Ser Glu Glu
                885                 890                 895

Gly Asp Val Gln Leu Asn Pro Ile Phe Pro Phe Asp Phe Lys Leu Gly
            900                 905                 910

Ser Ser Gly Glu Asp Arg Gly Lys Val Ile Val Thr Gln Asn Glu Asn
            915                 920                 925

Ile Val Tyr Asn Ser Met Tyr Glu Ser Phe Ser Ile Ser Phe Trp Ile
        930                 935                 940

Arg Ile Asn Lys Trp Val Ser Asn Leu Pro Gly Tyr Thr Ile Ile Asp
945                 950                 955                 960

Ser Val Lys Asn Asn Ser Gly Trp Ser Ile Gly Ile Ile Ser Asn Phe
                965                 970                 975

Leu Val Phe Thr Leu Lys Gln Asn Glu Asp Ser Glu Gln Ser Ile Asn
            980                 985                 990

Phe Ser Tyr Asp Ile Ser Asn Asn Ala Pro Gly Tyr Asn Lys Trp Phe
        995                 1000                1005

Phe Val Thr Val Thr Asn Asn Met Met Gly Asn Met Lys Ile Tyr Ile
            1010                1015                1020

Asn Gly Lys Leu Ile Asp Thr Ile Lys Val Lys Glu Leu Thr Gly Ile
1025                1030                1035                1040

Asn Phe Ser Lys Thr Ile Thr Phe Glu Ile Asn Lys Ile Pro Asp Thr
                1045                1050                1055

Gly Leu Ile Thr Ser Asp Ser Asp Asn Ile Asn Met Trp Ile Arg Asp
            1060                1065                1070

Phe Tyr Ile Phe Ala Lys Glu Leu Asp Gly Lys Asp Ile Asn Ile Leu
        1075                1080                1085

Phe Asn Ser Leu Gln Tyr Thr Asn Val Val Lys Asp Tyr Trp Gly Asn
        1090                1095                1100

Asp Leu Arg Tyr Asn Lys Glu Tyr Tyr Met Val Asn Ile Asp Tyr Leu
1105                1110                1115                1120

Asn Arg Tyr Met Tyr Ala Asn Ser Arg Gln Ile Val Phe Asn Thr Arg
                1125                1130                1135

Arg Asn Asn Asn Asp Phe Asn Glu Gly Tyr Lys Ile Ile Ile Lys Arg
            1140                1145                1150

Ile Arg Gly Asn Thr Asn Asp Thr Arg Val Arg Gly Gly Asp Ile Leu
        1155                1160                1165

Tyr Phe Asp Met Thr Ile Asn Asn Lys Ala Tyr Asn Leu Phe Met Lys
1170                1175                1180

Asn Glu Thr Met Tyr Ala Asp Asn His Ser Thr Glu Asp Ile Tyr Ala
1185                1190                1195                1200

Ile Gly Leu Arg Glu Gln Thr Lys Asp Ile Asn Asp Asn Ile Ile Phe
            1205                1210                1215

Gln Ile Gln Pro Met Asn Asn Thr Tyr Tyr Tyr Ala Ser Gln Ile Phe
            1220                1225                1230

Lys Ser Asn Phe Asn Gly Glu Asn Ile Ser Gly Ile Cys Ser Ile Gly
            1235                1240                1245

Thr Tyr Arg Phe Arg Leu Gly Gly Asp Trp Tyr Arg His Asn Tyr Leu
            1250                1255                1260

Val Pro Thr Val Lys Gln Gly Asn Tyr Ala Ser Leu Leu Glu Ser Thr
1265                1270                1275                1280

Ser Thr His Trp Gly Phe Val Pro Val Ser Glu
```

-continued

```
<210> SEQ ID NO 4
<211> LENGTH: 1276
<212> TYPE: PRT
<213> ORGANISM: Clostridium botulinum Serotype D
<220> FEATURE:
<221> NAME/KEY: DOMAIN
<222> LOCATION: (1)...(442)
<223> OTHER INFORMATION: Light chain comprising the enzymatic domain.
<221> NAME/KEY: DOMAIN
<222> LOCATION: (443)...(851)
<223> OTHER INFORMATION: Amino-terminal half of heavy chain comprising
      the translocation domain.
<221> NAME/KEY: DOMAIN
<222> LOCATION: (852)...(1276)
<223> OTHER INFORMATION: Carboxyl-terminal half of heavy chain
      comprising the binding domain.

<400> SEQUENCE: 4

Met Thr Trp Pro Val Lys Asp Phe Asn Tyr Ser Asp Pro Val Asn Asp
 1               5                  10                  15

Asn Asp Ile Leu Tyr Leu Arg Ile Pro Gln Asn Lys Leu Ile Thr Thr
            20                  25                  30

Pro Val Lys Ala Phe Met Ile Thr Gln Asn Ile Trp Val Ile Pro Glu
        35                  40                  45

Arg Phe Ser Ser Asp Thr Asn Pro Ser Leu Ser Lys Pro Pro Arg Pro
    50                  55                  60

Thr Ser Lys Tyr Gln Ser Tyr Tyr Asp Pro Ser Tyr Leu Ser Thr Asp
65                  70                  75                  80

Glu Gln Lys Asp Thr Phe Leu Lys Gly Ile Ile Lys Leu Phe Lys Arg
                85                  90                  95

Ile Asn Glu Arg Asp Ile Gly Lys Lys Leu Ile Asn Tyr Leu Val Val
            100                 105                 110

Gly Ser Pro Phe Met Gly Asp Ser Ser Thr Pro Glu Asp Thr Phe Asp
        115                 120                 125

Phe Thr Arg His Thr Thr Asn Ile Ala Val Glu Lys Phe Glu Asn Gly
    130                 135                 140

Ser Trp Lys Val Thr Asn Ile Ile Thr Pro Ser Val Leu Ile Phe Gly
145                 150                 155                 160

Pro Leu Pro Asn Ile Leu Asp Tyr Thr Ala Ser Leu Thr Leu Gln Gly
                165                 170                 175

Gln Gln Ser Asn Pro Ser Phe Glu Gly Phe Gly Thr Leu Ser Ile Leu
            180                 185                 190

Lys Val Ala Pro Glu Phe Leu Leu Thr Phe Ser Asp Val Thr Ser Asn
        195                 200                 205

Gln Ser Ser Ala Val Leu Gly Lys Ser Ile Phe Cys Met Asp Pro Val
    210                 215                 220

Ile Ala Leu Met His Glu Leu Thr His Ser Leu His Gln Leu Tyr Gly
225                 230                 235                 240

Ile Asn Ile Pro Ser Asp Lys Arg Ile Arg Pro Gln Val Ser Glu Gly
                245                 250                 255

Phe Phe Ser Gln Asp Gly Pro Asn Val Gln Phe Glu Glu Leu Tyr Thr
            260                 265                 270

Phe Gly Gly Leu Asp Val Glu Ile Ile Pro Gln Ile Glu Arg Ser Gln
        275                 280                 285

Leu Arg Glu Lys Ala Leu Gly His Tyr Lys Asp Ile Ala Lys Arg Leu
    290                 295                 300

Asn Asn Ile Asn Lys Thr Ile Pro Ser Ser Trp Ile Ser Asn Ile Asp
```

```
            305                 310                 315                 320
Lys Tyr Lys Lys Ile Phe Ser Glu Lys Tyr Asn Phe Asp Lys Asp Asn
                    325                 330                 335

Thr Gly Asn Phe Val Val Asn Ile Asp Lys Phe Asn Ser Leu Tyr Ser
                340                 345                 350

Asp Leu Thr Asn Val Met Ser Glu Val Val Tyr Ser Ser Gln Tyr Asn
            355                 360                 365

Val Lys Asn Arg Thr His Tyr Phe Ser Arg His Tyr Leu Pro Val Phe
        370                 375                 380

Ala Asn Ile Leu Asp Asp Asn Ile Tyr Thr Ile Arg Asp Gly Phe Asn
385                 390                 395                 400

Leu Thr Asn Lys Gly Phe Asn Ile Glu Asn Ser Gly Gln Asn Ile Glu
                405                 410                 415

Arg Asn Pro Ala Leu Gln Lys Leu Ser Ser Glu Ser Val Val Asp Leu
            420                 425                 430

Phe Thr Lys Val Cys Leu Arg Leu Thr Lys Asn Ser Arg Asp Asp Ser
        435                 440                 445

Thr Cys Ile Lys Val Lys Asn Asn Arg Leu Pro Tyr Val Ala Asp Lys
450                 455                 460

Asp Ser Ile Ser Gln Glu Ile Phe Glu Asn Lys Ile Ile Thr Asp Glu
465                 470                 475                 480

Thr Asn Val Gln Asn Tyr Ser Asp Lys Phe Ser Leu Asp Glu Ser Ile
                485                 490                 495

Leu Asp Gly Gln Val Pro Ile Asn Pro Glu Ile Val Asp Pro Leu Leu
            500                 505                 510

Pro Asn Val Asn Met Glu Pro Leu Asn Leu Pro Gly Glu Glu Ile Val
        515                 520                 525

Phe Tyr Asp Asp Ile Thr Lys Tyr Val Asp Tyr Leu Asn Ser Tyr Tyr
    530                 535                 540

Tyr Leu Glu Ser Gln Lys Leu Ser Asn Asn Val Glu Asn Ile Thr Leu
545                 550                 555                 560

Thr Thr Ser Val Glu Glu Ala Leu Gly Tyr Ser Asn Lys Ile Tyr Thr
                565                 570                 575

Phe Leu Pro Ser Leu Ala Glu Lys Val Asn Lys Gly Val Gln Ala Gly
            580                 585                 590

Leu Phe Leu Asn Trp Ala Asn Glu Val Val Glu Asp Phe Thr Thr Asn
        595                 600                 605

Ile Met Lys Lys Asp Thr Leu Asp Lys Ile Ser Asp Val Ser Val Ile
    610                 615                 620

Ile Pro Tyr Ile Gly Pro Ala Leu Asn Ile Gly Asn Ser Ala Leu Arg
625                 630                 635                 640

Gly Asn Phe Asn Gln Ala Phe Ala Thr Ala Gly Val Ala Phe Leu Leu
                645                 650                 655

Glu Gly Phe Pro Glu Phe Thr Ile Pro Ala Leu Gly Val Phe Thr Phe
            660                 665                 670

Tyr Ser Ser Ile Gln Glu Arg Glu Lys Ile Ile Lys Thr Ile Glu Asn
        675                 680                 685

Cys Leu Glu Gln Arg Val Lys Arg Trp Lys Asp Ser Tyr Gln Trp Met
    690                 695                 700

Val Ser Asn Trp Leu Ser Arg Ile Thr Thr Gln Phe Asn His Ile Asn
705                 710                 715                 720

Tyr Gln Met Tyr Asp Ser Leu Ser Tyr Gln Ala Asp Ala Ile Lys Ala
                725                 730                 735
```

```
Lys Ile Asp Leu Glu Tyr Lys Tyr Ser Gly Ser Asp Lys Glu Asn
        740                 745                 750

Ile Lys Ser Gln Val Glu Asn Leu Lys Asn Ser Leu Asp Val Lys Ile
            755                 760                 765

Ser Glu Ala Met Asn Asn Ile Asn Lys Phe Ile Arg Glu Cys Ser Val
    770                 775                 780

Thr Tyr Leu Phe Lys Asn Met Leu Pro Lys Val Ile Asp Glu Leu Asn
785                 790                 795                 800

Lys Phe Asp Leu Arg Thr Lys Thr Glu Leu Ile Asn Leu Ile Asp Ser
                805                 810                 815

His Asn Ile Ile Leu Val Gly Glu Val Asp Arg Leu Lys Ala Lys Val
            820                 825                 830

Asn Glu Ser Phe Glu Asn Thr Met Pro Phe Asn Ile Phe Ser Tyr Thr
    835                 840                 845

Asn Asn Ser Leu Leu Lys Asp Ile Ile Asn Glu Tyr Phe Asn Ser Ile
850                 855                 860

Asn Asp Ser Lys Ile Leu Ser Leu Gln Asn Lys Lys Asn Ala Leu Val
865                 870                 875                 880

Asp Thr Ser Gly Tyr Asn Ala Glu Val Arg Val Gly Asp Asn Val Gln
                885                 890                 895

Leu Asn Thr Ile Tyr Thr Asn Asp Phe Lys Leu Ser Ser Ser Gly Asp
            900                 905                 910

Lys Ile Ile Val Asn Leu Asn Asn Asn Ile Leu Tyr Ser Ala Ile Tyr
        915                 920                 925

Glu Asn Ser Ser Val Ser Phe Trp Ile Lys Ile Ser Lys Asp Leu Thr
    930                 935                 940

Asn Ser His Asn Glu Tyr Thr Ile Ile Asn Ser Ile Glu Gln Asn Ser
945                 950                 955                 960

Gly Trp Lys Leu Cys Ile Arg Asn Gly Asn Ile Glu Trp Ile Leu Gln
                965                 970                 975

Asp Val Asn Arg Lys Tyr Lys Ser Leu Ile Phe Asp Tyr Ser Glu Ser
            980                 985                 990

Leu Ser His Thr Gly Tyr Thr Asn Lys Trp Phe Phe Val Thr Ile Thr
        995                 1000                1005

Asn Asn Ile Met Gly Tyr Met Lys Leu Tyr Ile Asn Gly Glu Leu Lys
    1010                1015                1020

Gln Ser Gln Lys Ile Glu Asp Leu Asp Glu Val Lys Leu Asp Lys Thr
1025                1030                1035                1040

Ile Val Phe Gly Ile Asp Glu Asn Ile Asp Glu Asn Gln Met Leu Trp
                1045                1050                1055

Ile Arg Asp Phe Asn Ile Phe Ser Lys Glu Leu Ser Asn Glu Asp Ile
            1060                1065                1070

Asn Ile Val Tyr Glu Gly Gln Ile Leu Arg Asn Val Ile Lys Asp Tyr
        1075                1080                1085

Trp Gly Asn Pro Leu Lys Phe Asp Thr Glu Tyr Tyr Ile Ile Asn Asp
    1090                1095                1100

Asn Tyr Ile Asp Arg Tyr Ile Ala Pro Glu Ser Asn Val Leu Val Leu
1105                1110                1115                1120

Val Gln Tyr Pro Asp Arg Ser Lys Leu Tyr Thr Gly Asn Pro Ile Thr
                1125                1130                1135

Ile Lys Ser Val Ser Asp Lys Asn Pro Tyr Ser Arg Ile Leu Asn Gly
            1140                1145                1150

Asp Asn Ile Ile Leu His Met Leu Tyr Asn Ser Arg Lys Tyr Met Ile
        1155                1160                1165
```

```
Ile Arg Asp Thr Asp Thr Ile Tyr Ala Thr Gln Gly Gly Glu Cys Ser
    1170                1175                1180

Gln Asn Cys Val Tyr Ala Leu Lys Leu Gln Ser Asn Leu Gly Asn Tyr
1185                1190                1195                1200

Gly Ile Gly Ile Phe Ser Ile Lys Asn Ile Val Ser Lys Asn Lys Tyr
            1205                1210                1215

Cys Ser Gln Ile Phe Ser Ser Phe Arg Glu Asn Thr Met Leu Leu Ala
            1220                1225                1230

Asp Ile Tyr Lys Pro Trp Arg Phe Ser Phe Lys Asn Ala Tyr Thr Pro
            1235                1240                1245

Val Ala Val Thr Asn Tyr Glu Thr Lys Leu Leu Ser Thr Ser Ser Phe
    1250                1255                1260

Trp Lys Phe Ile Ser Arg Asp Pro Gly Trp Val Glu
1265                1270                1275

<210> SEQ ID NO 5
<211> LENGTH: 1252
<212> TYPE: PRT
<213> ORGANISM: Clostridium botulinum Serotype E
<220> FEATURE:
<221> NAME/KEY: DOMAIN
<222> LOCATION: (1)...(422)
<223> OTHER INFORMATION: Light chain comprising the enzymatic domain.
<221> NAME/KEY: DOMAIN
<222> LOCATION: (423)...(834)
<223> OTHER INFORMATION: Amino-terminal half of heavy chain comprising
      the translocation domain.
<221> NAME/KEY: DOMAIN
<222> LOCATION: (835)...(1252)
<223> OTHER INFORMATION: Carboxyl-terminal half of heavy chain
      comprising the binding domain.

<400> SEQUENCE: 5

Met Pro Lys Ile Asn Ser Phe Asn Tyr Asn Asp Pro Val Asn Asp Arg
 1               5                  10                  15

Thr Ile Leu Tyr Ile Lys Pro Gly Gly Cys Gln Glu Phe Tyr Lys Ser
            20                  25                  30

Phe Asn Ile Met Lys Asn Ile Trp Ile Ile Pro Glu Arg Asn Val Ile
        35                  40                  45

Gly Thr Thr Pro Gln Asp Phe His Pro Pro Thr Ser Leu Lys Asn Gly
    50                  55                  60

Asp Ser Ser Tyr Tyr Asp Pro Asn Tyr Leu Gln Ser Asp Glu Glu Lys
65                  70                  75                  80

Asp Arg Phe Leu Lys Ile Val Thr Lys Ile Phe Asn Arg Ile Asn Asn
                85                  90                  95

Asn Leu Ser Gly Gly Ile Leu Leu Glu Glu Leu Ser Lys Ala Asn Pro
            100                 105                 110

Tyr Leu Gly Asn Asp Asn Thr Pro Asp Asn Gln Phe His Ile Gly Asp
        115                 120                 125

Ala Ser Ala Val Glu Ile Lys Phe Ser Asn Gly Ser Gln Asp Ile Leu
    130                 135                 140

Leu Pro Asn Val Ile Ile Met Gly Ala Glu Pro Asp Leu Phe Glu Thr
145                 150                 155                 160

Asn Ser Ser Asn Ile Ser Leu Arg Asn Asn Tyr Met Pro Ser Asn His
                165                 170                 175

Gly Phe Gly Ser Ile Ala Ile Val Thr Phe Ser Pro Glu Tyr Ser Phe
            180                 185                 190

Arg Phe Asn Asp Asn Ser Met Asn Glu Phe Ile Gln Asp Pro Ala Leu
        195                 200                 205
```

```
Thr Leu Met His Glu Leu Ile His Ser Leu His Gly Leu Tyr Gly Ala
    210                 215                 220
Lys Gly Ile Thr Thr Lys Tyr Thr Ile Thr Gln Lys Gln Asn Pro Leu
225                 230                 235                 240
Ile Thr Asn Ile Arg Gly Thr Asn Ile Glu Glu Phe Leu Thr Phe Gly
            245                 250                 255
Gly Thr Asp Leu Asn Ile Ile Thr Ser Ala Gln Ser Asn Asp Ile Tyr
        260                 265                 270
Thr Asn Leu Leu Ala Asp Tyr Lys Lys Ile Ala Ser Lys Leu Ser Lys
    275                 280                 285
Val Gln Val Ser Asn Pro Leu Leu Asn Pro Tyr Lys Asp Val Phe Glu
290                 295                 300
Ala Lys Tyr Gly Leu Asp Lys Asp Ala Ser Gly Ile Tyr Ser Val Asn
305                 310                 315                 320
Ile Asn Lys Phe Asn Asp Ile Phe Lys Lys Leu Tyr Ser Phe Thr Glu
            325                 330                 335
Phe Asp Leu Ala Thr Lys Phe Gln Val Lys Cys Arg Gln Thr Tyr Ile
        340                 345                 350
Gly Gln Tyr Lys Tyr Phe Lys Leu Ser Asn Leu Leu Asn Asp Ser Ile
    355                 360                 365
Tyr Asn Ile Ser Glu Gly Tyr Asn Ile Asn Asn Leu Lys Val Asn Phe
370                 375                 380
Arg Gly Gln Asn Ala Asn Leu Asn Pro Arg Ile Ile Thr Pro Ile Thr
385                 390                 395                 400
Gly Arg Gly Leu Val Lys Lys Ile Ile Arg Phe Cys Lys Asn Ile Val
            405                 410                 415
Ser Val Lys Gly Ile Arg Lys Ser Ile Cys Ile Glu Ile Asn Asn Gly
        420                 425                 430
Glu Leu Phe Phe Val Ala Ser Glu Asn Ser Tyr Asn Asp Asp Asn Ile
    435                 440                 445
Asn Thr Pro Lys Glu Ile Asp Asp Thr Val Thr Ser Asn Asn Asn Tyr
450                 455                 460
Glu Asn Asp Leu Asp Gln Val Ile Leu Asn Phe Asn Ser Glu Ser Ala
465                 470                 475                 480
Pro Gly Leu Ser Asp Glu Lys Leu Asn Leu Thr Ile Gln Asn Asp Ala
            485                 490                 495
Tyr Ile Pro Lys Tyr Asp Ser Asn Gly Thr Ser Asp Ile Glu Gln His
        500                 505                 510
Asp Val Asn Glu Leu Asn Val Phe Phe Tyr Leu Asp Ala Gln Lys Val
    515                 520                 525
Pro Glu Gly Glu Asn Asn Val Asn Leu Thr Ser Ser Ile Asp Thr Ala
530                 535                 540
Leu Leu Glu Gln Pro Lys Ile Tyr Thr Phe Phe Ser Ser Glu Phe Ile
545                 550                 555                 560
Asn Asn Val Asn Lys Pro Val Gln Ala Ala Leu Phe Val Ser Trp Ile
            565                 570                 575
Gln Gln Val Leu Val Asp Phe Thr Thr Glu Ala Asn Gln Lys Ser Thr
        580                 585                 590
Val Asp Lys Ile Ala Asp Ile Ser Ile Val Val Pro Tyr Ile Gly Leu
    595                 600                 605
Ala Leu Asn Ile Gly Asn Glu Ala Gln Lys Gly Asn Phe Lys Asp Ala
610                 615                 620
Leu Glu Leu Leu Gly Ala Gly Ile Leu Leu Glu Phe Glu Pro Glu Leu
```

-continued

```
            625                 630                 635                 640
Leu Ile Pro Thr Ile Leu Val Phe Thr Ile Lys Ser Phe Leu Gly Ser
                    645                 650                 655
Ser Asp Asn Lys Asn Lys Val Ile Lys Ala Ile Asn Asn Ala Leu Lys
                660                 665                 670
Glu Arg Asp Glu Lys Trp Lys Glu Val Tyr Ser Phe Ile Val Ser Asn
            675                 680                 685
Trp Met Thr Lys Ile Asn Thr Gln Phe Asn Lys Arg Lys Glu Gln Met
        690                 695                 700
Tyr Gln Ala Leu Gln Asn Gln Val Asn Ala Ile Lys Thr Ile Ile Glu
705                 710                 715                 720
Ser Lys Tyr Asn Ser Tyr Thr Leu Glu Glu Lys Asn Glu Leu Thr Asn
                    725                 730                 735
Lys Tyr Asp Ile Lys Gln Ile Glu Asn Glu Leu Asn Gln Lys Val Ser
                740                 745                 750
Ile Ala Met Asn Asn Ile Asp Arg Phe Leu Thr Glu Ser Ser Ile Ser
            755                 760                 765
Tyr Leu Met Lys Leu Ile Asn Glu Val Lys Ile Asn Lys Leu Arg Glu
        770                 775                 780
Tyr Asp Glu Asn Val Lys Thr Tyr Leu Leu Asn Tyr Ile Ile Gln His
785                 790                 795                 800
Gly Ser Ile Leu Gly Glu Ser Gln Gln Glu Leu Asn Ser Met Val Thr
                    805                 810                 815
Asp Thr Leu Asn Asn Ser Ile Pro Phe Lys Leu Ser Ser Tyr Thr Asp
                820                 825                 830
Asp Lys Ile Leu Ile Ser Tyr Phe Asn Lys Phe Phe Lys Arg Ile Lys
            835                 840                 845
Ser Ser Ser Val Leu Asn Met Arg Tyr Lys Asn Asp Lys Tyr Val Asp
        850                 855                 860
Thr Ser Gly Tyr Asp Ser Asn Ile Asn Ile Asn Gly Asp Val Tyr Lys
865                 870                 875                 880
Tyr Pro Thr Asn Lys Asn Gln Phe Gly Ile Tyr Asn Asp Lys Leu Ser
                    885                 890                 895
Glu Val Asn Ile Ser Gln Asn Asp Tyr Ile Ile Tyr Asp Asn Lys Tyr
                900                 905                 910
Lys Asn Phe Ser Ile Ser Phe Trp Val Arg Ile Pro Asn Tyr Asp Asn
            915                 920                 925
Lys Ile Val Asn Val Asn Asn Glu Tyr Thr Ile Ile Asn Cys Met Arg
        930                 935                 940
Asp Asn Asn Ser Gly Trp Lys Val Ser Leu Asn His Asn Glu Ile Ile
945                 950                 955                 960
Trp Thr Leu Gln Asp Asn Ala Gly Ile Asn Gln Lys Leu Ala Phe Asn
                    965                 970                 975
Tyr Gly Asn Ala Asn Gly Ile Ser Asp Tyr Ile Asn Lys Trp Ile Phe
                980                 985                 990
Val Thr Ile Thr Asn Asp Arg Leu Gly Asp Ser Lys Leu Tyr Ile Asn
            995                 1000                1005
Gly Asn Leu Ile Asp Gln Lys Ser Ile Leu Asn Leu Gly Asn Ile His
        1010                1015                1020
Val Ser Asp Asn Ile Leu Phe Lys Ile Val Asn Cys Ser Tyr Thr Arg
1025                1030                1035                1040
Tyr Ile Gly Ile Arg Tyr Phe Asn Ile Phe Asp Lys Glu Leu Asp Glu
                    1045                1050                1055
```

```
Thr Glu Ile Gln Thr Leu Tyr Ser Asn Glu Pro Asn Thr Asn Ile Leu
            1060                1065                1070

Lys Asp Phe Trp Gly Asn Tyr Leu Leu Tyr Asp Lys Glu Tyr Tyr Leu
        1075                1080                1085

Leu Asn Val Leu Lys Pro Asn Asn Phe Ile Asp Arg Arg Lys Asp Ser
    1090                1095                1100

Thr Leu Ser Ile Asn Asn Ile Arg Ser Thr Ile Leu Leu Ala Asn Arg
1105                1110                1115                1120

Leu Tyr Ser Gly Ile Lys Val Lys Ile Gln Arg Val Asn Asn Ser Ser
                1125                1130                1135

Thr Asn Asp Asn Leu Val Arg Lys Asn Asp Gln Val Tyr Ile Asn Phe
            1140                1145                1150

Val Ala Ser Lys Thr His Leu Phe Pro Leu Tyr Ala Asp Thr Ala Thr
        1155                1160                1165

Thr Asn Lys Glu Lys Thr Ile Lys Ile Ser Ser Ser Gly Asn Arg Phe
    1170                1175                1180

Asn Gln Val Val Val Met Asn Ser Val Gly Asn Asn Cys Thr Met Asn
1185                1190                1195                1200

Phe Lys Asn Asn Asn Gly Asn Asn Ile Gly Leu Leu Gly Phe Lys Ala
                1205                1210                1215

Asp Thr Val Val Ala Ser Thr Trp Tyr Tyr Thr His Met Arg Asp His
            1220                1225                1230

Thr Asn Ser Asn Gly Cys Phe Trp Asn Phe Ile Ser Glu Glu His Gly
        1235                1240                1245

Trp Gln Glu Lys
    1250

<210> SEQ ID NO 6
<211> LENGTH: 1274
<212> TYPE: PRT
<213> ORGANISM: Clostridium botulinum Serotype F
<220> FEATURE:
<221> NAME/KEY: DOMAIN
<222> LOCATION: (1)...(436)
<223> OTHER INFORMATION: Light chain comprising the enzymatic domain.
<221> NAME/KEY: DOMAIN
<222> LOCATION: (437)...(852)
<223> OTHER INFORMATION: Amino-terminal half of heavy chain comprising
      the translocation domain.
<221> NAME/KEY: DOMAIN
<222> LOCATION: (853)...(1274)
<223> OTHER INFORMATION: Carboxyl-terminal half of heavy chain
      comprising the binding domain.

<400> SEQUENCE: 6

Met Pro Val Ala Ile Asn Ser Phe Asn Tyr Asn Asp Pro Val Asn Asp
 1               5                  10                  15

Asp Thr Ile Leu Tyr Met Gln Ile Pro Tyr Glu Glu Lys Ser Lys Lys
            20                  25                  30

Tyr Tyr Lys Ala Phe Glu Ile Met Arg Asn Val Trp Ile Ile Pro Glu
        35                  40                  45

Arg Asn Thr Ile Gly Thr Asn Pro Ser Asp Phe Asp Pro Pro Ala Ser
    50                  55                  60

Leu Lys Asn Gly Ser Ser Ala Tyr Tyr Asp Pro Asn Tyr Leu Thr Thr
65                  70                  75                  80

Asp Ala Glu Lys Asp Arg Tyr Leu Lys Thr Thr Ile Lys Leu Phe Lys
                85                  90                  95

Arg Ile Asn Ser Asn Pro Ala Gly Lys Val Leu Leu Gln Glu Ile Ser
            100                 105                 110
```

```
Tyr Ala Lys Pro Tyr Leu Gly Asn Asp His Thr Pro Ile Asp Glu Phe
        115                 120                 125

Ser Pro Val Thr Arg Thr Thr Ser Val Asn Ile Lys Leu Ser Thr Asn
130                 135                 140

Val Glu Ser Ser Met Leu Leu Asn Leu Leu Val Leu Gly Ala Gly Pro
145                 150                 155                 160

Asp Ile Phe Glu Ser Cys Cys Tyr Pro Val Arg Lys Leu Ile Asp Pro
                165                 170                 175

Asp Val Val Tyr Asp Pro Ser Asn Tyr Gly Phe Gly Ser Ile Asn Ile
                180                 185                 190

Val Thr Phe Ser Pro Glu Tyr Glu Tyr Thr Phe Asn Asp Ile Ser Gly
                195                 200                 205

Gly His Asn Ser Ser Thr Glu Ser Phe Ile Ala Asp Pro Ala Ile Ser
        210                 215                 220

Leu Ala His Glu Leu Ile His Ala Leu His Gly Leu Tyr Gly Ala Arg
225                 230                 235                 240

Gly Val Thr Tyr Glu Glu Thr Ile Glu Val Lys Gln Ala Pro Leu Met
                245                 250                 255

Ile Ala Glu Lys Pro Ile Arg Leu Glu Glu Phe Leu Thr Phe Gly Gly
                260                 265                 270

Gln Asp Leu Asn Ile Ile Thr Ser Ala Met Lys Glu Lys Ile Tyr Asn
                275                 280                 285

Asn Leu Leu Ala Asn Tyr Glu Lys Ile Ala Thr Arg Leu Ser Glu Val
290                 295                 300

Asn Ser Ala Pro Pro Glu Tyr Asp Ile Asn Tyr Lys Asp Tyr Phe
305                 310                 315                 320

Gln Trp Lys Tyr Gly Leu Asp Lys Asn Ala Asp Gly Ser Tyr Thr Val
                325                 330                 335

Asn Glu Asn Lys Phe Asn Glu Ile Tyr Lys Lys Leu Tyr Ser Phe Thr
                340                 345                 350

Glu Ser Asp Leu Ala Asn Lys Phe Lys Val Lys Cys Arg Asn Thr Tyr
                355                 360                 365

Phe Ile Lys Tyr Glu Phe Leu Lys Val Pro Asn Leu Leu Asp Asp
370                 375                 380

Ile Tyr Thr Val Ser Glu Gly Phe Asn Ile Gly Asn Leu Ala Val Asn
385                 390                 395                 400

Asn Arg Gly Gln Ser Ile Lys Leu Asn Pro Lys Ile Ile Asp Ser Ile
                405                 410                 415

Pro Asp Lys Gly Leu Val Glu Lys Ile Val Lys Phe Cys Lys Ser Val
                420                 425                 430

Ile Pro Arg Lys Gly Thr Lys Ala Pro Pro Arg Leu Cys Ile Arg Val
                435                 440                 445

Asn Asn Ser Glu Leu Phe Phe Val Ala Ser Glu Ser Ser Tyr Asn Glu
        450                 455                 460

Asn Asp Ile Asn Thr Pro Lys Glu Ile Asp Asp Thr Thr Asn Leu Asn
465                 470                 475                 480

Asn Asn Tyr Arg Asn Asn Leu Asp Glu Val Ile Leu Asp Tyr Asn Ser
                485                 490                 495

Gln Thr Ile Pro Gln Ile Ser Asn Arg Thr Leu Asn Thr Leu Val Gln
                500                 505                 510

Asp Asn Ser Tyr Val Pro Arg Tyr Asp Ser Asn Gly Thr Ser Glu Ile
                515                 520                 525

Glu Glu Tyr Asp Val Val Asp Phe Asn Val Phe Phe Tyr Leu His Ala
530                 535                 540
```

-continued

```
Gln Lys Val Pro Glu Gly Glu Thr Asn Ile Ser Leu Thr Ser Ser Ile
545                 550                 555                 560

Asp Thr Ala Leu Leu Glu Ser Lys Asp Ile Phe Phe Ser Ser Glu
                565                 570                 575

Phe Ile Asp Thr Ile Asn Lys Pro Val Asn Ala Ala Leu Phe Ile Asp
                580                 585                 590

Trp Ile Ser Lys Val Ile Arg Asp Phe Thr Thr Glu Ala Thr Gln Lys
                595                 600                 605

Ser Thr Val Asp Lys Ile Ala Asp Ile Ser Leu Ile Val Pro Tyr Val
                610                 615                 620

Gly Leu Ala Leu Asn Ile Ile Glu Ala Glu Lys Gly Asn Phe Glu
625                 630                 635                 640

Glu Ala Phe Glu Leu Leu Gly Val Gly Ile Leu Leu Glu Phe Val Pro
                645                 650                 655

Glu Leu Thr Ile Pro Val Ile Leu Val Phe Thr Ile Lys Ser Tyr Ile
                660                 665                 670

Asp Ser Tyr Glu Asn Lys Asn Lys Ala Ile Lys Ala Ile Asn Asn Ser
                675                 680                 685

Leu Ile Glu Arg Glu Ala Lys Trp Lys Glu Ile Tyr Ser Trp Ile Val
690                 695                 700

Ser Asn Trp Leu Thr Arg Ile Asn Thr Gln Phe Asn Lys Arg Lys Glu
705                 710                 715                 720

Gln Met Tyr Gln Ala Leu Gln Asn Gln Val Asp Ala Ile Lys Thr Ala
                725                 730                 735

Ile Glu Tyr Lys Tyr Asn Asn Tyr Thr Ser Asp Glu Lys Asn Arg Leu
                740                 745                 750

Glu Ser Glu Tyr Asn Ile Asn Asn Ile Glu Glu Leu Asn Lys Lys
                755                 760                 765

Val Ser Leu Ala Met Lys Asn Ile Glu Arg Phe Met Thr Glu Ser Ser
770                 775                 780

Ile Ser Tyr Leu Met Lys Leu Ile Asn Glu Ala Lys Val Gly Lys Leu
785                 790                 795                 800

Lys Lys Tyr Asp Asn His Val Lys Ser Asp Leu Leu Asn Tyr Ile Leu
                805                 810                 815

Asp His Arg Ser Ile Leu Gly Glu Gln Thr Asn Glu Leu Ser Asp Leu
                820                 825                 830

Val Thr Ser Thr Leu Asn Ser Ser Ile Pro Phe Glu Leu Ser Ser Tyr
                835                 840                 845

Thr Asn Asp Lys Ile Leu Ile Ile Tyr Phe Asn Arg Leu Tyr Lys Lys
                850                 855                 860

Ile Lys Asp Ser Ser Ile Leu Asp Met Arg Tyr Glu Asn Asn Lys Phe
865                 870                 875                 880

Ile Asp Ile Ser Gly Tyr Gly Ser Asn Ile Ser Ile Asn Gly Asn Val
                885                 890                 895

Tyr Ile Tyr Ser Thr Asn Arg Asn Gln Phe Gly Ile Tyr Asn Ser Arg
                900                 905                 910

Leu Ser Glu Val Asn Ile Ala Gln Asn Asn Asp Ile Ile Tyr Asn Ser
                915                 920                 925

Arg Tyr Gln Asn Phe Ser Ile Ser Phe Trp Val Arg Ile Pro Lys His
                930                 935                 940

Tyr Lys Pro Met Asn His Asn Arg Glu Tyr Thr Ile Ile Asn Cys Met
945                 950                 955                 960

Gly Asn Asn Asn Ser Gly Trp Lys Ile Ser Leu Arg Thr Val Arg Asp
```

-continued

```
                    965                 970                 975
Cys Glu Ile Ile Trp Thr Leu Gln Asp Thr Ser Gly Asn Lys Glu Asn
                980                 985                 990
Leu Ile Phe Arg Tyr Glu Glu Leu Asn Arg Ile Ser Asn Tyr Ile Asn
            995                1000                1005
Lys Trp Ile Phe Val Thr Ile Thr Asn Asn Arg Leu Gly Asn Ser Arg
       1010                1015                1020
Ile Tyr Ile Asn Gly Asn Leu Ile Val Glu Lys Ser Ile Ser Asn Leu
1025                1030                1035                1040
Gly Asp Ile His Val Ser Asp Asn Ile Leu Phe Lys Ile Val Gly Cys
                1045                1050                1055
Asp Asp Glu Thr Tyr Val Gly Ile Arg Tyr Phe Lys Val Phe Asn Thr
                1060                1065                1070
Glu Leu Asp Lys Thr Glu Ile Glu Thr Leu Tyr Ser Asn Glu Pro Asp
                1075                1080                1085
Pro Ser Ile Leu Lys Asn Tyr Trp Gly Asn Tyr Leu Leu Tyr Asn Lys
                1090                1095                1100
Lys Tyr Tyr Leu Phe Asn Leu Leu Arg Lys Asp Lys Tyr Ile Thr Leu
1105                1110                1115                1120
Asn Ser Gly Ile Leu Asn Ile Asn Gln Gln Arg Gly Val Thr Glu Gly
                1125                1130                1135
Ser Val Phe Leu Asn Tyr Lys Leu Tyr Glu Gly Val Glu Val Ile Ile
                1140                1145                1150
Arg Lys Asn Gly Pro Ile Asp Ile Ser Asn Thr Asp Asn Phe Val Arg
                1155                1160                1165
Lys Asn Asp Leu Ala Tyr Ile Asn Val Val Asp Arg Gly Val Glu Tyr
       1170                1175                1180
Arg Leu Tyr Ala Asp Thr Lys Ser Glu Lys Glu Lys Ile Ile Arg Thr
1185                1190                1195                1200
Ser Asn Leu Asn Asp Ser Leu Gly Gln Ile Ile Val Met Asp Ser Ile
                1205                1210                1215
Gly Asn Asn Cys Thr Met Asn Phe Gln Asn Asn Asn Gly Ser Asn Ile
                1220                1225                1230
Gly Leu Leu Gly Phe His Ser Asn Asn Leu Val Ala Ser Ser Trp Tyr
                1235                1240                1245
Tyr Asn Asn Ile Arg Arg Asn Thr Ser Ser Asn Gly Cys Phe Trp Ser
                1250                1255                1260
Ser Ile Ser Lys Glu Asn Gly Trp Lys Glu
1265                1270

<210> SEQ ID NO 7
<211> LENGTH: 1297
<212> TYPE: PRT
<213> ORGANISM: Clostridium botulinum Serotype G
<220> FEATURE:
<221> NAME/KEY: DOMAIN
<222> LOCATION: (1)...(442)
<223> OTHER INFORMATION: Light chain comprising the enzymatic domain.
<221> NAME/KEY: DOMAIN
<222> LOCATION: (443)...(852)
<223> OTHER INFORMATION: Amino-terminal half of heavy chain comprising
      the translocation domain.
<221> NAME/KEY: DOMAIN
<222> LOCATION: (853)...(1297)
<223> OTHER INFORMATION: Carboxyl-terminal half of heavy chain
      comprising the binding domain.

<400> SEQUENCE: 7

Met Pro Val Asn Ile Lys Asn Phe Asn Tyr Asn Asp Pro Ile Asn Asn
```

```
          1               5                   10                  15
Asp Asp Ile Ile Met Met Glu Pro Phe Asn Asp Pro Gly Pro Gly Thr
                    20                  25                  30

Tyr Tyr Lys Ala Phe Arg Ile Ile Asp Arg Ile Trp Ile Val Pro Glu
                    35                  40                  45

Arg Phe Thr Tyr Gly Phe Gln Pro Asp Gln Phe Asn Ala Ser Thr Gly
        50                  55                  60

Val Phe Ser Lys Asp Val Tyr Glu Tyr Asp Pro Thr Tyr Leu Lys
65                      70                  75                  80

Thr Asp Ala Glu Lys Asp Lys Phe Leu Lys Thr Met Ile Lys Leu Phe
                    85                  90                  95

Asn Arg Ile Asn Ser Lys Pro Ser Gly Gln Arg Leu Leu Asp Met Ile
                100                 105                 110

Val Asp Ala Ile Pro Tyr Leu Gly Asn Ala Ser Thr Pro Pro Asp Lys
                115                 120                 125

Phe Ala Ala Asn Val Ala Asn Val Ser Ile Asn Lys Lys Ile Ile Gln
                130                 135                 140

Pro Gly Ala Glu Asp Gln Ile Lys Gly Leu Met Thr Asn Leu Ile Ile
145                 150                 155                 160

Phe Gly Pro Gly Pro Val Leu Ser Asp Asn Phe Thr Asp Ser Met Ile
                165                 170                 175

Met Asn Gly His Ser Pro Ile Ser Glu Gly Phe Gly Ala Arg Met Met
                180                 185                 190

Ile Arg Phe Cys Pro Ser Cys Leu Asn Val Phe Asn Asn Val Gln Glu
                195                 200                 205

Asn Lys Asp Thr Ser Ile Phe Ser Arg Arg Ala Tyr Phe Ala Asp Pro
                210                 215                 220

Ala Leu Thr Leu Met His Glu Leu Ile His Val Leu His Gly Leu Tyr
225                 230                 235                 240

Gly Ile Lys Ile Ser Asn Leu Pro Ile Thr Pro Asn Thr Lys Glu Phe
                245                 250                 255

Phe Met Gln His Ser Asp Pro Val Gln Ala Glu Glu Leu Tyr Thr Phe
                260                 265                 270

Gly Gly His Asp Pro Ser Val Ile Ser Pro Ser Thr Asp Met Asn Ile
                275                 280                 285

Tyr Asn Lys Ala Leu Gln Asn Phe Gln Asp Ile Ala Asn Arg Leu Asn
                290                 295                 300

Ile Val Ser Ser Ala Gln Gly Ser Gly Ile Asp Ile Ser Leu Tyr Lys
305                 310                 315                 320

Gln Ile Tyr Lys Asn Lys Tyr Asp Phe Val Glu Asp Pro Asn Gly Lys
                325                 330                 335

Tyr Ser Val Asp Lys Asp Lys Phe Asp Lys Leu Tyr Lys Ala Leu Met
                340                 345                 350

Phe Gly Phe Thr Glu Thr Asn Leu Ala Gly Glu Tyr Gly Ile Lys Thr
                355                 360                 365

Arg Tyr Ser Tyr Phe Ser Glu Tyr Leu Pro Pro Ile Lys Thr Glu Lys
                370                 375                 380

Leu Leu Asp Asn Thr Ile Tyr Thr Gln Asn Glu Gly Phe Asn Ile Ala
385                 390                 395                 400

Ser Lys Asn Leu Lys Thr Glu Phe Asn Gly Gln Asn Lys Ala Val Asn
                405                 410                 415

Lys Glu Ala Tyr Glu Glu Ile Ser Leu Glu His Leu Val Ile Tyr Arg
                420                 425                 430
```

-continued

```
Ile Ala Met Cys Lys Pro Val Met Tyr Lys Asn Thr Gly Lys Ser Glu
        435                 440                 445

Gln Cys Ile Ile Val Asn Asn Glu Asp Leu Phe Phe Ile Ala Asn Lys
450                 455                 460

Asp Ser Phe Ser Lys Asp Leu Ala Lys Ala Glu Thr Ile Ala Tyr Asn
465                 470                 475                 480

Thr Gln Asn Asn Thr Ile Glu Asn Asn Phe Ser Ile Asp Gln Leu Ile
                485                 490                 495

Leu Asp Asn Asp Leu Ser Ser Gly Ile Asp Leu Pro Asn Glu Asn Thr
                500                 505                 510

Glu Pro Phe Thr Asn Phe Asp Asp Ile Asp Ile Pro Val Tyr Ile Lys
        515                 520                 525

Gln Ser Ala Leu Lys Lys Ile Phe Val Asp Gly Asp Ser Leu Phe Glu
530                 535                 540

Tyr Leu His Ala Gln Thr Phe Pro Ser Asn Ile Glu Asn Leu Gln Leu
545                 550                 555                 560

Thr Asn Ser Leu Asn Asp Ala Leu Arg Asn Asn Lys Val Tyr Thr
                565                 570                 575

Phe Phe Ser Thr Asn Leu Val Glu Lys Ala Asn Thr Val Gly Ala
                580                 585                 590

Ser Leu Phe Val Asn Trp Val Lys Gly Val Ile Asp Asp Phe Thr Ser
        595                 600                 605

Glu Ser Thr Gln Lys Ser Thr Ile Asp Lys Val Ser Asp Val Ser Ile
        610                 615                 620

Ile Ile Pro Tyr Ile Gly Pro Ala Leu Asn Val Gly Asn Glu Thr Ala
625                 630                 635                 640

Lys Glu Asn Phe Lys Asn Ala Phe Glu Ile Gly Gly Ala Ala Ile Leu
                645                 650                 655

Met Glu Phe Ile Pro Glu Leu Ile Val Pro Ile Val Gly Phe Phe Thr
                660                 665                 670

Leu Glu Ser Tyr Val Gly Asn Lys Gly His Ile Ile Met Thr Ile Ser
        675                 680                 685

Asn Ala Leu Lys Lys Arg Asp Gln Lys Trp Thr Asp Met Tyr Gly Leu
690                 695                 700

Ile Val Ser Gln Trp Leu Ser Thr Val Asn Thr Gln Phe Tyr Thr Ile
705                 710                 715                 720

Lys Glu Arg Met Tyr Asn Ala Leu Asn Asn Gln Ser Gln Ala Ile Glu
                725                 730                 735

Lys Ile Ile Glu Asp Gln Tyr Asn Arg Tyr Ser Glu Glu Asp Lys Met
                740                 745                 750

Asn Ile Asn Ile Asp Phe Asn Asp Ile Asp Phe Lys Leu Asn Gln Ser
        755                 760                 765

Ile Asn Leu Ala Ile Asn Asn Ile Asp Asp Phe Ile Asn Gln Cys Ser
        770                 775                 780

Ile Ser Tyr Leu Met Asn Arg Met Ile Pro Leu Ala Val Lys Lys Leu
785                 790                 795                 800

Lys Asp Phe Asp Asp Asn Leu Lys Arg Asp Leu Leu Glu Tyr Ile Asp
                805                 810                 815

Thr Asn Glu Leu Tyr Leu Leu Asp Glu Val Asn Ile Leu Lys Ser Lys
                820                 825                 830

Val Asn Arg His Leu Lys Asp Ser Ile Pro Phe Asp Leu Ser Leu Tyr
        835                 840                 845

Thr Lys Asp Thr Ile Leu Ile Gln Val Phe Asn Asn Tyr Ile Ser Asn
850                 855                 860
```

```
Ile Ser Ser Asn Ala Ile Leu Ser Leu Ser Tyr Arg Gly Gly Arg Leu
865                 870                 875                 880

Ile Asp Ser Ser Gly Tyr Gly Ala Thr Met Asn Val Gly Ser Asp Val
                885                 890                 895

Ile Phe Asn Asp Ile Gly Asn Gly Gln Phe Lys Leu Asn Ser Glu
            900                 905                 910

Asn Ser Asn Ile Thr Ala His Gln Ser Lys Phe Val Tyr Asp Ser
            915                 920                 925

Met Phe Asp Asn Phe Ser Ile Asn Phe Trp Val Arg Thr Pro Lys Tyr
            930                 935                 940

Asn Asn Asn Asp Ile Gln Thr Tyr Leu Gln Asn Glu Tyr Thr Ile Ile
945                 950                 955                 960

Ser Cys Ile Lys Asn Asp Ser Gly Trp Lys Val Ser Ile Lys Gly Asn
                965                 970                 975

Arg Ile Ile Trp Thr Leu Ile Asp Val Asn Ala Lys Ser Lys Ser Ile
                980                 985                 990

Phe Phe Glu Tyr Ser Ile Lys Asp Asn Ile Ser Asp Tyr Ile Asn Lys
                995                 1000                1005

Trp Phe Ser Ile Thr Ile Thr Asn Asp Arg Leu Gly Asn Ala Asn Ile
                1010                1015                1020

Tyr Ile Asn Gly Ser Leu Lys Lys Ser Glu Lys Ile Leu Asn Leu Asp
1025                1030                1035                1040

Arg Ile Asn Ser Ser Asn Asp Ile Asp Phe Lys Leu Ile Asn Cys Thr
                1045                1050                1055

Asp Thr Thr Lys Phe Val Trp Ile Lys Asp Phe Asn Ile Phe Gly Arg
                1060                1065                1070

Glu Leu Asn Ala Thr Glu Val Ser Ser Leu Tyr Trp Ile Gln Ser Ser
                1075                1080                1085

Thr Asn Thr Leu Lys Asp Phe Trp Gly Asn Pro Leu Arg Tyr Asp Thr
                1090                1095                1100

Gln Tyr Tyr Leu Phe Asn Gln Gly Met Gln Asn Ile Tyr Ile Lys Tyr
1105                1110                1115                1120

Phe Ser Lys Ala Ser Met Gly Glu Thr Ala Pro Arg Thr Asn Phe Asn
                1125                1130                1135

Asn Ala Ala Ile Asn Tyr Gln Asn Leu Tyr Leu Gly Leu Arg Phe Ile
                1140                1145                1150

Ile Lys Lys Ala Ser Asn Ser Arg Asn Ile Asn Asn Asp Asn Ile Val
                1155                1160                1165

Arg Glu Gly Asp Tyr Ile Tyr Leu Asn Ile Asp Asn Ile Ser Asp Glu
                1170                1175                1180

Ser Tyr Arg Val Tyr Val Leu Val Asn Ser Lys Glu Ile Gln Thr Gln
1185                1190                1195                1200

Leu Phe Leu Ala Pro Ile Asn Asp Asp Pro Thr Phe Tyr Asp Val Leu
                1205                1210                1215

Gln Ile Lys Lys Tyr Tyr Glu Lys Thr Thr Tyr Asn Cys Gln Ile Leu
                1220                1225                1230

Cys Glu Lys Asp Thr Lys Thr Phe Gly Leu Phe Gly Ile Gly Lys Phe
                1235                1240                1245

Val Lys Asp Tyr Gly Tyr Val Trp Asp Thr Tyr Asp Asn Tyr Phe Cys
                1250                1255                1260

Ile Ser Gln Trp Tyr Leu Arg Arg Ile Ser Glu Asn Ile Asn Lys Leu
1265                1270                1275                1280

Arg Leu Gly Cys Asn Trp Gln Phe Ile Pro Val Asp Glu Gly Trp Thr
```

Glu

```
<210> SEQ ID NO 8
<211> LENGTH: 1315
<212> TYPE: PRT
<213> ORGANISM: Clostridium tetani
<220> FEATURE:
<221> NAME/KEY: DOMAIN
<222> LOCATION: (1)...(441)
<223> OTHER INFORMATION: Light chain comprising the enzymatic domain.
<221> NAME/KEY: DOMAIN
<222> LOCATION: (442)...(870)
<223> OTHER INFORMATION: Amino-terminal half of heavy chain comprising
      the translocation domain.
<221> NAME/KEY: DOMAIN
<222> LOCATION: (871)...(1315)
<223> OTHER INFORMATION: Carboxyl-terminal half of heavy chain
      comprising the binding domain.
```

<400> SEQUENCE: 8

Met Pro Ile Thr Ile Asn Asn Phe Arg Tyr Ser Asp Pro Val Asn Asn
 1               5                  10                  15

Asp Thr Ile Ile Met Met Glu Pro Pro Tyr Cys Lys Gly Leu Asp Ile
             20                  25                  30

Tyr Tyr Lys Ala Phe Lys Ile Thr Asp Arg Ile Trp Ile Val Pro Glu
         35                  40                  45

Arg Tyr Glu Phe Gly Thr Lys Pro Glu Asp Phe Asn Pro Pro Ser Ser
     50                  55                  60

Leu Ile Glu Gly Ala Ser Glu Tyr Tyr Asp Pro Asn Tyr Leu Arg Thr
65                  70                  75                  80

Asp Ser Asp Lys Asp Arg Phe Leu Gln Thr Met Val Lys Leu Phe Asn
                 85                  90                  95

Arg Ile Lys Asn Asn Val Ala Gly Glu Ala Leu Leu Asp Lys Ile Ile
            100                 105                 110

Asn Ala Ile Pro Tyr Leu Gly Asn Ser Tyr Ser Leu Leu Asp Lys Phe
        115                 120                 125

Asp Thr Asn Ser Asn Ser Val Ser Phe Asn Leu Leu Glu Gln Asp Pro
    130                 135                 140

Ser Gly Ala Thr Thr Lys Ser Ala Met Leu Thr Asn Leu Ile Ile Phe
145                 150                 155                 160

Gly Pro Gly Pro Val Leu Asn Lys Asn Glu Val Arg Gly Ile Val Leu
                165                 170                 175

Arg Val Asp Asn Lys Asn Tyr Phe Pro Cys Arg Asp Gly Phe Gly Ser
            180                 185                 190

Ile Met Gln Met Ala Phe Cys Pro Glu Tyr Val Pro Thr Phe Asp Asn
        195                 200                 205

Val Ile Glu Asn Ile Thr Ser Leu Thr Ile Gly Lys Ser Lys Tyr Phe
    210                 215                 220

Gln Asp Pro Ala Leu Leu Leu Met His Glu Leu Ile His Val Leu His
225                 230                 235                 240

Gly Leu Tyr Gly Met Gln Val Ser Ser His Glu Ile Ile Pro Ser Lys
                245                 250                 255

Gln Glu Ile Tyr Met Gln His Thr Tyr Pro Ile Ser Ala Glu Glu Leu
            260                 265                 270

Phe Thr Phe Gly Gly Gln Asp Ala Asn Leu Ile Ser Ile Asp Ile Lys
        275                 280                 285

Asn Asp Leu Tyr Glu Lys Thr Leu Asn Asp Tyr Lys Ala Ile Ala Asn
    290                 295                 300

```
Lys Leu Ser Gln Val Thr Ser Cys Asn Asp Pro Asn Ile Asp Ile Asp
305                 310                 315                 320

Ser Tyr Lys Gln Ile Tyr Gln Gln Lys Tyr Gln Phe Asp Lys Asp Ser
            325                 330                 335

Asn Gly Gln Tyr Ile Val Asn Glu Asp Lys Phe Gln Ile Leu Tyr Asn
            340                 345                 350

Ser Ile Met Tyr Gly Phe Thr Glu Ile Glu Leu Gly Lys Lys Phe Asn
        355                 360                 365

Ile Lys Thr Arg Leu Ser Tyr Phe Ser Met Asn His Asp Pro Val Lys
    370                 375                 380

Ile Pro Asn Leu Leu Asp Asp Thr Ile Tyr Asn Asp Thr Glu Gly Phe
385                 390                 395                 400

Asn Ile Glu Ser Lys Asp Leu Lys Ser Glu Tyr Lys Gly Gln Asn Met
                405                 410                 415

Arg Val Asn Thr Asn Ala Phe Arg Asn Val Asp Gly Ser Gly Leu Val
            420                 425                 430

Ser Lys Leu Ile Gly Leu Cys Lys Lys Ile Ile Pro Pro Thr Asn Ile
            435                 440                 445

Arg Glu Asn Leu Tyr Asn Arg Thr Ala Ser Leu Thr Asp Leu Gly Gly
    450                 455                 460

Glu Leu Cys Ile Lys Ile Lys Asn Glu Asp Leu Thr Phe Ile Ala Glu
465                 470                 475                 480

Lys Asn Ser Phe Ser Glu Pro Phe Gln Asp Glu Ile Val Ser Tyr
                485                 490                 495

Asn Thr Lys Asn Lys Pro Leu Asn Phe Asn Tyr Ser Leu Asp Lys Ile
            500                 505                 510

Ile Val Asp Tyr Asn Leu Gln Ser Lys Ile Thr Leu Pro Asn Asp Arg
            515                 520                 525

Thr Thr Pro Val Thr Lys Gly Ile Pro Tyr Ala Pro Glu Tyr Lys Ser
    530                 535                 540

Asn Ala Ala Ser Thr Ile Glu Ile His Asn Ile Asp Asp Asn Thr Ile
545                 550                 555                 560

Tyr Gln Tyr Leu Tyr Ala Gln Lys Ser Pro Thr Thr Leu Gln Arg Ile
                565                 570                 575

Thr Met Thr Asn Ser Val Asp Asp Ala Leu Ile Asn Ser Thr Lys Ile
            580                 585                 590

Tyr Ser Tyr Phe Pro Ser Val Ile Ser Lys Val Asn Gln Gly Ala Gln
            595                 600                 605

Gly Ile Leu Phe Leu Gln Trp Val Arg Asp Ile Ile Asp Asp Phe Thr
    610                 615                 620

Asn Glu Ser Ser Gln Lys Thr Thr Ile Asp Lys Ile Ser Asp Val Ser
625                 630                 635                 640

Thr Ile Val Pro Tyr Ile Gly Pro Ala Leu Asn Ile Val Lys Gln Gly
                645                 650                 655

Tyr Glu Gly Asn Phe Ile Gly Ala Leu Glu Thr Thr Gly Val Val Leu
            660                 665                 670

Leu Leu Glu Tyr Ile Pro Glu Ile Thr Leu Pro Val Ile Ala Ala Leu
    675                 680                 685

Ser Ile Ala Glu Ser Ser Thr Gln Lys Glu Lys Ile Ile Lys Thr Ile
        690                 695                 700

Asp Asn Phe Leu Glu Lys Arg Tyr Glu Lys Trp Ile Glu Val Tyr Lys
705                 710                 715                 720

Leu Val Lys Ala Lys Trp Leu Gly Thr Val Asn Thr Gln Phe Gln Lys
```

```
                     725                 730                 735
Arg Ser Tyr Gln Met Tyr Arg Ser Leu Glu Tyr Gln Val Asp Ala Ile
        740                 745                 750
Lys Lys Ile Ile Asp Tyr Glu Tyr Lys Ile Tyr Ser Gly Pro Asp Lys
        755                 760                 765
Glu Gln Ile Ala Asp Glu Ile Asn Asn Leu Lys Asn Lys Leu Glu Glu
        770                 775                 780
Lys Ala Asn Lys Ala Met Ile Asn Ile Asn Ile Phe Met Arg Glu Ser
785                 790                 795                 800
Ser Arg Ser Phe Leu Val Asn Gln Met Ile Asn Glu Ala Lys Lys Gln
                805                 810                 815
Leu Leu Glu Phe Asp Thr Gln Ser Lys Asn Ile Leu Met Gln Tyr Ile
                820                 825                 830
Lys Ala Asn Ser Lys Phe Ile Gly Ile Thr Glu Leu Lys Lys Leu Glu
                835                 840                 845
Ser Lys Ile Asn Lys Val Phe Ser Thr Pro Ile Pro Phe Ser Tyr Ser
                850                 855                 860
Lys Asn Leu Asp Cys Trp Val Asp Asn Glu Glu Asp Ile Asp Val Ile
865                 870                 875                 880
Leu Lys Lys Ser Thr Ile Leu Asn Leu Asp Ile Asn Asn Asp Ile Ile
                885                 890                 895
Ser Asp Ile Ser Gly Phe Asn Ser Ser Val Ile Thr Tyr Pro Asp Ala
                900                 905                 910
Gln Leu Val Pro Gly Ile Asn Gly Lys Ala Ile His Leu Val Asn Asn
                915                 920                 925
Glu Ser Ser Glu Val Ile Val His Lys Ala Met Asp Ile Glu Tyr Asn
                930                 935                 940
Asp Met Phe Asn Asn Phe Thr Val Ser Phe Trp Leu Arg Val Pro Lys
945                 950                 955                 960
Val Ser Ala Ser His Leu Glu Gln Tyr Gly Thr Asn Glu Tyr Ser Ile
                965                 970                 975
Ile Ser Ser Met Lys Lys His Ser Leu Ser Ile Gly Ser Gly Trp Ser
                980                 985                 990
Val Ser Leu Lys Gly Asn Asn Leu Ile Trp Thr Leu Lys Asp Ser Ala
                995                 1000                1005
Gly Glu Val Arg Gln Ile Thr Phe Arg Asp Leu Pro Asp Lys Phe Asn
        1010                1015                1020
Ala Tyr Leu Ala Asn Lys Trp Val Phe Ile Thr Ile Thr Asn Asp Arg
1025                1030                1035                1040
Leu Ser Ser Ala Asn Leu Tyr Ile Asn Gly Val Leu Met Gly Ser Ala
                1045                1050                1055
Glu Ile Thr Gly Leu Gly Ala Ile Arg Glu Asp Asn Asn Ile Thr Leu
                1060                1065                1070
Lys Leu Asp Arg Cys Asn Asn Asn Asn Gln Tyr Val Ser Ile Asp Lys
                1075                1080                1085
Phe Arg Ile Phe Cys Lys Ala Leu Asn Pro Lys Glu Ile Glu Lys Leu
        1090                1095                1100
Tyr Thr Ser Tyr Leu Ser Ile Thr Phe Leu Arg Asp Phe Trp Gly Asn
1105                1110                1115                1120
Pro Leu Arg Tyr Asp Thr Glu Tyr Tyr Leu Ile Pro Val Ala Ser Ser
                1125                1130                1135
Ser Lys Asp Val Gln Leu Lys Asn Ile Thr Asp Tyr Met Tyr Leu Thr
                1140                1145                1150
```

```
Asn Ala Pro Ser Tyr Thr Asn Gly Lys Leu Asn Ile Tyr Tyr Arg Arg
        1155                1160                1165

Leu Tyr Asn Gly Leu Lys Phe Ile Ile Lys Arg Tyr Thr Pro Asn Asn
    1170                1175                1180

Glu Ile Asp Ser Phe Val Lys Ser Gly Asp Phe Ile Lys Leu Tyr Val
1185                1190                1195                1200

Ser Tyr Asn Asn Asn Glu His Ile Val Gly Tyr Pro Lys Asp Gly Asn
            1205                1210                1215

Ala Phe Asn Asn Leu Asp Arg Ile Leu Arg Val Gly Tyr Asn Ala Pro
        1220                1225                1230

Gly Ile Pro Leu Tyr Lys Lys Met Glu Ala Val Lys Leu Arg Asp Leu
    1235                1240                1245

Lys Thr Tyr Ser Val Gln Leu Lys Leu Tyr Asp Asp Lys Asn Ala Ser
1250                1255                1260

Leu Gly Leu Val Gly Thr His Asn Gly Gln Ile Gly Asn Asp Pro Asn
1265                1270                1275                1280

Arg Asp Ile Leu Ile Ala Ser Asn Trp Tyr Phe Asn His Leu Lys Asp
            1285                1290                1295

Lys Ile Leu Gly Cys Asp Trp Tyr Phe Val Pro Thr Asp Glu Gly Trp
        1300                1305                1310

Thr Asn Asp
        1315

<210> SEQ ID NO 9
<211> LENGTH: 1268
<212> TYPE: PRT
<213> ORGANISM: Clostridium baratii

<400> SEQUENCE: 9

Met Pro Val Asn Ile Asn Asn Phe Asn Tyr Asn Asp Pro Ile Asn Asn
1               5                   10                  15

Thr Thr Ile Leu Tyr Met Lys Met Pro Tyr Tyr Glu Asp Ser Asn Lys
            20                  25                  30

Tyr Tyr Lys Ala Phe Glu Ile Met Asp Asn Val Trp Ile Ile Pro Glu
        35                  40                  45

Arg Asn Ile Ile Gly Lys Lys Pro Ser Asp Phe Tyr Pro Pro Ile Ser
    50                  55                  60

Leu Asp Ser Gly Ser Ser Ala Tyr Tyr Asp Pro Asn Tyr Leu Thr Thr
65                  70                  75                  80

Asp Ala Glu Lys Asp Arg Phe Leu Lys Thr Val Ile Lys Leu Phe Asn
                85                  90                  95

Arg Ile Asn Ser Asn Pro Ala Gly Gln Val Leu Leu Glu Glu Ile Lys
            100                 105                 110

Asn Gly Lys Pro Tyr Leu Gly Asn Asp His Thr Ala Val Asn Glu Phe
        115                 120                 125

Cys Ala Asn Asn Arg Ser Thr Ser Val Glu Ile Lys Glu Ser Asn Gly
    130                 135                 140

Thr Thr Asp Ser Met Leu Leu Asn Leu Val Ile Leu Gly Pro Gly Pro
145                 150                 155                 160

Asn Ile Leu Glu Cys Ser Thr Phe Pro Val Arg Ile Phe Pro Asn Asn
                165                 170                 175

Ile Ala Tyr Asp Pro Ser Glu Lys Gly Phe Gly Ser Ile Gln Leu Met
            180                 185                 190

Ser Phe Ser Thr Glu Tyr Glu Tyr Ala Phe Asn Asp Asn Thr Asp Leu
        195                 200                 205
```

```
Phe Ile Ala Asp Pro Ala Ile Ser Leu Ala His Glu Leu Ile His Val
    210                 215                 220
Leu His Gly Leu Tyr Gly Ala Lys Gly Val Thr Asn Lys Lys Val Ile
225                 230                 235                 240
Glu Val Asp Gln Gly Ala Leu Met Ala Ala Glu Lys Asp Ile Lys Ile
                245                 250                 255
Glu Glu Phe Ile Thr Phe Gly Gly Gln Asp Leu Asn Ile Ile Thr Asn
                260                 265                 270
Ser Thr Asn Gln Lys Ile Tyr Val Ile Leu Leu Ser Asn Tyr Thr Ala
    275                 280                 285
Ile Ala Ser Arg Leu Ser Gln Val Asn Arg Asn Ser Ala Leu Asn
290                 295                 300
Thr Thr Tyr Tyr Lys Asn Phe Phe Gln Trp Lys Tyr Gly Leu Asp Gln
305                 310                 315                 320
Asp Ser Asn Gly Asn Tyr Thr Val Asn Ile Ser Lys Phe Asn Ala Ile
                325                 330                 335
Tyr Lys Lys Leu Phe Ser Phe Thr Glu Cys Asp Leu Ala Gln Lys Phe
                340                 345                 350
Gln Val Lys Asn Arg Ser Asn Tyr Leu Phe His Phe Lys Pro Phe Arg
                355                 360                 365
Leu Leu Asp Leu Leu Asp Asp Asn Ile Tyr Ser Ile Ser Glu Gly Phe
370                 375                 380
Asn Ile Gly Ser Leu Arg Val Asn Asn Gly Gln Asn Ile Asn Leu
385                 390                 395                 400
Asn Ser Arg Ile Val Gly Pro Ile Pro Asp Asn Gly Leu Val Glu Arg
                405                 410                 415
Phe Val Gly Leu Cys Lys Ser Ile Val Ser Lys Lys Gly Thr Lys Asn
                420                 425                 430
Ser Leu Cys Ile Lys Val Asn Asn Arg Asp Leu Phe Phe Val Ala Ser
                435                 440                 445
Glu Ser Ser Tyr Asn Glu Asn Gly Ile Asn Ser Pro Lys Glu Ile Asp
    450                 455                 460
Asp Thr Thr Ile Thr Asn Asn Tyr Lys Lys Asn Leu Asp Glu Val
465                 470                 475                 480
Ile Leu Asp Tyr Asn Ser Asp Ala Ile Pro Asn Leu Ser Ser Arg Leu
                485                 490                 495
Leu Asn Thr Thr Ala Gln Asn Asp Ser Tyr Val Pro Lys Tyr Asp Ser
                500                 505                 510
Asn Gly Thr Ser Glu Ile Lys Glu Tyr Thr Val Asp Lys Leu Asn Val
                515                 520                 525
Phe Phe Tyr Leu Tyr Ala Gln Lys Ala Pro Glu Gly Glu Ser Ala Ile
                530                 535                 540
Ser Leu Thr Ser Ser Val Asn Thr Ala Leu Leu Asp Ala Ser Lys Val
545                 550                 555                 560
Tyr Thr Phe Phe Ser Ser Asp Phe Ile Asn Thr Val Asn Lys Pro Val
                565                 570                 575
Gln Ala Ala Leu Phe Ile Ser Trp Ile Gln Gln Val Ile Asn Asp Phe
                580                 585                 590
Thr Thr Glu Ala Thr Gln Lys Ser Thr Ile Asp Lys Ile Ala Asp Ile
                595                 600                 605
Ser Leu Ile Val Pro Tyr Val Gly Leu Ala Leu Asn Ile Gly Asn Glu
                610                 615                 620
Val Gln Lys Gly Asn Phe Lys Glu Ala Ile Glu Leu Leu Gly Ala Gly
625                 630                 635                 640
```

Ile Leu Leu Glu Phe Val Pro Glu Leu Leu Ile Pro Thr Ile Leu Val
              645                 650                 655

Phe Thr Ile Lys Ser Phe Ile Asn Ser Asp Asp Ser Lys Asn Lys Ile
              660                 665                 670

Ile Lys Ala Ile Asn Asn Ala Leu Arg Glu Arg Glu Leu Lys Trp Lys
              675                 680                 685

Glu Val Tyr Ser Trp Ile Val Ser Asn Trp Leu Thr Arg Ile Asn Thr
              690                 695                 700

Gln Phe Asn Lys Arg Lys Glu Gln Met Tyr Gln Ala Leu Gln Asn Gln
705                 710                 715                 720

Val Asp Gly Ile Lys Lys Ile Glu Tyr Lys Tyr Asn Asn Tyr Thr
                  725                 730                 735

Leu Asp Glu Lys Asn Arg Leu Arg Ala Glu Tyr Asn Ile Tyr Ser Ile
              740                 745                 750

Lys Glu Glu Leu Asn Lys Val Ser Leu Ala Met Gln Asn Ile Asp
                  755                 760                 765

Arg Phe Leu Thr Glu Ser Ser Ile Ser Tyr Leu Met Lys Leu Ile Asn
              770                 775                 780

Glu Ala Lys Ile Asn Lys Leu Ser Glu Tyr Asp Lys Arg Val Asn Gln
785                 790                 795                 800

Tyr Leu Leu Asn Tyr Ile Leu Glu Asn Ser Ser Thr Leu Gly Thr Ser
                  805                 810                 815

Ser Val Pro Glu Leu Asn Asn Leu Val Ser Asn Thr Leu Asn Asn Ser
                  820                 825                 830

Ile Pro Phe Glu Leu Ser Glu Tyr Thr Asn Asp Lys Ile Leu Ile His
              835                 840                 845

Ile Leu Ile Arg Phe Tyr Lys Arg Ile Ile Asp Ser Ser Ile Leu Asn
              850                 855                 860

Met Lys Tyr Glu Asn Asn Arg Phe Ile Asp Ser Ser Gly Tyr Gly Ser
865                 870                 875                 880

Asn Ile Ser Ile Asn Gly Asp Ile Tyr Ile Tyr Ser Thr Asn Arg Asn
                  885                 890                 895

Gln Phe Gly Ile Tyr Ser Ser Arg Leu Ser Glu Val Asn Ile Thr Gln
              900                 905                 910

Asn Asn Thr Ile Ile Tyr Asn Ser Arg Tyr Gln Asn Phe Ser Val Ser
              915                 920                 925

Phe Trp Val Arg Ile Pro Lys Tyr Asn Asn Leu Lys Asn Leu Asn Asn
930                 935                 940

Glu Tyr Thr Ile Ile Asn Cys Met Arg Asn Asn Asn Ser Gly Trp Lys
945                 950                 955                 960

Ile Ser Leu Asn Tyr Asn Asn Ile Ile Trp Thr Leu Gln Asp Thr Thr
                  965                 970                 975

Gly Asn Asn Gln Lys Leu Val Phe Asn Tyr Thr Gln Met Ile Asp Ile
              980                 985                 990

Ser Asp Tyr Ile Asn Lys Trp Thr Phe Val Thr Ile Thr Asn Asn Arg
              995                 1000                1005

Leu Gly His Ser Lys Leu Tyr Ile Asn Gly Asn Leu Thr Asp Gln Lys
    1010                1015                1020

Ser Ile Leu Asn Leu Gly Asn Ile His Val Asp Asp Asn Ile Leu Phe
1025                1030                1035                1040

Lys Ile Val Gly Cys Asn Asp Thr Arg Tyr Val Gly Ile Arg Tyr Phe
              1045                1050                1055

Lys Ile Phe Asn Met Glu Leu Asp Lys Thr Glu Ile Glu Thr Leu Tyr

```
                    1060                1065                1070
His Ser Glu Pro Asp Ser Thr Ile Leu Lys Asp Phe Trp Gly Asn Tyr
            1075                1080                1085
Leu Leu Tyr Asn Lys Lys Tyr Tyr Leu Leu Asn Leu Leu Lys Pro Asn
            1090                1095                1100
Met Ser Val Thr Lys Asn Ser Asp Ile Leu Asn Ile Asn Arg Gln Arg
1105                1110                1115                1120
Gly Ile Tyr Ser Lys Thr Asn Ile Phe Ser Asn Ala Arg Leu Tyr Thr
            1125                1130                1135
Gly Val Glu Val Ile Ile Arg Lys Val Gly Ser Thr Asp Thr Ser Asn
            1140                1145                1150
Thr Asp Asn Phe Val Arg Lys Asn Asp Thr Val Tyr Ile Asn Val Val
            1155                1160                1165
Asp Gly Asn Ser Glu Tyr Gln Leu Tyr Ala Asp Val Ser Thr Ser Ala
            1170                1175                1180
Val Glu Lys Thr Ile Lys Leu Arg Arg Ile Ser Asn Ser Asn Tyr Asn
1185                1190                1195                1200
Ser Asn Gln Met Ile Ile Met Asp Ser Ile Gly Asp Asn Cys Thr Met
            1205                1210                1215
Asn Phe Lys Thr Asn Asn Gly Asn Asp Ile Gly Leu Leu Gly Phe His
            1220                1225                1230
Leu Asn Asn Leu Val Ala Ser Ser Trp Tyr Tyr Lys Asn Ile Arg Asn
            1235                1240                1245
Asn Thr Arg Asn Asn Gly Cys Phe Trp Ser Phe Ile Ser Lys Glu His
            1250                1255                1260
Gly Trp Gln Glu
1265

<210> SEQ ID NO 10
<211> LENGTH: 1251
<212> TYPE: PRT
<213> ORGANISM: Clostridium butyricum

<400> SEQUENCE: 10

Met Pro Thr Ile Asn Ser Phe Asn Tyr Asn Asp Pro Val Asn Asn Arg
1               5                   10                  15
Thr Ile Leu Tyr Ile Lys Pro Gly Gly Cys Gln Gln Phe Tyr Lys Ser
            20                  25                  30
Phe Asn Ile Met Lys Asn Ile Trp Ile Ile Pro Glu Arg Asn Val Ile
            35                  40                  45
Gly Thr Ile Pro Gln Asp Phe Leu Pro Pro Thr Ser Leu Lys Asn Gly
        50                  55                  60
Asp Ser Ser Tyr Tyr Asp Pro Asn Tyr Leu Gln Ser Asp Gln Glu Lys
65                  70                  75                  80
Asp Lys Phe Leu Lys Ile Val Thr Lys Ile Phe Asn Arg Ile Asn Asp
            85                  90                  95
Asn Leu Ser Gly Arg Ile Leu Leu Glu Glu Leu Ser Lys Ala Asn Pro
            100                 105                 110
Tyr Leu Gly Asn Asp Asn Thr Pro Asp Gly Asp Phe Ile Ile Asn Asp
            115                 120                 125
Ala Ser Ala Val Pro Ile Gln Phe Ser Asn Gly Ser Gln Ser Ile Leu
        130                 135                 140
Leu Pro Asn Val Ile Ile Met Gly Ala Glu Pro Asp Leu Phe Glu Thr
145                 150                 155                 160
Asn Ser Ser Asn Ile Ser Leu Arg Asn Asn Tyr Met Pro Ser Asn His
```

```
                165                 170                 175
Gly Phe Gly Ser Ile Ala Ile Val Thr Phe Ser Pro Glu Tyr Ser Phe
                180                 185                 190

Arg Phe Lys Asp Asn Ser Met Asn Glu Phe Ile Gln Asp Pro Ala Leu
                195                 200                 205

Thr Leu Met His Glu Leu Ile His Ser Leu His Gly Leu Tyr Gly Ala
                210                 215                 220

Lys Gly Ile Thr Thr Lys Tyr Thr Ile Thr Gln Lys Gln Asn Pro Leu
225                 230                 235                 240

Ile Thr Asn Ile Arg Gly Thr Asn Ile Glu Glu Phe Leu Thr Phe Gly
                245                 250                 255

Gly Thr Asp Leu Asn Ile Ile Thr Ser Ala Gln Ser Asn Asp Ile Tyr
                260                 265                 270

Thr Asn Leu Leu Ala Asp Tyr Lys Lys Ile Ala Ser Lys Leu Ser Lys
                275                 280                 285

Val Gln Val Ser Asn Pro Leu Leu Asn Pro Tyr Lys Asp Val Phe Glu
                290                 295                 300

Ala Lys Tyr Gly Leu Asp Lys Asp Ala Ser Gly Ile Tyr Ser Val Asn
305                 310                 315                 320

Ile Asn Lys Phe Asn Asp Ile Phe Lys Lys Leu Tyr Ser Phe Thr Glu
                325                 330                 335

Phe Asp Leu Ala Thr Lys Phe Gln Val Lys Cys Arg Gln Thr Tyr Ile
                340                 345                 350

Gly Gln Tyr Lys Tyr Phe Lys Leu Ser Asn Leu Leu Asn Asp Ser Ile
                355                 360                 365

Tyr Asn Ile Ser Glu Gly Tyr Asn Ile Asn Asn Leu Lys Val Asn Phe
                370                 375                 380

Arg Gly Gln Asn Ala Asn Leu Asn Pro Arg Ile Ile Thr Pro Ile Thr
385                 390                 395                 400

Gly Arg Gly Leu Val Lys Lys Ile Ile Arg Phe Cys Lys Asn Ile Val
                405                 410                 415

Ser Val Lys Gly Ile Arg Lys Ser Ile Cys Ile Glu Ile Asn Asn Gly
                420                 425                 430

Glu Leu Phe Phe Val Ala Ser Glu Asn Ser Tyr Asn Asp Asp Asn Ile
                435                 440                 445

Asn Thr Pro Lys Glu Ile Asp Asp Thr Val Thr Ser Asn Asn Asn Tyr
                450                 455                 460

Glu Asn Asp Leu Asp Gln Val Ile Leu Asn Phe Asn Ser Glu Ser Ala
465                 470                 475                 480

Pro Gly Leu Ser Asp Glu Lys Leu Asn Leu Thr Ile Gln Asn Asp Ala
                485                 490                 495

Tyr Ile Pro Lys Tyr Asp Ser Asn Gly Thr Ser Asp Ile Glu Gln His
                500                 505                 510

Asp Val Asn Glu Leu Asn Val Phe Phe Tyr Leu Asp Ala Gln Lys Val
                515                 520                 525

Pro Glu Gly Glu Asn Asn Val Asn Leu Thr Ser Ser Ile Asp Thr Ala
                530                 535                 540

Leu Leu Glu Gln Pro Lys Ile Tyr Thr Phe Phe Ser Ser Glu Phe Ile
545                 550                 555                 560

Asn Asn Val Asn Lys Pro Val Gln Ala Ala Leu Phe Val Gly Trp Ile
                565                 570                 575

Gln Gln Val Leu Val Asp Phe Thr Thr Glu Ala Asn Gln Lys Ser Thr
                580                 585                 590
```

-continued

Val Asp Lys Ile Ala Asp Ile Ser Ile Val Val Pro Tyr Ile Gly Leu
            595                 600                 605

Ala Leu Asn Ile Gly Asn Glu Ala Gln Lys Gly Asn Phe Lys Asp Ala
            610                 615                 620

Leu Glu Leu Leu Gly Ala Gly Ile Leu Leu Glu Phe Glu Pro Glu Leu
625                 630                 635                 640

Leu Ile Pro Thr Ile Leu Val Phe Thr Ile Lys Ser Phe Leu Gly Ser
            645                 650                 655

Ser Asp Asn Lys Asn Lys Val Ile Lys Ala Ile Asn Asn Ala Leu Lys
            660                 665                 670

Glu Arg Asp Glu Lys Trp Lys Glu Val Tyr Ser Phe Ile Val Ser Asn
            675                 680                 685

Trp Met Thr Lys Ile Asn Thr Gln Phe Asn Lys Arg Lys Glu Gln Met
            690                 695                 700

Tyr Gln Ala Leu Gln Asn Gln Val Asn Ala Leu Lys Ala Ile Ile Glu
705                 710                 715                 720

Ser Lys Tyr Asn Ser Tyr Thr Leu Glu Glu Lys Asn Glu Leu Thr Asn
            725                 730                 735

Lys Tyr Asp Ile Glu Gln Ile Glu Asn Glu Leu Asn Gln Lys Val Ser
            740                 745                 750

Ile Ala Met Asn Asn Ile Asp Arg Phe Leu Thr Glu Ser Ser Ile Ser
            755                 760                 765

Tyr Leu Met Lys Leu Ile Asn Glu Val Lys Ile Asn Lys Leu Arg Glu
            770                 775                 780

Tyr Asp Glu Asn Val Lys Thr Tyr Leu Leu Asp Tyr Ile Ile Lys His
785                 790                 795                 800

Gly Ser Ile Leu Gly Glu Ser Gln Gln Glu Leu Asn Ser Met Val Ile
            805                 810                 815

Asp Thr Leu Asn Asn Ser Ile Pro Phe Lys Leu Ser Ser Tyr Thr Asp
            820                 825                 830

Asp Lys Ile Leu Ile Ser Tyr Phe Asn Lys Phe Phe Lys Arg Ile Lys
            835                 840                 845

Ser Ser Ser Val Leu Asn Met Arg Tyr Lys Asn Asp Lys Tyr Val Asp
850                 855                 860

Thr Ser Gly Tyr Asp Ser Asn Ile Asn Ile Asn Gly Asp Val Tyr Lys
865                 870                 875                 880

Tyr Pro Thr Asn Lys Asn Gln Phe Gly Ile Tyr Asn Asp Lys Leu Ser
            885                 890                 895

Glu Val Asn Ile Ser Gln Asn Asp Tyr Ile Ile Tyr Asp Asn Lys Tyr
            900                 905                 910

Lys Asn Phe Ser Ile Ser Phe Trp Val Arg Ile Pro Asn Tyr Asp Asn
            915                 920                 925

Lys Ile Val Asn Val Asn Asn Glu Tyr Thr Ile Ile Asn Cys Met Arg
930                 935                 940

Asp Asn Asn Ser Gly Trp Lys Val Ser Leu Asn His Asn Glu Ile Ile
945                 950                 955                 960

Trp Thr Leu Gln Asp Asn Ser Gly Ile Asn Gln Lys Leu Ala Phe Asn
            965                 970                 975

Tyr Gly Asn Ala Asn Gly Ile Ser Asp Tyr Ile Asn Lys Trp Ile Phe
            980                 985                 990

Val Thr Ile Thr Asn Asp Arg Leu Gly Asp Ser Lys Leu Tyr Ile Asn
            995                1000                1005

Gly Asn Leu Ile Asp Lys Lys Ser Ile Leu Asn Leu Gly Asn Ile His
            1010                1015                1020

Val Ser Asp Asn Ile Leu Phe Lys Ile Val Asn Cys Ser Tyr Thr Arg
1025 1030 1035 1040

Tyr Ile Gly Ile Arg Tyr Phe Asn Ile Phe Asp Lys Glu Leu Asp Glu
1045 1050 1055

Thr Glu Ile Gln Thr Leu Tyr Asn Asn Glu Pro Asn Ala Asn Ile Leu
1060 1065 1070

Lys Asp Phe Trp Gly Asn Tyr Leu Leu Tyr Asp Lys Glu Tyr Tyr Leu
1075 1080 1085

Leu Asn Val Leu Lys Pro Asn Asn Phe Ile Asn Arg Arg Thr Asp Ser
1090 1095 1100

Thr Leu Ser Ile Asn Asn Ile Arg Ser Thr Ile Leu Leu Ala Asn Arg
1105 1110 1115 1120

Leu Tyr Ser Gly Ile Lys Val Lys Ile Gln Arg Val Asn Asn Ser Ser
1125 1130 1135

Thr Asn Asp Asn Leu Val Arg Lys Asn Asp Gln Val Tyr Ile Asn Phe
1140 1145 1150

Val Ala Ser Lys Thr His Leu Leu Pro Leu Tyr Ala Asp Thr Ala Thr
1155 1160 1165

Thr Asn Lys Glu Lys Thr Ile Lys Ile Ser Ser Ser Gly Asn Arg Phe
1170 1175 1180

Asn Gln Val Val Val Met Asn Ser Val Gly Asn Cys Thr Met Asn Phe
1185 1190 1195 1200

Lys Asn Asn Asn Gly Asn Asn Ile Gly Leu Leu Gly Phe Lys Ala Asp
1205 1210 1215

Thr Val Val Ala Ser Thr Trp Tyr Tyr Thr His Met Arg Asp Asn Thr
1220 1225 1230

Asn Ser Asn Gly Phe Phe Trp Asn Phe Ile Ser Glu Glu His Gly Trp
1235 1240 1245

Gln Glu Lys
1250

<210> SEQ ID NO 11
<211> LENGTH: 25
<212> TYPE: PRT
<213> ORGANISM: Artificial Sequence
<220> FEATURE:
<221> NAME/KEY: DOMAIN
<222> LOCATION: (1)...(25)
<223> OTHER INFORMATION: BoNT/A di-chain loop region

<400> SEQUENCE: 11

Cys Val Arg Gly Ile Ile Thr Ser Lys Thr Lys Ser Leu Asp Lys Gly
1 5 10 15

Tyr Asn Lys Ala Leu Asn Asp Leu Cys
20 25

<210> SEQ ID NO 12
<211> LENGTH: 10
<212> TYPE: PRT
<213> ORGANISM: Artificial Sequence
<220> FEATURE:
<221> NAME/KEY: DOMAIN
<222> LOCATION: (1)...(10)
<223> OTHER INFORMATION: BoNT/B di-chain loop region

<400> SEQUENCE: 12

Cys Lys Ser Val Lys Ala Pro Gly Ile Cys
1 5 10

```
<210> SEQ ID NO 13
<211> LENGTH: 17
<212> TYPE: PRT
<213> ORGANISM: Artificial Sequence
<220> FEATURE:
<221> NAME/KEY: DOMAIN
<222> LOCATION: (1)...(17)
<223> OTHER INFORMATION: BoNT/C1 di-chain loop region

<400> SEQUENCE: 13

Cys His Lys Ala Ile Asp Gly Arg Ser Leu Tyr Asn Lys Thr Leu Asp
 1               5                  10                  15

Cys

<210> SEQ ID NO 14
<211> LENGTH: 14
<212> TYPE: PRT
<213> ORGANISM: Artificial Sequence
<220> FEATURE:
<221> NAME/KEY: DOMAIN
<222> LOCATION: (1)...(14)
<223> OTHER INFORMATION: BoNT/D di-chain loop region

<400> SEQUENCE: 14

Cys Leu Arg Leu Thr Lys Asn Ser Arg Asp Asp Ser Thr Cys
 1               5                  10

<210> SEQ ID NO 15
<211> LENGTH: 15
<212> TYPE: PRT
<213> ORGANISM: Artificial Sequence
<220> FEATURE:
<221> NAME/KEY: DOMAIN
<222> LOCATION: (1)...(15)
<223> OTHER INFORMATION: BoNT/E di-chain loop region

<400> SEQUENCE: 15

Cys Lys Asn Ile Val Ser Val Lys Gly Ile Arg Lys Ser Ile Cys
 1               5                  10                  15

<210> SEQ ID NO 16
<211> LENGTH: 17
<212> TYPE: PRT
<213> ORGANISM: Artificial Sequence
<220> FEATURE:
<221> NAME/KEY: DOMAIN
<222> LOCATION: (1)...(17)
<223> OTHER INFORMATION: BoNT/F di-chain loop region

<400> SEQUENCE: 16

Cys Lys Ser Val Ile Pro Arg Lys Gly Thr Lys Ala Pro Pro Arg Leu
 1               5                  10                  15

Cys

<210> SEQ ID NO 17
<211> LENGTH: 15
<212> TYPE: PRT
<213> ORGANISM: Artificial Sequence
<220> FEATURE:
<221> NAME/KEY: DOMAIN
<222> LOCATION: (1)...(15)
<223> OTHER INFORMATION: BoNT/G di-chain loop region

<400> SEQUENCE: 17

Cys Lys Pro Val Met Tyr Lys Asn Thr Gly Lys Ser Glu Gln Cys
 1               5                  10                  15

<210> SEQ ID NO 18
```

```
<211> LENGTH: 29
<212> TYPE: PRT
<213> ORGANISM: Artificial Sequence
<220> FEATURE:
<221> NAME/KEY: DOMAIN
<222> LOCATION: (1)...(29)
<223> OTHER INFORMATION: TeNT di-chain loop region

<400> SEQUENCE: 18
```

Cys Lys Lys Ile Ile Pro Pro Thr Asn Ile Arg Glu Asn Leu Tyr Asn
1 5 10 15

Arg Thr Ala Ser Leu Thr Asp Leu Gly Gly Glu Leu Cys
20 25

<210> SEQ ID NO 19
<211> LENGTH: 15
<212> TYPE: PRT
<213> ORGANISM: Artificial Sequence
<220> FEATURE:
<221> NAME/KEY: DOMAIN
<222> LOCATION: (1)...(15)
<223> OTHER INFORMATION: BaNT di-chain loop region

<400> SEQUENCE: 19

Cys Lys Ser Ile Val Ser Lys Lys Gly Thr Lys Asn Ser Leu Cys
1 5 10 15

<210> SEQ ID NO 20
<211> LENGTH: 15
<212> TYPE: PRT
<213> ORGANISM: Artificial Sequence
<220> FEATURE:
<221> NAME/KEY: DOMAIN
<222> LOCATION: (1)...(15)
<223> OTHER INFORMATION: BuNT di-chain loop region

<400> SEQUENCE: 20

Cys Lys Asn Ile Val Ser Val Lys Gly Ile Arg Lys Ser Ile Cys
1 5 10 15

<210> SEQ ID NO 21
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Bovine enterokinase protease cleavage site.

<400> SEQUENCE: 21

Asp Asp Asp Asp Lys
1 5

<210> SEQ ID NO 22
<211> LENGTH: 7
<212> TYPE: PRT
<213> ORGANISM: Artificial Sequence
<220> FEATURE:
<221> NAME/KEY: SITE
<222> LOCATION: (1)...(1)
<223> OTHER INFORMATION: Tobacco Etch Virus protease cleavage site consensus sequence
<221> NAME/KEY: VARIANT
<222> LOCATION: (2)...(3)
<223> OTHER INFORMATION: Xaa can be amino amino acid
<221> NAME/KEY: VARIANT
<222> LOCATION: (5)...(5)
<223> OTHER INFORMATION: Xaa can be amino amino acid

<400> SEQUENCE: 22

```
Glu Xaa Xaa Tyr Xaa Gln Gly
 1               5

<210> SEQ ID NO 23
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site
      consensus sequence
<221> NAME/KEY: VARIANT
<222> LOCATION: (2)...(3)
<223> OTHER INFORMATION: Xaa can be any amino acid
<221> NAME/KEY: VARIANT
<222> LOCATION: (5)...(5)
<223> OTHER INFORMATION: Xaa can be any amino acid

<400> SEQUENCE: 23

Glu Xaa Xaa Tyr Xaa Gln Ser
 1               5

<210> SEQ ID NO 24
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 24

Glu Asn Leu Tyr Phe Gln Gly
 1               5

<210> SEQ ID NO 25
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 25

Glu Asn Leu Tyr Phe Gln Ser
 1               5

<210> SEQ ID NO 26
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 26

Glu Asn Ile Tyr Thr Gln Gly
 1               5

<210> SEQ ID NO 27
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.
```

```
<400> SEQUENCE: 27

Glu Asn Ile Tyr Thr Gln Ser
1               5

<210> SEQ ID NO 28
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 28

Glu Asn Ile Tyr Leu Gln Gly
1               5

<210> SEQ ID NO 29
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 29

Glu Asn Ile Tyr Leu Gln Ser
1               5

<210> SEQ ID NO 30
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 30

Glu Asn Val Tyr Phe Gln Gly
1               5

<210> SEQ ID NO 31
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 31

Glu Asn Val Tyr Ser Gln Ser
1               5

<210> SEQ ID NO 32
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Etch Virus protease cleavage site.

<400> SEQUENCE: 32

Glu Asn Val Tyr Ser Gln Gly
1               5
```

```
<210> SEQ ID NO 33
<211> LENGTH: 7
<212> TYPE: PRT
<213> ORGANISM: Artificial Sequence
<220> FEATURE:
<221> NAME/KEY: SITE
<222> LOCATION: (0)...(0)
<223> OTHER INFORMATION: Tobacco Etch Virus protease cleavage site.

<400> SEQUENCE: 33

Glu Asn Val Tyr Ser Gln Ser
 1               5

<210> SEQ ID NO 34
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for a Tobacco Vein Mottling
      Virus protease cleavage site
<221> NAME/KEY: VARIANT
<222> LOCATION: (1)...(2)
<223> OTHER INFORMATION: Xaa can be any amino acid

<400> SEQUENCE: 34

Xaa Xaa Val Arg Phe Gln Gly
 1               5

<210> SEQ ID NO 35
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus sequence for a Tobacco Vein Mottling
      Virus protease cleavage site
<221> NAME/KEY: VARIANT
<222> LOCATION: (1)...(2)
<223> OTHER INFORMATION: Xaa can be any amino acid

<400> SEQUENCE: 35

Xaa Xaa Val Arg Phe Gln Ser
 1               5

<210> SEQ ID NO 36
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Vein Mottling Virus protease cleavage
      site

<400> SEQUENCE: 36

Glu Thr Val Arg Phe Gln Gly
 1               5

<210> SEQ ID NO 37
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Vein Mottling Virus protease cleavage
      site
```

```
<400> SEQUENCE: 37

Glu Thr Val Arg Phe Gln Ser
 1               5

<210> SEQ ID NO 38
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Vein Mottling Virus protease cleavage
      site

<400> SEQUENCE: 38

Asn Asn Val Arg Phe Gln Gly
 1               5

<210> SEQ ID NO 39
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Tobacco Vein Mottling Virus protease cleavage
      site

<400> SEQUENCE: 39

Asn Asn Val Arg Phe Gln Ser
 1               5

<210> SEQ ID NO 40
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Consensus Sequence for human rhinovirus 3C
      protease cleavage site
<221> NAME/KEY: VARIANT
<222> LOCATION: (1)...(1)
<223> OTHER INFORMATION: Xaa can be any amino acid
<221> NAME/KEY: VARIANT
<222> LOCATION: (2)...(2)
<223> OTHER INFORMATION: Xaa can be G, A, V, L, I, M, S or T

<400> SEQUENCE: 40

Xaa Xaa Leu Phe Gln Gly Pro
 1               5

<210> SEQ ID NO 41
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human rhinovirus 3C protease cleavage site

<400> SEQUENCE: 41

Glu Ala Leu Phe Gln Gly Pro
 1               5

<210> SEQ ID NO 42
<211> LENGTH: 7
<212> TYPE: PRT
<213> ORGANISM: Artificial Sequence
<220> FEATURE:
```

```
<221> NAME/KEY: SITE
<222> LOCATION: (1)...(7)
<223> OTHER INFORMATION: Human Rhinovirus 3C protease cleavage site.

<400> SEQUENCE: 42

Glu Val Leu Phe Gln Gly Pro
  1               5

<210> SEQ ID NO 43
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C protease cleavage site.

<400> SEQUENCE: 43

Glu Leu Leu Phe Gln Gly Pro
  1               5

<210> SEQ ID NO 44
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C protease cleavage site.

<400> SEQUENCE: 44

Asp Ala Leu Phe Gln Gly Pro
  1               5

<210> SEQ ID NO 45
<211> LENGTH: 7
<212> TYPE: PRT
<213> ORGANISM: Artificial Sequence
<220> FEATURE:
<221> NAME/KEY: SITE
<222> LOCATION: (1)...(7)
<223> OTHER INFORMATION: Human Rhinovirus 3C protease cleavage site.

<400> SEQUENCE: 45

Asp Val Leu Phe Gln Gly Pro
  1               5

<210> SEQ ID NO 46
<211> LENGTH: 7
<212> TYPE: PRT
<213> ORGANISM: Artificial Sequence
<220> FEATURE:
<221> NAME/KEY: SITE
<222> LOCATION: (0)...(0)
<223> OTHER INFORMATION: Human Rhinovirus 3C protease cleavage site.

<400> SEQUENCE: 46

Asp Leu Leu Phe Gln Gly Pro
  1               5

<210> SEQ ID NO 47
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: subtilisin cleavage site consensus sequence
<221> NAME/KEY: VARIANT
<222> LOCATION: (1)...(4)
```

```
<223> OTHER INFORMATION: Xaa can be any amino acid

<400> SEQUENCE: 47

Xaa Xaa Xaa Xaa His Tyr
 1               5

<210> SEQ ID NO 48
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Conseqnsus sequence for a subtilisin cleavage
      site
<221> NAME/KEY: VARIANT
<222> LOCATION: (1)...(4)
<223> OTHER INFORMATION: Xaa can be any amino acid

<400> SEQUENCE: 48

Xaa Xaa Xaa Xaa Tyr His
 1               5

<210> SEQ ID NO 49
<211> LENGTH: 2
<212> TYPE: PRT
<213> ORGANISM: Artificial Sequence
<220> FEATURE:
<221> NAME/KEY: SITE
<222> LOCATION: (1)...(2)
<223> OTHER INFORMATION: subtilisin cleavage site

<400> SEQUENCE: 49

His Tyr
 1

<210> SEQ ID NO 50
<211> LENGTH: 2
<212> TYPE: PRT
<213> ORGANISM: Artificial Sequence
<220> FEATURE:
<221> NAME/KEY: SITE
<222> LOCATION: (1)...(2)
<223> OTHER INFORMATION: Subtilisin cleavage site

<400> SEQUENCE: 50

Tyr His
 1

<210> SEQ ID NO 51
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Subtilisin cleavage site

<400> SEQUENCE: 51

Pro Gly Ala Ala His Tyr
 1               5

<210> SEQ ID NO 52
<211> LENGTH: 2
<212> TYPE: PRT
<213> ORGANISM: Artificial Sequence
<220> FEATURE:
<221> NAME/KEY: SITE
<222> LOCATION: (1)...(2)
<223> OTHER INFORMATION: Hydroxylamine cleavage site
```

```
<400> SEQUENCE: 52

Asn Gly
 1

<210> SEQ ID NO 53
<211> LENGTH: 4
<212> TYPE: PRT
<213> ORGANISM: Artificial Sequence
<220> FEATURE:
<221> NAME/KEY: SITE
<222> LOCATION: (1)...(4)
<223> OTHER INFORMATION: Hydroxylamine cleavage site

<400> SEQUENCE: 53

Asn Gly Asn Gly
 1

<210> SEQ ID NO 54
<211> LENGTH: 6
<212> TYPE: PRT
<213> ORGANISM: Artificial Sequence
<220> FEATURE:
<221> NAME/KEY: SITE
<222> LOCATION: (1)...(6)
<223> OTHER INFORMATION: Hydroxylamine cleavage site

<400> SEQUENCE: 54

Asn Gly Asn Gly Asn Gly
 1               5

<210> SEQ ID NO 55
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Consensus sequence for a SUMO/ULP-1 protease
      cleavage site
<221> NAME/KEY: VARIANT
<222> LOCATION: (3)...(5)
<223> OTHER INFORMATION: Xaa can be any amino acid

<400> SEQUENCE: 55

Gly Gly Xaa Xaa Xaa
 1               5

<210> SEQ ID NO 56
<211> LENGTH: 98
<212> TYPE: PRT
<213> ORGANISM: Artificial Sequence
<220> FEATURE:
<221> NAME/KEY: SITE
<222> LOCATION: (1)...(98)
<223> OTHER INFORMATION: SUMO/ULP-1 protease cleavage site.

<400> SEQUENCE: 56

Met Ala Asp Ser Glu Val Asn Gln Glu Ala Lys Pro Glu Val Lys Pro
 1               5                  10                  15

Glu Val Lys Pro Glu Thr His Ile Asn Leu Lys Val Ser Asp Gly Ser
                20                  25                  30

Ser Glu Ile Phe Phe Lys Ile Lys Lys Thr Thr Pro Leu Arg Arg Leu
            35                  40                  45

Met Glu Ala Phe Ala Lys Arg Gln Gly Lys Glu Met Asp Ser Leu Arg
        50                  55                  60

Phe Leu Tyr Asp Gly Ile Arg Ile Gln Ala Asp Gln Thr Pro Glu Asp
```

```
               65                  70                  75                  80
Leu Asp Met Glu Asp Asn Asp Ile Ile Glu Ala His Arg Glu Gln Ile
                    85                  90                  95

Gly Gly

<210> SEQ ID NO 57
<211> LENGTH: 5
<212> TYPE: PRT
<213> ORGANISM: Artificial Sequence
<220> FEATURE:
<221> NAME/KEY: SITE
<222> LOCATION: (1)...(6)
<223> OTHER INFORMATION: Non-human Caspase 3 consensus sequence
<221> NAME/KEY: VARIANT
<222> LOCATION: (2)...(2)
<223> OTHER INFORMATION: Xaa can be any amino acid, with E preferred
<221> NAME/KEY: VARIANT
<222> LOCATION: (3)...(3)
<223> OTHER INFORMATION: Xaa can be any amino acid
<221> NAME/KEY: VARIANT
<222> LOCATION: (5)...(5)
<223> OTHER INFORMATION: Xaa can be any amino acid, with G or S
      preferred

<400> SEQUENCE: 57

Asp Xaa Xaa Asp Xaa
1               5

<210> SEQ ID NO 58
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Non-human Caspase 3 protease cleavage site

<400> SEQUENCE: 58

Asp Glu Val Asp Gly
1               5

<210> SEQ ID NO 59
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Non-human Caspase 3 protease cleavage site

<400> SEQUENCE: 59

Asp Glu Val Asp Ser
1               5

<210> SEQ ID NO 60
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Non-human Caspase 3 protease cleavage site

<400> SEQUENCE: 60

Asp Glu Pro Asp Gly
1               5

<210> SEQ ID NO 61
<211> LENGTH: 5
```

```
<212> TYPE: PRT
<213> ORGANISM: Artificial Sequence
<220> FEATURE:
<221> NAME/KEY: SITE
<222> LOCATION: (1)...(5)
<223> OTHER INFORMATION: Non-human Caspase 3 protease cleavage site

<400> SEQUENCE: 61

Asp Glu Pro Asp Ser
 1               5

<210> SEQ ID NO 62
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Non-human Caspase 3 protease cleavage site

<400> SEQUENCE: 62

Asp Glu Leu Asp Gly
 1               5

<210> SEQ ID NO 63
<211> LENGTH: 5
<212> TYPE: PRT
<213> ORGANISM: Artificial Sequence
<220> FEATURE:
<221> NAME/KEY: SITE
<222> LOCATION: (1)...(5)
<223> OTHER INFORMATION: Non-human Caspase 3 protease cleavage site

<400> SEQUENCE: 63

Asp Glu Leu Asp Ser
 1               5

<210> SEQ ID NO 64
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: flexible G-spacer

<400> SEQUENCE: 64

Gly Gly Gly Gly Ser
 1               5

<210> SEQ ID NO 65
<211> LENGTH: 5
<212> TYPE: PRT
<213> ORGANISM: Artificial Sequence
<220> FEATURE:
<221> NAME/KEY: DOMAIN
<222> LOCATION: (1)...(5)
<223> OTHER INFORMATION: flexible A-spacer

<400> SEQUENCE: 65

Glu Ala Ala Ala Lys
 1               5

<210> SEQ ID NO 66
<211> LENGTH: 5
<212> TYPE: PRT
<213> ORGANISM: Artificial Sequence
<220> FEATURE:
<221> NAME/KEY: ZN_FING
<222> LOCATION: (1)...(5)
```

-continued

```
<223> OTHER INFORMATION: Zinc-finger motif
<221> NAME/KEY: VARIANT
<222> LOCATION: (3)...(4)
<223> OTHER INFORMATION: Xaa can be any amino acid

<400> SEQUENCE: 66

His Glu Xaa Xaa His
 1               5

<210> SEQ ID NO 67
<211> LENGTH: 44
<212> TYPE: DNA
<213> ORGANISM: Artificial Sequence
<220> FEATURE:
<221> NAME/KEY: primer_bind
<222> LOCATION: (1)...(44)
<223> OTHER INFORMATION: Oligonucleotide primer

<400> SEQUENCE: 67
gactggtgga cagcaagtcg accggaagct ttacgacgat gacg            44

<210> SEQ ID NO 68
<211> LENGTH: 44
<212> TYPE: DNA
<213> ORGANISM: Artificial Sequence
<220> FEATURE:
<221> NAME/KEY: primer_bind
<222> LOCATION: (1)...(44)
<223> OTHER INFORMATION: Oligonucleotide primer

<400> SEQUENCE: 68
cgtcatcgtc gtaaagcttc cggtcgactt gctgtccacc agtc            44

<210> SEQ ID NO 69
<211> LENGTH: 30
<212> TYPE: DNA
<213> ORGANISM: Artificial Sequence
<220> FEATURE:
<221> NAME/KEY: primer_bind
<222> LOCATION: (1)...(30)
<223> OTHER INFORMATION: Oligonucleotide primer

<400> SEQUENCE: 69
aatagatcta gatcattaac agatttagga                            30

<210> SEQ ID NO 70
<211> LENGTH: 27
<212> TYPE: DNA
<213> ORGANISM: Artificial Sequence
<220> FEATURE:
<221> NAME/KEY: primer_bind
<222> LOCATION: (1)...(27)
<223> OTHER INFORMATION: Oligonucleotide primer

<400> SEQUENCE: 70
ttctaaagat ctatacattt gataact                               27

<210> SEQ ID NO 71
<211> LENGTH: 27
<212> TYPE: DNA
<213> ORGANISM: Artificial Sequence
<220> FEATURE:
<221> NAME/KEY: primer_bind
<222> LOCATION: (1)...(27)
<223> OTHER INFORMATION: Oligonucleotide primer

<400> SEQUENCE: 71
atgtatagat ctttagaata tcaagta                               27
```

-continued

```
<210> SEQ ID NO 72
<211> LENGTH: 45
<212> TYPE: DNA
<213> ORGANISM: Artificial Sequence
<220> FEATURE:
<221> NAME/KEY: primer_bind
<222> LOCATION: (1)...(45)
<223> OTHER INFORMATION: Oligonucleotide primer

<400> SEQUENCE: 72
atcgataagc ttttatcagt cgacccaaca atccagattt ttaga            45

<210> SEQ ID NO 73
<211> LENGTH: 65
<212> TYPE: PRT
<213> ORGANISM: Artificial Sequence
<220> FEATURE:
<221> NAME/KEY: DOMAIN
<222> LOCATION: (1)...(65)
<223> OTHER INFORMATION: Modified di-chain loop region

<400> SEQUENCE: 73

Ser Lys Leu Ile Gly Leu Cys Lys Lys Ile Ile Pro Pro Thr Asn Ile
 1               5                  10                  15

Arg Glu Asn Leu Tyr Asn Arg Thr Ala Gly Glu Lys Leu Tyr Asp Asp
                20                  25                  30

Asp Asp Lys Asp Arg Trp Gly Ser Ser Arg Ser Leu Thr Asp Leu Gly
            35                  40                  45

Gly Glu Leu Cys Ile Lys Asn Glu Asp Leu Thr Phe Ile Ala Glu Lys
        50                  55                  60

Asn
65

<210> SEQ ID NO 74
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 74
aatagaactg caggagaaaa gctttacgac gatgac                      36

<210> SEQ ID NO 75
<211> LENGTH: 36
<212> TYPE: DNA
<213> ORGANISM: Artificial Sequence
<220> FEATURE:
<223> OTHER INFORMATION: Oligonucleotide primer

<400> SEQUENCE: 75
gtcatcgtcg taaagctttt ctcctgcagt tctatt                      36

<210> SEQ ID NO 76
<211> LENGTH: 4016
<212> TYPE: DNA
<213> ORGANISM: Clostridia botulinum serotype E

<400> SEQUENCE: 76
gaattcaagt agtagataat aaaaataatg ccacagattt ttattattaa taatgatata   60
tttatctcta actgtttaac tttaacttat aacaatgtaa atatatattt gtctataaaa  120
aatcaagatt acaattgggt tatatgtgat cttaatcatg atataccaaa aaagtcatat  180
ctatggatat taaaaatat ataaatttaa aattaggaga tgctgtatat gccaaaaatt  240
```

| | |
|---|---|
| aatagttta attataatga tcctgttaat gatagaacaa ttttatatat taaaccaggc | 300 |
| ggttgtcaag aattttataa atcatttaat attatgaaaa atatttggat aattccagag | 360 |
| agaaatgtaa ttggtacaac cccccaagat tttcatccgc ctacttcatt aaaaaatgga | 420 |
| gatagtagtt attatgaccc taattattta caaagtgatg aagaaaagga tagatttta | 480 |
| aaaatagtca caaaaatatt taatagaata aataataatc tttcaggagg gattttatta | 540 |
| gaagaactgt caaaagctaa tccatattta gggaatgata atactccaga taatcaattc | 600 |
| catattggtg atgcatcagc agttgagatt aaattctcaa atggtagcca agacatacta | 660 |
| ttacctaatg ttattataat gggagcagag cctgatttat ttgaaactaa cagttccaat | 720 |
| atttctctaa gaaataatta tatgccaagc aatcaccgtt ttggatcaat agctatagta | 780 |
| acattctcac ctgaatattc ttttagattt aatgataatt gtatgaatga atttattcaa | 840 |
| gatcctgctc ttacattaat gcatgaatta atacattcat tacatggact atatggggct | 900 |
| aaagggatta ctacaaagta tactataaca caaaaacaaa atcccctaat aacaaatata | 960 |
| agaggtacaa atattgaaga attcttaact tttggaggta ctgatttaaa cattattact | 1020 |
| agtgctcagt ccaatgatat ctatactaat cttctagctg attataaaaa aatagcgtct | 1080 |
| aaacttagca agtacaagt atctaatcca ctacttaatc cttataaaga tgtttttgaa | 1140 |
| gcaaagtatg gattagataa agatgctagc ggaatttatt cggtaaatat aaacaaattt | 1200 |
| aatgatattt ttaaaaaatt atacagcttt acggaatttg atttacgaac taaatttcaa | 1260 |
| gttaaatgta ggcaaactta tattggacag tataaatact tcaaacttc aaacttgtta | 1320 |
| aatgattcta tttataatat atcagaaggc tataatataa ataatttaaa ggtaaatttt | 1380 |
| agaggacaga atgcaaattt aaatcctaga attattacac caattacagg tagaggacta | 1440 |
| gtaaaaaaaa tcattagatt ttgtaaaaat attgtttctg taaaaggcat aaggaaatca | 1500 |
| atatgtatcg aaataaataa tggtgagtta ttttttgtgg cttccagaaa tagttataat | 1560 |
| gatgataata taaatactcc taaagaaatt gacgatacag taacttcaaa aataaattat | 1620 |
| gaaaatgatt tagatcaggt tattttaaat tttaatagtg aatcagcacc tggactttca | 1680 |
| gatgaaaaat taaatttaac tatccaaaat gatgcttata taccaaaata tgattctaat | 1740 |
| ggaacaagtg atatagaaca acatgatgtt aatgaactta atgtattttt ctatttagat | 1800 |
| gcacagaaag tgcccgaagg tgaaaataat gtcaatctca cctcttcaat tgatacagca | 1860 |
| ttattagaac aacctaaaat atatacattt ttttcatcag aatttattaa taatgtcaat | 1920 |
| aaacctgtgc aagcagcatt atttgtaagc tggatacaac aagtgttagt agattttact | 1980 |
| actgaagcta accaaaaaag tactgttgat aaaattgcag atatttctat agttgttcca | 2040 |
| tatataggtc ttgctttaaa tataggaaat gaagcacaaa aaggaaattt taaagatgca | 2100 |
| cttgaattat taggagcagg tatttatta gaatttgaac ccgagctttt aattcctaca | 2160 |
| attttagtat tcacgataaa atctttttta ggttcatctg ataataaaaa taagttatt | 2220 |
| aaagcaataa ataatgcatt gaaagaaaga gatgaaaaat ggaaagaagt atatagtttt | 2280 |
| atagtatcga attggatgac taaaattaat acacaattta taaaagaaa agaacaaatg | 2340 |
| tatcaagctt tacaaaatca agtaaatgca attaaaacaa taatagaatc taagtataat | 2400 |
| agttatactt tagaggaaaa aaatgagctt acaaataaat atgatattaa gcaaatagaa | 2460 |
| aatgaactta atcaaaaggt ttctatagca atgaataata tagacaggtt cttaactgaa | 2520 |
| agttctatat cctatttaat gaaaataata aatgaagtaa aaattaataa attaagagaa | 2580 |
| tatgatgaga atgtcaaaac gtatttattg aattatatta tacaacatgg atcaatcttg | 2640 |

```
ggagagagtc agcaagaact aaattctatg gtaactgata ccctaaataa tagtattcct    2700
tttaagcttt cttcttatac agatgataaa attttaattt catattttaa taaattcttt    2760
aagagaatta aaagtagttc agttttaaat atgagatata aaatgataaa atacgtagat    2820
acttcaggat atgattcaaa tataaatatt aatggagatg tatataaata tccaactaat    2880
aaaaatcaat ttggaatata taatgataaa cttagtgaag ttaatatatc tcaaaatgat    2940
tacattatat atgataataa atataaaaat tttagtatta gttttttgggt aagaattcct    3000 aactatgata ataagatagt aaatgttaat aatgaataca ctataataaa ttgtatgaga    3060
gataataatt caggatggaa agtatctctt aatcataatg aaataatttg acattcgaa     3120 gataatcgag gaattaatca aaaattagca tttaactatg gtaacgcaaa tggtatttct    3180
gattatataa ataagtggat ttttgtaact ataactaatg atagattagg agattctaaa    3240
ctttatatta atggaaattt aatagatcaa aaatcaattt taaatttagg taatattcat    3300
gttagtgaca atatattatt taaaatagtt aattgtagtt atacaagata tattggtatt    3360
agatatttta atattttgga taagaattta gatgaaacag aaattcaaac tttatatagc    3420
aatgaaccta atacaaatat tttgaaggat ttttggggaa attatttgct ttatgacaaa    3480
gaatactatt tattaaatgt gttaaaacca ataactttta ttgataggag aaaagattct    3540
actttaagca ttaataatat aagaagcact attcttttag ctaatagatt atatagtgga    3600
ataaaagtta aaatacaaag agttaataat agtagtacta acgataatct tgttagaaag    3660
aatgatcagg tatatattaa ttttgtagcc agcaaaactc acttatttcc attatatgct    3720
gatacagcta ccacaaataa agagaaaaca ataaaaatat catcatctgg caatagattt    3780
aatcaagtag tagttatgaa ttcagtagga aattgtacaa tgaattttaa aaataataat    3840
ggaaataata ttgggttgtt aggtttcaag gcagatactg tcgttgctag tacttggtat    3900
tatacacata tgagagatca tacaaacagc aatggatgtt tttggaactt tatttctgaa    3960
gaacatggat ggcaagaaaa ataaaaatta gattaaacgg ctaaagtcat aaattc        4016
```

<210> SEQ ID NO 77
<211> LENGTH: 37
<212> TYPE: DNA
<213> ORGANISM: Artificial Sequence
<220> FEATURE:
<221> NAME/KEY: primer_bind
<222> LOCATION: (1)...(37)
<223> OTHER INFORMATION: Oligonucleotide primer

<400> SEQUENCE: 77
cccggatccc caaaaattaa tagttttaat tataatg                             37

<210> SEQ ID NO 78
<211> LENGTH: 36
<212> TYPE: DNA
<213> ORGANISM: Artificial Sequence
<220> FEATURE:
<221> NAME/KEY: primer_bind
<222> LOCATION: (1)...(36)
<223> OTHER INFORMATION: Oligonucleotide primer

<400> SEQUENCE: 78
cccctgcagt cattttttctt gccatccatg ttcttc                             36

<210> SEQ ID NO 79
<211> LENGTH: 31
<212> TYPE: DNA
<213> ORGANISM: Artificial Sequence
<220> FEATURE:
<221> NAME/KEY: primer_bind
<222> LOCATION: (1)...(31)
<223> OTHER INFORMATION: Oligonucleotide primer

<400> SEQUENCE: 79
cagttaatac attcattaca tggactatat g                                                31

<210> SEQ ID NO 80
<211> LENGTH: 26
<212> TYPE: DNA
<213> ORGANISM: Artificial Sequence
<220> FEATURE:
<221> NAME/KEY: primer_bind
<222> LOCATION: (1)...(26)
<223> OTHER INFORMATION: Oligonucleotide primer

<400> SEQUENCE: 80
atgcattaat gtaagagcag gatctt                                                      26

<210> SEQ ID NO 81
<211> LENGTH: 13
<212> TYPE: PRT
<213> ORGANISM: Homo sapiens

<400> SEQUENCE: 81

Ser Tyr Ser Met Glu His Phe Arg Trp Gly Lys Pro Val
 1               5                  10

<210> SEQ ID NO 82
<211> LENGTH: 16
<212> TYPE: PRT
<213> ORGANISM: Homo sapiens

<400> SEQUENCE: 82

Asp Glu Gly Pro Tyr Arg Met Glu His Phe Arg Trp Gly Ser Pro Pro
 1               5                  10                  15

<210> SEQ ID NO 83
<211> LENGTH: 11
<212> TYPE: PRT
<213> ORGANISM: Homo sapiens

<400> SEQUENCE: 83

Tyr Val Met Gly His Phe Arg Trp Asp Arg Phe
 1               5                  10

<210> SEQ ID NO 84
<211> LENGTH: 39
<212> TYPE: PRT
<213> ORGANISM: Homo sapiens

<400> SEQUENCE: 84

Ser Tyr Ser Met Glu His Phe Arg Trp Gly Lys Pro Val Gly Lys Lys
 1               5                  10                  15

Arg Arg Pro Val Lys Val Tyr Pro Asn Gly Ala Glu Asp Glu Ser Ala
                20                  25                  30

Glu Ala Phe Pro Leu Glu Phe
                35

<210> SEQ ID NO 85
<211> LENGTH: 21
<212> TYPE: PRT
<213> ORGANISM: Homo sapiens

<400> SEQUENCE: 85

```
Pro Val Lys Val Tyr Pro Asn Gly Ala Glu Asp Glu Ser Ala Glu Ala
 1               5                  10                  15

Phe Pro Leu Glu Phe
            20

<210> SEQ ID NO 86
<211> LENGTH: 89
<212> TYPE: PRT
<213> ORGANISM: Homo sapiens

<400> SEQUENCE: 86

Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Glu His Phe
        35                  40                  45

Arg Trp Gly Ser Pro Pro Lys Asp Lys Arg Tyr Gly Phe Met Thr
 50                  55                  60

Ser Glu Lys Ser Gln Thr Pro Leu Val Thr Leu Phe Lys Asn Ala Ile
65                  70                  75                  80

Ile Lys Asn Ala Tyr Lys Lys Gly Glu
                85

<210> SEQ ID NO 87
<211> LENGTH: 56
<212> TYPE: PRT
<213> ORGANISM: Homo sapiens

<400> SEQUENCE: 87

Glu Leu Thr Gly Gln Arg Leu Arg Glu Gly Asp Gly Pro Asp Gly Pro
 1               5                  10                  15

Ala Asp Asp Gly Ala Gly Ala Gln Ala Asp Leu Glu His Ser Leu Leu
            20                  25                  30

Val Ala Ala Glu Lys Lys Asp Glu Gly Pro Tyr Arg Met Glu His Phe
        35                  40                  45

Arg Trp Gly Ser Pro Pro Lys Asp
 50                  55

<210> SEQ ID NO 88
<211> LENGTH: 30
<212> TYPE: PRT
<213> ORGANISM: Homo sapiens

<400> SEQUENCE: 88

Glu Asp Val Ser Ala Gly Glu Asp Cys Gly Pro Leu Pro Glu Gly Gly
 1               5                  10                  15

Pro Glu Pro Arg Ser Asp Gly Ala Lys Pro Gly Pro Arg Glu
            20                  25                  30

<210> SEQ ID NO 89
<211> LENGTH: 23
<212> TYPE: PRT
<213> ORGANISM: Homo sapiens

<400> SEQUENCE: 89

Ser Ser Glu Met Ala Arg Asp Glu Asp Gly Gly Gln Asp Gly Asp Gln
 1               5                  10                  15

Val Gly His Glu Asp Leu Tyr
            20
```

<210> SEQ ID NO 90
<211> LENGTH: 76
<212> TYPE: PRT
<213> ORGANISM: Homo sapiens

<400> SEQUENCE: 90

Trp Cys Leu Glu Ser Ser Gln Cys Gln Asp Leu Thr Thr Glu Ser Asn
1               5                   10                  15

Leu Leu Glu Cys Ile Arg Ala Cys Lys Pro Asp Leu Ser Ala Glu Thr
            20                  25                  30

Pro Met Phe Pro Gly Asn Gly Asp Glu Gln Pro Leu Thr Glu Asn Pro
        35                  40                  45

Arg Lys Tyr Val Met Gly His Phe Arg Trp Asp Arg Phe Gly Arg Arg
    50                  55                  60

Asn Ser Ser Ser Ser Gly Ser Ser Gly Ala Gly Gln
65                  70                  75

<210> SEQ ID NO 91
<211> LENGTH: 30
<212> TYPE: PRT
<213> ORGANISM: Homo sapiens

<400> SEQUENCE: 91

Gly Trp Thr Leu Asn Ser Ala Gly Tyr Leu Leu Gly Pro His Ala Val
1               5                   10                  15

Gly Asn His Arg Ser Phe Ser Asp Lys Asn Gly Leu Thr Ser
            20                  25                  30

<210> SEQ ID NO 92
<211> LENGTH: 59
<212> TYPE: PRT
<213> ORGANISM: Homo sapiens

<400> SEQUENCE: 92

Glu Leu Arg Pro Glu Asp Asp Met Lys Pro Gly Ser Phe Asp Arg Ser
1               5                   10                  15

Ile Pro Glu Asn Asn Ile Met Arg Thr Ile Ile Glu Phe Leu Ser Phe
            20                  25                  30

Leu His Leu Lys Glu Ala Gly Ala Leu Asp Arg Leu Leu Asp Leu Pro
        35                  40                  45

Ala Ala Ala Ser Ser Glu Asp Ile Glu Arg Ser
    50                  55

<210> SEQ ID NO 93
<211> LENGTH: 112
<212> TYPE: PRT
<213> ORGANISM: Homo sapiens

<400> SEQUENCE: 93

Leu Pro Val Asn Ser Pro Met Asn Lys Gly Asp Thr Glu Val Met Lys
1               5                   10                  15

Cys Ile Val Glu Val Ile Ser Asp Thr Leu Ser Lys Pro Ser Pro Met
            20                  25                  30

Pro Val Ser Gln Glu Cys Phe Glu Thr Leu Arg Gly Asp Glu Arg Ile
        35                  40                  45

Leu Ser Ile Leu Arg His Gln Asn Leu Leu Lys Glu Leu Gln Asp Leu
    50                  55                  60

Ala Leu Gln Gly Ala Lys Glu Arg Ala His Gln Gln Lys Lys His Ser
65                  70                  75                  80

```
Gly Phe Glu Asp Glu Leu Ser Glu Val Leu Glu Asn Gln Ser Gln
                85                  90                  95

Ala Glu Leu Lys Glu Ala Val Glu Glu Pro Ser Ser Lys Asp Val Met
            100                 105                 110
```

<210> SEQ ID NO 94
<211> LENGTH: 76
<212> TYPE: PRT
<213> ORGANISM: Homo sapiens

<400> SEQUENCE: 94

```
Leu Pro Val Asn Ser Pro Met Asn Lys Gly Asp Thr Glu Val Met Lys
 1               5                  10                  15

Cys Ile Val Glu Val Ile Ser Asp Thr Leu Ser Lys Pro Ser Pro Met
            20                  25                  30

Pro Val Ser Gln Glu Cys Phe Glu Thr Leu Arg Gly Asp Glu Arg Ile
            35                  40                  45

Leu Ser Ile Leu Arg His Gln Asn Leu Leu Lys Glu Leu Gln Asp Leu
            50                  55                  60

Ala Leu Gln Gly Ala Lys Glu Arg Ala His Gln Gln
65                  70                  75
```

<210> SEQ ID NO 95
<211> LENGTH: 20
<212> TYPE: PRT
<213> ORGANISM: Homo sapiens

<400> SEQUENCE: 95

```
Ser Gly Glu Ala Thr Asp Gly Ala Arg Pro Gln Ala Leu Pro Glu Pro
 1               5                  10                  15

Met Gln Glu Ser
            20
```

<210> SEQ ID NO 96
<211> LENGTH: 53
<212> TYPE: PRT
<213> ORGANISM: Homo sapiens

<400> SEQUENCE: 96

```
Gly Glu Ser Arg Ser Glu Ala Leu Ala Val Asp Gly Ala Gly Lys Pro
 1               5                  10                  15

Gly Ala Glu Glu Ala Gln Asp Pro Gly Lys Gly Glu Gln Glu His
            20                  25                  30

Ser Gln Gln Lys Glu Glu Glu Glu Met Ala Val Val Pro Gln Gly
        35                  40                  45

Leu Phe Arg Gly Gly
    50
```

<210> SEQ ID NO 97
<211> LENGTH: 14
<212> TYPE: PRT
<213> ORGANISM: Homo sapiens

<400> SEQUENCE: 97

```
Trp Ser Lys Met Asp Gln Leu Ala Lys Glu Leu Thr Ala Glu
 1               5                  10
```

<210> SEQ ID NO 98
<211> LENGTH: 21
<212> TYPE: PRT
<213> ORGANISM: Homo sapiens

<400> SEQUENCE: 98

Ser Ser Met Lys Leu Ser Phe Arg Ala Arg Ala Tyr Gly Phe Arg Gly
1               5                   10                  15

Pro Gly Pro Gln Leu
            20

<210> SEQ ID NO 99
<211> LENGTH: 72
<212> TYPE: PRT
<213> ORGANISM: Homo sapiens

<400> SEQUENCE: 99

Leu Ser Phe Arg Ala Arg Ala Tyr Gly Phe Arg Gly Pro Gly Pro Gln
1               5                   10                  15

Leu Arg Arg Gly Trp Arg Pro Ser Ser Arg Glu Asp Ser Leu Glu Ala
            20                  25                  30

Gly Leu Pro Leu Gln Val Arg Gly Tyr Pro Glu Glu Lys Lys Glu Glu
        35                  40                  45

Glu Gly Ser Ala Asn Arg Arg Pro Glu Asp Gln Glu Leu Glu Ser Leu
    50                  55                  60

Ser Ala Ile Glu Ala Glu Leu Glu
65                  70

<210> SEQ ID NO 100
<211> LENGTH: 25
<212> TYPE: PRT
<213> ORGANISM: Homo sapiens

<400> SEQUENCE: 100

Gly Trp Arg Pro Ser Ser Arg Glu Asp Ser Leu Glu Ala Gly Leu Pro
1               5                   10                  15

Leu Gln Val Arg Gly Tyr Pro Glu Glu
            20                  25

<210> SEQ ID NO 101
<211> LENGTH: 67
<212> TYPE: PRT
<213> ORGANISM: Homo sapiens

<400> SEQUENCE: 101

Arg Val Gln Glu Ser Gln Arg Asp Lys Ala Arg Arg Arg Leu Pro Gly
1               5                   10                  15

Glu Leu Arg Asn Tyr Leu Asp Tyr Gly Glu Glu Lys Gly Glu Glu Ala
            20                  25                  30

Ala Arg Gly Lys Trp Gln Pro Gln Gly Asp Pro Arg Asp Ala Asp Glu
        35                  40                  45

Asn Arg Glu Glu Ala Arg Leu Arg Gly Lys Gly Tyr Ala Pro His His
    50                  55                  60

Ile Thr Glu
65

<210> SEQ ID NO 102
<211> LENGTH: 14
<212> TYPE: PRT
<213> ORGANISM: Homo sapiens

<400> SEQUENCE: 102

Gln Tyr Asp Arg Val Ala Gln Leu Asp Gln Leu Leu His Tyr
1               5                   10

```
<210> SEQ ID NO 103
<211> LENGTH: 14
<212> TYPE: PRT
<213> ORGANISM: Bos taurus

<400> SEQUENCE: 103

Gln Tyr Asp Arg Val Ala Glu Leu Asp Gln Leu Leu His Tyr
1               5                   10

<210> SEQ ID NO 104
<211> LENGTH: 11
<212> TYPE: PRT
<213> ORGANISM: Homo sapiens

<400> SEQUENCE: 104

Gln Lys Ile Ala Glu Lys Phe Ser Gln Arg Gly
1               5                   10

<210> SEQ ID NO 105
<211> LENGTH: 13
<212> TYPE: PRT
<213> ORGANISM: Homo sapiens

<400> SEQUENCE: 105

Gln Lys Ile Ala Glu Lys Phe Ser Gly Thr Arg Arg Gly
1               5                   10

<210> SEQ ID NO 106
<211> LENGTH: 33
<212> TYPE: PRT
<213> ORGANISM: Homo sapiens

<400> SEQUENCE: 106

Thr Asn Glu Ile Val Glu Glu Gln Tyr Thr Pro Gln Ser Leu Ala Thr
1               5                   10                  15

Leu Glu Ser Val Phe Gln Glu Leu Gly Lys Leu Thr Gly Pro Asn Asn
            20                  25                  30

Gln

<210> SEQ ID NO 107
<211> LENGTH: 11
<212> TYPE: PRT
<213> ORGANISM: Homo sapiens

<400> SEQUENCE: 107

Arg Pro Lys Pro Gln Gln Phe Phe Gly Leu Met
1               5                   10

<210> SEQ ID NO 108
<211> LENGTH: 12
<212> TYPE: PRT
<213> ORGANISM: Homo sapiens

<400> SEQUENCE: 108

Arg Pro Lys Pro Gln Gln Phe Phe Gly Leu Met Gly
1               5                   10

<210> SEQ ID NO 109
<211> LENGTH: 13
<212> TYPE: PRT
<213> ORGANISM: Homo sapiens

<400> SEQUENCE: 109

Arg Pro Lys Pro Gln Gln Phe Phe Gly Leu Met Gly Lys
```

```
                1               5                  10
```

<210> SEQ ID NO 110
<211> LENGTH: 14
<212> TYPE: PRT
<213> ORGANISM: Homo sapiens

<400> SEQUENCE: 110

```
Arg Pro Lys Pro Gln Gln Phe Phe Gly Leu Met Gly Lys Arg
1               5                   10
```

<210> SEQ ID NO 111
<211> LENGTH: 36
<212> TYPE: PRT
<213> ORGANISM: Homo sapiens

<400> SEQUENCE: 111

```
Asp Ala Asp Ser Ser Ile Glu Lys Gln Val Ala Leu Leu Lys Ala Leu
1               5                   10                  15

Tyr Gly His Gly Gln Ile Ser His Lys Arg His Lys Thr Asp Ser Phe
            20                  25                  30

Val Gly Leu Met
        35
```

<210> SEQ ID NO 112
<211> LENGTH: 19
<212> TYPE: PRT
<213> ORGANISM: Homo sapiens

<400> SEQUENCE: 112

```
Gly His Gly Gln Ile Ser His Lys Arg His Lys Thr Asp Ser Phe Val
1               5                   10                  15

Gly Leu Met
```

<210> SEQ ID NO 113
<211> LENGTH: 10
<212> TYPE: PRT
<213> ORGANISM: Homo sapiens

<400> SEQUENCE: 113

```
His Lys Thr Asp Ser Phe Val Gly Leu Met
1               5                   10
```

<210> SEQ ID NO 114
<211> LENGTH: 10
<212> TYPE: PRT
<213> ORGANISM: Rattus norvegicus

<400> SEQUENCE: 114

```
Asp Met His Asp Phe Phe Val Gly Leu Met
1               5                   10
```

<210> SEQ ID NO 115
<211> LENGTH: 10
<212> TYPE: PRT
<213> ORGANISM: Homo sapiens

<400> SEQUENCE: 115

```
Ser Arg Thr Arg Gln Phe Tyr Gly Leu Met
1               5                   10
```

<210> SEQ ID NO 116
<211> LENGTH: 10
<212> TYPE: PRT

<213> ORGANISM: Homo sapiens

<400> SEQUENCE: 116

Gly Lys Ala Ser Gln Phe Phe Gly Leu Met
1               5                   10

<210> SEQ ID NO 117
<211> LENGTH: 14
<212> TYPE: PRT
<213> ORGANISM: Homo sapiens

<400> SEQUENCE: 117

Lys Lys Ala Tyr Gln Leu Glu His Thr Phe Gln Gly Leu Leu
1               5                   10

<210> SEQ ID NO 118
<211> LENGTH: 14
<212> TYPE: PRT
<213> ORGANISM: Homo sapiens

<400> SEQUENCE: 118

Val Gly Ala Tyr Gln Leu Glu His Thr Phe Gln Gly Leu Leu
1               5                   10

<210> SEQ ID NO 119
<211> LENGTH: 36
<212> TYPE: PRT
<213> ORGANISM: Homo sapiens

<400> SEQUENCE: 119

Tyr Pro Ser Lys Pro Asp Asn Pro Gly Glu Asp Ala Pro Ala Glu Asp
1               5                   10                  15

Met Ala Arg Tyr Tyr Ser Ala Leu Arg His Tyr Ile Asn Leu Ile Thr
            20                  25                  30

Arg Gln Arg Tyr
        35

<210> SEQ ID NO 120
<211> LENGTH: 36
<212> TYPE: PRT
<213> ORGANISM: Homo sapiens

<400> SEQUENCE: 120

Tyr Pro Ile Lys Pro Glu Ala Pro Gly Glu Asp Ala Ser Pro Glu Glu
1               5                   10                  15

Leu Asn Arg Tyr Tyr Ala Ser Leu Arg His Tyr Leu Asn Leu Val Thr
            20                  25                  30

Arg Gln Arg Tyr
        35

<210> SEQ ID NO 121
<211> LENGTH: 33
<212> TYPE: PRT
<213> ORGANISM: Homo sapiens

<400> SEQUENCE: 121

Glu Pro Val Tyr Pro Gly Asp Asn Ala Thr Pro Glu Gln Met Ala Gln
1               5                   10                  15

Tyr Ala Ala Asp Leu Arg Arg Tyr Ile Asn Met Leu Thr Arg Pro Arg
            20                  25                  30

Tyr

<210> SEQ ID NO 122
<211> LENGTH: 36
<212> TYPE: PRT
<213> ORGANISM: Homo sapiens

<400> SEQUENCE: 122

```
Ala Pro Leu Glu Pro Val Tyr Pro Gly Asp Asn Ala Thr Pro Glu Gln
 1               5                  10                  15

Met Ala Gln Tyr Ala Ala Asp Leu Arg Arg Tyr Ile Asn Met Leu Thr
            20                  25                  30

Arg Pro Arg Tyr
        35
```

<210> SEQ ID NO 123
<211> LENGTH: 20
<212> TYPE: PRT
<213> ORGANISM: Homo sapiens

<400> SEQUENCE: 123

```
His Lys Glu Asp Thr Leu Ala Phe Ser Glu Trp Gly Ser Pro His Ala
 1               5                  10                  15

Ala Val Pro Arg
            20
```

<210> SEQ ID NO 124
<211> LENGTH: 926
<212> TYPE: PRT
<213> ORGANISM: Artificial Sequence
<220> FEATURE:
<221> NAME/KEY: PEPTIDE
<222> LOCATION: (1)...(926)
<223> OTHER INFORMATION: BoNT/A-TEV-alphaMSHAP4A

<400> SEQUENCE: 124

```
Met Gly Pro Arg Arg Leu Leu Leu Val Ala Ala Cys Phe Ser Leu Cys
 1               5                  10                  15

Gly Pro Leu Leu Ser Ala Arg Thr Arg Ala Arg Arg Pro Glu Ser Lys
            20                  25                  30

Ala Thr Asn Ala Thr Asp Asp Asp Asp Lys Ser Tyr Ser Met Glu His
        35                  40                  45

Phe Arg Trp Gly Lys Pro Val Ala Leu Asn Asp Leu Cys Ile Lys Val
    50                  55                  60

Asn Asn Trp Asp Leu Phe Phe Ser Pro Ser Glu Asp Asn Phe Thr Asn
65                  70                  75                  80

Asp Leu Asn Lys Gly Glu Glu Ile Thr Ser Asp Thr Asn Ile Glu Ala
                85                  90                  95

Ala Glu Glu Asn Ile Ser Leu Asp Leu Ile Gln Gln Tyr Tyr Leu Thr
            100                 105                 110

Phe Asn Phe Asp Asn Glu Pro Glu Asn Ile Ser Ile Glu Asn Leu Ser
        115                 120                 125

Ser Asp Ile Ile Gly Gln Leu Glu Leu Met Pro Asn Ile Glu Arg Phe
    130                 135                 140

Pro Asn Gly Lys Lys Tyr Glu Leu Asp Lys Tyr Thr Met Phe His Tyr
145                 150                 155                 160

Leu Arg Ala Gln Glu Phe Glu His Gly Lys Ser Arg Ile Ala Leu Thr
                165                 170                 175

Asn Ser Val Asn Glu Ala Leu Leu Asn Pro Ser Arg Val Tyr Thr Phe
            180                 185                 190

Phe Ser Ser Asp Tyr Val Lys Lys Val Asn Lys Ala Thr Glu Ala Ala
        195                 200                 205
```

```
Met Phe Leu Gly Trp Val Glu Gln Leu Val Tyr Asp Phe Thr Asp Glu
    210                 215                 220
Thr Ser Glu Val Ser Thr Thr Asp Lys Ile Ala Asp Ile Thr Ile Ile
225                 230                 235                 240
Ile Pro Tyr Ile Gly Pro Ala Leu Asn Ile Gly Asn Met Leu Tyr Lys
                245                 250                 255
Asp Asp Phe Val Gly Ala Leu Ile Phe Ser Gly Ala Val Ile Leu Leu
                260                 265                 270
Glu Phe Ile Pro Glu Ile Ala Ile Pro Val Leu Gly Thr Phe Ala Leu
            275                 280                 285
Val Ser Tyr Ile Ala Asn Lys Val Leu Thr Val Gln Thr Ile Asp Asn
        290                 295                 300
Ala Leu Ser Lys Arg Asn Glu Lys Trp Asp Glu Val Tyr Lys Tyr Ile
305                 310                 315                 320
Val Thr Asn Trp Leu Ala Lys Val Asn Thr Gln Ile Asp Leu Ile Arg
                325                 330                 335
Lys Lys Met Lys Glu Ala Leu Glu Asn Gln Ala Glu Ala Thr Lys Ala
            340                 345                 350
Ile Ile Asn Tyr Gln Tyr Asn Gln Tyr Thr Glu Glu Lys Asn Asn
        355                 360                 365
Ile Asn Phe Asn Ile Asp Asp Leu Ser Ser Lys Leu Asn Glu Ser Ile
370                 375                 380
Asn Lys Ala Met Ile Asn Ile Asn Lys Phe Leu Asn Gln Cys Ser Val
385                 390                 395                 400
Ser Tyr Leu Met Asn Ser Met Ile Pro Tyr Gly Val Lys Arg Leu Glu
                405                 410                 415
Asp Phe Asp Ala Ser Leu Lys Asp Ala Leu Leu Lys Tyr Ile Tyr Asp
            420                 425                 430
Asn Arg Gly Thr Leu Ile Gly Gln Val Asp Arg Leu Lys Asp Lys Val
        435                 440                 445
Asn Asn Thr Leu Ser Thr Asp Ile Pro Phe Gln Leu Ser Lys Tyr Val
        450                 455                 460
Asp Asn Gln Arg Leu Leu Ser Thr Phe Thr Glu Tyr Ile Lys Glu Asn
465                 470                 475                 480
Leu Tyr Phe Gln Gly Pro Phe Val Asn Lys Gln Phe Asn Tyr Lys Asp
                485                 490                 495
Pro Val Asn Gly Val Asp Ile Ala Tyr Ile Lys Ile Pro Asn Ala Gly
                500                 505                 510
Gln Met Gln Pro Val Lys Ala Phe Lys Ile His Asn Lys Ile Trp Val
        515                 520                 525
Ile Pro Glu Arg Asp Thr Phe Thr Asn Pro Glu Glu Gly Asp Leu Asn
        530                 535                 540
Pro Pro Pro Glu Ala Lys Gln Val Pro Val Ser Tyr Tyr Asp Ser Thr
545                 550                 555                 560
Tyr Leu Ser Thr Asp Asn Glu Lys Asp Asn Tyr Leu Lys Gly Val Thr
                565                 570                 575
Lys Leu Phe Glu Arg Ile Tyr Ser Thr Asp Leu Gly Arg Met Leu Leu
            580                 585                 590
Thr Ser Ile Val Arg Gly Ile Pro Phe Trp Gly Gly Ser Thr Ile Asp
        595                 600                 605
Thr Glu Leu Lys Val Ile Asp Thr Asn Cys Ile Asn Val Ile Gln Pro
    610                 615                 620
Asp Gly Ser Tyr Arg Ser Glu Glu Leu Asn Leu Val Ile Ile Gly Pro
```

```
                625                 630                 635                 640
Ser Ala Asp Ile Ile Gln Phe Glu Cys Lys Ser Phe Gly His Glu Val
                    645                 650                 655

Leu Asn Leu Thr Arg Asn Gly Tyr Gly Ser Thr Gln Tyr Ile Arg Phe
            660                 665                 670

Ser Pro Asp Phe Thr Phe Gly Phe Glu Glu Ser Leu Glu Val Asp Thr
        675                 680                 685

Asn Pro Leu Leu Gly Ala Gly Lys Phe Ala Thr Asp Pro Ala Val Thr
    690                 695                 700

Leu Ala His Glu Leu Ile His Ala Gly His Arg Leu Tyr Gly Ile Ala
705                 710                 715                 720

Ile Asn Pro Asn Arg Val Phe Lys Val Asn Thr Asn Ala Tyr Tyr Glu
                725                 730                 735

Met Ser Gly Leu Glu Val Ser Phe Glu Glu Leu Arg Thr Phe Gly Gly
            740                 745                 750

His Asp Ala Lys Phe Ile Asp Ser Leu Gln Glu Asn Glu Phe Arg Leu
        755                 760                 765

Tyr Tyr Tyr Asn Lys Phe Lys Asp Ile Ala Ser Thr Leu Asn Lys Ala
    770                 775                 780

Lys Ser Ile Val Gly Thr Thr Ala Ser Leu Gln Tyr Met Lys Asn Val
785                 790                 795                 800

Phe Lys Glu Lys Tyr Leu Leu Ser Glu Asp Thr Ser Gly Lys Phe Ser
                805                 810                 815

Val Asp Lys Leu Lys Phe Asp Lys Leu Tyr Lys Met Leu Thr Glu Ile
            820                 825                 830

Tyr Thr Glu Asp Asn Phe Val Lys Phe Phe Lys Val Leu Asn Arg Lys
        835                 840                 845

Thr Tyr Leu Asn Phe Asp Lys Ala Val Phe Lys Ile Asn Ile Val Pro
    850                 855                 860

Lys Val Asn Tyr Thr Ile Tyr Asp Gly Phe Asn Leu Arg Asn Thr Asn
865                 870                 875                 880

Leu Ala Ala Asn Phe Asn Gly Gln Asn Thr Glu Ile Asn Asn Met Asn
                885                 890                 895

Phe Thr Lys Leu Lys Asn Phe Thr Gly Leu Phe Glu Phe Tyr Lys Leu
            900                 905                 910

Leu Cys Val Arg Gly Ile Ile Thr Ser Lys Thr Lys Ser Leu
        915                 920                 925

<210> SEQ ID NO 125
<211> LENGTH: 928
<212> TYPE: PRT
<213> ORGANISM: Artificial Sequence
<220> FEATURE:
<221> NAME/KEY: PEPTIDE
<222> LOCATION: (1)...(928)
<223> OTHER INFORMATION: BoNT/A-TEV-alphaMSHAP4B

<400> SEQUENCE: 125

Met Gly Pro Arg Arg Leu Leu Leu Val Ala Ala Cys Phe Ser Leu Cys
1               5                   10                  15

Gly Pro Leu Leu Ser Ala Arg Thr Arg Ala Arg Pro Glu Ser Lys
            20                  25                  30

Ala Thr Asn Ala Thr Asp Asp Asp Lys Ser Tyr Ser Met Glu His
        35                  40                  45

Phe Arg Trp Gly Lys Pro Val Pro Phe Val Asn Lys Gln Phe Asn Tyr
    50                  55                  60
```

-continued

```
Lys Asp Pro Val Asn Gly Val Asp Ile Ala Tyr Ile Lys Ile Pro Asn
 65                  70                  75                  80

Ala Gly Gln Met Gln Pro Val Lys Ala Phe Lys Ile His Asn Lys Ile
                 85                  90                  95

Trp Val Ile Pro Glu Arg Asp Thr Phe Thr Asn Pro Glu Glu Gly Asp
            100                 105                 110

Leu Asn Pro Pro Glu Ala Lys Gln Val Pro Val Ser Tyr Tyr Asp
        115                 120                 125

Ser Thr Tyr Leu Ser Thr Asp Asn Glu Lys Asp Asn Tyr Leu Lys Gly
        130                 135                 140

Val Thr Lys Leu Phe Glu Arg Ile Tyr Ser Thr Asp Leu Gly Arg Met
145                 150                 155                 160

Leu Leu Thr Ser Ile Val Arg Gly Ile Pro Phe Trp Gly Gly Ser Thr
                165                 170                 175

Ile Asp Thr Glu Leu Lys Val Ile Asp Thr Asn Cys Ile Asn Val Ile
            180                 185                 190

Gln Pro Asp Gly Ser Tyr Arg Ser Glu Glu Leu Asn Leu Val Ile Ile
        195                 200                 205

Gly Pro Ser Ala Asp Ile Ile Gln Phe Glu Cys Lys Ser Phe Gly His
210                 215                 220

Glu Val Leu Asn Leu Thr Arg Asn Gly Tyr Gly Ser Thr Gln Tyr Ile
225                 230                 235                 240

Arg Phe Ser Pro Asp Phe Thr Phe Gly Phe Glu Glu Ser Leu Glu Val
                245                 250                 255

Asp Thr Asn Pro Leu Leu Gly Ala Gly Lys Phe Ala Thr Asp Pro Ala
            260                 265                 270

Val Thr Leu Ala His Glu Leu Ile His Ala Gly His Arg Leu Tyr Gly
        275                 280                 285

Ile Ala Ile Asn Pro Asn Arg Val Phe Lys Val Asn Thr Asn Ala Tyr
        290                 295                 300

Tyr Glu Met Ser Gly Leu Glu Val Ser Phe Glu Glu Leu Arg Thr Phe
305                 310                 315                 320

Gly Gly His Asp Ala Lys Phe Ile Asp Ser Leu Gln Glu Asn Glu Phe
                325                 330                 335

Arg Leu Tyr Tyr Tyr Asn Lys Phe Lys Asp Ile Ala Ser Thr Leu Asn
            340                 345                 350

Lys Ala Lys Ser Ile Val Gly Thr Thr Ala Ser Leu Gln Tyr Met Lys
        355                 360                 365

Asn Val Phe Lys Glu Lys Tyr Leu Leu Ser Glu Asp Thr Ser Gly Lys
        370                 375                 380

Phe Ser Val Asp Lys Leu Lys Phe Asp Lys Leu Tyr Lys Met Leu Thr
385                 390                 395                 400

Glu Ile Tyr Thr Glu Asp Asn Phe Val Lys Phe Phe Lys Val Leu Asn
                405                 410                 415

Arg Lys Thr Tyr Leu Asn Phe Asp Lys Ala Val Phe Lys Ile Asn Ile
            420                 425                 430

Val Pro Lys Val Asn Tyr Thr Ile Tyr Asp Gly Phe Asn Leu Arg Asn
        435                 440                 445

Thr Asn Leu Ala Ala Asn Phe Asn Gly Gln Asn Thr Glu Ile Asn Asn
        450                 455                 460

Met Asn Phe Thr Lys Leu Lys Asn Phe Thr Gly Leu Phe Glu Phe Tyr
465                 470                 475                 480

Lys Leu Leu Cys Val Arg Gly Ile Ile Thr Ser Lys Thr Lys Ser Leu
                485                 490                 495
```

```
Glu Asn Leu Tyr Phe Gln Gly Ala Leu Asn Asp Leu Cys Ile Lys Val
            500                 505                 510
Asn Asn Trp Asp Leu Phe Phe Ser Pro Ser Glu Asp Asn Phe Thr Asn
            515                 520                 525
Asp Leu Asn Lys Gly Glu Glu Ile Thr Ser Asp Thr Asn Ile Glu Ala
            530                 535                 540
Ala Glu Glu Asn Ile Ser Leu Asp Leu Ile Gln Gln Tyr Tyr Leu Thr
545                 550                 555                 560
Phe Asn Phe Asp Asn Glu Pro Glu Asn Ile Ser Ile Glu Asn Leu Ser
                565                 570                 575
Ser Asp Ile Ile Gly Gln Leu Glu Leu Met Pro Asn Ile Glu Arg Phe
                580                 585                 590
Pro Asn Gly Lys Lys Tyr Glu Leu Asp Lys Tyr Thr Met Phe His Tyr
                595                 600                 605
Leu Arg Ala Gln Glu Phe Glu His Gly Lys Ser Arg Ile Ala Leu Thr
            610                 615                 620
Asn Ser Val Asn Glu Ala Leu Leu Asn Pro Ser Arg Val Tyr Thr Phe
625                 630                 635                 640
Phe Ser Ser Asp Tyr Val Lys Lys Val Asn Lys Ala Thr Glu Ala Ala
                645                 650                 655
Met Phe Leu Gly Trp Val Glu Gln Leu Val Tyr Asp Phe Thr Asp Glu
                660                 665                 670
Thr Ser Glu Val Ser Thr Thr Asp Lys Ile Ala Asp Ile Thr Ile Ile
            675                 680                 685
Ile Pro Tyr Ile Gly Pro Ala Leu Asn Ile Gly Asn Met Leu Tyr Lys
            690                 695                 700
Asp Asp Phe Val Gly Ala Leu Ile Phe Ser Gly Ala Val Ile Leu Leu
705                 710                 715                 720
Glu Phe Ile Pro Glu Ile Ala Ile Pro Val Leu Gly Thr Phe Ala Leu
                725                 730                 735
Val Ser Tyr Ile Ala Asn Lys Val Leu Thr Val Gln Thr Ile Asp Asn
            740                 745                 750
Ala Leu Ser Lys Arg Asn Glu Lys Trp Asp Glu Val Tyr Lys Tyr Ile
            755                 760                 765
Val Thr Asn Trp Leu Ala Lys Val Asn Thr Gln Ile Asp Leu Ile Arg
            770                 775                 780
Lys Lys Met Lys Glu Ala Leu Glu Asn Gln Ala Glu Ala Thr Lys Ala
785                 790                 795                 800
Ile Ile Asn Tyr Gln Tyr Asn Gln Tyr Thr Glu Glu Glu Lys Asn Asn
                805                 810                 815
Ile Asn Phe Asn Ile Asp Asp Leu Ser Ser Lys Leu Asn Glu Ser Ile
                820                 825                 830
Asn Lys Ala Met Ile Asn Ile Asn Lys Phe Leu Asn Gln Cys Ser Val
            835                 840                 845
Ser Tyr Leu Met Asn Ser Met Ile Pro Tyr Gly Val Lys Arg Leu Glu
            850                 855                 860
Asp Phe Asp Ala Ser Leu Lys Asp Ala Leu Leu Lys Tyr Ile Tyr Asp
865                 870                 875                 880
Asn Arg Gly Thr Leu Ile Gly Gln Val Asp Arg Leu Lys Asp Lys Val
                885                 890                 895
Asn Asn Thr Leu Ser Thr Asp Ile Pro Phe Gln Leu Ser Lys Tyr Val
                900                 905                 910
Asp Asn Gln Arg Leu Leu Ser Thr Phe Thr Glu Tyr Ile Lys Asn Ile
```

915 920 925

<210> SEQ ID NO 126
<211> LENGTH: 926
<212> TYPE: PRT
<213> ORGANISM: Artificial Sequence
<220> FEATURE:
<221> NAME/KEY: PEPTIDE
<222> LOCATION: (1)...(926)
<223> OTHER INFORMATION: BoNT/A-ENT-NPYCP5A

<400> SEQUENCE: 126

Met Pro Phe Val Asn Lys Gln Phe Asn Tyr Lys Asp Pro Val Asn Gly
1 5 10 15

Val Asp Ile Ala Tyr Ile Lys Ile Pro Asn Ala Gly Gln Met Gln Pro
20 25 30

Val Lys Ala Phe Lys Ile His Asn Lys Ile Trp Val Ile Pro Glu Arg
35 40 45

Asp Thr Phe Thr Asn Pro Glu Glu Gly Asp Leu Asn Pro Pro Pro Glu
50 55 60

Ala Lys Gln Val Pro Val Ser Tyr Tyr Asp Ser Thr Tyr Leu Ser Thr
65 70 75 80

Asp Asn Glu Lys Asp Asn Tyr Leu Lys Gly Val Thr Lys Leu Phe Glu
85 90 95

Arg Ile Tyr Ser Thr Asp Leu Gly Arg Met Leu Leu Thr Ser Ile Val
100 105 110

Arg Gly Ile Pro Phe Trp Gly Gly Ser Thr Ile Asp Thr Glu Leu Lys
115 120 125

Val Ile Asp Thr Asn Cys Ile Asn Val Ile Gln Pro Asp Gly Ser Tyr
130 135 140

Arg Ser Glu Glu Leu Asn Leu Val Ile Ile Gly Pro Ser Ala Asp Ile
145 150 155 160

Ile Gln Phe Glu Cys Lys Ser Phe Gly His Glu Val Leu Asn Leu Thr
165 170 175

Arg Asn Gly Tyr Gly Ser Thr Gln Tyr Ile Arg Phe Ser Pro Asp Phe
180 185 190

Thr Phe Gly Phe Glu Glu Ser Leu Glu Val Asp Thr Asn Pro Leu Leu
195 200 205

Gly Ala Gly Lys Phe Ala Thr Asp Pro Ala Val Thr Leu Ala His Glu
210 215 220

Leu Ile His Ala Gly His Arg Leu Tyr Gly Ile Ala Ile Asn Pro Asn
225 230 235 240

Arg Val Phe Lys Val Asn Thr Asn Ala Tyr Tyr Glu Met Ser Gly Leu
245 250 255

Glu Val Ser Phe Glu Glu Leu Arg Thr Phe Gly Gly His Asp Ala Lys
260 265 270

Phe Ile Asp Ser Leu Gln Glu Asn Glu Phe Arg Leu Tyr Tyr Tyr Asn
275 280 285

Lys Phe Lys Asp Ile Ala Ser Thr Leu Asn Lys Ala Lys Ser Ile Val
290 295 300

Gly Thr Thr Ala Ser Leu Gln Tyr Met Lys Asn Val Phe Lys Glu Lys
305 310 315 320

Tyr Leu Leu Ser Glu Asp Thr Ser Gly Lys Phe Ser Val Asp Lys Leu
325 330 335

Lys Phe Asp Lys Leu Tyr Lys Met Leu Thr Glu Ile Tyr Thr Glu Asp
340 345 350

```
Asn Phe Val Lys Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
                420                 425                 430

Gly Ile Ile Thr Ser Lys Thr Lys Ser Leu Asp Asp Asp Lys Tyr
            435                 440                 445

Pro Ser Lys Pro Asp Asn Pro Gly Glu Asp Ala Pro Ala Glu Asp Met
450                 455                 460

Ala Arg Tyr Tyr Ser Ala Leu Arg His Tyr Ile Asn Leu Ile Thr Arg
465                 470                 475                 480

Gln Arg Tyr Ala Leu Ala Gly Gly Gly Ser Gly Gly Gly Ser
                485                 490                 495

Gly Gly Gly Gly Ser Ala Leu Asn Asp Leu Cys Ile Lys Val Asn Asn
            500                 505                 510

Trp Asp Leu Phe Phe Ser Pro Ser Glu Asp Asn Phe Thr Asn Asp Leu
            515                 520                 525

Asn Lys Gly Glu Glu Ile Thr Ser Asp Thr Asn Ile Glu Ala Ala Glu
530                 535                 540

Glu Asn Ile Ser Leu Asp Leu Ile Gln Gln Tyr Tyr Leu Thr Phe Asn
545                 550                 555                 560

Phe Asp Asn Glu Pro Glu Asn Ile Ser Ile Glu Asn Leu Ser Ser Asp
                565                 570                 575

Ile Ile Gly Gln Leu Glu Leu Met Pro Asn Ile Glu Arg Phe Pro Asn
                580                 585                 590

Gly Lys Lys Tyr Glu Leu Asp Lys Tyr Thr Met Phe His Tyr Leu Arg
                595                 600                 605

Ala Gln Glu Phe Glu His Gly Lys Ser Arg Ile Ala Leu Thr Asn Ser
610                 615                 620

Val Asn Glu Ala Leu Leu Asn Pro Ser Arg Val Tyr Thr Phe Phe Ser
625                 630                 635                 640

Ser Asp Tyr Val Lys Lys Val Asn Lys Ala Thr Glu Ala Ala Met Phe
                645                 650                 655

Leu Gly Trp Val Glu Gln Leu Val Tyr Asp Phe Thr Asp Glu Thr Ser
                660                 665                 670

Glu Val Ser Thr Thr Asp Lys Ile Ala Asp Ile Thr Ile Ile Pro
            675                 680                 685

Tyr Ile Gly Pro Ala Leu Asn Ile Gly Asn Met Leu Tyr Lys Asp Asp
690                 695                 700

Phe Val Gly Ala Leu Ile Phe Ser Gly Ala Val Ile Leu Leu Glu Phe
705                 710                 715                 720

Ile Pro Glu Ile Ala Ile Pro Val Leu Gly Thr Phe Ala Leu Val Ser
                725                 730                 735

Tyr Ile Ala Asn Lys Val Leu Thr Val Gln Thr Ile Asp Asn Ala Leu
                740                 745                 750

Ser Lys Arg Asn Glu Lys Trp Asp Glu Val Tyr Lys Tyr Ile Val Thr
            755                 760                 765

Asn Trp Leu Ala Lys Val Asn Thr Gln Ile Asp Leu Ile Arg Lys Lys
770                 775                 780
```

```
Met Lys Glu Ala Leu Glu Asn Gln Ala Glu Ala Thr Lys Ala Ile Ile
785                 790                 795                 800

Asn Tyr Gln Tyr Asn Gln Tyr Thr Glu Glu Glu Lys Asn Asn Ile Asn
                805                 810                 815

Phe Asn Ile Asp Asp Leu Ser Ser Lys Leu Asn Glu Ser Ile Asn Lys
            820                 825                 830

Ala Met Ile Asn Ile Asn Lys Phe Leu Asn Gln Cys Ser Val Ser Tyr
        835                 840                 845

Leu Met Asn Ser Met Ile Pro Tyr Gly Val Lys Arg Leu Glu Asp Phe
    850                 855                 860

Asp Ala Ser Leu Lys Asp Ala Leu Leu Lys Tyr Ile Tyr Asp Asn Arg
865                 870                 875                 880

Gly Thr Leu Ile Gly Gln Val Asp Arg Leu Lys Asp Lys Val Asn Asn
                885                 890                 895

Thr Leu Ser Thr Asp Ile Pro Phe Gln Leu Ser Lys Tyr Val Asp Asn
            900                 905                 910

Gln Arg Leu Leu Ser Thr Phe Thr Glu Tyr Ile Lys Asn Ile
        915                 920                 925

<210> SEQ ID NO 127
<211> LENGTH: 932
<212> TYPE: PRT
<213> ORGANISM: Artificial Sequence
<220> FEATURE:
<221> NAME/KEY: PEPTIDE
<222> LOCATION: (1)...(932)
<223> OTHER INFORMATION: BoNT/A-ENT-NPYCP5B

<400> SEQUENCE: 127

Met Glu Ala Ala Ala Lys Glu Ala Ala Ala Lys Ala Leu Asn Asp Leu
 1               5                  10                  15

Cys Ile Lys Val Asn Asn Trp Asp Leu Phe Phe Ser Pro Ser Glu Asp
            20                  25                  30

Asn Phe Thr Asn Asp Leu Asn Lys Gly Glu Glu Ile Thr Ser Asp Thr
        35                  40                  45

Asn Ile Glu Ala Ala Glu Glu Asn Ile Ser Leu Asp Leu Ile Gln Gln
    50                  55                  60

Tyr Tyr Leu Thr Phe Asn Phe Asp Asn Glu Pro Glu Asn Ile Ser Ile
65                  70                  75                  80

Glu Asn Leu Ser Ser Asp Ile Ile Gly Gln Leu Glu Leu Met Pro Asn
                85                  90                  95

Ile Glu Arg Phe Pro Asn Gly Lys Lys Tyr Glu Leu Asp Lys Tyr Thr
            100                 105                 110

Met Phe His Tyr Leu Arg Ala Gln Glu Phe Glu His Gly Lys Ser Arg
        115                 120                 125

Ile Ala Leu Thr Asn Ser Val Asn Glu Ala Leu Leu Asn Pro Ser Arg
    130                 135                 140

Val Tyr Thr Phe Phe Ser Ser Asp Tyr Val Lys Lys Val Asn Lys Ala
145                 150                 155                 160

Thr Glu Ala Ala Met Phe Leu Gly Trp Val Glu Gln Leu Val Tyr Asp
                165                 170                 175

Phe Thr Asp Glu Thr Ser Glu Val Ser Thr Thr Asp Lys Ile Ala Asp
            180                 185                 190

Ile Thr Ile Ile Ile Pro Tyr Ile Gly Pro Ala Leu Asn Ile Gly Asn
        195                 200                 205

Met Leu Tyr Lys Asp Asp Phe Val Gly Ala Leu Ile Phe Ser Gly Ala
```

```
                  210                 215                 220
Val Ile Leu Leu Glu Phe Ile Pro Glu Ile Ala Ile Pro Val Leu Gly
225                 230                 235                 240

Thr Phe Ala Leu Val Ser Tyr Ile Ala Asn Lys Val Leu Thr Val Gln
                    245                 250                 255

Thr Ile Asp Asn Ala Leu Ser Lys Arg Asn Glu Lys Trp Asp Glu Val
                260                 265                 270

Tyr Lys Tyr Ile Val Thr Asn Trp Leu Ala Lys Val Asn Thr Gln Ile
            275                 280                 285

Asp Leu Ile Arg Lys Lys Met Lys Glu Ala Leu Glu Asn Gln Ala Glu
        290                 295                 300

Ala Thr Lys Ala Ile Ile Asn Tyr Gln Tyr Asn Gln Tyr Thr Glu Glu
305                 310                 315                 320

Glu Lys Asn Asn Ile Asn Phe Asn Ile Asp Asp Leu Ser Ser Lys Leu
                    325                 330                 335

Asn Glu Ser Ile Asn Lys Ala Met Ile Asn Ile Asn Lys Phe Leu Asn
                340                 345                 350

Gln Cys Ser Val Ser Tyr Leu Met Asn Ser Met Ile Pro Tyr Gly Val
            355                 360                 365

Lys Arg Leu Glu Asp Phe Asp Ala Ser Leu Lys Asp Ala Leu Leu Lys
        370                 375                 380

Tyr Ile Tyr Asp Asn Arg Gly Thr Leu Ile Gly Gln Val Asp Arg Leu
385                 390                 395                 400

Lys Asp Lys Val Asn Asn Thr Leu Ser Thr Asp Ile Pro Phe Gln Leu
                    405                 410                 415

Ser Lys Tyr Val Asp Asn Gln Arg Leu Leu Ser Thr Phe Thr Glu Tyr
                420                 425                 430

Ile Lys Asn Ile Asp Asp Asp Lys Tyr Pro Ser Lys Pro Asp Asn
            435                 440                 445

Pro Gly Glu Asp Ala Pro Ala Glu Asp Met Ala Arg Tyr Tyr Ser Ala
        450                 455                 460

Leu Arg His Tyr Ile Asn Leu Ile Thr Arg Gln Arg Tyr Ala Leu Ala
465                 470                 475                 480

Gly Gly Gly Gly Ser Gly Gly Gly Ser Gly Gly Gly Ser Pro
                    485                 490                 495

Phe Val Asn Lys Gln Phe Asn Tyr Lys Asp Pro Val Asn Gly Val Asp
                500                 505                 510

Ile Ala Tyr Ile Lys Ile Pro Asn Ala Gly Gln Met Gln Pro Val Lys
            515                 520                 525

Ala Phe Lys Ile His Asn Lys Ile Trp Val Ile Pro Glu Arg Asp Thr
        530                 535                 540

Phe Thr Asn Pro Glu Glu Gly Asp Leu Asn Pro Pro Glu Ala Lys
545                 550                 555                 560

Gln Val Pro Val Ser Tyr Asp Ser Thr Tyr Leu Ser Thr Asp Asn
                    565                 570                 575

Glu Lys Asp Asn Tyr Leu Lys Gly Val Thr Lys Leu Phe Glu Arg Ile
                580                 585                 590

Tyr Ser Thr Asp Leu Gly Arg Met Leu Leu Thr Ser Ile Val Arg Gly
            595                 600                 605

Ile Pro Phe Trp Gly Gly Ser Thr Ile Asp Thr Glu Leu Lys Val Ile
        610                 615                 620

Asp Thr Asn Cys Ile Asn Val Ile Gln Pro Asp Gly Ser Tyr Arg Ser
625                 630                 635                 640
```

-continued

```
Glu Glu Leu Asn Leu Val Ile Ile Gly Pro Ser Ala Asp Ile Ile Gln
                645                 650                 655

Phe Glu Cys Lys Ser Phe Gly His Glu Val Leu Asn Leu Thr Arg Asn
            660                 665                 670

Gly Tyr Gly Ser Thr Gln Tyr Ile Arg Phe Ser Pro Asp Phe Thr Phe
        675                 680                 685

Gly Phe Glu Glu Ser Leu Glu Val Asp Thr Asn Pro Leu Leu Gly Ala
    690                 695                 700

Gly Lys Phe Ala Thr Asp Pro Ala Val Thr Leu Ala His Glu Leu Ile
705                 710                 715                 720

His Ala Gly His Arg Leu Tyr Gly Ile Ala Ile Asn Pro Asn Arg Val
                725                 730                 735

Phe Lys Val Asn Thr Asn Ala Tyr Tyr Glu Met Ser Gly Leu Glu Val
            740                 745                 750

Ser Phe Glu Glu Leu Arg Thr Phe Gly Gly His Asp Ala Lys Phe Ile
        755                 760                 765

Asp Ser Leu Gln Glu Asn Glu Phe Arg Leu Tyr Tyr Tyr Asn Lys Phe
    770                 775                 780

Lys Asp Ile Ala Ser Thr Leu Asn Lys Ala Lys Ser Ile Val Gly Thr
785                 790                 795                 800

Thr Ala Ser Leu Gln Tyr Met Lys Asn Val Phe Lys Glu Lys Tyr Leu
                805                 810                 815

Leu Ser Glu Asp Thr Ser Gly Lys Phe Ser Val Asp Lys Leu Lys Phe
            820                 825                 830

Asp Lys Leu Tyr Lys Met Leu Thr Glu Ile Tyr Thr Glu Asp Asn Phe
        835                 840                 845

Val Lys Phe Phe Lys Val Leu Asn Arg Lys Thr Tyr Leu Asn Phe Asp
    850                 855                 860

Lys Ala Val Phe Lys Ile Asn Ile Val Pro Lys Val Asn Tyr Thr Ile
865                 870                 875                 880

Tyr Asp Gly Phe Asn Leu Arg Asn Thr Asn Leu Ala Ala Asn Phe Asn
                885                 890                 895

Gly Gln Asn Thr Glu Ile Asn Asn Met Asn Phe Thr Lys Leu Lys Asn
            900                 905                 910

Phe Thr Gly Leu Phe Glu Phe Tyr Lys Leu Leu Cys Val Arg Gly Ile
        915                 920                 925

Ile Thr Ser Lys
    930

<210> SEQ ID NO 128
<211> LENGTH: 922
<212> TYPE: PRT
<213> ORGANISM: Artificial Sequence
<220> FEATURE:
<221> NAME/KEY: PEPTIDE
<222> LOCATION: (1)...(922)
<223> OTHER INFORMATION: BoNT/A-TEV-GalaninXP6A

<400> SEQUENCE: 128

Met Pro Phe Val Asn Lys Gln Phe Asn Tyr Lys Asp Pro Val Asn Gly
 1               5                  10                  15

Val Asp Ile Ala Tyr Ile Lys Ile Pro Asn Ala Gly Gln Met Gln Pro
            20                  25                  30

Val Lys Ala Phe Lys Ile His Asn Lys Ile Trp Val Ile Pro Glu Arg
        35                  40                  45

Asp Thr Phe Thr Asn Pro Glu Glu Gly Asp Leu Asn Pro Pro Pro Glu
    50                  55                  60
```

-continued

```
Ala Lys Gln Val Pro Val Ser Tyr Tyr Asp Ser Thr Tyr Leu Ser Thr
 65                  70                  75                  80

Asp Asn Glu Lys Asp Asn Tyr Leu Lys Gly Val Thr Lys Leu Phe Glu
                 85                  90                  95

Arg Ile Tyr Ser Thr Asp Leu Gly Arg Met Leu Leu Thr Ser Ile Val
            100                 105                 110

Arg Gly Ile Pro Phe Trp Gly Gly Ser Thr Ile Asp Thr Glu Leu Lys
        115                 120                 125

Val Ile Asp Thr Asn Cys Ile Asn Val Ile Gln Pro Asp Gly Ser Tyr
130                 135                 140

Arg Ser Glu Glu Leu Asn Leu Val Ile Gly Pro Ser Ala Asp Ile
145                 150                 155                 160

Ile Gln Phe Glu Cys Lys Ser Phe Gly His Glu Val Leu Asn Leu Thr
                165                 170                 175

Arg Asn Gly Tyr Gly Ser Thr Gln Tyr Ile Arg Phe Ser Pro Asp Phe
            180                 185                 190

Thr Phe Gly Phe Glu Glu Ser Leu Glu Val Asp Thr Asn Pro Leu Leu
        195                 200                 205

Gly Ala Gly Lys Phe Ala Thr Asp Pro Ala Val Thr Leu Ala His Glu
210                 215                 220

Leu Ile His Ala Gly His Arg Leu Tyr Gly Ile Ala Ile Asn Pro Asn
225                 230                 235                 240

Arg Val Phe Lys Val Asn Thr Asn Ala Tyr Tyr Glu Met Ser Gly Leu
                245                 250                 255

Glu Val Ser Phe Glu Glu Leu Arg Thr Phe Gly Gly His Asp Ala Lys
            260                 265                 270

Phe Ile Asp Ser Leu Gln Glu Asn Glu Phe Arg Leu Tyr Tyr Tyr Asn
        275                 280                 285

Lys Phe Lys Asp Ile Ala Ser Thr Leu Asn Lys Ala Lys Ser Ile Val
290                 295                 300

Gly Thr Thr Ala Ser Leu Gln Tyr Met Lys Asn Val Phe Lys Glu Lys
305                 310                 315                 320

Tyr Leu Leu Ser Glu Asp Thr Ser Gly Lys Phe Ser Val Asp Lys Leu
                325                 330                 335

Lys Phe Asp Lys Leu Tyr Lys Met Leu Thr Glu Ile Tyr Thr Glu Asp
            340                 345                 350

Asn Phe Val Lys Phe Phe Lys Val Leu Asn Arg Lys Thr Tyr Leu Asn
        355                 360                 365

Phe Asp Lys Ala Val Phe Lys Ile Asn Ile Val Pro Lys Val Asn Tyr
370                 375                 380

Thr Ile Tyr Asp Gly Phe Asn Leu Arg Asn Thr Asn Leu Ala Ala Asn
385                 390                 395                 400

Phe Asn Gly Gln Asn Thr Glu Ile Asn Asn Met Asn Phe Thr Lys Leu
                405                 410                 415

Lys Asn Phe Thr Gly Leu Phe Glu Phe Tyr Lys Leu Leu Cys Val Arg
            420                 425                 430

Gly Ile Ile Thr Ser Lys Thr Lys Ser Leu Glu Asn Leu Tyr Phe Gln
        435                 440                 445

Gly Ala Leu Asn Asp Leu Cys Ile Lys Val Asn Asn Trp Asp Leu Phe
450                 455                 460

Phe Ser Pro Ser Glu Asp Asn Phe Thr Asn Asp Leu Asn Lys Gly Glu
465                 470                 475                 480

Glu Ile Thr Ser Asp Thr Asn Ile Glu Ala Ala Glu Glu Asn Ile Ser
```

```
                485                 490                 495
Leu Asp Leu Ile Gln Gln Tyr Tyr Leu Thr Phe Asn Phe Asp Asn Glu
                500                 505                 510

Pro Glu Asn Ile Ser Ile Glu Asn Leu Ser Ser Asp Ile Ile Gly Gln
                515                 520                 525

Leu Glu Leu Met Pro Asn Ile Glu Arg Phe Pro Asn Gly Lys Lys Tyr
                530                 535                 540

Glu Leu Asp Lys Tyr Thr Met Phe His Tyr Leu Arg Ala Gln Glu Phe
545                 550                 555                 560

Glu His Gly Lys Ser Arg Ile Ala Leu Thr Asn Ser Val Asn Glu Ala
                565                 570                 575

Leu Leu Asn Pro Ser Arg Val Tyr Thr Phe Phe Ser Ser Asp Tyr Val
                580                 585                 590

Lys Lys Val Asn Lys Ala Thr Glu Ala Ala Met Phe Leu Gly Trp Val
                595                 600                 605

Glu Gln Leu Val Tyr Asp Phe Thr Asp Glu Thr Ser Glu Val Ser Thr
                610                 615                 620

Thr Asp Lys Ile Ala Asp Ile Thr Ile Ile Pro Tyr Ile Gly Pro
625                 630                 635                 640

Ala Leu Asn Ile Gly Asn Met Leu Tyr Lys Asp Asp Phe Val Gly Ala
                645                 650                 655

Leu Ile Phe Ser Gly Ala Val Ile Leu Leu Glu Phe Ile Pro Glu Ile
                660                 665                 670

Ala Ile Pro Val Leu Gly Thr Phe Ala Leu Val Ser Tyr Ile Ala Asn
                675                 680                 685

Lys Val Leu Thr Val Gln Thr Ile Asp Asn Ala Leu Ser Lys Arg Asn
                690                 695                 700

Glu Lys Trp Asp Glu Val Tyr Lys Tyr Ile Val Thr Asn Trp Leu Ala
705                 710                 715                 720

Lys Val Asn Thr Gln Ile Asp Leu Ile Arg Lys Lys Met Lys Glu Ala
                725                 730                 735

Leu Glu Asn Gln Ala Glu Ala Thr Lys Ala Ile Ile Asn Tyr Gln Tyr
                740                 745                 750

Asn Gln Tyr Thr Glu Glu Lys Asn Asn Ile Asn Phe Asn Ile Asp
                755                 760                 765

Asp Leu Ser Ser Lys Leu Asn Glu Ser Ile Asn Lys Ala Met Ile Asn
                770                 775                 780

Ile Asn Lys Phe Leu Asn Gln Cys Ser Val Ser Tyr Leu Met Asn Ser
785                 790                 795                 800

Met Ile Pro Tyr Gly Val Lys Arg Leu Glu Asp Phe Asp Ala Ser Leu
                805                 810                 815

Lys Asp Ala Leu Leu Lys Tyr Ile Tyr Asp Asn Arg Gly Thr Leu Ile
                820                 825                 830

Gly Gln Val Asp Arg Leu Lys Asp Lys Val Asn Asn Thr Leu Ser Thr
                835                 840                 845

Asp Ile Pro Phe Gln Leu Ser Lys Tyr Val Asp Asn Gln Arg Leu Leu
                850                 855                 860

Ser Thr Phe Thr Glu Tyr Ile Lys Asn Ile Ala Leu Ala Gly Gly Gly
865                 870                 875                 880

Gly Ser Gly Gly Gly Ser Gly Gly Gly Ser Gly Trp Thr Leu
                885                 890                 895

Asn Ser Ala Gly Tyr Leu Leu Gly Pro His Ala Val Gly Asn His Arg
                900                 905                 910
```

```
Ser Phe Ser Asp Lys Asn Gly Leu Thr Ser
            915                 920

<210> SEQ ID NO 129
<211> LENGTH: 923
<212> TYPE: PRT
<213> ORGANISM: Artificial Sequence
<220> FEATURE:
<221> NAME/KEY: PEPTIDE
<222> LOCATION: (1)...(923)
<223> OTHER INFORMATION: BoNT/A-TEV-GalaninXP6B

<400> SEQUENCE: 129

Met Glu Ala Ala Ala Lys Glu Ala Ala Lys Ala Leu Asn Asp Leu
 1               5                  10                  15

Cys Ile Lys Val Asn Asn Trp Asp Leu Phe Phe Ser Pro Ser Glu Asp
            20                  25                  30

Asn Phe Thr Asn Asp Leu Asn Lys Gly Glu Glu Ile Thr Ser Asp Thr
        35                  40                  45

Asn Ile Glu Ala Ala Glu Glu Asn Ile Ser Leu Asp Leu Ile Gln Gln
    50                  55                  60

Tyr Tyr Leu Thr Phe Asn Phe Asp Asn Glu Pro Glu Asn Ile Ser Ile
 65                 70                  75                  80

Glu Asn Leu Ser Ser Asp Ile Ile Gly Gln Leu Glu Leu Met Pro Asn
                85                  90                  95

Ile Glu Arg Phe Pro Asn Gly Lys Lys Tyr Glu Leu Asp Lys Tyr Thr
            100                 105                 110

Met Phe His Tyr Leu Arg Ala Gln Glu Phe Glu His Gly Lys Ser Arg
        115                 120                 125

Ile Ala Leu Thr Asn Ser Val Asn Glu Ala Leu Leu Asn Pro Ser Arg
    130                 135                 140

Val Tyr Thr Phe Phe Ser Ser Asp Tyr Val Lys Lys Val Asn Lys Ala
145                 150                 155                 160

Thr Glu Ala Ala Met Phe Leu Gly Trp Val Glu Gln Leu Val Tyr Asp
                165                 170                 175

Phe Thr Asp Glu Thr Ser Glu Val Ser Thr Thr Asp Lys Ile Ala Asp
            180                 185                 190

Ile Thr Ile Ile Ile Pro Tyr Ile Gly Pro Ala Leu Asn Ile Gly Asn
        195                 200                 205

Met Leu Tyr Lys Asp Asp Phe Val Gly Ala Leu Ile Phe Ser Gly Ala
    210                 215                 220

Val Ile Leu Leu Glu Phe Ile Pro Glu Ile Ala Ile Pro Val Leu Gly
225                 230                 235                 240

Thr Phe Ala Leu Val Ser Tyr Ile Ala Asn Lys Val Leu Thr Val Gln
                245                 250                 255

Thr Ile Asp Asn Ala Leu Ser Lys Arg Asn Glu Lys Trp Asp Glu Val
            260                 265                 270

Tyr Lys Tyr Ile Val Thr Asn Trp Leu Ala Lys Val Asn Thr Gln Ile
        275                 280                 285

Asp Leu Ile Arg Lys Lys Met Lys Glu Ala Leu Glu Asn Gln Ala Glu
    290                 295                 300

Ala Thr Lys Ala Ile Ile Asn Tyr Gln Tyr Asn Gln Tyr Thr Glu Glu
305                 310                 315                 320

Glu Lys Asn Asn Ile Asn Phe Asn Ile Asp Asp Leu Ser Ser Lys Leu
                325                 330                 335

Asn Glu Ser Ile Asn Lys Ala Met Ile Asn Ile Asn Lys Phe Leu Asn
            340                 345                 350
```

```
Gln Cys Ser Val Ser Tyr Leu Met Asn Ser Met Ile Pro Tyr Gly Val
        355                 360                 365
Lys Arg Leu Glu Asp Phe Asp Ala Ser Leu Lys Asp Ala Leu Leu Lys
    370                 375                 380
Tyr Ile Tyr Asp Asn Arg Gly Thr Leu Ile Gly Gln Val Asp Arg Leu
385                 390                 395                 400
Lys Asp Lys Val Asn Asn Thr Leu Ser Thr Asp Ile Pro Phe Gln Leu
                405                 410                 415
Ser Lys Tyr Val Asp Asn Gln Arg Leu Leu Ser Thr Phe Thr Glu Tyr
            420                 425                 430
Ile Lys Asn Ile Glu Asn Leu Tyr Phe Gln Gly Pro Phe Val Asn Lys
        435                 440                 445
Gln Phe Asn Tyr Lys Asp Pro Val Asn Gly Val Asp Ile Ala Tyr Ile
    450                 455                 460
Lys Ile Pro Asn Ala Gly Gln Met Gln Pro Val Lys Ala Phe Lys Ile
465                 470                 475                 480
His Asn Lys Ile Trp Val Ile Pro Glu Arg Asp Thr Phe Thr Asn Pro
                485                 490                 495
Glu Glu Gly Asp Leu Asn Pro Pro Glu Ala Lys Gln Val Pro Val
            500                 505                 510
Ser Tyr Tyr Asp Ser Thr Tyr Leu Ser Thr Asp Asn Glu Lys Asp Asn
        515                 520                 525
Tyr Leu Lys Gly Val Thr Lys Leu Phe Glu Arg Ile Tyr Ser Thr Asp
    530                 535                 540
Leu Gly Arg Met Leu Leu Thr Ser Ile Val Arg Gly Ile Pro Phe Trp
545                 550                 555                 560
Gly Gly Ser Thr Ile Asp Thr Glu Leu Lys Val Ile Asp Thr Asn Cys
                565                 570                 575
Ile Asn Val Ile Gln Pro Asp Gly Ser Tyr Arg Ser Glu Glu Leu Asn
        580                 585                 590
Leu Val Ile Ile Gly Pro Ser Ala Asp Ile Ile Gln Phe Glu Cys Lys
    595                 600                 605
Ser Phe Gly His Glu Val Leu Asn Leu Thr Arg Asn Gly Tyr Gly Ser
610                 615                 620
Thr Gln Tyr Ile Arg Phe Ser Pro Asp Phe Thr Phe Gly Phe Glu Glu
625                 630                 635                 640
Ser Leu Glu Val Asp Thr Asn Pro Leu Leu Gly Ala Gly Lys Phe Ala
                645                 650                 655
Thr Asp Pro Ala Val Thr Leu Ala His Glu Leu Ile His Ala Gly His
            660                 665                 670
Arg Leu Tyr Gly Ile Ala Ile Asn Pro Asn Arg Val Phe Lys Val Asn
        675                 680                 685
Thr Asn Ala Tyr Tyr Glu Met Ser Gly Leu Glu Val Ser Phe Glu Glu
    690                 695                 700
Leu Arg Thr Phe Gly Gly His Asp Ala Lys Phe Ile Asp Ser Leu Gln
705                 710                 715                 720
Glu Asn Glu Phe Arg Leu Tyr Tyr Tyr Asn Lys Phe Lys Asp Ile Ala
                725                 730                 735
Ser Thr Leu Asn Lys Ala Lys Ser Ile Val Gly Thr Thr Ala Ser Leu
            740                 745                 750
Gln Tyr Met Lys Asn Val Phe Lys Glu Lys Tyr Leu Leu Ser Glu Asp
        755                 760                 765
Thr Ser Gly Lys Phe Ser Val Asp Lys Leu Lys Phe Asp Lys Leu Tyr
```

-continued

```
                770                 775                 780
Lys Met Leu Thr Glu Ile Tyr Thr Glu Asp Asn Phe Val Lys Phe Phe
785                     790                     795                 800

Lys Val Leu Asn Arg Lys Thr Tyr Leu Asn Phe Asp Lys Ala Val Phe
                805                     810                     815

Lys Ile Asn Ile Val Pro Lys Val Asn Tyr Thr Ile Tyr Asp Gly Phe
                820                     825                     830

Asn Leu Arg Asn Thr Asn Leu Ala Ala Asn Phe Asn Gly Gln Asn Thr
            835                     840                     845

Glu Ile Asn Asn Met Asn Phe Thr Lys Leu Lys Asn Phe Thr Gly Leu
        850                     855                     860

Phe Glu Phe Tyr Lys Leu Leu Cys Val Arg Gly Ile Ile Thr Gly Gly
865                     870                     875                     880

Gly Gly Ser Gly Gly Gly Ser Gly Gly Gly Ser Gly Trp Thr
                885                     890                     895

Leu Asn Ser Ala Gly Tyr Leu Leu Gly Pro His Ala Val Gly Asn His
                900                     905                     910

Arg Ser Phe Ser Asp Lys Asn Gly Leu Thr Ser
            915                     920

<210> SEQ ID NO 130
<211> LENGTH: 17
<212> TYPE: PRT
<213> ORGANISM: Artificial Sequence
<220> FEATURE:
<223> OTHER INFORMATION: Linker

<400> SEQUENCE: 130

Gly Glu Lys Leu Tyr Asp Asp Asp Asp Lys Asp Arg Trp Gly Ser Ser
1               5                   10                  15

Arg
```

What is claimed is:

1. A recombinant single-chain polypeptide comprising:
   a) a first amino acid sequence region comprising
      i) a first domain comprising a binding element comprising a granin peptide able to preferentially interact with a granin peptide receptor under physiological conditions; and
      ii) a second domain comprising a translocation element comprising a Clostridial neurotoxin translocation domain able to facilitate the transfer of a Clostridial toxin light chain across a vesicular membrane;
   b) a second amino acid sequence region comprising a therapeutic element comprising a Clostridial neurotoxin light chain having biological activity when released into the cytoplasm of said target cell;
   c) a third amino acid sequence region comprising an exogenous protease cleavage site;
      wherein said first and second amino acid sequence regions are separated by said third amino acid sequence region.

2. The polypeptide of claim 1, wherein said granin peptide comprises a chromogranin A, a chromogranin B, or a chromogranin C.

3. The polypeptide of claim 2, wherein said chromogranin A comprises a β-granin, a vasostatin, a chromostatin, a pancreastatin, a WE-14, a catestatin, a parastatin or a GE-25.

4. The polypeptide of claim 2, wherein said chromogranin A comprises SEQ ID NO: 93, SEQ ID NO: 94, SEQ ID NO: 95, SEQ ID NO: 96, SEQ ID NO: 97, SEQ ID NO: 98, SEQ ID NO: 99 or SEQ ID NO: 100.

5. The polypeptide of claim 2, wherein said chromogranin B comprises a GAWK peptide, an adrenomedullary peptide or a secretolytin.

6. The polypeptide of claim 2, wherein said chromogranin B comprises SEQ ID NO: 101, SEQ ID NO: 102, SEQ ID NO: 103, SEQ ID NO: 104 or SEQ ID NO: 105.

7. The polypeptide of claim 2, wherein said chromogranin C comprises a secretoneurin.

8. The polypeptide of claim 2, wherein said chromogranin C comprises SEQ ID NO: 106.

9. The polypeptide of claim 1, wherein said translocation element comprises a *Clostridium botulinum* neurotoxin translocation domain.

10. The polypeptide of claim 9, wherein said *Clostridium botulinum* neurotoxin translocation domain is selected from the group consisting of a *Clostridium botulinum* serotype A neurotoxin translocation domain, a *Clostridium botulinum* serotype B neurotoxin translocation domain, a *Clostridium botulinum* serotype C1 neurotoxin translocation domain, a *Clostridium botulinum* serotype D neurotoxin translocation domain, a *Clostridium botulinum* serotype E neurotoxin translocation domain, a *Clostridium botulinum* serotype F neurotoxin translocation domain and a *Clostridium botulinum* serotype G neurotoxin translocation domain.

11. The polypeptide of claim 1, wherein said translocation element comprises a *Clostridium tetani* neurotoxin translocation domain.

12. The polypeptide of claim 1, wherein said therapeutic element comprises a *Clostridium botulinum* neurotoxin light chain.

13. The polypeptide of claim 12, wherein said *Clostridium botulinum* neurotoxin light chain therapeutic element is selected from the group consisting of a *Clostridium botulinum* serotype A neurotoxin light chain, a *Clostridium botulinum* serotype B neurotoxin light chain, a *Clostridium botulinum* serotype C1 neurotoxin light chain, a *Clostridium botulinum* serotype D neurotoxin light chain, a *Clostridium botulinum* serotype E neurotoxin light chain, a *Clostridium botulinum* serotype F neurotoxin light chain and a *Clostridium botulinum* serotype G neurotoxin light chain.

14. The polypeptide of claim 1, wherein said therapeutic element comprises a *Clostridium tetani* neurotoxin light chain.

15. The polypeptide of claim 1, wherein said exogenous protease cleavage site comprises a non-human enterokinase cleavage site, a tobacco etch virus protease cleavage site, a tobacco vein mottling virus protease cleavage site, a human rhinovirus 3C protease cleavage site, a human enterovirus 3C protease cleavage site, a subtilisin cleavage site, a SUMO/ULP-1 protease cleavage site, or a non-human Caspase 3 protease cleavage site.

16. The polypeptide of claim 15, wherein said non-human enterokinase cleavage site comprises SEQ ID NO: 21.

17. The polypeptide of claim 15, wherein said tobacco etch virus protease cleavage site comprises SEQ ID NO: 22 or SEQ ID NO: 23.

18. The polypeptide of claim 15, wherein said tobacco etch virus protease cleavage site comprises SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32 or SEQ ID NO: 33.

19. The polypeptide of claim 15, wherein said tobacco vein mottling virus protease cleavage site comprises SEQ ID NO: 34 or SEQ ID NO: 35.

20. The polypeptide of claim 15, wherein said tobacco vein mottling virus protease cleavage site comprises SEQ ID NO: 36, SEQ ID NO: 37, SEQ ID NO: 38, or SEQ ID NO: 39.

21. The polypeptide of claim 15, wherein said human rhinovirus 3C protease cleavage site comprises SEQ ID NO: 40.

22. The polypeptide of claim 15, wherein said human rhinovirus 3C protease cleavage site comprises SEQ ID NO: 41, SEQ ID NO: 42, SEQ ID NO: 43, SEQ ID NO: 44, SEQ ID NO: 45 or SEQ ID NO: 46.

23. The polypeptide of claim 15, wherein said subtilisin cleavage site comprises SEQ ID NO: 47 or SEQ ID NO: 48.

24. The polypeptide of claim 15, wherein said subtilisin cleavage site comprises SEQ ID NO: 49, SEQ ID NO: 50, or SEQ ID NO: 51.

25. The polypeptide of claim 15, wherein said non-human Caspase 3 protease cleavage site comprises SEQ ID NO: 57.

26. The polypeptide of claim 15, wherein said non-human Caspase 3 protease cleavage site comprises SEQ ID NO: 58, SEQ ID NO: 59, SEQ ID NO: 60, SEQ ID NO: 61, SEQ ID NO: 62 or SEQ ID NO: 63.

27. The polypeptide of claim 1, wherein said polypeptide further comprises a fourth amino acid sequence region comprising a target-binding portion of a binding tag.

28. A method of activating a single-chain polypeptide, the method comprising the step of incubating the single-chain polypeptide according to claim 1 with an exogenous protease; wherein the exogenous protease cleaves the exogenous protease cleavage site; and wherein cleavage of the single-chain polypeptide by the exogenous protease converts the single-chain polypeptide into a di-chain form, thereby activating the single-chain polypeptide.

29. A pharmaceutical composition comprising a carrier and a di-chain polypeptide obtained by the method according to claim 28.

* * * * *

UNITED STATES PATENT AND TRADEMARK OFFICE
CERTIFICATE OF CORRECTION

| | |
|---|---|
| PATENT NO. | : 7,897,157 B2 |
| APPLICATION NO. | : 11/845252 |
| DATED | : March 1, 2011 |
| INVENTOR(S) | : Lance E. Steward et al. |

It is certified that error appears in the above-identified patent and that said Letters Patent is hereby corrected as shown below:

On the first page, in field (56), in column 2, under "Other Publications", line 31, delete "interation" and insert -- interaction --, therefor.

On page 2, in column 2, under "Other Publications", line 6, delete "Neurotoxiicity" and insert -- Neurotoxicity --, therefor.

On page 2, in column 2, under "Other Publications", line 12, delete "Cahins" and insert -- Chains --, therefor.

On page 2, in column 2, under "Other Publications", line 19, delete "Proetin" and insert -- Protein --, therefor.

In column 1, line 12, delete "Aug. 8," and insert -- Aug. 25, --, therefor.

In column 1, line 15, delete "Aug. 5," and insert -- Aug. 25, --, therefor.

In column 3, line 2, delete "bephlarospasm" and insert -- blepharospasm --, therefor.

In column 5, line 31, delete "chromotography" and insert -- chromatography --, therefor.

In column 5, line 58, delete "zeamatus," and insert -- zeamais, --, therefor.

In column 5, line 59, delete "crustacian" and insert -- crustacean --, therefor.

In column 5, line 62, delete "amyliquifaciens," and insert -- amyloliquefaciens, --, therefor.

In column 6, line 66, after "and" delete "a".

In column 7, line 45, before "amino" delete "and".

Signed and Sealed this
Seventh Day of February, 2012

David J. Kappos
*Director of the United States Patent and Trademark Office*

In column 7, line 61, delete "Commassie" and insert -- Coomassie --, therefor.

In column 8, line 25, delete "diaphrams" and insert -- diaphragms --, therefor.

In column 14, line 18, delete "zeamatus," and insert -- zeamais, --, therefor.

In column 14, line 19, delete "crustacian" and insert -- crustacean --, therefor.

In column 14, line 23, delete "amyliquifaciens," and insert -- amyloliquefaciens, --, therefor.

In column 14, line 47, delete "crustacian" and insert -- crustacean --, therefor.

In column 15, line 13, delete "crustacian" and insert -- crustacean --, therefor.

In column 21, line 41, delete "perioxysome" and insert -- peroxisome --, therefor.

In column 22, line 6, delete "$Glu_{26}$," and insert -- $Glu_{261}$ --, therefor.

In column 82, line 19, delete "calmodilin" and insert -- calmodulin --, therefor.

In column 82, line 21, delete "hemagluttinin" and insert -- hemagglutinin --, therefor.

In column 82, line 33, delete "Manual" and insert -- Manual: --, therefor.

In column 83, line 9, delete "hemagluttinin" and insert -- hemagglutinin --, therefor.

In column 83, line 26, delete "hemagluttinin" and insert -- hemagglutinin --, therefor.

In column 87, line 16, delete "Hind III" and insert -- HindIII --, therefor.

In column 87, line 17, delete "Hind III" and insert -- HindIII --, therefor.

In column 87, line 24, delete "Sal I Hind III" and insert -- SalI HindIII --, therefor.

In column 87, line 29, delete "Hind III Sal I" and insert -- HindIII SalI --, therefor.

In column 87, line 30, delete "Sal I and Hind III" and insert -- SalI and HindIII --, therefor.

In column 87, line 45, delete "Sal I and Hind III," and insert -- SalI and HindIII, --, therefor.

In column 87, line 47-48, delete "Sal I and Hind III" and insert -- SalI and HindIII --, therefor.

In column 88, line 8-9, delete "Hind III and a Sal I" and insert -- HindIII and a SalI --, therefor.

CERTIFICATE OF CORRECTION (continued)
U.S. Pat. No. 7,897,157 B2

In column 88, line 34, delete "Hind III" and insert -- HindIII --, therefor.

In column 88, line 36, delete "Hind III" and insert -- HindIII --, therefor.

In column 88, line 41, delete "Sal I" and insert -- SalI --, therefor.

In column 88, line 43, delete "Sal I" and insert -- SalI --, therefor.

In column 88, line 57, delete "Hind III and Sal I," and insert -- HindIII and SalI, --, therefor.

In column 89, line 2, delete "ER" and insert -- EK --, therefor.

In column 92, line 46, delete "typsin" and insert -- trypsin --, therefor.

In column 93, line 10, delete "pH7.4," and insert -- pH 7.4, --, therefor.

In column 94, line 1, delete "Adivity" and insert -- Activity --, therefor.

In column 94, line 6, delete "LD50" and insert -- $LD_{50}$ --, therefor.

In column 95, line 48, delete "H," and insert -- $H_C$ --, therefor.

In column 95, line 8, delete "tranferase" and insert -- transferase --, therefor.

In column 96, line 26, delete "Hind III" and insert -- HindIII --, therefor.

In column 96, line 57, after "X62089)" insert -- . --.

In column 101, line 13, delete "Talone" and insert -- Talon® --, therefor.

In column 101, line 28, delete "Quiagen" and insert -- Qiagen --, therefor.

In column 101, line 49, delete "Quiagen," and insert -- Qiagen, --, therefor.

In column 101, line 51, delete "Commassie" and insert -- Coomassie --, therefor.

In column 106, line 35, after "BoNT/G-TEV-αMSHAP4A" insert -- , --.

In column 115, line 28, delete "Pro Tease" and insert -- Protease --, therefor.

In column 122, line 44, delete "monolaureate," and insert -- monolaurate, --, therefor.

In column 122, line 48-49, delete "monolaureate)" and insert -- monolaurate) --, therefor.

CERTIFICATE OF CORRECTION (continued)
U.S. Pat. No. 7,897,157 B2

Page 4 of 4

In column 197-198, line 34-41, delete "
```
<223> OTHER INFORMATION: Consensus sequence for a Tobacco Vein Mottling
      Virus protease cleavage site
<221> NAME/KEY: VARIANT
<222> LOCATION: (1)...(2)
<223> OTHER INFORMATION: Xaa can be any amino acid

<400> SEQUENCE: 35

Xaa Xaa Val Arg Phe Gln Ser
 1               5
```
" and insert --
```
<223> human rhinovirus 3C protease cleavage site
      consensus sequence
<221> VARIANT
<222> (1)...(1)
<223> Xaa can be amino acid, with D or E preferred
<221> VARIANT
<222> (2)...(2)
<223> Xaa can be G, A, V, L, I, M, S or T
<400> 35
Xaa Xaa Leu Phe Gln Gly Pro
 1               5
```
--, therefor.